US009580503B2

(12) United States Patent
Landes et al.

(10) Patent No.: US 9,580,503 B2
(45) Date of Patent: *Feb. 28, 2017

(54) ANTIBODIES AGAINST T CELL IMMUNOGLOBULIN DOMAIN AND MUCIN DOMAIN 1 (TIM-1) ANTIGEN AND USES THEREOF

(75) Inventors: Gregory M. Landes, The Woodlands, TX (US); Francine Chen, San Francisco, CA (US); Binyam Bezabeh, Oakland, CA (US); Ian Foltz, Burnaby (CA); Kam Fai Tse, Clinton, CT (US); Michael Jeffers, Branford, CT (US); Mehdi Mesri, Branford, CT (US); Gary Starling, Clinton, CT (US); Peter Mezes, Old Lyme, CT (US); Nikolia Khramtsov, Branford, CT (US)

(73) Assignees: Celldex Therapeutics, Inc., Hampton, NJ (US); Amgen Fremont Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/305,898

(22) Filed: Nov. 29, 2011

(65) Prior Publication Data
US 2012/0251555 A1    Oct. 4, 2012

Related U.S. Application Data

(62) Division of application No. 10/805,177, filed on Mar. 19, 2004, now Pat. No. 8,067,544.

(60) Provisional application No. 60/456,652, filed on Mar. 19, 2003.

(51) Int. Cl.
*A61K 39/395*      (2006.01)
*C07K 16/28*       (2006.01)
*A61K 39/00*       (2006.01)

(52) U.S. Cl.
CPC .......... *C07K 16/2803* (2013.01); *C07K 16/28* (2013.01); *C07K 16/2809* (2013.01); *A61K 2039/505* (2013.01); *C07K 2316/96* (2013.01); *C07K 2317/21* (2013.01); *C07K 2317/31* (2013.01); *C07K 2317/34* (2013.01); *C07K 2317/50* (2013.01); *C07K 2317/56* (2013.01); *C07K 2317/622* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 6,664,385 B1 | 12/2003 | Sanicola-Nadel et al. |
| 7,662,387 B2 | 2/2010 | Law et al. |
| 2003/0124114 A1 | 7/2003 | McIntire et al. |
| 2004/0162413 A1 | 8/2004 | Watkins et al. |

FOREIGN PATENT DOCUMENTS

| WO | WO-9744460 A1 | 11/1997 |
| WO | WO-02098920 A1 | 12/2002 |
| WO | WO-03002722 A2 | 1/2003 |
| WO | WO-03080856 A2 | 10/2003 |
| WO | WO-2004084823 A2 | 10/2004 |
| WO | WO-2005001092 A2 | 1/2005 |

OTHER PUBLICATIONS

White et al. (2001, Ann. Rev. Med., 2001, 52:125-145).*
Casset et al. "A Peptide Mimetic of an Anti-CD4 Monoclonal Antibody by Rational Design." Biochem. Biophys. Res. Commun. 307.1(2003):198-205.
Chen et al. "Selection and Analysis of an Optimized Anti-VEGF Antibody: Crystal Structure of an Affinity-Matured Fab in Complex with Antigen." J. Mol. Biol. 293.4(1999):865-881.
Feigelstock et al. "The Human Homolog of HAVcr-1 Codes for a Hepatitis A Virus Cellular Receptor." J. Virol. 72.8(1998):6621-6628.
Holm et al. "Functional Mapping and Single Chain Construction of the Anti-Cytokeratin 8 Monoclonal Antibody TS1." Mol. Immunol. 44.6(2007):1075-1084.
Kuchroo et al. "The TIM Gene Family: Emerging Roles in Immunity and Disease." Nat. Rev. Immunol. 3.6(2003):454-462.
Lederman et al. "A Single Amino Acid Substitution in a Common African Allele of the CD4 Molecule Ablates Binding of the Monoclonal Antibody, OKT4." Mol. Immunol. 28.11(1991):1171-1181.
MacCallum et al. "Antibody-Antigen Interactions: Contact Analysis and Binding Site Topography." J. Mol. Biol. 262.5(1996):732-745.
McIntire et al. "Identification of Tapr (an Airway Hyperreactivity locus) and the Linked Tim Gene Family." Nat. Immunol. 2.12(2001):1109-1116.
Mueller et al. "Expression of Tissue Factor by Melanoma Cells Promotes Efficient Hematogenous Metastasis." PNAS. 89.24(1992):11832-11836.
Rudikoff et al. "Single Amino Acid Substitition Altering Antigen-Binding Specificity." PNAS. 79.6(1982):1979-1983.
Shevach. "CD4+ CD25+ Suppressor T Cells: More Questions than Answers." Nat. Rev. Immunol. 2.6(2002):389-400.

(Continued)

*Primary Examiner* — Laura B Goddard
*Assistant Examiner* — Meera Natarajan
(74) *Attorney, Agent, or Firm* — Mintz Levin Cohn Ferris Glovsky and Popeo, P.C.; Fred C. Hernandez; Linyu L. Mitra

(57) ABSTRACT

The invention described herein is related to antibodies directed to the antigen TIM-1 and uses of such antibodies. In particular, there are provided fully human monoclonal antibodies directed to the antigen TIM-1. Isolated polynucleotide sequences encoding, and amino acid sequences comprising, heavy and light chain immunoglobulin molecules, particularly sequences corresponding to contiguous heavy and light chain sequences spanning the framework regions (FR's) and/or complementarity determining regions (CDR's), specifically from FR1 through FR4 or CDR1 through CDR3, are provided. Hybridomas or other cell lines expressing such immunoglobulin molecules and monoclonal antibodies are also provided.

16 Claims, 32 Drawing Sheets

(56) References Cited

OTHER PUBLICATIONS

Vadjos et al. "Comprehensive Functional Maps of the Antigen-Binding Site of an Anti-ErbB2 Antibody Obtained with Shotgun Scanning Mutagenesis." *J. Mol. Biol.* 320.2(2002):415-428.
Winter et al. "Humanized Antibodies." *Immunol. Today.* 14(1993):243-246.
Wu et al. "Humanization of a Murine Monoclonal Activity by Simultaneous Optimization of Framework and CDR Residues." *J. Mol. Biol.* 294.1(1999):151-162.
Doronina, Svetlana O. et al., "Development of potent monoclonal antibody auristatin conjugates for cancer therapy," Nature Biotechnology, vol. 21.7 (2003):778-784.
Francisco, Joseph A. et al., "cAC10-vcMMAE, an anti-CD30-monomethyl auristatin E conjugate with potent and selective antitumor activity," Blood, vol. 102 (2003):1458-1465.
Hamblett, Kevin J. et al., "Effects of Drug Loading on the Antitumor Activity of a Monoclonal Antibody Drug Conjugate," Clinical Cancer Research, vol. 10 (2004):7063-7070.
Wu, Anna M. et al., "Arming antibodies: prospects and challenges for immunoconjugates," Nature Biotechnology, vol. 23.9 (2005):1137-1146.
De Pascalis et al. "Grafting of "Abbreviated" Complementary-Determining Regions Containing Specificity-Determining Residues Essential for Ligand Contact to Engineer a Less Immunogenic Humanized Monoclonal Antibody". J. lmmunol. 169(2002): 3076-3084.
Bailly et al., Shedding of kidney injury molecule-1, a putative adhesion protein involved in renal regeneration. J Biol Chem. Oct. 18, 2002;277(42):39739-48.

* cited by examiner

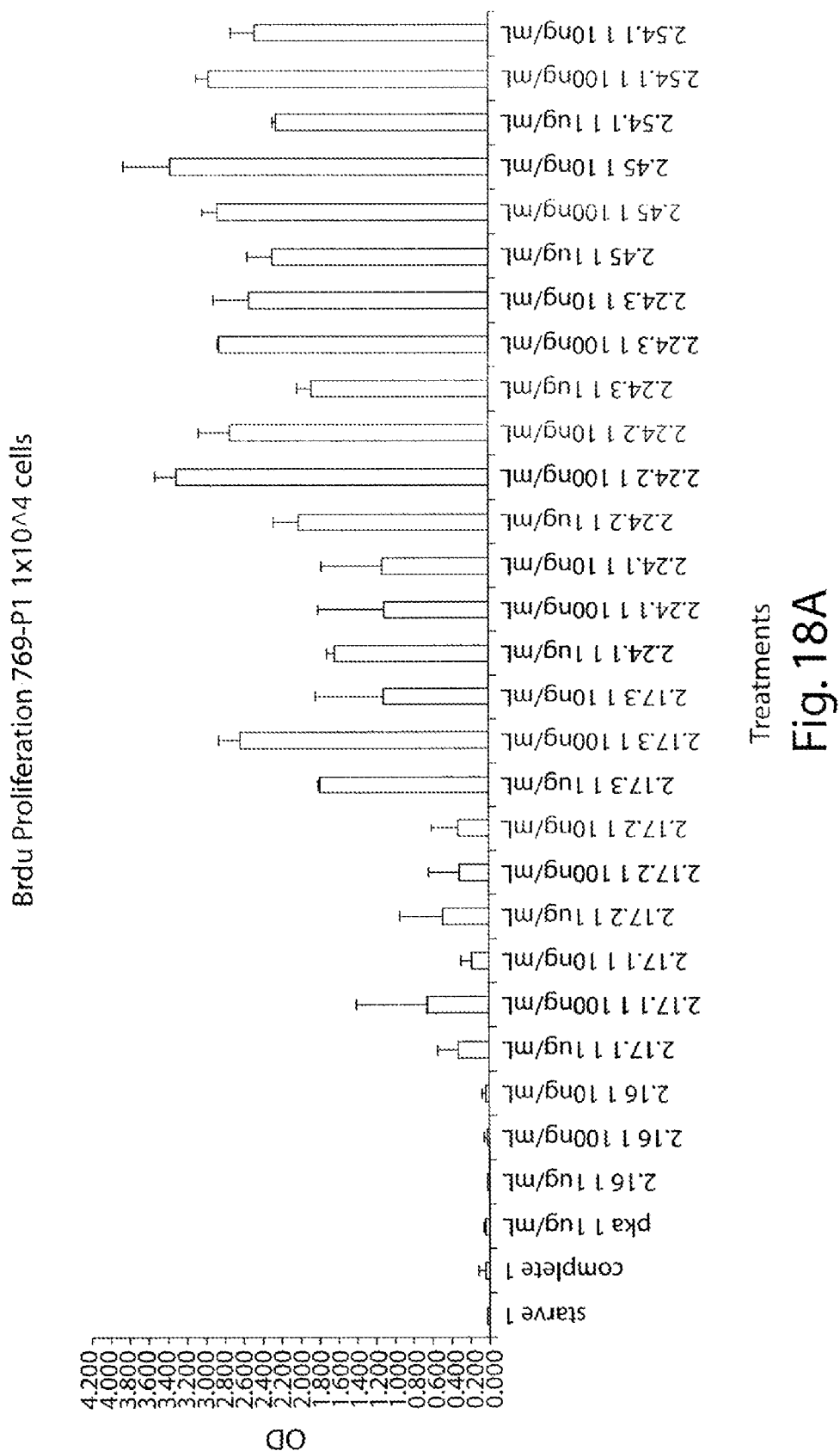

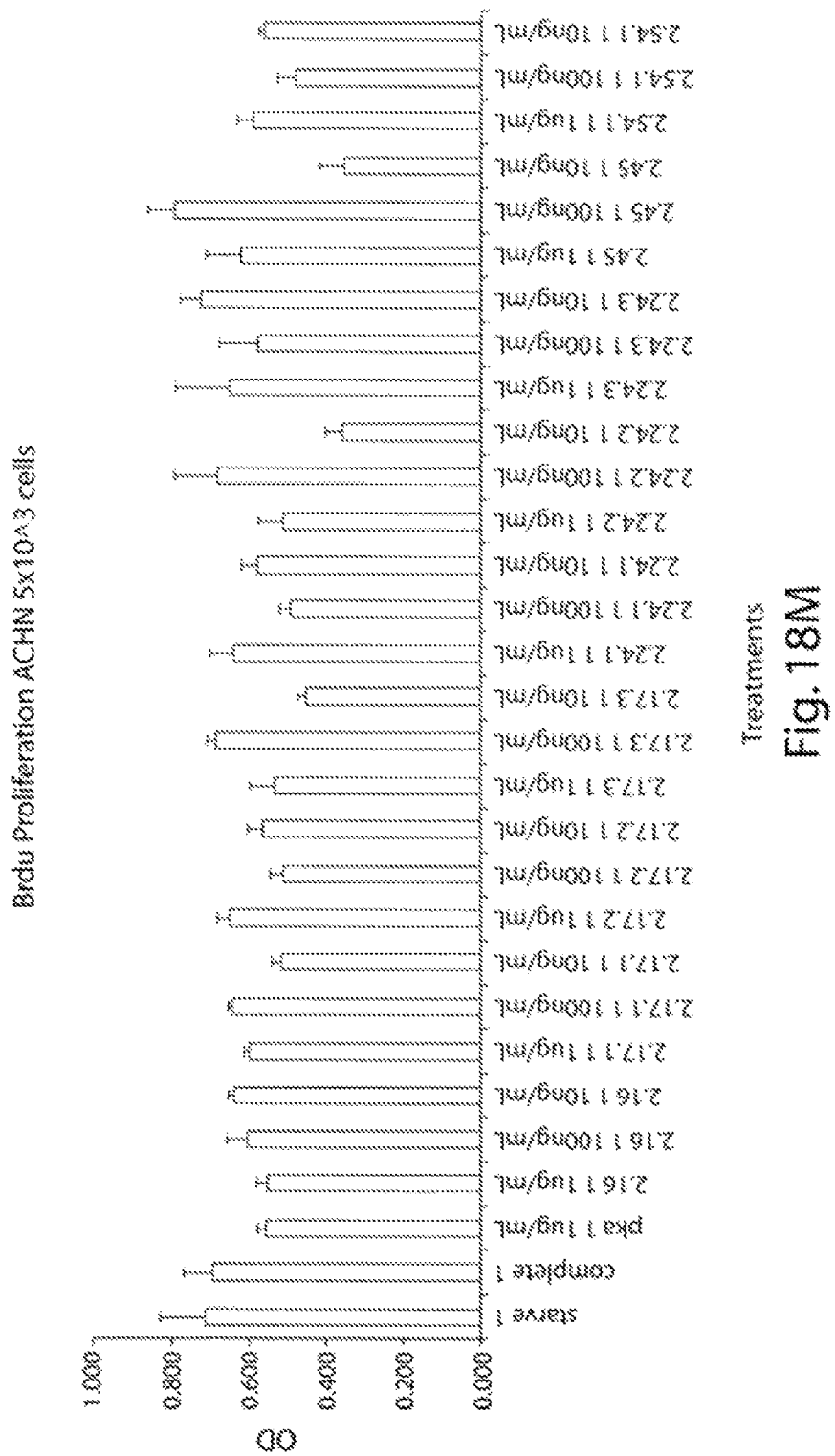

400
ANTIBODIES AGAINST T CELL IMMUNOGLOBULIN DOMAIN AND MUCIN DOMAIN 1 (TIM-1) ANTIGEN AND USES THEREOF

RELATED APPLICATIONS

This application is a division of U.S. patent application Ser. No. 10/805,177, filed Mar. 19, 2004 and now issued as U.S. Pat. No. 8,067,544, which claims the benefit of priority under 35 U.S.C. §119(e) to U.S. Provisional Application No. 60/456,652, filed Mar. 19, 2003, each of which is hereby expressly incorporated by reference.

INCORPORATION BY REFERENCE OF SEQUENCE LISTING

The contents of the text file named "Cura965C4US.txt," which was created on Jun 5, 2012 and is 144 KB in size, are hereby incorporated by reference in their entirety.

BACKGROUND OF THE INVENTION

Field of the Invention

The invention disclosed herein is related to antibodies directed to the antigen T cell, immunoglobulin domain and mucin domain 1 (TIM-1) proteins and uses of such antibodies. In particular, there are provided fully human monoclonal antibodies directed to the antigen TIM-1. Nucleotide sequences encoding, and amino acid sequences comprising, heavy and light chain immunoglobulin molecules, particularly sequences corresponding to contiguous heavy and light chain sequences spanning the framework regions and/or complementarity determining regions (CDRs), specifically from FR1 through FR4 or CDR1 through CDR3, are provided. Hybridomas or other cell lines expressing such immunoglobulin molecules and monoclonal antibodies are also provided.

Description of the Related Art

A new family of genes encoding T cell, immunoglobulin domain and mucin domain (TIM) proteins (three in humans and eight in mice) have been described recently with emerging roles in immunity. Kuchroo et al., *Nat Rev Immunol* 3:454-462 (2003); McIntire et al., *Nat Immunol* 2:1109-1116 (2001). The TIM gene family members reside in chromosomal regions, 5q33.2 in human and 11B1.1 in mouse, and have been linked to allergy and autoimmune diseases. Shevach, *Nat Rev Immunol* 2:389-400 (2002); Wills-Karp et al., *Nat Immunol* 4:1050-1052 (2003).

One TIM family member, TIM-1, is also known as Hepatitis A virus cellular receptor (HAVcr-1) and was originally discovered as a receptor for Hepatitis A virus (HAV) (Kaplan et al, *EMBO J* 15(16):4282-96 (1996)). This gene was later cloned as kidney injury molecule 1 (KIM-1) (Ichimura et al., *J Biol Chem* 273:4135-4142 (1998); Han et al., *Kidney Int* 62:237-244 (2002)).

Kaplan et al. isolated the cellular receptor for hepatitis A virus from a cDNA library from a primary African Green Monkey Kidney (AGMK) cell line expressing the receptor. See U.S. Pat. No. 5,622,861. The disclosed utility of the polypeptides and nucleic acids was to diagnose infection by hepatitis A virus, to separate hepatitis A virus from impurities in a sample, to treat infection as well as to prevent infection by hepatitis A virus. Furthermore, the polypeptides could be expressed in transformed cells and used to test efficacy of compounds in an anti-hepatitis A virus binding assay.

The human homolog, hHAVcr-1 (aka TIM-1), was described by Feigelstock et al., *J Virology* 72(8): 6621-6628 (1998). The same molecules were described in PCT Publication Nos: WO 97/44460 and WO 98/53071 and U.S. Pat. No. 6,664,385 as Kidney Injury-related Molecules (KIM) that were found to be upregulated in renal tissue after injury to the kidney. The molecules were described as being useful in a variety of therapeutic interventions, specifically, renal disease, disorder or injury. For example, PCT Publication No. WO 02/098920 describes antibodies to KIM and describes antibodies that inhibit the shedding of KIM-1 polypeptide from KIM-1 expressing cells e.g., renal cells, or renal cancer cells.

TIM-1 is a type 1 membrane protein that contains a novel six-cysteine immunoglobulin-like domain and a mucin threonine/serine.proline-rich (T/S/P) domain. TIM-1 was originally identified in rat. TIM-1 has been found in mouse, African green monkey, and humans (Feigelstock et al., *J Virol* 72(8):6621-8 (1998). The African green monkey ortholog is most closely related to human TIM-1 showing 77.6% amino acid identity over 358 aligned amino acids. Rat and mouse orthologs exhibit 50% (155/310) and 45.6% (126/276) amino acid identity respectively, although over shorter segments of aligned sequence than for African green monkey. Monoclonal antibodies to the Ig-like domain of TIM-1 have been shown to be protective against Hepatitis A Virus infection in vitro. Silberstein et al., *J Virol* 75(2):717-25 (2001). In addition, Kim-1 was shown to be expressed at low levels in normal kidney but its expression is increased dramatically in postischemic kidney. Ichimura et al., *J Biol Chem* 273(7):4135-42 (1998). HAVCR-1 is also expressed at elevated levels in clear cell carcinomas and cancer cell lines derived from the same.

TIM-1 shows homology to the P-type "trefoil" domain suggesting that it may have similar biological activity to other P-type trefoil family members. Some trefoil domain containing proteins have been shown to induce cellular scattering and invasion when used to treat kidney, colon and breast tumor cell lines. Prest et al., *FASEB J* 16(6):592-4 (2002). In addition, some trefoil containing proteins confer cellular resistance to anoikis, an anchorage-related apoptosis phenomenon in epithelium. Chen et al., *Biochem Biophys Res Commun* 274(3):576-82 (2000).

TIM-1 maps to a region of human chromosome 5 known as Tapr in the murine sytenic region that has been implicated in asthma. Tapr, a major T cell regulatory locus, controls the development of airway hyperreactivity. Wills-Karp, *Nature Immunology* 2:1095-1096 (2001); McIntire et al., *Nature Immunology* 2:1109-1116 (2001).

SUMMARY OF THE INVENTION

Embodiments of the invention described herein are based upon the development of human monoclonal antibodies, or binding fragments thereof, that bind TIM-1 and affect TIM-1 function. TIM-1 is expressed at elevated levels in pathologies, such as neoplasms and inflammatory diseases. Inhibition of the biological activity of TIM-1 can thus prevent inflammation and other desired effects, including TIM-1 induced cell proliferation. Embodiments of the invention are based upon the generation and identification of isolated antibodies, or binding fragments thereof, that bind specifically to TIM-1.

Accordingly, one embodiment of the invention includes isolated antibodies, or fragments of those antibodies, that specifically bind to TIM-1. As known in the art, the antibodies can advantageously be, for example, monoclonal, chimeric and/or fully human antibodies. Embodiments of the invention described herein also provide cells for producing these antibodies.

Some embodiments of the invention described herein relate to monoclonal antibodies that bind TIM-1 and affect TIM-1 function. Other embodiments relate to fully human anti-TIM-1 antibodies and anti-TIM-1 antibody preparations with desirable properties from a therapeutic perspective, including strong binding affinity for TIM-1, the ability to neutralize TIM-1 in vitro and in vivo, and the ability to inhibit TIM-1 induced cell proliferation.

In a preferred embodiment, antibodies described herein bind to TIM-1 with very high affinities (Kd). For example a human, rabbit, mouse, chimeric or humanized antibody that is capable of binding TIM-1 with a Kd less than, but not limited to, $10^{-7}$, $10^{-8}$, $10^{-9}$, $10^{-10}$, $10^{-11}$, $10^{-12}$, $10^{-13}$ or $10^{-14}$ M, or any range or value therein. Affinity and/or avidity measurements can be measured by KinEXA® and/or BIACORE®, as described herein.

In one embodiment, the invention provides an isolated antibody that specifically binds to T cell, immunoglobulin domain and mucin domain 1 (TIM-1). In some embodiments, the isolated antibody has a heavy chain polypeptide comprising an amino acid sequence selected from the group consisting of SEQ ID NOs: 2, 6, 10, 14, 18, 22, 26, 30, 34, 38, 42, 46, and 50.

In another embodiment, the invention provides an isolated antibody that specifically binds to T cell, immunoglobulin domain and mucin domain 1 (TIM-1) and has a light chain polypeptide comprising an amino acid sequence selected from the group consisting of SEQ ID NOs: 4, 8, 12, 16, 20, 24, 28, 32, 36, 40, 44, 48, and 52.

In yet another embodiment, the invention provides an isolated antibody that specifically binds to TIM-1 and has a heavy chain polypeptide comprising an amino acid sequence selected from the group consisting of SEQ ID NOs: 2, 6, 10, 14, 18, 22, 26, 30, 34, 38, 42, 46, and 50 and has a light chain polypeptide comprising an amino acid sequence selected from the group consisting of SEQ ID NOs: 4, 8, 12, 16, 20, 24, 28, 32, 36, 40, 44, 48, and 52.

Another embodiment of the invention is a fully human antibody that specifically binds to TIM-1 and has a heavy chain polypeptide comprising an amino acid sequence comprising the complementarity determining region (CDR) with one of the sequences shown in Table 4. It is noted that CDR determinations can be readily accomplished by those of ordinary skill in the art. See for example, Kabat et al., *Sequences of Proteins of Immunological Interest*, Fifth Edition, NIH Publication 91-3242, Bethesda Md. [1991], vols. 1-3.

Yet another embodiment is an antibody that specifically binds to TIM-1 and has a light chain polypeptide comprising an amino acid sequence comprising a CDR comprising one of the sequences shown in Table 5. In certain embodiments the antibody is a fully human monoclonal antibody.

A further embodiment is an antibody that binds to TIM-1 and comprises a heavy chain polypeptide comprising an amino acid sequence comprising one of the CDR sequences shown in Table 4 and a light chain polypeptide comprising an amino acid sequence comprising one of the CDR sequences shown in Table 5. In certain embodiments the antibody is a fully human monoclonal antibody.

Another embodiment of the invention is a fully human antibody that binds to orthologs of TIM-1. A further embodiment herein is an antibody that cross-competes for binding to TIM-1 with the fully human antibodies described herein.

Other embodiments includes methods of producing high affinity antibodies to TIM-1 by immunizing a mammal with human TIM-1, or a fragment thereof, and one or more orthologous sequences or fragments thereof.

It will be appreciated that embodiments of the invention are not limited to any particular form of an antibody. For example, the anti-TIM-1 antibody can be a full length antibody (e.g., having an intact human Fc region) or an antibody fragment (e.g., a Fab, Fab', F(ab')$_2$, Fv, or single chain antibodies). In addition, the antibody can be manufactured from a hybridoma that secretes the antibody, or from a recombinantly produced cell that has been transformed or transfected with a gene or genes encoding the antibody.

Some embodiments of the invention include isolated nucleic acid molecules encoding any of the anti-TIM-1 antibodies described herein, vectors having an isolated nucleic acid molecule encoding the anti-TIM-1 antibody, and a host cell transformed with such a nucleic acid molecule. In addition, one embodiment of the invention is a method of producing an anti-TIM-1 antibody by culturing host cells under conditions wherein a nucleic acid molecule is expressed to produce the antibody followed by recovering the antibody from the host cell.

In other embodiments the invention provides compositions, including an antibody, or functional fragment thereof, and a pharmaceutically acceptable carrier.

In some embodiments, the invention includes pharmaceutical compositions having an effective amount of an anti-TIM-1 antibody in admixture with a pharmaceutically acceptable carrier or diluent. In yet other embodiments, the anti-TIM-1 antibody, or a fragment thereof, is conjugated to a therapeutic agent. The therapeutic agent can be, for example, a toxin, a radioisotope, or a chemotherapeutic agent. Preferably, such antibodies can be used for the treatment of pathologies, including for example, tumors and cancers, such as ovarian, stomach, endometrial, salivary gland, lung, kidney, colon, colorectal, thyroid, pancreatic, prostate and bladder cancer, as well as other inflammatory conditions. More preferably, the antibodies can be used to treat renal and ovarian carcinomas.

In still further embodiments, the antibodies described herein can be used for the preparation of a medicament for the effective treatment of TIM-1 induced cell proliferation in an animal, wherein said monoclonal antibody specifically binds to TIM-1.

Yet another embodiment is the use of an anti-TIM-1 antibody in the preparation of a medicament for the treatment of diseases such as neoplasms and inflammatory conditions. In one embodiment, the neoplasm includes, without limitation, tumors and cancers, such as ovarian, stomach, endometrial, salivary gland, lung, kidney, colon, colorectal, thyroid, pancreatic, prostate and bladder cancer.

In yet another aspect, the invention includes a method for effectively treating pathologies associated with the expression of TIM-1. These methods include selecting an animal in need of treatment for a condition associated with the expression of TIM-1, and administering to said animal a therapeutically effective dose of a fully human monoclonal antibody, wherein said antibody specifically binds to TIM-1.

Preferably a mammal and, more preferably, a human, receives the anti-TIM-1 antibody. In a preferred embodiment, neoplasms are treated, including, without limitation, renal and pancreatic tumors, head and neck cancer, ovarian cancer, gastric (stomach) cancer, melanoma, lymphoma, prostate cancer, liver cancer, lung cancer, renal cancer, bladder cancer, colon cancer, esophageal cancer, and brain cancer.

Further embodiments of the invention include the use of an antibody of in the preparation of medicament for the effective treatment of neoplastic disease in an animal, wherein said monoclonal antibody specifically binds to TIM-1. Treatable neoplastic diseases include, for example, ovarian cancer, bladder cancer, lung cancer, glioblastoma, stomach cancer, endometrial cancer, kidney cancer, colon cancer, pancreatic cancer, and prostrate cancer.

In some embodiments, the invention includes a method for inhibiting cell proliferation associated with the expression of TIM-1. These methods include selecting an animal in need of treatment for TIM-1 induced cell proliferation and administering to said animal a therapeutically effective dose of a fully human monoclonal antibody, wherein the antibody specifically binds TIM-1. In other embodiments, cells expressing TIM-1 are treated with an effective amount of an anti-TIM-1 antibody or a fragment thereof. The method can be performed in vivo.

The methods can be performed in vivo and the patient is preferably a human patient. In a preferred embodiment, the methods concern the treatment of neoplastic diseases, for example, tumors and cancers, such as renal (kidney) cancer, pancreatic cancer, head and neck cancer, ovarian cancer, gastric (stomach) cancer, melanoma, lymphoma, prostate cancer, liver cancer, breast cancer, lung cancer, bladder cancer, colon cancer, esophageal cancer, and brain cancer.

In some embodiments, the anti-TIM-1 antibody is administered to a patient, followed by administration of a clearing agent to remove excess circulating antibody from the blood.

In some embodiments, anti-TIM-1 antibodies can be modified to enhance their capability of fixing complement and participating in complement-dependent cytotoxicity (CDC). In one embodiment, anti-TIM-1 antibodies can be modified, such as by an amino acid substitution, to alter their clearance from the body. Alternatively, some other amino acid substitutions can slow clearance of the antibody from the body.

In another embodiment, the invention provides an article of manufacture including a container. The container includes a composition containing an anti-TIM-1 antibody, and a package insert or label indicating that the composition can be used to treat neoplastic or inflammatory diseases characterized by the overexpression of TIM-1.

Yet another embodiment provides methods for assaying the level of TIM-1 in a patient sample, comprising contacting an anti-TIM-1 antibody with a biological sample from a patient, and detecting the level of binding between said antibody and TIM-1 in said sample. In more specific embodiments, the biological sample is blood.

In one embodiment, the invention includes an assay kit for detecting TIM-1 and TIM-1 orthologs in mammalian tissues or cells to screen for neoplastic diseases or inflammatory conditions. The kit includes an antibody that binds to TIM-1 and a means for indicating the reaction of the antibody with TIM-1, if present. Preferably the antibody is a monoclonal antibody. In one embodiment, the antibody that binds TIM-1 is labeled. In another embodiment the antibody is an unlabeled first antibody and the kit further includes a means for detecting the first antibody. In one embodiment, the means includes a labeled second antibody that is an anti-immunoglobulin. Preferably the antibody is labeled with a marker selected from the group consisting of a fluorochrome, an enzyme, a radionuclide and a radiopaque material.

Another embodiment of the invention includes a method of diagnosing diseases or conditions in which an antibody prepared as described herein is utilized to detect the level of TIM-1 in a patient sample. In one embodiment, the patient sample is blood or blood serum. In further embodiments, methods for the identification of risk factors, diagnosis of disease, and staging of disease is presented which involves the identification of the overexpression of TIM-1 using anti-TIM-1 antibodies.

Embodiments of the invention described herein also pertain to variants of a TIM-1 protein that function as either TIM-1 agonists (mimetics) or as TIM-1 antagonists.

Another embodiment of the invention is the use of monoclonal antibodies directed against the TIM-1 antigen coupled to cytotoxic chemotherapic agents or radiotherapic agents such as anti-tumor therapeutics.

One embodiment provides an isolated antibody that blocks simultaneous binding to TIM-1 antigen by an antibody having a heavy chain sequence comprising an the amino acid sequence selected from the group consisting of SEQ ID NOS: 2, 6, 10, 14, 18, 22, 26, 30, 34, 38, 42, 46, and 50. Another embodiment provides an isolated antibody that binds to TIM-1 antigen and that cross reacts with an antibody having a heavy chain sequence comprising the amino acid sequence from the group consisting of SEQ ID NOS: 2, 6, 10, 14, 18, 22, 26, 30, 34, 38, 42, 46, and 50.

Another embodiment of the invention provides an isolated antibody that binds to an epitope of SEQ ID NO: 87 on the TIM-1 antigen of SEQ ID NO: 54, and that cross reacts with an antibody having a heavy chain sequence comprising the amino acid sequence selected from the group consisting of SEQ ID NOS: 2, 6, 10, 14, 18, 22, 26, 30, 34, 38, 42, 46, and 50. In still another embodiment, the invention provides an isolated antibody that binds to an epitope of SEQ ID NO: 87 on the TIM-1 antigen of SEQ ID NO: 54, wherein said antibody blocks simultaneous binding to TIM-1 antigen by an antibody having a heavy chain sequence comprising the amino acid sequence selected from the group comprising SEQ ID NOS: 2, 6, 10, 14, 18, 22, 26, 30, 34, 38, 42, 46, and 50.

DETAILED DESCRIPTION OF THE PREFERRED EMBODIMENT

Figure 1:
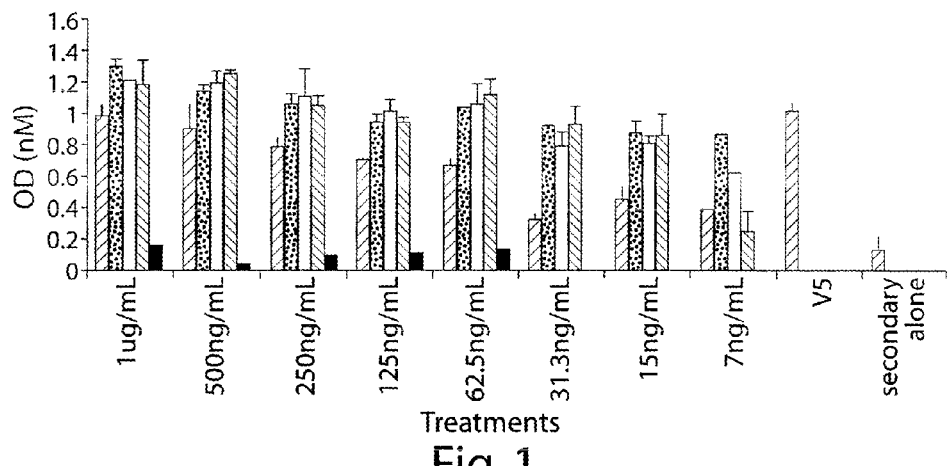
FIG. 1 is a bar graph of the results of an ELISA assay of anti-TIM-1 monoclonal antibodies 1.29, 2.56.2, 2.59.2, and 2.45.1 against the TIM-1 antigen.

Embodiments of the invention described herein are based upon the generation and identification of isolated antibodies that bind specifically to T cell, immunoglobulin domain and mucin domain 1 (TIM-1). As discussed below, TIM-1 is expressed at elevated levels in clear cell carcinomas and cancer cell lines derived from the same. Accordingly, antibodies that bind to TIM-1 are useful for the treatment and inhibition of carcinomas. In addition, antibodies that bind TIM-1 are also useful for reducing cell migration and enhancing apoptosis of kidney cancer cells.

Accordingly, embodiments of the invention described herein provide isolated antibodies, or fragments of those antibodies, that bind to TIM-1. As known in the art, the antibodies can advantageously be, e.g., monoclonal, chimeric and/or human antibodies. Embodiments of the invention described herein also provide cells for producing these antibodies.

Another embodiment of the invention provides for using these antibodies for diagnostic or therapeutic purposes. For example, embodiments of the invention provide methods and antibodies for inhibiting the expression of TIM-1 associated with cell proliferation. Preferably, the antibodies are used to treat neoplasms such as renal and pancreatic tumors, head and neck cancer, ovarian cancer, gastric (stomach) cancer, melanoma, lymphoma, prostate cancer, liver cancer, breast cancer, lung cancer, renal cancer, bladder cancer, colon cancer, esophageal cancer, and brain cancer. In association with such treatment, articles of manufacture comprising these antibodies are provided. Additionally, an assay kit comprising these antibodies is provided to screen for cancers or tumors.

Additionally, the nucleic acids described herein, and fragments and variants thereof, may be used, by way of nonlimiting example, (a) to direct the biosynthesis of the corresponding encoded proteins, polypeptides, fragments and variants as recombinant or heterologous gene products, (b) as probes for detection and quantification of the nucleic acids disclosed herein, (c) as sequence templates for preparing antisense molecules, and the like. Such uses are described more fully in the following disclosure.

Furthermore, the TIM-1 proteins and polypeptides described herein, and fragments and variants thereof, may be used, in ways that include (a) serving as an immunogen to stimulate the production of an anti-TIM-1 antibody, (b) a capture antigen in an immunogenic assay for such an antibody, (c) as a target for screening for substances that bind to a TIM-1 polypeptide described herein, and (d) a target for a TIM-1 specific antibody such that treatment with the antibody affects the molecular and/or cellular function mediated by the target. TIM-1 polypeptide expression or activity can promote cell survival and/or metastatic potential. Conversely, a decrease in TIM-1 polypeptide expression or inhibition of its function reduces tumor cell survival and invasiveness in a therapeutically beneficial manner.

Single chain antibodies (scFv's) and bispecific antibodies specific for TIM-1 are useful particularly because it may more readily penetrate a tumor mass due to its smaller size relative to a whole IgG molecule. Studies comparing the tumor penetration between whole IgG molecules and scFv's have been have been described in the literature. The scFv can be derivatized with a toxin or radionuclide in order to destroy tumor cells expressing the TIM-1 antigen, in a manner similar to the IgG2 or IgG4 anti-TIM-1 toxin labeled or radionuclide derivatized whole antibodies already discussed, but with the advantage of being able to penetrate the tumor more fully, which may translate into increased efficacy in eradicating the tumor. A specific example of a biologically active anti-TIM-1 scFv is provided herein.

Sequence Listing

The heavy chain and light chain variable region nucleotide and amino acid sequences of representative human anti-TIM-1 antibodies are provided in the sequence listing, the contents of which are summarized in Table 1 below.

TABLE 1

| mAb ID No.: | Sequence | SEQ ID NO: |
|---|---|---|
| 1.29 | Nucleotide sequence encoding the variable region and a portion of the constant region of the heavy chain | 1 |
| | Amino acid sequence of the variable region of the heavy chain | 2 |
| | Nucleotide sequence encoding the variable region and a portion of the constant region of the light chain | 3 |
| | Amino acid sequence of the variable region of the light chain | 4 |

TABLE 1-continued

| mAb ID No.: | Sequence | SEQ ID NO: |
|---|---|---|
| 1.37 | Nucleotide sequence encoding the variable region and a portion of the constant region of the heavy chain | 5 |
| | Amino acid sequence of the variable region of the heavy chain | 6 |
| | Nucleotide sequence encoding the variable region and a portion of the constant region of the light chain | 7 |
| | Amino acid sequence of the variable region of the light chain | 8 |
| 2.16 | Nucleotide sequence encoding the variable region and a portion of the constant region of the heavy chain | 9 |
| | Amino acid sequence of the variable region of the heavy chain | 10 |
| | Nucleotide sequence encoding the variable region and a portion of the constant region of the light chain | 11 |
| | Amino acid sequence of the variable region of the light chain | 12 |
| 2.17 | Nucleotide sequence encoding the variable region and a portion of the constant region of the heavy chain | 13 |
| | Amino acid sequence of the variable region of the heavy chain | 14 |
| | Nucleotide sequence encoding the variable region and a portion of the constant region of the light chain | 15 |
| | Amino acid sequence of the variable region of the light chain | 16 |
| 2.24 | Nucleotide sequence encoding the variable region and a portion of the constant region of the heavy chain | 17 |
| | Amino acid sequence of the variable region of the heavy chain | 18 |
| | Nucleotide sequence encoding the variable region and a portion of the constant region of the light chain | 19 |
| | Amino acid sequence of the variable region of the light chain | 20 |
| 2.45 | Nucleotide sequence encoding the variable region and a portion of the constant region of the heavy chain | 21 |
| | Amino acid sequence of the variable region of the heavy chain | 22 |
| | Nucleotide sequence encoding the variable region and a portion of the constant region of the light chain | 23 |
| | Amino acid sequence of the variable region of the light chain | 24 |
| 2.54 | Nucleotide sequence encoding the variable region and a portion of the constant region of the heavy chain | 25 |
| | Amino acid sequence of the variable region of the heavy chain | 26 |
| | Nucleotide sequence encoding the variable region and a portion of the constant region of the light chain | 27 |
| | Amino acid sequence of the variable region of the light chain | 28 |
| 2.56 | Nucleotide sequence encoding the variable region and a portion of the constant region of the heavy chain | 29 |
| | Amino acid sequence of the variable region of the heavy chain | 30 |
| | Nucleotide sequence encoding the variable region and a portion of the constant region of the light chain | 31 |
| | Amino acid sequence of the variable region of the light chain | 32 |
| 2.59 | Nucleotide sequence encoding the variable region and a portion of the constant region of the heavy chain | 33 |
| | Amino acid sequence of the variable region of the heavy chain | 34 |
| | Nucleotide sequence encoding the variable region and a portion of the constant region of the light chain | 35 |
| | Amino acid sequence of the variable region of the light chain | 36 |
| 2.61 | Nucleotide sequence encoding the variable region and a portion of the constant region of the heavy chain | 37 |
| | Amino acid sequence of the variable region of the heavy chain | 38 |
| | Nucleotide sequence encoding the variable region and a portion of the constant region of the light chain | 39 |
| | Amino acid sequence of the variable region of the light chain | 40 |
| 2.70 | Nucleotide sequence encoding the variable region and a portion of the constant region of the heavy chain | 41 |
| | Amino acid sequence of the variable region of the heavy chain | 42 |
| | Nucleotide sequence encoding the variable region and a portion of the constant region of the light chain | 43 |
| | Amino acid sequence of the variable region of the light chain | 44 |
| 2.76 | Nucleotide sequence encoding the variable region and a portion of the constant region of the heavy chain | 45 |
| | Amino acid sequence of the variable region of the heavy chain | 46 |
| | Nucleotide sequence encoding the variable region and a portion of the constant region of the light chain | 47 |
| | Amino acid sequence of the variable region of the light chain | 48 |
| 2.70.2 | Nucleotide sequence encoding the variable region and a portion of the constant region of the heavy chain | 49 |
| | Amino acid sequence of the variable region and a porition of the constant region of the heavy chain | 50 |
| | Nucleotide sequence encoding the variable region and a portion of the constant region of the light chain | 51 |
| | Amino acid sequence of the variable region and a porition of the constant region of the light chain | 52 |

Definitions

Unless otherwise defined, scientific and technical terms used in connection with the invention described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. *Molecular Cloning: A Laboratory Manual* (2d ed., Cold Spring Harbor Laboratory Press, Cold Spring Harbor, N.Y. (1989)), which is incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The term "TIM-1" refers to T cell, immunoglobulin domain and mucin domain 1. In one embodiment, TIM-1 refers to a polypeptide comprising the amino acid sequence of SEQ ID NO: 54.

The term "polypeptide" is used herein as a generic term to refer to native protein, fragments, or analogs of a polypeptide sequence. Hence, native protein, fragments, and analogs are species of the polypeptide genus. Preferred polypeptides in accordance with the invention comprise human heavy chain immunoglobulin molecules and human kappa light chain immunoglobulin molecules, as well as antibody molecules formed by combinations comprising the heavy chain immunoglobulin molecules with light chain immunoglobulin molecules, such as the kappa light chain immunoglobulin molecules, and vice versa, as well as fragments and analogs thereof.

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

The term "isolated polynucleotide" as used herein shall mean a polynucleotide of genomic, cDNA, or synthetic origin or some combination thereof, which by virtue of its origin the isolated polynucleotide (1) is not associated with all or a portion of a polynucleotide in which the isolated polynucleotide is found in nature, (2) is operably linked to a polynucleotide which it is not linked to in nature, or (3) does not occur in nature as part of a larger sequence.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of murine proteins, (3) is expressed by a cell from a different species, or (4) does not occur in nature.

The term "oligonucleotide" referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g. for probes; although oligonucleotides may be double stranded, e.g. for use in the construction of a gene mutant. Oligonucleotides described herein can be either sense or antisense oligonucleotides.

Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as upstream sequences; sequence regions on the DNA strand having the same sequence as the RNA and which are 3' to the 3' end of the RNA transcript are referred to as downstream sequences.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al., *Nucl. Acids Res.* 14:9081 (1986); Stec et al., *J. Am. Chem. Soc.* 106:6077 (1984); Stein et al., *Nucl. Acids Res.* 16:3209 (1988); Zon et al., *Anti-Cancer Drug Design* 6:539 (1991); Zon et al., *Oligonucleotides and Analogues: A Practical Approach*, pp. 87-108 (F. Eckstein, ed., Oxford University Press, Oxford England (1991)); Stec et al., U.S. Pat. No. 5,151,510; Uhlmann and Peyman, *Chemical Reviews* 90:543 (1990), the disclosures of which are hereby incorporated by reference. An oligonucleotide can include a label for detection, if desired.

The term "operably linked" as used herein refers to positions of components so described are in a relationship permitting them to function in their intended manner. A control sequence operably linked to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term control sequences is intended to include, at a minimum, all components whose presence is essential for expression and processing, and can also include additional components whose presence is advantageous, for example, leader sequences and fusion partner sequences.

The term "selectively hybridize" referred to herein means to detectably and specifically bind. Polynucleotides, oligonucleotides and fragments thereof described herein selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments described herein and a nucleic acid sequence of interest will be at least 80%, and more typically with preferably increasing homologies of at least 85%, 90%, 95%, 99%, and 100%.

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in *Atlas of Protein Sequence and Structure*, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence.

In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA."

The following terms are used to describe the sequence relationships between two or more polynucleotide or amino acid sequences: "reference sequence," "comparison window," "sequence identity," "percentage of sequence identity," and "substantial identity." A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a comparison window to identify and compare local regions of sequence similarity. A "comparison window," as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman, *Adv. Appl. Math.*, 2:482 (1981), by the homology alignment algorithm of Needleman and Wunsch, *J. Mol. Biol.*, 48:443 (1970), by the search for similarity method of Pearson and Lipman, *Proc. Natl. Acad. Sci. (U.S.A.)*, 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term percentage of sequence identity is calculated by comparing two optimally aligned sequences over the window of comparison, determining the number of positions at which the identical nucleic acid base (e.g., A, T, C, G, U, or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See *Immunology—A Synthesis* ($2^{nd}$ Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides described herein. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

As discussed herein, minor variations in the amino acid sequences of antibodies or immunoglobulin molecules are contemplated as being encompassed by the invention described herein, providing that the variations in the amino acid sequence maintain at least 75%, more preferably at least 80%, 90%, 95%, and most preferably 99% sequence identity to the antibodies or immunoglobin molecules described herein. In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al., *Science,* 253:164 (1991). Thus, the foregoing examples demonstrate that those of skill in the art can recognize sequence motifs and structural conformations that may be used to define structural and functional domains described herein.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts). A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden and J. Tooze, eds., Garland Publishing, New York, N.Y. (1991)); and Thornton et al., *Nature,* 354:105 (1991), which are each incorporated herein by reference.

The term "polypeptide fragment" as used herein refers to a polypeptide that has an amino-terminal and/or carboxy-terminal deletion, but where the remaining amino acid sequence is identical to the corresponding positions in the naturally-occurring sequence deduced, for example, from a full-length cDNA sequence. Fragments typically are at least 5, 6, 8 or 10 amino acids long, preferably at least 14 amino acids long, more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has at least one of the following properties: (1) specific binding to a TIM-1, under suitable binding conditions, (2) ability to block appropriate TIM-1 binding, or (3) ability to inhibit the growth and/or survival of TIM-1 expressing cells in vitro or in vivo. Typically, polypeptide analogs comprise a conservative amino acid substitution (or addition or deletion) with respect to the naturally occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compounds are termed peptide mimetics or peptidomimetics. Fauchere, *J. Adv. Drug Res.*, 15:29 (1986); Veber and Freidinger, *TINS*, p. 392 (1985); and Evans et al., *J. Med. Chem.*, 30:1229 (1987), which are incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —$CH_2NH$—, —$CH_2S$—, —$CH_2$—$CH_2$—, —CH=CH—(cis and trans), —$COCH_2$—, —CH(OH)$CH_2$—, and —$CH_2SO$—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch, *Ann. Rev. Biochem.*, 61:387 (1992), incorporated herein by reference); for example, by adding internal cysteine residues capable of forming intramolecular disulfide bridges which cyclize the peptide.

"Antibody" or "antibody peptide(s)" refer to an intact antibody, or a binding fragment thereof that competes with the intact antibody for specific binding. Binding fragments are produced by recombinant DNA techniques, or by enzymatic or chemical cleavage of intact antibodies. Binding fragments include Fab, Fab', F(ab')$_2$, Fv, and single-chain antibodies. An antibody other than a bispecific or bifunctional antibody is understood to have each of its binding sites identical. An antibody substantially inhibits adhesion of a receptor to a counterreceptor when an excess of antibody reduces the quantity of receptor bound to counterreceptor by at least about 20%, 40%, 60% or 80%, and more usually greater than about 85% (as measured in an in vitro competitive binding assay).

Digestion of antibodies with the enzyme, papain, results in two identical antigen-binding fragments, known also as "Fab" fragments, and a "Fc" fragment, having no antigen-binding activity but having the ability to crystallize. Digestion of antibodies with the enzyme, pepsin, results in the a "F(ab')$_2$" fragment in which the two arms of the antibody molecule remain linked and comprise two-antigen binding sites. The F(ab')$_2$ fragment has the ability to crosslink antigen.

"Fv" when used herein refers to the minimum fragment of an antibody that retains both antigen-recognition and antigen-binding sites.

"Fab" when used herein refers to a fragment of an antibody which comprises the constant domain of the light chain and the CH1 domain of the heavy chain.

The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is ≤1 µM, preferably ≤100 nM and most preferably ≤10 nM.

The term "agent" is used herein to denote a chemical compound, a mixture of chemical compounds, a biological macromolecule, or an extract made from biological materials.

The term "pharmaceutical agent" or "drug" as used herein refers to a chemical compound or composition capable of inducing a desired therapeutic effect when properly administered to a patient. Other chemistry terms herein are used according to conventional usage in the art, as exemplified by *The McGraw-Hill Dictionary of Chemical Terms* (Parker, S., Ed., McGraw-Hill, San Francisco (1985)), incorporated herein by reference).

The term "antineoplastic agent" is used herein to refer to agents that have the functional property of inhibiting a development or progression of a neoplasm in a human, particularly a malignant (cancerous) lesion, such as a carcinoma, sarcoma, lymphoma, or leukemia. Inhibition of metastasis is frequently a property of antineoplastic agents.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

"Active" or "activity" in regard to a TIM-1 polypeptide refers to a portion of a TIM-1 polypeptide which has a biological or an immunological activity of a native TIM-1 polypeptide. "Biological" when used herein refers to a biological function that results from the activity of the native TIM-1 polypeptide. A preferred biological activity includes, for example, regulation of cellular growth.

"Label" or "labeled" as used herein refers to the addition of a detectable moiety to a polypeptide, for example, a radiolabel, fluorescent label, enzymatic label chemiluminescent labeled or a biotinyl group. Radioisotopes or radionuclides may include $^3$H, $^{14}$C, $^{15}$N, $^{35}$S, $^{90}$Y, $^{99}$Tc, $^{111}$In, $^{125}$I, $^{131}$I, fluorescent labels may include rhodamine, lanthanide phosphors or FITC and enzymatic labels may include horseradish peroxidase, β-galactosidase, luciferase, alkaline phosphatase.

"Mammal" when used herein refers to any animal that is considered a mammal. Preferably, the mammal is human.

"Liposome" when used herein refers to a small vesicle that may be useful for delivery of drugs that may include the TIM-1 polypeptide described herein or antibodies to such a TIM-1 polypeptide to a mammal.

The term "patient" includes human and veterinary subjects.

Antibody Structure

The basic whole antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable domain of about 100 to 110 or more amino acids primarily responsible for antigen recognition. The carboxy-terminal portion of each chain defines a constant region primarily responsible for effector function. Human light chains are classified as kappa and lambda light chains. Human heavy chains are classified as mu, delta, gamma, alpha, or epsilon, and define the antibody's isotype as IgM, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2d ed. Raven Press, N.Y. (1989)) (incorporated by reference in its entirety for all purposes). The variable regions of each light/heavy chain pair form the antibody binding site.

The variable domains all exhibit the same general structure of relatively conserved framework regions (FR) joined by three hyper variable regions, also called complementarity determining regions or CDRs. The CDRs from the heavy and light chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each region is in accordance with the definitions of Kabat, *Sequences of Proteins of Immunological Interest* (National Institutes of Health, Bethesda, Md. (1987 and 1991)), or Chothia & Lesk, *J. Mol. Biol.* 196:901-917 (1987); Chothia et al., *Nature* 342:878-883 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79: 315-321 (1990), Kostelny et al., *J. Immunol.* 148:1547-1553 (1992). Bispecific antibodies do not exist in the form of fragments having a single binding site (e.g., Fab, Fab', and Fv).

It will be appreciated that such bifunctional or bispecific antibodies are contemplated and encompassed by the invention. A bispecific single chain antibody with specificity to TIM-1 and to the CD3 antigen on cytotoxic T lymphocytes can be used to direct these T cells to tumor cells expressing TIM-1 and cause apoptosis and eradication of the tumor. Two bispecific scFv constructs for this purpose are described herein. The scFv components specific for TIM-1 can be derived from anti-TIM-1 antibodies described herein. In some embodiments, the anti-TIM-1 antibody components disclosed in Tables 4 and 5 can be used to generate a biologically active scFv directed against TIM-1. In a preferred embodiment, the scFv components are derived from mAb 2.70. The anti-CD3 scFv component of the therapeutic bispecific scFv was derived from a sequence deposited in Genbank (accession number CAE85148). Alternative antibodies known to target CD3 or other T cell antigens may similarly be effective in treating malignancies when coupled with anti-TIM-1, whether on a single-chain backbone or a full IgG.

Human Antibodies and Humanization of Antibodies

Embodiments of the invention described herein contemplate and encompass human antibodies. Human antibodies avoid certain of the problems associated with antibodies that possess murine or rat variable and/or constant regions. The presence of such murine or rat derived proteins can lead to the rapid clearance of the antibodies or can lead to the generation of an immune response against the antibody by a mammal other than a rodent.

Human Antibodies

The ability to clone and reconstruct megabase-sized human loci in YACs and to introduce them into the mouse germline provides a powerful approach to elucidating the functional components of very large or crudely mapped loci as well as generating useful models of human disease. An important practical application of such a strategy is the "humanization" of the mouse humoral immune system. Introduction of human immunoglobulin (Ig) loci into mice in which the endogenous Ig genes have been inactivated offers the opportunity to develop human antibodies in the mouse. Fully human antibodies are expected to minimize the immunogenic and allergic responses intrinsic to mouse or mouse-derivatized Mabs and thus to increase the efficacy and safety of the antibodies administered to humans. The use of fully human antibodies can be expected to provide a substantial advantage in the treatment of chronic and recurring human diseases, such as inflammation, autoimmunity, and cancer, which require repeated antibody administrations.

One approach toward this goal was to engineer mouse strains deficient in mouse antibody production with large fragments of the human Ig loci in anticipation that such mice would produce a large repertoire of human antibodies in the absence of mouse antibodies. This general strategy was demonstrated in connection with our generation of the first XenoMouse® strains as published in 1994. See Green et al., *Nature Genetics* 7:13-21 (1994). The XenoMouse® strains were engineered with yeast artificial chromosomes (YACs) containing 245 kb and 190 kb-sized germline configuration fragments of the human heavy chain locus and kappa light chain locus, respectively, which contained core variable and constant region sequences. Id. The XENOMOUSE® strains are available from Abgenix, Inc. (Fremont, Calif.). Greater than approximately 80% of the human antibody repertoire has been introduced through introduction of megabase sized, germline configuration YAC fragments of the human heavy chain loci and kappa light chain loci, respectively, to produce XenoMouse® mice.

The production of the XENOMOUSE® is further discussed and delineated in U.S. patent application Ser. Nos. 07/466,008, filed Jan. 12, 1990, 07/610,515, filed Nov. 8, 1990, 07/919,297, filed Jul. 24, 1992, 07/922,649, filed Jul. 30, 1992, filed 08/031,801, filed Mar. 15, 1993, 08/112,848, filed Aug. 27, 1993, 08/234,145, filed Apr. 28, 1994, 08/376, 279, filed Jan. 20, 1995, 08/430, 938, Apr. 27, 1995, 08/464, 584, filed Jun. 5, 1995, 08/464,582, filed Jun. 5, 1995, 08/463,191, filed Jun. 5, 1995, 08/462,837, filed Jun. 5, 1995, 08/486,853, filed Jun. 5, 1995, 08/486,857, filed Jun. 5, 1995, 08/486,859, filed Jun. 5, 1995, 08/462,513, filed Jun. 5, 1995, 08/724,752, filed Oct. 2, 1996, and 08/759,620, filed Dec. 3, 1996 and U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2. See also Mendez et al., *Nature Genetics* 15:146-156 (1997) and Green and Jakobovits, *J. Exp. Med.* 188:483-495 (1998). See also European Patent No. EP 0 463 151 B1, grant published Jun. 12, 1996, International Patent Application No., WO 94/02602, published Feb. 3, 1994, International Patent Application No., WO 96/34096, published Oct. 31, 1996, WO 98/24893, published Jun. 11, 1998, WO 00/76310, published Dec. 21, 2000. The disclosures of each of the above-cited patents, applications, and references are hereby incorporated by reference in their entirety.

Alternative approaches have utilized a "minilocus" approach, in which an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661,016, 5,770,429, 5,789,650, 5,814,318, 5,877,397, 5,874,299, and 6,255,458 each to Lonberg and Kay, U.S. Pat. Nos. 5,591,669 and 6,023,010 to Krimpenfort and Berns, U.S. Pat. Nos. 5,612,205, 5,721,367, and 5,789, 215 to Berns et al., and U.S. Pat. No. 5,643,763 to Choi and Dunn, and GenPharm International U.S. patent application Ser. Nos. 07/574,748, filed Aug. 29, 1990, 07/575,962, filed Aug. 31, 1990, 07/810,279, filed Dec. 17, 1991, 07/853,408, filed Mar. 18, 1992, 07/904,068, filed Jun. 23, 1992, 07/990, 860, filed Dec. 16, 1992, 08/053,131, filed Apr. 26, 1993, 08/096,762, filed Jul. 22, 1993, 08/155,301, filed Nov. 18, 1993, 08/161,739, filed Dec. 3, 1993, 08/165,699, filed Dec. 10, 1993, 08/209,741, filed Mar. 9, 1994, the disclosures of which are hereby incorporated by reference. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175, the disclosures of which are hereby incorporated by reference in their entirety. See further Taylor et al., 1992, Chen et al., 1993, Tuaillon et al., 1993, Choi et al., 1993, Lonberg et al., (1994), Taylor et al., (1994), and Tuaillon et al., (1995), Fishwild et al., (1996), the disclosures of which are hereby incorporated by reference in their entirety.

While chimeric antibodies have a human constant region and a murine variable region, it is expected that certain human anti-chimeric antibody (HACA) responses will be observed, particularly in chronic or multi-dose utilizations of the antibody. Thus, it would be desirable to provide fully human antibodies against TIM-1 in order to vitiate concerns and/or effects of human anti-mouse antibody (HAMA) or HACA response.

Humanization and Display Technologies

Antibodies with reduced immunogenicity can be generated using humanization and library display techniques. It will be appreciated that antibodies can be humanized or primatized using techniques well known in the art. See e.g., Winter and Harris, *Immunol Today* 14:43-46 (1993) and Wright et al., *Crit, Reviews in Immunol.* 12:125-168 (1992). The antibody of interest can be engineered by recombinant DNA techniques to substitute the CH1, CH2, CH3, hinge domains, and/or the framework domain with the corresponding human sequence (see WO 92/02190 and U.S. Pat. Nos. 5,530,101, 5,585,089, 5,693,761, 5,693,792, 5,714,350, and 5,777,085). Also, the use of Ig cDNA for construction of chimeric immunoglobulin genes is known in the art (Liu et al., *P.N.A.S.* 84:3439 (1987) and *J. Immunol.* 139:3521 (1987)). mRNA is isolated from a hybridoma or other cell producing the antibody and used to produce cDNA. The cDNA of interest can be amplified by the polymerase chain reaction using specific primers (U.S. Pat. Nos. 4,683,195 and 4,683,202). Alternatively, an expression library is made and screened to isolate the sequence of interest encoding the variable region of the antibody is then fused to human constant region sequences. The sequences of human constant regions genes can be found in Kabat et al., "Sequences of Proteins of Immunological Interest," N.I.H. publication no. 91-3242 (1991). Human C region genes are readily available from known clones. The choice of isotype will be guided by the desired effector functions, such as complement fixation, or activity in antibody-dependent cellular cytotoxicity. Preferred isotypes are IgG1, IgG2 and IgG4. Either of the human light chain constant regions, kappa or lambda, can be used. The chimeric, humanized antibody is then expressed by conventional methods. Expression vectors include plasmids, retroviruses, YACs, EBV derived episomes, and the like.

Antibody fragments, such as Fv, F(ab')$_2$ and Fab can be prepared by cleavage of the intact protein, e.g., by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions can be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody can be joined to any strong promoter, including retroviral LTRs, e.g., SV-40 early promoter, (Okayama et al., *Mol. Cell. Bio.* 3:280 (1983)), Rous sarcoma virus LTR (Gorman et al., *P.N.A.S.* 79:6777 (1982)), and moloney murine leukemia virus LTR (Grosschedl et al., *Cell* 41:885 (1985)). Also, as will be appreciated, native Ig promoters and the like can be used.

Further, human antibodies or antibodies from other species can be generated through display-type technologies, including, without limitation, phage display, retroviral display, ribosomal display, and other techniques, using techniques well known in the art and the resulting molecules can be subjected to additional maturation, such as affinity maturation, as such techniques are well known in the art. Wright and Harris, supra., Hanes and Plucthau, *PNAS USA* 94:4937-4942 (1997) (ribosomal display), Parmley and Smith, *Gene* 73:305-318 (1988) (phage display), Scott, *TIBS* 17:241-245 (1992), Cwirla et al., *PNAS USA* 87:6378-6382 (1990), Russel et al., *Nucl. Acids Res.* 21:1081-1085 (1993), Hoganboom et al., *Immunol. Reviews* 130:43-68 (1992), Chiswell and McCafferty, *TIBTECH* 10:80-84 (1992), and U.S. Pat. No. 5,733,743. If display technologies are utilized to produce antibodies that are not human, such antibodies can be humanized as described above.

Using these techniques, antibodies can be generated to TIM-1 expressing cells, TIM-1 itself, forms of TIM-1, epitopes or peptides thereof, and expression libraries thereto (see e.g. U.S. Pat. No. 5,703,057) which can thereafter be screened as described above for the activities described above.

Antibody Therapeutics

In certain respects, it can be desirable in connection with the generation of antibodies as therapeutic candidates against TIM-1 that the antibodies be capable of fixing complement and participating in complement-dependent cytotoxicity (CDC). Such antibodies include, without limitation, the following: murine IgM, murine IgG2a, murine IgG2b, murine IgG3, human IgM, human IgG1, and human IgG3. It will be appreciated that antibodies that are generated need not initially possess such an isotype but, rather, the antibody as generated can possess any isotype and the antibody can be isotype switched thereafter using conventional techniques that are well known in the art. Such techniques include the use of direct recombinant techniques (see, e.g., U.S. Pat. No. 4,816,397), cell-cell fusion techniques (see, e.g., U.S. Pat. Nos. 5,916,771 and 6,207,418), among others.

In the cell-cell fusion technique, a myeloma or other cell line is prepared that possesses a heavy chain with any desired isotype and another myeloma or other cell line is prepared that possesses the light chain. Such cells can, thereafter, be fused and a cell line expressing an intact antibody can be isolated.

By way of example, the TIM-1 antibody discussed herein is a human anti-TIM-1 IgG2 antibody. If such antibody possessed desired binding to the TIM-1 molecule, it could be readily isotype switched to generate a human IgM, human IgG1, or human IgG3 isotype, while still possessing the same variable region (which defines the antibody's specificity and some of its affinity). Such molecule would then be capable of fixing complement and participating in CDC.

Design and Generation of Other Therapeutics

Due to their association with renal and pancreatic tumors, head and neck cancer, ovarian cancer, gastric (stomach) cancer, melanoma, lymphoma, prostate cancer, liver cancer, breast cancer, lung cancer, renal cancer, bladder cancer, colon cancer, esophageal cancer, and brain cancer, antineoplastic agents comprising anti-TIM-1 antibodies are contemplated and encompassed by the invention.

Moreover, based on the activity of the antibodies that are produced and characterized herein with respect to TIM-1, the design of other therapeutic modalities beyond antibody moieties is facilitated. Such modalities include, without limitation, advanced antibody therapeutics, such as bispecific antibodies, immunotoxins, and radiolabeled therapeutics, generation of peptide therapeutics, gene therapies, particularly intrabodies, antisense therapeutics, and small molecules.

In connection with the generation of advanced antibody therapeutics, where complement fixation is a desirable attribute, it can be possible to sidestep the dependence on complement for cell killing through the use of bispecifics, immunotoxins, or radiolabels, for example.

For example, in connection with bispecific antibodies, bispecific antibodies can be generated that comprise (i) two antibodies one with a specificity to TIM-1 and another to a second molecule that are conjugated together, (ii) a single antibody that has one chain specific to TIM-1 and a second chain specific to a second molecule, or (iii) a single chain antibody that has specificity to TIM-1 and the other molecule. Such bispecific antibodies can be generated using techniques that are well known for example, in connection with (i) and (ii) see, e.g., Fanger et al., *Immunol Methods* 4:72-81 (1994) and Wright and Harris, supra and in connection with (iii) see, e.g., Traunecker et al., *Int. J. Cancer (Suppl.)* 7:51-52 (1992). In each case, the second specificity can be made to the heavy chain activation receptors, including, without limitation, CD16 or CD64 (see, e.g., Deo et al., 18:127 (1997)) or CD89 (see, e.g., Valerius et al., *Blood* 90:4485-4492 (1997)). Bispecific antibodies prepared in accordance with the foregoing would be likely to kill cells expressing TIM-1, and particularly those cells in which the TIM-1 antibodies described herein are effective.

With respect to immunotoxins, antibodies can be modified to act as immunotoxins utilizing techniques that are well known in the art. See, e.g., Vitetta, *Immunol Today* 14:252 (1993). See also U.S. Pat. No. 5,194,594. In connection with the preparation of radiolabeled antibodies, such modified antibodies can also be readily prepared utilizing techniques that are well known in the art. See, e.g., Junghans et al., in *Cancer Chemotherapy and Biotherapy* 655-686 (2d ed., Chafner and Longo, eds., Lippincott Raven (1996)). See also U.S. Pat. Nos. 4,681,581, 4,735,210, 5,101,827, 5,102,990 (RE 35,500), 5,648,471, and 5,697,902. Each of immunotoxins and radiolabeled molecules would be likely to kill cells expressing TIM-1, and particularly those cells in which the antibodies described herein are effective.

In connection with the generation of therapeutic peptides, through the utilization of structural information related to TIM-1 and antibodies thereto, such as the antibodies described herein (as discussed below in connection with small molecules) or screening of peptide libraries, therapeutic peptides can be generated that are directed against TIM-1. Design and screening of peptide therapeutics is discussed in connection with Houghten et al., Biotechniques 13:412-421 (1992), Houghten, *PNAS USA* 82:5131-5135 (1985), Pinalla et al., *Biotechniques* 13:901-905 (1992), Blake and Litzi-Davis, *BioConjugate Chem.* 3:510-513 (1992). Immunotoxins and radiolabeled molecules can also be prepared, and in a similar manner, in connection with peptidic moieties as discussed above in connection with antibodies.

Assuming that the TIM-1 molecule (or a form, such as a splice variant or alternate form) is functionally active in a disease process, it will also be possible to design gene and antisense therapeutics thereto through conventional techniques. Such modalities can be utilized for modulating the function of TIM-1. In connection therewith the antibodies, as described herein, facilitate design and use of functional assays related thereto. A design and strategy for antisense therapeutics is discussed in detail in International Patent Application No. WO 94/29444. Design and strategies for gene therapy are well known. However, in particular, the use of gene therapeutic techniques involving intrabodies could prove to be particularly advantageous. See, e.g., Chen et al., *Human Gene Therapy* 5:595-601 (1994) and Marasco, *Gene Therapy* 4:11-15 (1997). General design of and considerations related to gene therapeutics is also discussed in International Patent Application No. WO 97/38137.

Small molecule therapeutics can also be envisioned. Drugs can be designed to modulate the activity of TIM-1, as described herein. Knowledge gleaned from the structure of the TIM-1 molecule and its interactions with other molecules, as described herein, such as the antibodies described herein, and others can be utilized to rationally design additional therapeutic modalities. In this regard, rational drug design techniques such as X-ray crystallography, computer-aided (or assisted) molecular modeling (CAMM), quantitative or qualitative structure-activity relationship (QSAR), and similar technologies can be utilized to focus drug discovery efforts. Rational design allows prediction of protein or synthetic structures which can interact with the molecule or specific forms thereof which can be used to modify or modulate the activity of TIM-1. Such structures can be synthesized chemically or expressed in biological systems. This approach has been reviewed in Capsey et al., *Genetically Engineered Human Therapeutic Drugs* (Stockton Press, NY (1988)). Further, combinatorial libraries can be designed and synthesized and used in screening programs, such as high throughput screening efforts.

TIM-1 Agonists And Antagonists

Embodiments of the invention described herein also pertain to variants of a TIM-1 protein that function as either TIM-1 agonists (mimetics) or as TIM-1 antagonists. Variants of a TIM-1 protein can be generated by mutagenesis, e.g., discrete point mutation or truncation of the TIM-1 protein. An agonist of the TIM-1 protein can retain substantially the same, or a subset of, the biological activities of the naturally occurring form of the TIM-1 protein. An antagonist of the TIM-1 protein can inhibit one or more of the activities of the naturally occurring form of the TIM-1 protein by, for example, competitively binding to a downstream or upstream member of a cellular signaling cascade which includes the TIM-1 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the TIM-1 protein.

Variants of the TIM-1 protein that function as either TIM-1 agonists (mimetics) or as TIM-1 antagonists can be identified by screening combinatorial libraries of mutants, e.g., truncation mutants, of the TIM-1 protein for protein agonist or antagonist activity. In one embodiment, a variegated library of TIM-1 variants is generated by combinatorial mutagenesis at the nucleic acid level and is encoded by a variegated gene library. A variegated library of TIM-1 variants can be produced by, for example, enzymatically ligating a mixture of synthetic oligonucleotides into gene sequences such that a degenerate set of potential TIM-1 sequences is expressible as individual polypeptides, or alternatively, as a set of larger fusion proteins (e.g., for phage display) containing the set of TIM-1 sequences therein. There are a variety of methods which can be used to produce libraries of potential TIM-1 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential TIM-1 variant sequences. Methods for synthesizing degenerate oligonucleotides are known in the art (see, e.g., Narang, *Tetrahedron* 39:3 (1983); Itakura et al., *Annu. Rev. Biochem.* 53:323 (1984); Itakura et al., *Science* 198:1056 (1984); Ike et al., *Nucl. Acid Res.* 11:477 (1983).

Radioimmuno & Immunochemotherapeutic Antibodies

Cytotoxic chemotherapy or radiotherapy of cancer is limited by serious, sometimes life-threatening, side effects that arise from toxicities to sensitive normal cells because the therapies are not selective for malignant cells. Therefore, there is a need to improve the selectivity. One strategy is to couple therapeutics to antibodies that recognize tumor-associated antigens. This increases the exposure of the malignant cells to the ligand-targeted therapeutics but reduces the exposure of normal cells to the same agent. See Allen, *Nat. Rev. Cancer* 2(10):750-63 (2002).

The TIM-1 antigen is one of these tumor-associated antigens, as shown by its specific expression on cellular membranes of tumor cells by FACS and IHC. Therefore one embodiment of the invention is to use monoclonal antibodies directed against the TIM-1 antigen coupled to cytotoxic chemotherapic agents or radiotherapic agents as anti-tumor therapeutics.

Radiolabels are known in the art and have been used for diagnostic or therapeutic radioimmuno conjugates. Examples of radiolabels includes, but are not limited to, the following: radioisotopes or radionuclides (e.g., 3H, 14C, 15N, 35S, 90Y, 99Tc, 111In, 125I, 131I, 177Lu, Rhenium-186, Rhenium-188, Samarium-153, Copper-64, Scandium-47). For example, radionuclides which have been used in radioimmunoconjugate guided clinical diagnosis include, but are not limited to: 131 I, 125 I, 123 I, 99 Tc, 67Ga, as well as 111 In. Antibodies have also been labeled with a variety of radionuclides for potential use in targeted immunotherapy (see Peirersz et al., 1987). Monoclonal antibody conjugates have also been used for the diagnosis and treatment of cancer (e.g., *Immunol. Cell Biol.* 65:111-125). These radionuclides include, for example, 188 Re and 186 Re as well as 90 Y, and to a lesser extent 199 Au and 67 Cu. 1-(131) have also been used for therapeutic purposes. U.S. Pat. No. 5,460,785 provides a listing of such radioisotopes. Radiotherapeutic chelators and chelator conjugates are known in the art. See U.S. Pat. Nos. 4,831,175, 5,099,069, 5,246,692, 5,286,850, and 5,124,471.

Immunoradiopharmaceuticals utilizing anti-TIM-1 antibodies can be prepared utilizing techniques that are well known in the art. See, e.g., Junghans et al., in Cancer Chemotherapy and Biotherapy 655-686 (2d ed., Chafner and Longo, eds., Lippincott Raven (1996)), U.S. Pat. Nos. 4,681,581, 4,735,210, 5,101,827, RE 35,500, 5,648,471, and 5,697,902.

Cyotoxic immunoconjugates are known in the art and have been used as therapeutic agents. Such immunoconjugates may for example, use maytansinoids (U.S. Pat. No. 6,441,163), tubulin polymerization inhibitor, auristatin (Mohammad et al., *Int. J. Oncol.* 15(2):367-72 (1999); Doronina et al., *Nature Biotechnology* 21(7):778-784 (2003)), dolastatin derivatives (Ogawa et al., *Toxicol Lett.* 121(2):97-106 (2001); 21(3)778-784), Mylotarg® (Wyeth Laboratories, Philidelphia, Pa.); maytansinoids (DM1), taxane or mertansine (ImmunoGen Inc.). Immunotoxins utilizing anti-TIM-1 antibodies may be prepared by techniques that are well known in the art. See, e.g., Vitetta, *Immunol Today* 14:252 (1993); U.S. Pat. No. 5,194,594.

Bispecific antibodies may be generated using techniques that are well known in the art for example, see, e.g., Fanger et al., *Immunol Methods* 4:72-81 (1994); Wright and Harris, supra; Traunecker et al., *Int. J. Cancer (Suppl.)* 7:51-52 (1992). In each case, the first specificity is to TIM-1, the second specificity may be made to the heavy chain activation receptors, including, without limitation, CD16 or CD64 (see, e.g., Deo et al., 18:127 (1997)) or CD89 (see, e.g., Valerius et al., *Blood* 90:4485-4492 (1997)). Bispecific antibodies prepared in accordance with the foregoing would kill cells expressing TIM-1.

Depending on the intended use of the antibody, i.e., as a diagnostic or therapeutic reagent, radiolabels are known in the art and have been used for similar purposes. For example, radionuclides which have been used in clinical diagnosis include, but are not limited to: $^{131}$I, $^{125}$I, $^{123}$I, $^{99}$Tc, $^{67}$Ga, as well as $^{111}$In. Antibodies have also been labeled with a variety of radionuclides for potential use in targeted immunotherapy. See Peirersz et al., (1987). Monoclonal antibody conjugates have also been used for the diagnosis and treatment of cancer. See, e.g., *Immunol. Cell Biol.* 65:111-125. These radionuclides include, for example, $^{188}$Re and $^{186}$Re as well as $^{90}$Y, and to a lesser extent $^{199}$Au and $^{67}$Cu. 1-(131) have also been used for therapeutic purposes. U.S. Pat. No. 5,460,785 provides a listing of such radioisotopes.

Patents relating to radiotherapeutic chelators and chelator conjugates are known in the art. For example, U.S. Pat. No. 4,831,175 of Gansow is directed to polysubstituted diethylenetriaminepentaacetic acid chelates and protein conjugates containing the same, and methods for their preparation. U.S. Pat. Nos. 5,099,069, 5,246,692, 5,286,850, and 5,124,471 of Gansow also relate to polysubstituted DTPA chelates.

Cytotoxic chemotherapies are known in the art and have been used for similar purposes. For example, U.S. Pat. No. 6,441,163 describes the process for the production of cytotoxic conjugates of maytansinoids and antibodies. The antitumor activity of a tubulin polymerization inhibitor, auristatin PE, is also known in the art. Mohammad et al., Int. J. Oncol. 15(2):367-72 (August 1999).

Preparation of Antibodies

Briefly, XenoMouse® lines of mice were immunized with TIM-1 protein, lymphatic cells (such as B-cells) were recovered from the mice that express antibodies and were fused with a myeloid-type cell line to prepare immortal hybridoma cell lines, and such hybridoma cell lines were screened and selected to identify hybridoma cell lines that produce antibodies specific to TIM-1. Alternatively, instead of being fused to myeloma cells to generate hybridomas, the recovered B cells, isolated from immunized XenoMouse® lines of mice, with reactivity against TIM-1 (determined by e.g. ELISA with TIM-1-His protein), were then isolated using a TIM-1-specific hemolytic plaque assay. Babcook et al., *Proc. Natl. Acad. Sci. USA*, 93:7843-7848 (1996). In this assay, target cells such as sheep red blood cells (SRBCs) were coated with the TIM-1 antigen. In the presence of a B cell culture secreting the anti-TIM-1 antibody and complement, the formation of a plaque indicates specific TIM-1-mediated lysis of the target cells. Single antigen-specific plasma cells in the center of the plaques were isolated and the genetic information that encodes the specificity of the antibody isolated from single plasma cells.

Using reverse-transcriptase PCR, the DNA encoding the variable region of the antibody secreted was cloned and inserted into a suitable expression vector, preferably a vector cassette such as a pcDNA, more preferably the pcDNA vector containing the constant domains of immunoglobulin heavy and light chain. The generated vector was then be transfected into host cells, preferably CHO cells, and cultured in conventional nutrient media modified as appropriate for inducing promoters, selecting transformants, or amplifying the genes encoding the desired sequences.

In general, antibodies produced by the above-mentioned cell lines possessed fully human IgG2 heavy chains with human kappa light chains. The antibodies possessed high affinities, typically possessing Kd's of from about 10-6 through about 10-11 M, when measured by either solid phase and solution phase. These mAbs can be stratified into groups or "bins" based on antigen binding competition studies, as discussed below.

As will be appreciated, antibodies, as described herein, can be expressed in cell lines other than hybridoma cell lines. Sequences encoding particular antibodies can be used for transformation of a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference). The transformation procedure used depends upon the host to be transformed. Methods for introduction of heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. Cell lines of particular preference are selected through determining which cell lines have high expression levels and produce antibodies with constitutive TIM-1 binding properties.

Therapeutic Administration and Formulations

The compounds of the invention are formulated according to standard practice, such as prepared in a carrier vehicle. The term "pharmacologically acceptable carrier" means one or more organic or inorganic ingredients, natural or synthetic, with which the mutant proto-oncogene or mutant oncoprotein is combined to facilitate its application. A suitable carrier includes sterile saline although other aqueous and non-aqueous isotonic sterile solutions and sterile suspensions known to be pharmaceutically acceptable are known to those of ordinary skill in the art. In this regard, the term "carrier" encompasses liposomes and the antibody (See Chen et al., *Anal. Biochem.* 227: 168-175 (1995) as well as any plasmid and viral expression vectors.

Any of the novel polypeptides of this invention may be used in the form of a pharmaceutically acceptable salt. Suitable acids and bases which are capable of forming salts with the polypeptides of the present invention are well known to those of skill in the art, and include inorganic and organic acids and bases.

A compound of the invention is administered to a subject in a therapeutically-effective amount, which means an amount of the compound which produces a medically desirable result or exerts an influence on the particular condition being treated. An effective amount of a compound of the invention is capable of ameliorating or delaying progression of the diseased, degenerative or damaged condition. The effective amount can be determined on an individual basis and will be based, in part, on consideration of the physical attributes of the subject, symptoms to be treated and results sought. An effective amount can be determined by one of ordinary skill in the art employing such factors and using no more than routine experimentation.

The compounds of the invention may be administered in any manner which is medically acceptable. This may include injections, by parenteral routes such as intravenous, intravascular, intraarterial, subcutaneous, intramuscular, intratumor, intraperitoneal, intraventricular, intraepidural, or others as well as oral, nasal, ophthalmic, rectal, or topical. Sustained release administration is also specifically included in the invention, by such means as depot injections or erodible implants. Localized delivery is particularly contemplated, by such means as delivery via a catheter to one or more arteries, such as the renal artery or a vessel supplying a localized tumor.

Biologically active anti-TIM-1 antibodies as described herein can be used in a sterile pharmaceutical preparation or formulation to reduce the level of serum TIM-1 thereby effectively treating pathological conditions where, for example, serum TIM-1 is abnormally elevated. Anti-TIM-1 antibodies preferably possess adequate affinity to potently suppress TIM-1 to within the target therapeutic range, and preferably have an adequate duration of action to allow for infrequent dosing. A prolonged duration of action will allow for less frequent and more convenient dosing schedules by alternate parenteral routes such as subcutaneous or intramuscular injection.

When used for in vivo administration, the antibody formulation must be sterile. This is readily accomplished, for example, by filtration through sterile filtration membranes, prior to or following lyophilization and reconstitution. The antibody ordinarily will be stored in lyophilized form or in solution. Therapeutic antibody compositions generally are placed into a container having a sterile access port, for example, an intravenous solution bag or vial having an adapter that allows retrieval of the formulation, such as a stopper pierceable by a hypodermic injection needle.

The route of antibody administration is in accord with known methods, e.g., injection or infusion by intravenous, intraperitoneal, intracerebral, intramuscular, intraocular, intraarterial, intrathecal, inhalation or intralesional routes, or by sustained release systems as noted below. The antibody is preferably administered continuously by infusion or by bolus injection.

An effective amount of antibody to be employed therapeutically will depend, for example, upon the therapeutic objectives, the route of administration, and the condition of the patient. Accordingly, it is preferred that the therapist titer the dosage and modify the route of administration as required to obtain the optimal therapeutic effect. Typically, the clinician will administer antibody until a dosage is reached that achieves the desired effect. The progress of this therapy is easily monitored by conventional assays or by the assays described herein.

Antibodies, as described herein, can be prepared in a mixture with a pharmaceutically acceptable carrier. This therapeutic composition can be administered intravenously or through the nose or lung, preferably as a liquid or powder aerosol (lyophilized). The composition can also be administered parenterally or subcutaneously as desired. When administered systemically, the therapeutic composition should be sterile, pyrogen-free and in a parenterally acceptable solution having due regard for pH, isotonicity, and stability. These conditions are known to those skilled in the art. Briefly, dosage formulations of the compounds described herein are prepared for storage or administration by mixing the compound having the desired degree of purity with physiologically acceptable carriers, excipients, or stabilizers. Such materials are non-toxic to the recipients at the dosages and concentrations employed, and include buffers such as TRIS HCl, phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium and/or nonionic surfactants such as TWEEN, PLURONICS or polyethyleneglycol.

Sterile compositions for injection can be formulated according to conventional pharmaceutical practice as described in *Remington: The Science and Practice of Pharmacy* (20$^{th}$ ed, Lippincott Williams & Wilkens Publishers (2003)). For example, dissolution or suspension of the active compound in a vehicle such as water or naturally occurring vegetable oil like sesame, peanut, or cottonseed oil or a synthetic fatty vehicle like ethyl oleate or the like can be desired. Buffers, preservatives, antioxidants and the like can be incorporated according to accepted pharmaceutical practice.

Suitable examples of sustained-release preparations include semipermeable matrices of solid hydrophobic polymers containing the polypeptide, which matrices are in the form of shaped articles, films or microcapsules. Examples of sustained-release matrices include polyesters, hydrogels (e.g., poly(2-hydroxyethyl-methacrylate) as described by Langer et al., *J. Biomed Mater. Res.*, (1981) 15:167-277 and Langer, *Chem. Tech.*, (1982) 12:98-105, or poly(vinylalcohol)), polylactides (U.S. Pat. No. 3,773,919, EP 58,481), copolymers of L-glutamic acid and gamma ethyl-L-glutamate (Sidman et al., *Biopolymers*, (1983) 22:547-556), non-degradable ethylene-vinyl acetate (Langer et al., supra), degradable lactic acid-glycolic acid copolymers such as the LUPRON Depot™ (injectable microspheres composed of lactic acid-glycolic acid copolymer and leuprolide acetate), and poly-D-(−)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they can denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through disulfide interchange, stabilization can be achieved by modifying sulfhydryl residues, lyophilizing from acidic solutions, controlling moisture content, using appropriate additives, and developing specific polymer matrix compositions.

Sustained-released compositions also include preparations of crystals of the antibody suspended in suitable formulations capable of maintaining crystals in suspension. These preparations when injected subcutaneously or intraperitonealy can produce a sustained release effect. Other compositions also include liposomally entrapped antibodies. Liposomes containing such antibodies are prepared by methods known per se: U.S. Pat. No. DE 3,218,121; Epstein et al., *Proc. Natl. Acad. Sci. USA*, (1985) 82:3688-3692; Hwang et al., *Proc. Natl. Acad. Sci. USA*, (1980) 77:4030-4034; EP 52,322; EP 36,676; EP 88,046; EP 143,949; 142,641; Japanese patent application 83-118008; U.S. Pat. Nos. 4,485,045 and 4,544,545; and EP 102,324.

The dosage of the antibody formulation for a given patient will be determined by the attending physician taking into consideration various factors known to modify the action of drugs including severity and type of disease, body weight, sex, diet, time and route of administration, other medications and other relevant clinical factors. Therapeutically effective dosages can be determined by either in vitro or in vivo methods.

An effective amount of the antibodies, described herein, to be employed therapeutically will depend, for example, upon the therapeutic objectives, the route of administration, and the condition of the patient. Accordingly, it is preferred for the therapist to titer the dosage and modify the route of administration as required to obtain the optimal therapeutic effect. A typical daily dosage might range from about 0.001 mg/kg to up to 100 mg/kg or more, depending on the factors mentioned above. Typically, the clinician will administer the therapeutic antibody until a dosage is reached that achieves the desired effect. The progress of this therapy is easily monitored by conventional assays or as described herein.

It will be appreciated that administration of therapeutic entities in accordance with the compositions and methods herein will be administered with suitable carriers, excipients, and other agents that are incorporated into formulations to provide improved transfer, delivery, tolerance, and the like. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures can be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." *Regul. Toxicol. Pharmacol.* 32(2):210-8 (2000), Wang W. "Lyophilization and development of solid protein pharmaceuticals." *Int. J. Pharm.* 203(1-2):1-60 (2000), Charman W N "Lipids, lipophilic drugs, and oral drug delivery-some emerging concepts." *J Pharm Sci.* 89(8):967-78 (2000), Powell et al. "Compendium of excipients for parenteral formulations" *PDA J Pharm Sci Technol.* 52:238-311 (1998) and the citations therein for additional information related to formulations, excipients and carriers well known to pharmaceutical chemists.

It is expected that the antibodies described herein will have therapeutic effect in treatment of symptoms and conditions resulting from TIM-1 expression. In specific embodiments, the antibodies and methods herein relate to the treatment of symptoms resulting from TIM-1 expression including symptoms of cancer. Further embodiments, involve using the antibodies and methods described herein to treat cancers, such as cancer of the lung, colon, stomach, kidney, prostrate, or ovary.

Diagnostic Use

TIM-1 has been found to be expressed at low levels in normal kidney but its expression is increased dramatically in postischemic kidney. Ichimura et al., *J. Biol. Chem.* 273(7): 4135-42 (1998). As immunohistochemical staining with anti-TIM-1 antibody shows positive staining of renal, kidney, prostate and ovarian carcinomas (see below), TIM-1 overexpression relative to normal tissues can serve as a diagnostic marker of such diseases.

Antibodies, including antibody fragments, can be used to qualitatively or quantitatively detect the expression of TIM-1 proteins. As noted above, the antibody preferably is equipped with a detectable, e.g., fluorescent label, and binding can be monitored by light microscopy, flow cytometry, fluorimetry, or other techniques known in the art. These techniques are particularly suitable if the amplified gene encodes a cell surface protein, e.g., a growth factor. Such binding assays are performed as known in the art.

In situ detection of antibody binding to the TIM-1 protein can be performed, for example, by immunofluorescence or immunoelectron microscopy. For this purpose, a tissue specimen is removed from the patient, and a labeled antibody is applied to it, preferably by overlaying the antibody on a biological sample. This procedure also allows for determining the distribution of the marker gene product in the tissue examined. It will be apparent for those skilled in the art that a wide variety of histological methods are readily available for in situ detection.

Epitope Mapping

The specific part of the protein immunogen recognized by an antibody may be determined by assaying the antibody reactivity to parts of the protein, for example an N terminal and C terminal half. The resulting reactive fragment can then be further dissected, assaying consecutively smaller parts of the immunogen with the antibody until the minimal reactive peptide is defined. Anti-TIM-1 mAb 2.70.2 was assayed for reactivity against overlapping peptides designed from the antigen sequence and was found to specifically recognize the amino acid sequence PLPRQNHE (SEQ ID NO:96) corresponding to amino acids 189-202 of the TIM-1 immunogen (SEQ ID NO:54). Furthermore using an alanine scanning technique, it has been determined that the second proline and the asparagine residues appear to be important for mAb 2.70.2 binding.

Alternatively, the epitope that is bound by the anti-TIM-1 antibodies of the invention may be determined by subjecting the TIM-1 immunogen to SDS-PAGE either in the absence or presence of a reduction agent and analyzed by immunoblotting. Epitope mapping may also be performed using SELDI. SELDI ProteinChip® (LumiCyte) arrays used to define sites of protein-protein interaction. TIM-1 protein antigen or fragments thereof may be specifically captured by antibodies covalently immobilized onto the PROTEINCHIP array surface. The bound antigens may be detected by a laser-induced desorption process and analyzed directly to determine their mass.

The epitope recognized by anti-TIM-1 antibodies described herein may be determined by exposing the PROTEINCHIP Array to a combinatorial library of random peptide 12-mer displayed on Filamentous phage (New England Biolabs). Antibody-bound phage are eluted and then amplified and taken through additional binding and amplification cycles to enrich the pool in favor of binding sequences. After three or four rounds, individual binding clones are further tested for binding by phage ELISA assays performed on antibody-coated wells and characterized by specific DNA sequencing of positive clones.

EXAMPLES

The following examples, including the experiments conducted and results achieved are provided for illustrative purposes only and are not to be construed as limiting upon the invention described herein.

Example 1

Preparation of Monoclonal Antibodies that Bind TIM-1

The soluble extracellular domain of TIM-1 was used as the immunogen to stimulate an immune response in Xeno-Mouse® animals. A DNA (CG57008-02), which encodes the amino acid sequence for the TIM-1 extracellular domain (minus the predicted N-terminal signal peptide) was subcloned to the baculovirus expression vector, pMelV5His (CuraGen Corp., New Haven, Conn.), expressed using the pBlueBac baculovirus expression system (Invitrogen Corp., Carlsbad, Calif.), and confirmed by Western blot analyses. The nucleotide sequence below encodes the polypeptide used to generate antibodies.

(SEQ ID NO: 53)
```
TCTGTAAAGGTTGGTGGAGAGGCAGGTCCATCTGTCACACTACCCTGCC

ACTACAGTGGAGCTGTCACATCAATGTGCTGGAATAGAGGCTCATGTTC

TCTATTCACATGCCAAAATGGCATTGTCTGGACCAATGGAACCCACGTC

ACCTATCGGAAGGACACACGCTATAAGCTATTGGGGGACCTTTCAAGAA

GGGATGTCTCTTTGACCATAGAAAATACAGCTGTGTCTGACAGTGGCGT

ATATTGTTGCCGTGTTGAGCACCGTGGGTGGTTCAATGACATGAAAATC

ACCGTATCATTGGAGATTGTGCCACCCAAGGTCACGACTACTCCAATTG

TCACAACTGTTCCAACCGTCACGACTGTTCGAACGAGCACCACTGTTCC

AACGACAACGACTGTTCCAACGACAACTGTTCCAACAACAATGAGCATT

CCAACGACAACGACTGTTCCGACGACAATGACTGTTTCAACGACAACGA

GCGTTCCAACGACAACGAGCATTCCAACAACAACAAGTGTTCCAGTGAC

AACAACGGTCTCTACCTTTGTTCCTCCAATGCCTTTGCCCAGGCAGAAC

CATGAACCAGTAGCCACTTCACCATCTTCACCTCAGCCAGCAGAAACCC

ACCCTACGACACTGCAGGGAGCAATAAGGAGAGAACCCACCAGCTCACC

ATTGTACTCTTACACAACAGATGGGAATGACACCGTGACAGAGTCTTCA

GATGGCCTTTGGAATAACAATCAAACTCAACTGTTCCTAGAACATAGTC

TACTG
```

The amino acid sequence encoded thereby is as follows:

(SEQ ID NO: 54)
```
SVKVGGEAGPSVTLPCHYSGAVTSMCWNRGSCSLFTCQNGIVWTNGTHVTYRKDTRY

KLLGDLSRRDVSLTIENTAVSDSGVYCCRVEHRGWFNDMKITVSLEIVPPKVTTTPIVTT

VPTVTTVRTSTTVPTTTTVPTTTVPTTMSIPTTTTVPTTMTVSTTTSVPTTTSIPTTTSVPVT

TTVSTFVPPMPLPRQNHEPVATSPSSPQPAETHPTTLQGAIRREPTSSPLYSYTTDGNDTV

TESSDGLWNNNQTQLFLEHSLL
```

To facilitate purification of recombinant TIM-1, the expression construct can incorporate coding sequences for the V5 binding domain V5 and a HIS tag. Fully human IgG2 and IgG4 monoclonal antibodies (mAb), directed against TIM-1 were generated from human antibody-producing XenoMouse® strains engineered to be deficient in mouse antibody production and to contain the majority of the human antibody gene repertoire on megabase-sized fragments from the human heavy and kappa light chain loci as previously described in Yang et al., Cancer Res. (1999). Two XenoMouse® strains, an hIgG2 (xmg-2) strain and an IgG4 (3C-1) strain, were immunized with the TIM-1 antigen (SEQ ID NO: 54). Both strains responded well to immunization (Tables 2 and 3).

TABLE 2

Serum titer of XENOMOUSE ® hIgG$_2$ strain immunized with TIM-1 antigen.
Group 1: 5 mice (hIgG$_2$ strain); mode of immunization = footpad

| Mouse ID | Reactivity to TIM-1 Titers via hIgG | |
|---|---|---|
| | Bleed After 4 inj. | Bleed After 6 inj. |
| M716-1 | 600,000 | 600,000 |
| M716-2 | 600,000 | 500,000 |
| M716-3 | 200,000 | 400,000 |
| M716-4 | 300,000 | 200,000 |
| M716-5 | 400,000 | 400,000 |
| Negative Control | 75 | 110 |
| Positive Control | — | 600,000 |

TABLE 3

Serum titer of XENOMOUSE ® IgG$_4$ strain immunized with TIM-1 antigen
Group 2: 5 mice (IgG$_4$ strain); mode of immunization = footpad

| Mouse ID | Reactivity to TIM-1 Titers via hIgG | |
|---|---|---|
| | Bleed After 4 inj. | Bleed After 6 inj. |
| M326-2 | 15,000 | 73,000 |
| M326-3 | 7,500 | 60,000 |
| M329-1 | 27,000 | 30,000 |
| M329-3 | 6,500 | 50,000 |
| M337-1 | 2,500 | 16,000 |
| Negative Control | <100 | 90 |
| Positive Control | — | 600,000 |

Hybridoma cell lines were generated from the immunized mice. Selected hybridomas designated 1.29, 1.37, 2.16, 2.17, 2.24, 2.45, 2.54 2.56, 2.59, 2.61, 2.70, and 2.76 (and subclones thereof) were further characterized. The antibodies produced by cell lines 1.29 and 1.37 possess fully human IgG2 heavy chains with human kappa light chains while those antibodies produced by cell lines 2.16, 2.17, 2.24, 2.45, 2.54 2.56, 2.59, 2.61, 2.70, and 2.76 possess fully human IgG4 heavy chains with human kappa light chains.

The amino acid sequences of the heavy chain variable domain regions of twelve anti-TIM-1 antibodies with their respective germline sequences are shown in Table 4 below. The corresponding light chain variable domain regions amino acid sequence is shown in Table 5 below. "X" indicates any amino acid, preferably the germline sequence in the corresponding amino acid position. The CDRs (CDR1, CDR2, and CDR3) and FRs (FR1, FR2, and FR3) in the immunoglobulins are shown under the respective column headings.

TABLE 4

Heavy Chain Analysis

| mAb | SEQ ID NO: | D | FR1 | CDR1 | FR2 | CDR2 | FR3 | CDR3 | J |
|---|---|---|---|---|---|---|---|---|---|
|  | 55 | Germline | QVQLVESGGGVVQP GRSLRLSCAAS | GFTFSS YGMH | WVRQAPGKG LEWVA | VIWYDGSNKY YADSVKG | RFTISRDNSKNTLYLQ MNSLRAEDTAVYYCAR | XXDY | WGQGTLVTVSSA |
| 2.54 | 26 | VH3-33/--/ JH4b | QVQLEQSGGGVVQP GRSLRLSCAAS | GFTFTN YGLH | WVRQAPGKG LDWVA | VIWYDGSHKF YADSVKG | RFTISRDNSKNTLFLQ MNSLRAEDTAVYYCTR | DLDY | WGQGTLVTVSSA |
|  | 56 | Germline | QVQLVESGGGVVQP GRSLRLSCAAS | GFTFSS YGMH | WVRQAPGKG LEWVA | VIWYDGSNKY YADSVKG | RFTISRDNSKNTLYLQ MNSLRAEDTAVYYCAX | XXYDSSX XXYGMDV | WGQGTLVTVSSA |
| 2.76 | 46 | VH3-33/D3-22/JH6b | XXXXEQSGGGVVQP GRSLRLSCAAS | GFTFSS YGMY | WVRQAPGKG LEWVA | VIWYDGSNKY YADSVKG | RFTISRDNSKNTLYLQ MNSLRAEDTAVYYCAR | DFYDSSR YHYGMDV | WGQGTLVTVSSA |
|  | 57 | Germline | QVQLQESGPGLVKP SQTLSLTCTVS | GGSISS GGYYWS | WIRQHPGKG LEWIG | YIYYSGSTYY NPSLKS | RVTISVDTSKNQFSLK LSSVTAADTAVYYCAR | XXXXSSS WYXXFDY | WGQGTLVTVSSA |
| 2.59 | 34 | VH4-31/D6-13/JH4b | XXXXXQSGPRLVKP SQTLSLTCTVS | GGSISS DGYYWS | WIRQHPGKG LEWIG | YIYYSGSTFY NPSLKS | RVAISVDTSKNQFSLK LSSVTAADTAVYYCAR | ESPHSSN WYSGFDC | WGQGTLVTVSSA |
|  | 58 | Germline | QVQLVESGGGVVQP GRSLRLSCAAS | GFTFSS YGMH | WVRQAPGKG LEWVA | VIWYDGSNKY YADSVKG | RFTISRDNSKNTLYLQ MNSLRAEDTAVYYCAR | DYYDSSX XXXXFDY | WGQGTLVTVSSA |
| 2.70 | 42 | VH3-33/D3-22/JH4b | QVQLVESGGGVVQP GRSLRLSCAAS | GFIFSR YGMH | WVRQAPGKG LKWVA | VIWYDGSNKL YADSVKG | RFTISRDNSKNTLYLQ MNSLRAEDTAVYYCAR | DYYDNSR HHWGFDY | WGQGTLVTVSSA |
| 2.24 | 18 |  | QVQLEQSGGGVVQP GRSLRLSCAAS | GFTFSR YGMH | WVRQAPGKG LKWVA | VIWYDGSNKL YADSVKG | RFTISRDNSKNTLYLQ MNSLRAEDTAVYYCAR | DYYDNSR HHWGFDY | WGQGTLVTVSSA |
| 2.61 | 38 |  | QVQLVEAGGGVVQP GRSLRLSCAAS | GFTFRS YGMH | WVRQAPGKG LKWVA | VIWYDGSNKY YTDSVKG | RFTISRDNSKNTLYLQ MNSLRAEDTAVYYCVR | DYYDNSR HHWGFDY | WGQGTLVTVSSA |
| 2.56 | 30 |  | QVQLVESGGGVVQP GRSLRLSCAAS | GFTFSS YGMH | WVRQAPGKG LEWVA | VIWYDGSHKY YADSVKG | RFTISRDNSKNTLYLQ MNSLRAEDTAVYYSAR | DYYDTSR HHWGFDC | WGQGTLVTVSSA |
|  | 59 | Germline | EVQLVESGGGLVKP GGSLRLSCAAS | GFTFSN AWMS | WVRQAPGKG LEWVG | RIKSKTDGGT TDYAAPVKG | RFTISRDDSKNTLYLQ MNSLKTEDTAVYYCTX | XDXXXDY | WGQGTLVTVSSA |
| 2.16 | 10 | VH3-15/D3-16/JH4b | XXXXEQSGGGVVKP GGSLRLSCAAS | GFTFSN AWMT | WVRQAPGKG LEWVG | RIKRRTDGGT TDYAAPVKG | RFTISRDDSKNTLYLQ MNNLKNEDTAVYYCTS | VDNDVDY | WGQGTLVTVSSA |
|  | 60 | Germline | QVQLQESGPGLVKP SETLSLTCTVS | GGSVSS GGYYWS | WIRQPPGKG LEWIG | YIYYSGSTNY NPSLKS | RVTISVDTSKNQFSLK LSSVTAADTAVYYCAR | XXXWXXX FDY | WGQGTLVTVSSA |
| 1.29 | 2 | VH4-61/D1-7/JH4b | QVQLQESGPGLVKP SETLSLTCTVS | GGSVSS GGYYWS | WIRQPPGKG LEWIG | FIYYTGSTNY NPSLKS | RVSISVDTSKNQFSLK LSSVTAADAAVYYCAR | DYDWSFH FDY | WGQGTLVTVSSA |
|  | 61 | Germline | EVQLVESGGGLVKP GGSLRLSCAAS | GFTFSN AWMS | WVRQAPGKG LEWVG | RIKSKTDGGT TDYAAPVKG | RFTISRDDSKNTLYLQ MNSLKTEDTAVYYCTT | XXXSGDY | WGQGTLVTVSSA |
| 2.45 | 22 | VH3-15/D6-19/JH4b | XXXXXQSGGGLVKP GGSLRLSCAAS | GFTFSN AWMT | WVRQAPGKG LEWVG | RIKRKTDGGT TDYAAPVKG | RFTISRDDSENTLYLQ MNSLETEDTAVYYCTT | VDNSGDY | WGQGTLVTVSSA |
|  | 62 | Germline | EVQLVESGGGLVQP GGSLRLSCAAS | GFTFSS YWMS | WVRQAPGKG LEWVA | NIKQDGSEKY YVDSVKG | RFTISRDNAKNSLYLQ MNSLRAEDTAVYYCAR | XDY | WGQGTLVTVSSA |
| 1.37 | 6 | VH3-7/--/ JH4b | EVQLVESGGGLVQP GGSLRLSCAAS | GFTFTN YWMS | WVRQAPGKG LEWVA | NIQQDSEKY YVDSVRG | RFTISRDNAKNSLYLQ MNSLRAEDSAVYYCAR | WDY | WGQGTLVTVSSA |
|  | 63 | Germline | EVQLVESGGGLVQP GGSLRLSCAAS | GFTFSS YSMN | WVRQAPGKG LEWVS | YISSSSSTIY YADSVKG | RFTISRDNAKNSLYLQ MNSLRDEDTAVYYCAX | XFDY | WGQGTLVTVSSA |
| 2.17 | 14 | VH3-48/--/ JH4b | QVQLEQSGGGLVQP GGSLRLSCAAS | GFTFST YSMN | WVRQAPGKG LEWVS | YIRSSTSTIY YAESLKG | RFTISSDNAKNSLYLQ MNSLRDEDTAVYYCAR | DFDY | WGQGTLVTVSSA |

TABLE 5

Light Chain Analysis

| mAb | SEQ ID NO: | J | FR1 | CDR1 | FR2 | CDR2 | FR3 | CDR3 | J |
|---|---|---|---|---|---|---|---|---|---|
|  | 64 | Germline | ETQLTQSPGTLSLS PGERATLSC | RASQSVSSSYL A | WYQQKPGQ APRLLIY | GASSRAT | GIPDRFSGSGSGTDFT LTISRLEPEDFAVYYC | QQYGSSXXLT | FGGGTKVEIKR |
| 2.54 | 28 | A27/JK4 | ETQLTQSPGTLSLS PGERVTLSC | RASQSVSNNYL A | WYQQKPGQ APRLLIY | GASSRAT | GIPDRFSGSGSGTDFT LTISRLEPEDCAECYC | QQYGSSLPLT | FGGGTKVEIKR |
|  | 65 | Germline | DIVMTQSPLSLPVT PGEPASISC | RSSQSLLHSNG YNYLD | WYLQKPGQ SPQLLIY | LGSNRAS | GVPDRFSGSGSGTDFT LKISRVEAEDVGVYYC | MQALQTXXT | FGGGTKVEIKR |
| 2.16 | 12 | A3/JK4 | XXXLTQSPLSLPVT PGEPASISC | RSSQSLLHSNG YNYLD | WYLQKPGQ SPQLLIY | LGSNRAS | GVPDRFSGSGSGTDFT LKISRVEAEDIGLYYC | MQALQTPLT | FGGGTKVDIKR |

TABLE 5-continued

Light Chain Analysis

| mAb | SEQ ID NO: | J | FR1 | CDR1 | FR2 | CDR2 | FR3 | CDR3 | J |
|---|---|---|---|---|---|---|---|---|---|
| 2.45 | 24 | | XXXXTQSPLSLPVT PGEPASISC | RSSQSLLHSNG YNYLD | WYLQKPGQ SPQLLIY | LGSNRAS | GVPDRFSGSGSGTDFT LKISRVEAEDVGVYYC | MQALQTPLT | FGGGTKVEIKR |
| | 66 | Germline | DIQMTQSPSSLSAS VGDRVTITC | RASQGIRNDLG | WYQQKPGK APKRLIY | AASSLQS | GVPSRFSGSGSGTEFT LTISSLQPEDFATYYC | LQHNSYPLT | FGGGTKVEIKR |
| 1.29 | 4 | A30/JK4 | DIQMTQSPSSLSAS IGDRVTITC | RASQGIRNDLG | WYQQKPGK APKRLIY | AASSLQS | GVPSRFSGSGSGTEFT LTISSLQPEDFATYYC | LQHNSYPLT | FGGGTKVEIKR |
| | 67 | Germline | DIVMTQTPLSSPVT LGQPASISC | RSSQSLVHSDG NTYLS | WLQQRPGQ PPRLLIY | KISNRFS | GVPDRFSGSGAGTDFT LKISRVEAEDVGVYYC | MQATQFPXIT | FGQGTRLEIKR |
| 2.17 | 16 | A23/JK5 | EIQLTQSPLSSPVT LGQPASISC | RSSQSLVHSDG DTYLN | WLQQRPGQ PPRLLIY | KISTRFS | GVPDRFSGSGAGTDFT LKISRVETDDVGIYYC | MQTTQIPQIT | FGQGTRLEIKR |
| | 68 | Germline | DIQMTQSPSSLSAS VGDRVTITC | RASQSISSYLN | WYQQKPGK APKLLIY | AASSLQS | GVPSRFSGSGSGTDFT LTISSLQPEDFATYYC | QQSYSTPPT | FGQGTKVEIKR |
| 2.24 | 20 | O12/JK1 | DIQLTQSPSSLSAS VGDRVTITC | RASQSIYSYLN | WYQQKPGK APKLLIY | AASSLQS | GVPSRFSGSGSGTDFT LTISSLQPEDFATYYC | QQSYSTPPT | FGQGTKVEIKR |
| | 69 | Germline | DIVMTQTPLSSPVT LGQPASISC | RSSQSLVHSDG NTYLS | WLQQRPGQ PPRLLIY | KISNRFS | GVPDRFSGSGAGTDFT LKISRVEAEDVGVYYC | MQATQFPQT | FGQGTKVEIKR |
| 1.37 | 8 | A23/JK1 | DIVMTQTPLSSTVI LGQPASISC | RSSQSLVHSDG NTYLN | WLQQRPGQ PPRLLIY | MISNRFS | GVPDRFSGSGAGTDFT LKISRVEAEDVGVYYC | MQATESPQT | FGQGTKVEIKR |
| | 70 | Germline | DIVMTQTPLSLPVT PGEPASISC | RSSQSLLDSDD GNTYLD | WYLQKPGQ SPQLLIY | TLSYRAS | GVPDRFSGSGSGTDFT LKISRVEAEDVGVYYC | MQRIEFPIT | FGQGTRLEIKR |
| 2.70 | 44 | O1/JK5 | DIVMTQTPLSLPVT PGEPASISC | RSSRSLLDSDD GNTYLD | WYLQKPGQ SPQLLIY | TLSYRAS | GVPDRFSGSGSGTDFT LKISRVEAEDVGVYYC | MQRVEFPIT | FGQGTRLEIKR |
| 2.56 | 32 | | EIVMTQTPLSLPVT PGEPASISC | RSSQSLLDSED GNTYLD | WYLQKPGQ SPQLLIY | TLSHRAS | GVPDRFSGSGSGTDFT LKISRVEAEDVGVYCC | MQRVEFPIT | FGQGTRLEIKR |
| 2.76 | 48 | | XXXXTQCPLSLPVT PGEPASISC | RSSQSLLDSDD GNTYLD | WYLQKPGQ SPQLLIY | TVSYRAS | GVPDRFSGSGSGTDFT LKISRVEAEDVGVYYC | MQRIEFPIT | FGQGTRLEIKR |
| | 71 | Germline | EIVLTQSPDFQSVT PKEKVTITC | RASQSIGSSLH | WYQQKPDQ SPKLLIK | YASQSFS | GVPSRFSGSGSGTDFT LTINSLEAEDAATYYC | HQSSSLPFT | FGPGTKVDIKR |
| 2.59 | 36 | A26/JK3 | XXXXTQSPDFQSVT PKEKVTITC | RASQSIGSRLH | WYQQKPDQ SPKLLIK | YASQSFS | GVPSRFSGSGSGTDFT LTINSLEAEDAATYYC | HQSSNLPFT | FGPGTKVDIKR |
| | 72 | Germline | DIQMTQSPSSLSAS VGDRVTITC | RASQGIRNDLG | WYQQKPGK APKRLIY | AASSLQS | GVPSRFSGSGSGTEFT LTISSLQPEDFATYYC | LQHNSYPXX | FGQGTKLEIKR |
| 2.61 | 40 | A30/JK2 | DIQMTQSPSSRCAS VGDRVTITC | RASQGIRNDLA APK | WYQQKPGK RLIY | AASSLQS | GVPSRFSGSRSGTEFT LTISSLQPEDFAAYYC | LQHNSYPPS | FGQGTKLEIKR |

Human antibody heavy chain VH3-33 was frequently selected in productive rearrangement for producing antibody successfully binding to TIM-1. Any variants of a human antibody VH3-33 germline in a productive rearrangement making antibody to TIM-1 is within the scope of the invention. Other heavy chain V regions selected in TIM-1 binding antibodies included: VH4-31, VH3-15, VH4-61, VH3-7 and VH3-48. The light chain V regions selected included: A27, A3, A30, A23, O12, O1, and A26. It is understood that the λκ XenoMouse® may be used to generate anti-TIM-1 antibodies utilizing lambda V regions.

The heavy chain variable domain germ line usage of the twelve anti-TIM-1 antibodies is shown in Table 6. The light chain variable domain germ line usage is shown in Table 7 (below).

TABLE 6

Germ Line Usage of the Heavy Chain Variable Domain Regions

| mAb | V Heavy | V Sequence | #N's | N | D1 | D1 Sequence | #N's | N | D2 | D2 Sequence |
|---|---|---|---|---|---|---|---|---|---|---|
| 2.16 | VH3-15 | TGTACC (1-285) | 5 | TCA GT | D3-16 (291-296) | CGATAA | -N.A- | -N.A- | -N.A- | -N.A- |
| 2.70 | VH3-33 | GAGAGA (1-290) | 0 | | D3-22 (291-306) | TTACTATGAT AATAGT (SEQ ID NO: 73) | -N.A- | -N.A- | -N.A- | -N.A- |
| 2.59 | VH4-31 | GAGAGA (2-284) | 8 | ATC CCC TC | D6-13 (293-309) | ATAGCAGCAA CTGGTAC (SEQ ID NO: 75) | -N.A- | -N.A- | -N.A- | -N.A- |

TABLE 6-continued

Germ Line Usage of the Heavy Chain Variable Domain Regions

| 2.24 | VH3-33 (1-296) | GAGAGA | 0 | | D3-22 (297-312) | TTACTATGAT AATAGT (SEQ ID NO: 76) | -N.A- | -N.A- | -N.A- | -N.A- |
|---|---|---|---|---|---|---|---|---|---|---|
| 1.29 | VH4-61 (1-293) | GAGAGA | 5 | TTA TG | D1-7 (299-304) | ACTGGA | -N.A- | -N.A- | -N.A- | -N.A- |
| 2.61 | VH3-33 (1-296) | GAGAGA | 0 | | D3-22 (297-312) | TTACTATGAT AATAGT (SEQ ID NO: 78) | -N.A- | -N.A- | -N.A- | -N.A- |
| 2.76 | VH3-33 (1-281) | TGCGAG | 6 | GGA TTT | D3-22 (288-300) | CTATGATAGT AGT (SEQ ID NO: 80) | -N.A- | -N.A- | -N.A- | -N.A- |
| 2.54 | VH3-33 (1-296) | GCGAGA | -N.A- | -N.A- | -N.A- | -N.A- | -N.A- | -N.A- | -N.A- | -N.A- |
| 1.37 | VH3-7 (7-300) | GCGAGA | -N.A- | -N.A- | -N.A- | -N.A- | -N.A- | -N.A- | -N.A- | -N.A- |
| 2.17 | VH3-48 (2-291) | TGTGCG | -N.A- | -N.A- | -N.A- | -N.A- | -N.A- | -N.A- | -N.A- | -N.A- |
| 2.45 | VH3-15 (2-286) | CCACAG | 7 | TCG ATA A | D6-19 (294-299) | CAGTGG | -N.A- | -N.A- | -N.A- | -N.A- |
| 2.56 | VH3-33 (1-290) | GAGAGA | 0 | | D3-22 (291-301) | TTACTATGATA (SEQ ID NO: 81) | -N.A- | -N.A- | -N.A- | -N.A- |

| | mAb | #N's | N | JH | J Sequence | Constant Region | CDR1 | CDR2 | CDR3 |
|---|---|---|---|---|---|---|---|---|---|
| | 2.16 | 7 | TGACGTG | JH4b (304-343) | GACTAC | G4 (344-529) | 64-93 | 136-192 | 289-309 |
| | 2.70 | 15 | AGACATCA CTGGGGG (SEQ ID NO: 74) | JH4b (322-364) | TTTGAC | G4 (365-502) | 70-99 | 142-192 | 289-330 |
| | 2.59 | 5 | TCGGG | JH4b (315-358) | CTTTGA | G4 (359-545) | 61-96 | 139-186 | 283-324 |
| | 2.24 | 15 | AGACATCA CTGGGGG (SEQ ID NO: 77) | JH4b (328-370) | TTTGAC | G4 (371-568) | 76-105 | 148-198 | 295-336 |
| | 1.29 | 6 | GCTTCC | JH4b (311-355) | ACTTTG | G2 (356-491) | 70-105 | 148-195 | 292-321 |
| | 2.61 | 15 | AGACATCA CTGGGGG (SEQ ID NO: 79) | JH4b (328-370) | TTTGAC | G4 (371-534) | 76-105 | 148-198 | 295-336 |
| | 2.76 | 7 | CGTTACC | JH6b (308-358) | ACTACG | G4 (359-544) | 64-93 | 136-186 | 283-324 |
| | 2.54 | 2 | TC | JH4b) (299-340 | TTGACT | G4 (341-537) | 76-105 | 148-198 | 295-306 |
| | 1.37 | 3 | TGG | JH4b (304-343) | GACTAC | G2 (344-469) | 82-111 | 154-204 | 301-309 |
| | 2.17 | 5 | CGGGA | JH4b (297-340) | CTTTGA | G4 (341-538) | 76-105 | 148-198 | 295-306 |
| | 2.45 | 0 | | JH4b (300-340) | TGACTA | G4 (341-526) | 61-90 | 133-189 | 286-306 |
| | 2.56 | 20 | CGAGTCGG CATCACTG GGGG (SEQ ID NO: 82) | JH4b (322-364) | TTTGAC | G4 (365-527) | 70-99 | 142-192 | 289-330 |

TABLE 7

Germ Line Usage of the Light Chain Variable Domain Regions

| mAb | VL | V Sequence | #N's | N | JL | J Sequence | Constant Region | CDR1 | CDR2 | CDR3 |
|---|---|---|---|---|---|---|---|---|---|---|
| 2.70 | O1 (46-348) | TTTCCT | 0 | | JK5 (349-385) | ATCACC | IGKC (386-522) | 115-165 | 211-231 | 328-354 |
| 2.59 | A26 (1-272) | TTTACC | 0 | | JK3 (273-310) | ATTCAC | IGKC (311-450) | 58-90 | 136-156 | 253-279 |
| 2.24 | O12 (1-287) | CCCTCC | 0 | | JK1 (288-322) | GACGTT | IGKC (323-472) | 70-102 | 148-168 | 265-291 |
| 1.29 | A30 (46-331) | ACCCTC | 0 | | JK4 (332-367) | TCACTT | IGKC (368-504) | 115-147 | 193-213 | 310-336 |
| 2.56 | O1 (46-348) | TTTCCT | 0 | | JK5 (349-385) | ATCACC | IGKC (386-521) | 115-165 | 211-231 | 328-354 |
| 2.61 | A30 (1-287) | CCCTCC | 3 | CAG | JK2 (291-322) | TTTTGG | IGKC (323-470) | 70-102 | 148-168 | 265-291 |
| 2.76 | O1 (1-290) | GTTTCC | 0 | | JK5 (291-328) | GATCAC | IGKC (329-419) | 58-108 | 154-174 | 271-297 |
| 1.37 | A23 (43-344) | TCCTCA | 0 | | JK1 (345-379) | GACGTT | IGKC (380-454) | 112-159 | 205-225 | 322-348 |
| 2.17 | A23 (1-302) | TCCTCA | 1 | A | JK5 (304-340) | ATCACC | IGKC (341-490) | 70-117 | 163-183 | 280-309 |
| 2.54 | A27 (1-286) | GCTCAC | 4 | TCCC | JK4 (291-328) | GCTCAC | IGKC (329-480) | 70-105 | 151-171 | 268-297 |
| 2.16 | A3 (2-290) | AACTCC | 2 | GC | JK4 (293-328) | TCACTT | IGKC (329-447) | 61-108 | 154-174 | 271-297 |
| 2.45 | A3 (1-287) | AACTCC | 2 | GC | JK4 (290-325) | TCACTT | IGKC (326-465) | 58-105 | 151-171 | 268-294 |

The sequences encoding monoclonal antibodies 1.29, 1.37, 2.16, 2.17, 2.24, 2.45, 2.54 2.56, 2.59, 2.61, 2.70, and 2.76, respectively, including the heavy chain nucleotide sequence (A), heavy chain amino acid sequence (B) and the light chain nucleotide sequence (C) with the encoded amino acid sequence (D) are provided in the sequence listing as summarized in Table 1 above. A particular monoclonal antibody, 2.70, was further subcloned and is designated 2.70.2, see Table 1.

Example 2

Antibody Reactivity with Membrane Bound TIM-1 Protein by FACS

Fluorescent Activated Cell Sorter (FACS) analysis was performed to demonstrate the specificity of the anti-TIM-1 antibodies for cell membrane-bound TIM-1 antigen and to identify preferred antibodies for use as a therapeutic or diagnostic agent. The analysis was performed on two renal cancer cell lines, ACHN (ATCC#:CRL-1611) and CAKI-2 (ATCC#:HTB-47). A breast cancer cell line that does not express the TIM-1 antigen, BT549, was used as a control. Table 8 shows that both antibodies 2.59.2 and 2.70.2 specifically bound to TIM-1 antigen expressed on ACHN and CAKI-2 cells, but not antigen negative BT549 cells. Based on the Geo Mean Ratios normalized to the irrelevant antibody isotype control (pK16), ACHN cells had a higher cell surface expression of TIM-1 protein than CAKI-2 cells.

TABLE 8

| | Geo Mean Ratio (relative to negative control) | | | |
|---|---|---|---|---|
| Antibody | BIN | ACHN | CAKI-2 | BT549 |
| 2.59.2 | 1 | 15.2 | 7.7 | 1.4 |
| 2.70.2 | 6 | 19.4 | 8.8 | 1.8 |
| 1.29 | 1 | 17.9 | | 1.2 |
| 2.16.1 | 2 | 7.9 | | 1.5 |

TABLE 8-continued

| | Geo Mean Ratio (relative to negative control) | | | |
|---|---|---|---|---|
| Antibody | BIN | ACHN | CAKI-2 | BT549 |
| 2.56.2 | 5 | 12.2 | | 1.5 |
| 2.45.1 | 8 | 4.3 | | 1.1 |

Example 3

Specificity of the Anti-TIM-1 Monoclonal Antibodies

Figure 2:
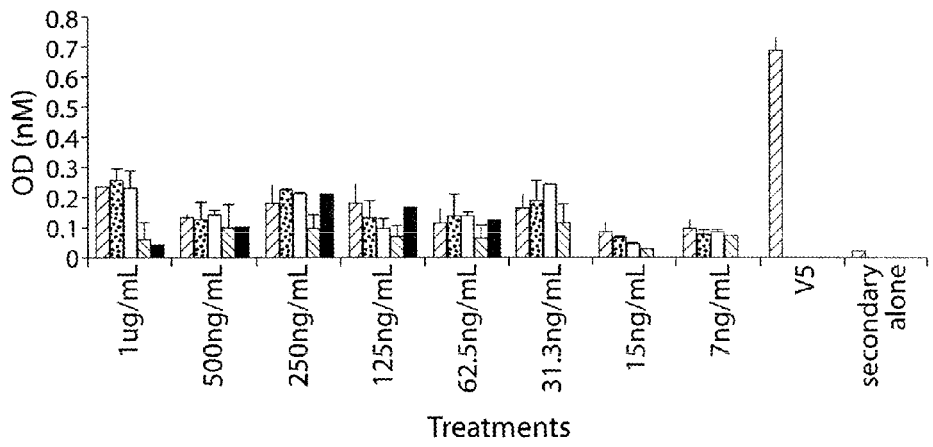
FIG. 2 is a bar graph of the results of an ELISA assay of anti-TIM-1 monoclonal antibodies 1.29, 2.56.2, 2.59.2, and 2.45.1 against irrelevant protein.

The anti-TIM-1 antibodies bound specifically to TIM-1 protein but not an irrelevant protein in an ELISA assay. TIM-1 antigen (with a V5-HIS tag) specific binding results for four of the anti-TIM-1 monoclonal antibodies (1.29, 2.56.2, 2.59.2, and 2.45.1) as well as an isotype matched control mAb PK16.3 are shown in FIG. 1. The X axis depicts the antibodies used in the order listed above and the Y axis is the optical density. The respective binding of these antibodies to the irrelevant protein (also with a V5-HIS tag) is shown in FIG. 2.

ELISA Protocol.

A 96-well high protein binding ELISA plate (Corning Costar cat. no. 3590) was coated with 50 μL of the TIM-1 antigen at a concentration of 5 μg/mL diluted in coating buffer (0.1M Carbonate, pH9.5), and incubated overnight at 4° C. The wells were then washed five times with 200-300 μL of 0.5% Tween-20 in PBS. Next, plates were blocked with 200 μL of assay diluent (Pharmingen, San Diego, Calif., cat. no. 26411E) for at least 1 hour at room temperature. Anti-TIM-1 monoclonal antibodies were then diluted in assay diluent with the final concentrations of 7, 15, 31.3, 62.5, 125, 250, 500 and 1000 ng/mL. An anti-V5-HRP antibody was used at 1:1000 to detect the V5 containing peptide as the positive control for the ELISA. Plates were then washed again as described above. Next 50 μL of each antibody dilution was added to the proper wells, then incubated for at least 2 hours at room temp. Plates were washed again as described above, then 50 μL of secondary antibody (goat anti-human-HRP) was added at 1:1000 and allowed to incubate for 1 hour at room temp. Plates were washed again as described above then developed with 100 μL of TMB substrate solution/well (1:1 ratio of solution A+B) (Pharmingen, San Diego, Calif., cat. no. 2642KK). Finally, the reaction was stopped with 50 μL sulfuric acid and the plates read at 450 nm with a correction of 550 nm.

Example 4

Antibody Sequences

In order to analyze structures of antibodies, as described herein, genes encoding the heavy and light chain fragments out of the particular hybridoma were cloned. Gene cloning and sequencing was accomplished as follows. Poly(A)+ mRNA was isolated from approximately 2×105 hybridoma cells derived from immunized XenoMouse® mice using a Fast-Track kit (Invitrogen). The generation of random primed cDNA was followed by PCR. Human VH or human VK family specific variable domain primers (Marks et. al., 1991) or a universal human VH primer, MG-30 (CAGGT-GCAGCTGGAGCAGTCIGG) (SEQ ID NO:83) were used in conjunction with primers specific for the human:

Cγ2 constant region (MG-40d; 5'-GCT GAG GGA GTA GAG TCC TGA GGA-3' (SEQ ID NO: 84));

Cγ1 constant region (HG1; 5' CAC ACC GCG GTC ACA TGG C (SEQ ID NO: 85));
or

Cγ3 constant region (HG3; 5' CTA CTC TAG GGC ACC TGT CC (SEQ ID NO: 86))

or the human Cκ constant domain (hκP2; as previously described in Green et al., 1994). Sequences of human MAbs-derived heavy and kappa chain transcripts from hybridomas were obtained by direct sequencing of PCR products generated from poly(A⁺) RNA using the primers described above. PCR products were also cloned into pCRII using a TA cloning kit (Invitrogen) and both strands were sequenced using Prism dye-terminator sequencing kits and an ABI 377 sequencing machine. All sequences were analyzed by alignments to the "V BASE sequence directory" (Tomlinson et al., MRC Centre for Protein Engineering, Cambridge, UK) using MacVector and Geneworks software programs.

In each of Tables 4-7 above, CDR domains were determined in accordance with the Kabat numbering system. See Kabat, Sequences of Proteins of Immunological Interest (National Institutes of Health, Bethesda, Md. (1987 and 1991)).

Example 5

Epitope Binning and BiaCore® Affinity Determination

Epitope Binning
Certain antibodies, described herein were "binned" in accordance with the protocol described in U.S. Patent Application Publication No. 20030157730, published on Aug. 21, 2003, entitled "Antibody Categorization Based on Binding Characteristics."
MxhIgG conjugated beads were prepared for coupling to primary antibody. The volume of supernatant needed was calculated using the following formula: (n+10)×50 μL (where n=total number of samples on plate). Where the concentration was known, 0.5 μg/mL was used. Bead stock was gently vortexed, then diluted in supernatant to a concentration of 2500 of each bead per well or 0.5×105/mL and incubated on a shaker in the dark at room temperature overnight, or 2 hours if at a known concentration of 0.5 μg/mL. Following aspiration, 504, of each bead was added to each well of a filter plate, then washed once by adding 100 μL/well wash buffer and aspirating. Antigen and controls were added to the filter plate 50 μL/well then covered and allowed to incubate in the dark for 1 hour on shaker. Following a wash step, a secondary unknown antibody was added at 50 μL/well using the same dilution (or concentration if known) as used for the primary antibody. The plates were then incubated in the dark for 2 hours at room temperature on shaker followed by a wash step. Next, 50 μL/well biotinylated mxhIgG diluted 1:500 was added and allowed to incubate in the dark for 1 hour on shaker at room temperature. Following a wash step, 50 μL/well Streptavidin-PE was added at 1:1000 and allowed to incubate in the dark for 15 minutes on shaker at room temperature. Following a wash step, each well was resuspended in 804, blocking buffer and read using a Luminex system.

Table 9 shows that the monoclonal antibodies generated belong to eight distinct bins. Antibodies bound to at least three distinct epitopes on the TIM-1 antigen.

Determination of Anti-TIM-1 mAb Affinity Using BiaCore® Analysis

BiaCore® analysis was used to determine binding affinity of anti-TIM-1 antibody to TIM-1 antigen. The analysis was performed at 25° C. using a BiaCore® 2000 biosensor equipped with a research-grade CM5 sensor chip. A high-density goat a human antibody surface over a CM5 BiaCore® chip was prepared using routine amine coupling. Antibody supernatents were diluted to ~5 μg/mL in HBS-P running buffer containing 100 μg/mL BSA and 10 mg/mL carboxymethyldextran. The antibodies were then captured individually on a separate surface using a 2 minute contact time, and a 5 minute wash for stabilization of antibody baseline.

TIM-1 antigen was injected at 292 nM over each surface for 75 seconds, followed by a 3-minute dissociation. Double-referenced binding data were obtained by subtracting the signal from a control flow cell and subtracting the baseline drift of a buffer inject just prior to the TIM-1 injection. TIM-1 binding data for each mAb were normalized for the amount of mAb captured on each surface. The normalized, drift-corrected responses were also measured. The kinetic analysis results of anti-TIM-1 mAB binding at 25° C. are listed in Table 9 below.

TABLE 9

Competition Bins and $K_D$, for TIM-1-specific mAbs

| Bin | Antibody | Affinity nM by BIAcore |
|---|---|---|
| 1 | 2.59 | 0.38 |
|   | 1.29 | 3.64 |
| 2 | 2.16 | 0.79 |

TABLE 9-continued

Competition Bins and K$_{Ds}$ for TIM-1-specific mAbs

| Bin | Antibody | Affinity nM by BIAcore |
|---|---|---|
| 3 | 2.17 | 2.42 |
| 4 | 1.37 | 2.78 |
|   | 2.76 | 0.57 |
|   | 2.61 | 1.0 |
| 5 | 2.24 | 2.42 |
|   | 2.56 | 1.1 |
| 6 | 2.70 | 2.71 |
| 7 | 2.54 | 3.35 |
| 8 | 2.45 | 1.15 |

Example 6

Epitope Mapping

Anti-TIM-1 mAb 2.70.2 was assayed for reactivity against overlapping peptides designed from the TIM-1 antigen sequence. Assay plates were coated with the TIM-1 fragment peptides, using irrelevant peptide or no peptide as controls. Anti-TIM-1 mAb 2.70.2 was added to the plates, incubated, washed and then bound antibody was detected using anti-human Ig HRP conjugate. Human antibody not specific to TIM-1, an isotype control antibody or no antibody served as controls. Results showed that mAb 2.70.2 specifically reacted with a peptide having the amino acid sequence PMPLPRQNHEPVAT (SEQ ID NO:87), corresponding to amino acids 189-202 of the TIM-1 immunogen (SEQ ID NO:54).

Specificity of mAb 2.70.2 was further defined by assaying against the following peptides:

```
A) PMPLPRQNHEPVAT    (SEQ ID NO: 87)

B) PMPLPRQNHEPV     (SEQ ID NO: 88)

C) PMPLPRQNHE      (SEQ ID NO: 89)

D) PMPLPRQN       (SEQ ID NO: 90)

E) PMPLPR        (SEQ ID NO: 91)

F) PLPRQNHEPVAT    (SEQ ID NO: 92)

G) PRQNHEPVAT     (SEQ ID NO: 93)

H) QNHEPVAT      (SEQ ID NO: 94)

I) HEPVAT       (SEQ ID NO: 95)
```

Results showed mAb 2.70.2 specifically bound to peptides A, B, C, and F, narrowing the antibody epitope to PLPRNHE (SEQ ID NO:96)

As shown in Table 10, synthetic peptides were made in which each amino acid residue of the epitope was replace with an alanine and were assayed for reactivity with mAb 2.70.2. In this experiment, the third proline and the asparagines residues were determined to be critical for mAb 2.70.2 binding. Furthermore, assays of peptides with additional N or C terminal residues removed showed mAb 2.70.2 binding was retained by the minimal epitope LPRQNH (SEQ ID NO:97)

TABLE 10

| | | | | | | | | | SEQ ID NO: | mAb 2.70.2 Reactivity |
|---|---|---|---|---|---|---|---|---|---|---|
| P | M | P | L | P | R | Q | N | H | E | 89 | + |
| P | M | P | A | P | R | Q | N | H | E | 98 | + |
| P | M | P | L | A | R | Q | N | H | E | 99 | − |
| P | M | P | L | P | A | Q | N | H | E | 100 | + |
| P | M | P | L | P | R | A | N | H | E | 101 | + |
| P | M | P | L | P | R | Q | A | H | E | 102 | − |
| P | M | P | L | P | R | Q | N | A | E | 103 | + |
|   | P | L | P | R | Q | N | H | E |   | 104 | + |
|   |   | L | P | R | Q | N | H | E |   | 105 | + |
|   | P | L | P | R | Q | N | H | E |   | 106 | + |
|   |   | L | P | R | Q | N | H | E |   | 107 | + |

Example 7

Immunohistochemical (IHC) Analysis of TIM-1 Expression in Normal and Tumor Tissues Immunohistochemical (IHC) analysis of TIM-1 expression in normal and tumor tissue specimens was performed with techniques known in the art. Biotinylated fully human anti-TIM-1 antibodies 2.59.2, 2.16.1 and 2.45.1 were analyzed. Streptavidin-HRP was used for detection.

Briefly, tissues were deparaffinized using conventional techniques, and then processed using a heat-induced epitope retrieval process to reveal antigenic epitopes within the tissue sample. Sections were incubated with 10% normal goat serum for 10 minutes. Normal goat serum solution was drained and wiped to remove excess solution. Sections were incubated with the biotinylated anti-TIM-1 mAb at 5 µg/mL for 30 minutes at 25° C., and washed thoroughly with PBS. After incubation with streptavidin-HRP conjugate for 10 minutes, a solution of diaminobenzidine (DAB) was applied onto the sections to visualize the immunoreactivity. For the isotype control, sections were incubated with a biotinylated isotype matched negative control mAb at 5 µg/mL for 30 minutes at 25° C. instead of biotinylated anti-TIM-1 mAb. The results of the IHC studies are summarized in Tables 11 and 12.

Figure 3A:
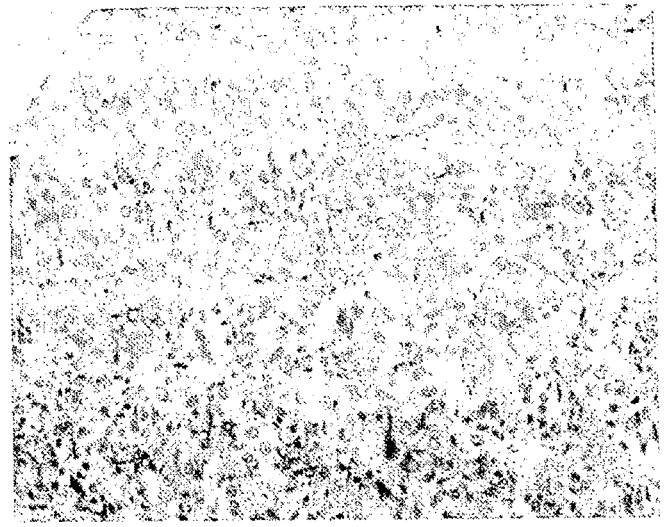
FIG. 3 shows staining of Renal Cell Cancer (3A) and Pancreatic Cancer (3B) with the anti-TIM-1 mAb 2.59.2.
Figure 3B:
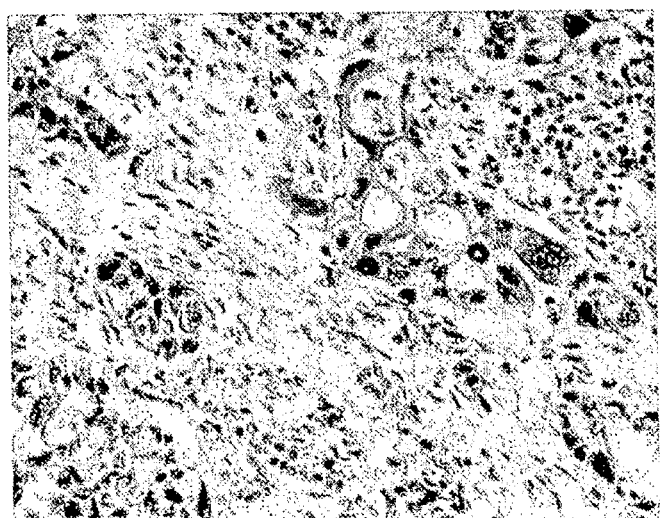

The specimens were graded on a scale of 0-3, with a score of 1+ indicating that the staining is above that observed in control tissues stained with an isotype control irrelevant antibody. The corresponding histological specimens from one renal tumor and the pancreatic tumor are shown in FIGS. 3 (A and B). In addition to these the renal and pancreatic tumors, specimens from head and neck cancer, ovarian cancer, gastric cancer, melanoma, lymphoma, prostate cancer, liver cancer, breast cancer, lung cancer, bladder cancer, colon cancer, esophageal cancer, and brain cancer, as well the corresponding normal tissues were stained with anti-TIM-1 mAb 2.59.2. Overall, renal cancer tissue samples and pancreatic cancer tissue samples highly positive when stained with anti-TIM-1 mAb 2.59.2. No staining in normal tissues was seen. These results indicate that TIM-1 is a marker of cancer in these tissues and that anti-TIM-1 mAb can be used to differentiate cancers from normal tissues and to target TIM-1 expressing cells in vivo.

TABLE 11

Immunohistology Renal tumors expression of TIM-1 protein detected by anti-TIM-1 mAb 2.59.2

| Specimen | Cell Type | Histology | Score |
|---|---|---|---|
| 1 | Malignant cells | Not known | 0 |
| 1 | Other | Not cell associated | 2 |
| 2 | Malignant cells | Clear Cell | 2 |
| 3 | Malignant cells | Clear Cell | 0 |
| 4 | Malignant cells | Clear Cell | 3 |
| 5 | Malignant cells | Clear Cell | 2 (occasional) |
| 6 | Malignant cells | Not known | 2 |
| 7 | Malignant cells | Clear Cell | 2 |
| 8 | Malignant cells | Clear Cell | 0 |
| 9 | Malignant cells | Clear Cell | 2 (occasional) |
| 10 | Malignant cells | Clear Cell | 1-2 |
| 11 | Malignant cells | Not known | 3 (many) |
| 12 | Malignant cells | Clear Cell | 1-2 |
| 12 | Other | Not cell associated | 2 |
| 13 | Malignant cells | Clear Cell | 2 (occasional) |
| 14 | Malignant cells | Clear Cell | 1-2 |
| 15 | Malignant cells | Clear Cell | 3-4 |
| 16 | Malignant cells | Not known | 1-2 |
| 17 | Malignant cells | Not known | 4 (occasional) |
| 18 | Malignant cells | Not known | 1-2 |
| 19 | Malignant cells | Clear Cell | 0 |
| 20 | Malignant cells | Clear Cell | 3-4 |
| 21 | Malignant cells | Clear Cell | 2 (occasional) |
| 22 | Malignant cells | Clear Cell | 3 |
| 23 | Malignant cells | Clear Cell | 2 |
| 24 | Malignant cells | Not known | 3-4 occasional |
| 25 | Malignant cells | Not known | 2-3 |
| 26 | Malignant cells | Not known | 3 |
| 27 | Malignant cells | Clear Cell | 2 |
| 27 | Other | Not cell associated | 2 |
| 28 | Malignant cells | Not known | 2 |
| 29 | Malignant cells | Clear Cell | 2-3 |
| 30 | Malignant cells | Clear Cell | 2 |
| 31 | Malignant cells | Clear Cell | 2-3 |
| 32 | Malignant cells | Clear Cell | 0 |
| 33 | Malignant cells | Clear Cell | 0 |
| 34 | Malignant cells | Clear Cell | 2 |
| 34 | Other | Not cell associated | 2 |
| 35 | Malignant cells | Clear Cell | 2-3 |
| 36 | Malignant cells | Clear Cell | 3 |
| 37 | Malignant cells | Not known | 3 |
| 38 | Malignant cells | Clear Cell | 3 |
| 39 | Malignant cells | Not known | 2 |
| 40 | Malignant cells | Clear Cell | 2-3 |

TABLE 12

Normal Human Tissue Immunohistology with anti-TIM-1 mAb 2.59.2

| Tissue | Specimen 1 | Specimen 2 |
|---|---|---|
| Adrenal Cortex | 0 | 0 |
| Adrenal Medulla | 0 | 1 |
| Bladder: Smooth muscle | 0 | 0 |
| Bladder: Transitional Epithelium | 3 | 0 |
| Brain cortex: Blia | 0 | 0 |
| Brain cortex: Neurons | 0 | 0 |
| Breast: Epithelium | 0 | 0 |
| Breast: Stroma | 0 | 0 |
| Colon: Epithelium | 0 | 0 |
| Colon: Ganglia | 0 | NA |
| Colon: Inflammatory compartment | 3-4 (occasional) | 3 (occasional) |
| Colon: Smooth muscle | 1 (occasional) | 0 |
| Heart: Cardiac myocytes | 0 | 0 |
| Kidney cortex: Glomeruli | 2-3 | 2 |
| Kidney cortex: Tubular epithelium | 2 | 2-3 |
| Kidney medulla:Tubular epithelium | 2 | 0 |
| Kidney medulla: other | NA | 2-3 |
| Liver: Bile duct epithelium | 0 | 0 |
| Liver: Hepatocytes | 1-2 | 1 |
| Liver: Kupffer cells | 0 | 0 |
| Lung: Airway epithelium | 0 | 0 |
| Lung: Alveolar macrophages | 2 (occasional)-3 | 2-3 (occasional) |
| Lung: other | 3 | NA |
| Lung: Pneumocytes | 2-3 (occasional) | 2-3 (occasional) |
| Ovary: Follicle | 2 (occasional) | 1-2 |
| Ovary: Stroma | 1 | 1 (occasional) |
| Pancreas: Acinar epithelium | 0 | 1 (occasional) |
| Pancreas: Ductal epithelium | 0 | 0 |
| Pancreas: Islets of Langerhans | 0 | 0 |
| Placenta: Stroma | 0 | 0 |
| Placenta: Trophoblasts | 0 | 0 |
| Prostate: Fibromuscular stroma | 0 | 0 |
| Prostate: Glandular epithelium | 0 | 0 |
| Skeletal muscle: Myocytes | 0 | 0 |
| Skin: Dermis | 0 | 0 |
| Skin: Epidermis | 0 | 0 |
| Small intestine: Epithelium | 0 | 0 |
| Small intestine: Ganglion | 0 | 0 |
| Small intestine: Inflammatory compartment | 0 | 0 |
| Small intestine: Smooth muscle cells | 0 | 0 |
| Spleen: Red pulp | 0 | 2 (rare) |
| Spleen: white pulp | 0 | 0 |
| Stomach: Epithelium | 0 | 0 |
| Stomach: Smooth Muscle Cells | 0 | 0 |
| Tstis: Leydig cells | 2 | 1-2 |
| Testis: Seminiferous epithelium | 1 | 2 |
| Thymus: Epithelium | 0 | 0 |
| Thymus: Lymphocytes | 2 (rare) | 2 (occasional) |
| Thyroid: Follicular epithelium | 0 | 0 |
| Tonsil: Epithelium | 0 | 0 |
| Tonsil: Lymphocytes | 3 (occasional) | 2 (occasional) |
| Uterus: Endometrium | 0 | 0 |
| Uterus: Myometrium | 0 | 0 |

Example 8

Antibody Mediated Toxin Killing

A clonogenic assay as described in the art was used to determine whether primary antibodies can induce cancer cell death when used in combination with a saporin toxin conjugated secondary antibody reagent. Kohls and Lappi, *Biotechniques,* 28(1):162-5 (2000).

Assay Protocol

ACHN and BT549 cells were plated onto flat bottom tissue culture plates at a density of 3000 cells per well. On day 2 or when cells reached ~25% confluency, 100 ng/well secondary mAb-toxin (goat anti-human IgG-saporin; Advanced Targeting Systems; HUM-ZAP; cat. no. IT-22) was added. A positive control anti-EGFR antibody, mAb 2.7.2, mAb 2.59.2, or an isotype control mAb was then added to each well at the desired concentration (typically 1 to 500 ng/mL). On day 5, the cells were trypsinized, transferred to a 150 mm tissue culture dish, and incubated at 37° C. Plates were examined daily. On days 10-12, all plates were Giemsa stained and colonies on the plates were counted. Plating efficiency was determined by comparing the number of cells prior to transfer to 150 mm plates to the number of colonies that eventually formed.

Figure 4:
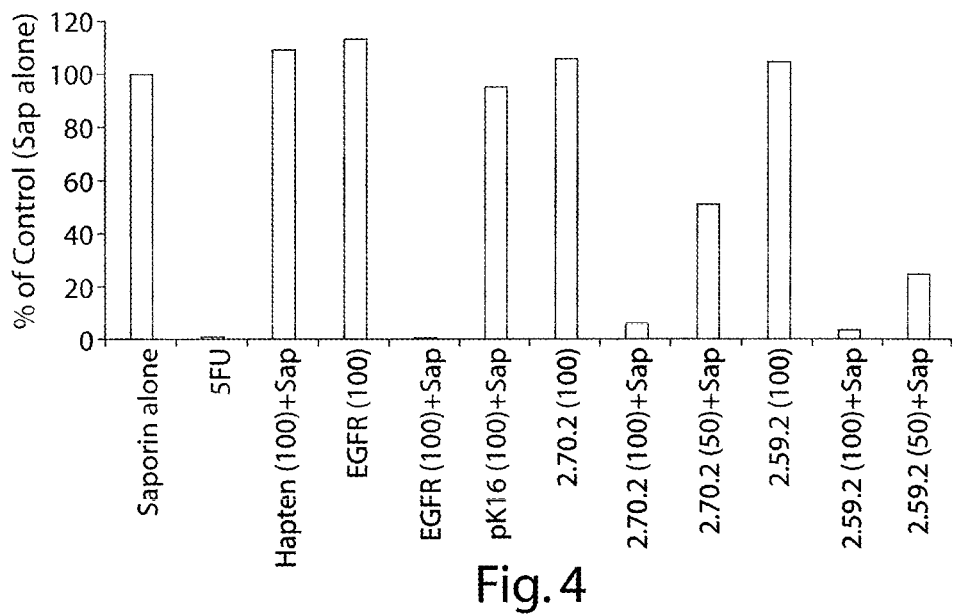
FIG. 4 is a bar graph of clonogenic assay results of anti-TIM-1 monoclonal antibody mediated toxin killing in the ACHN kidney cancer cell line.
Figure 5:
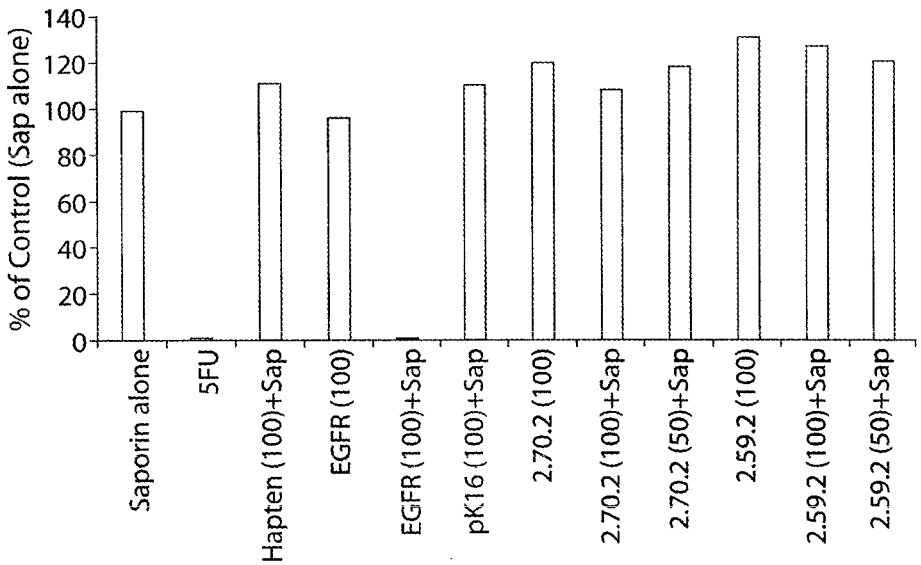
FIG. 5 is a bar graph of clonogenic assay results of anti-TIM-1 monoclonal antibody mediated toxin killing in the BT549 breast cancer cell line.

The percent viability in antigen positive ACHN and antigen negative BT549 cell lines are presented in FIG. 4 and FIG. 5 respectively. In this study, the cytotoxic chemotherapy reagent 5 Fluorouracil (5-FU) was used as the positive control and induced almost complete killing, whereas the saporin conjugated-goat anti-human secondary antibody alone had no effect. A monoclonal antibody (Neo-Markers MS-269-PABX) generated against the EGF receptor expressed by both cell lines was used to demonstrate primary antibody and secondary antibody-saporin conjugate specific killing. The results indicate that both cell lines were susceptible to EGFR mAb mediated toxin killing at 100 ng/mL. At the same dose, both the anti-TIM-1 mAb 2.59.2 and the anti-TIM-1 mAb 2.70.2 induced over 90% ACHN cell death as compared to 0% BT549 cell death.

Antibody Toxin Conjugate Mediated Killing: Clonogenic Assay

CAKI-1 and BT549 cells were plated onto flat bottom tissue culture plates at a density of 3000 cells per well. On day 2 or when cells reach ~25% confluency, various concentrations (typically 1 to 1000 ng/ml) of unconjugated and Auristatin E (AE)-conjugated mAb, which included anti-EGFR, anti-TIM-1 mAb 2.7.2, anti-TIM-1 mAb 2.59.2 or isotype control mAb, were added to cells. Each of these antibodies was conjugated to AE. The monoclonal antibody (NeoMarkers MS-269-PABX) generated against the EGF receptor, which is expressed by both cell lines, was used as a positive control to demonstrate specific killing mediated by AE-conjugated antibody. On day 5, the cells were trypsinized, transferred to a 150 mm tissue culture dish, and incubated at 37° C. Plates were examined daily. On days 10-12, all plates were Giemsa stained and colonies on the plates were counted. Plating efficiency was determined by counting the cells prior to transfer to 150 mm plates and compared to the number of colonies that eventually formed.

Figure 6:
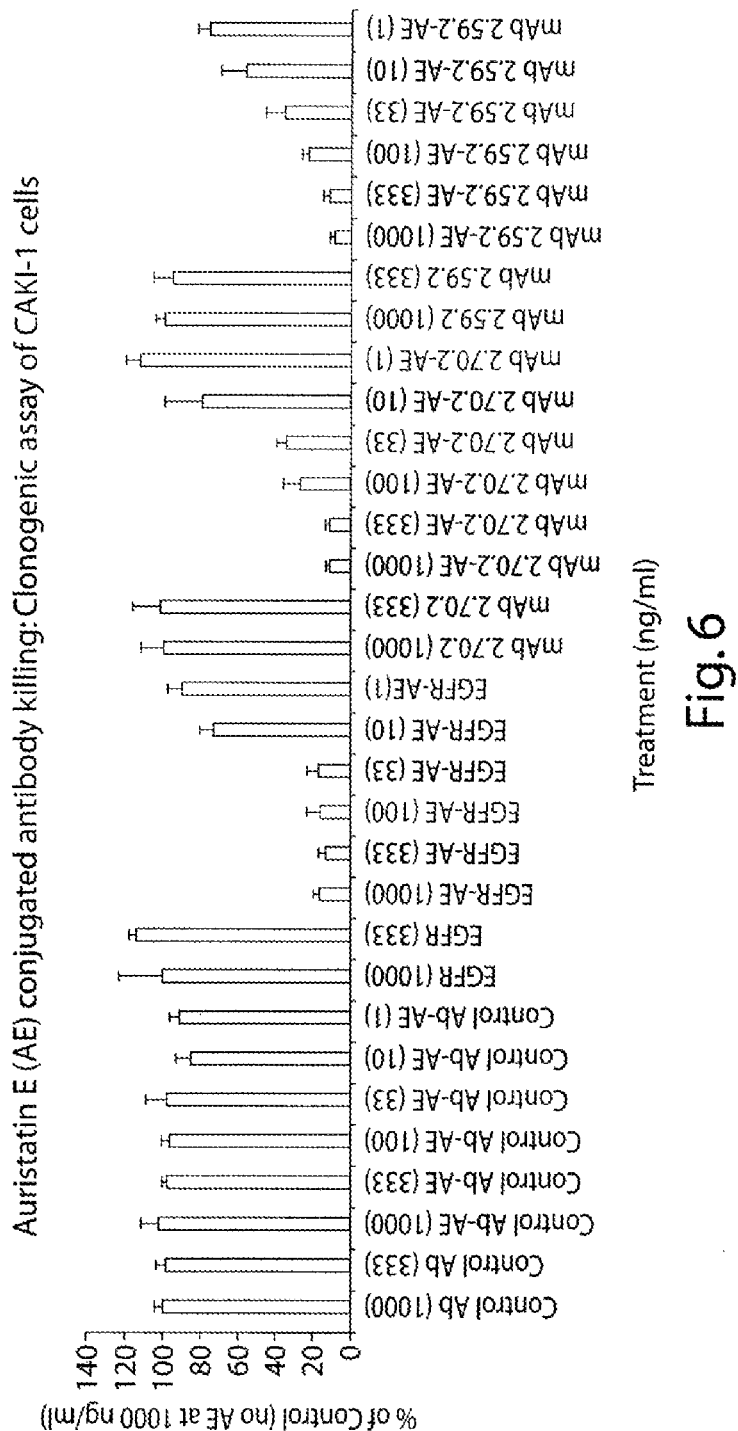
FIG. 6 is a bar graph of the results of a clonogenic assay of CAKI-1 cells treated with Auristatin E (AE) conjugated antibodies.
Figure 7:
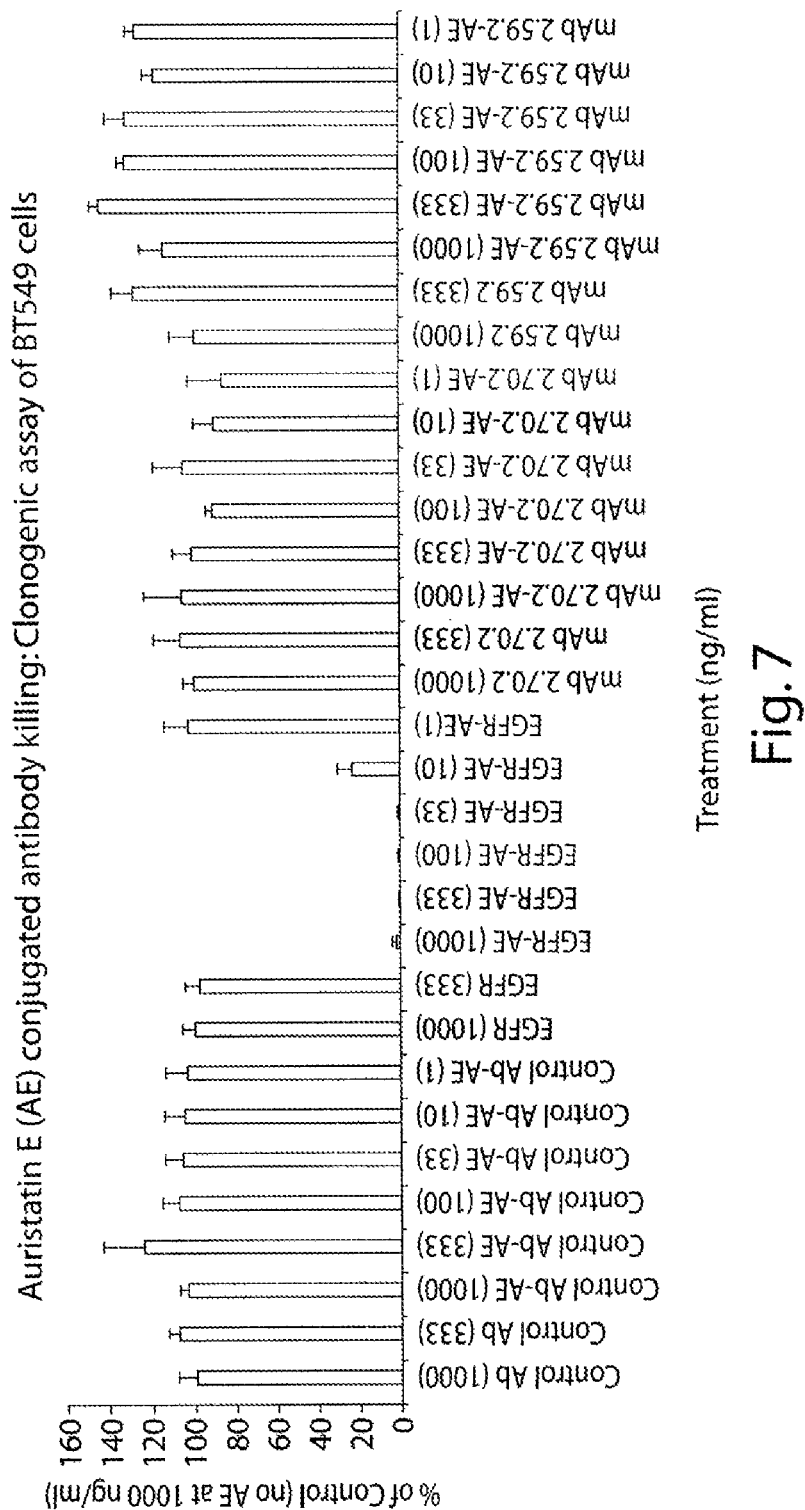
FIG. 7 is a bar graph of the results of a clonogenic assay of BT549 cells treated with Auristatin E (AE) conjugated antibodies.
Figure 8:
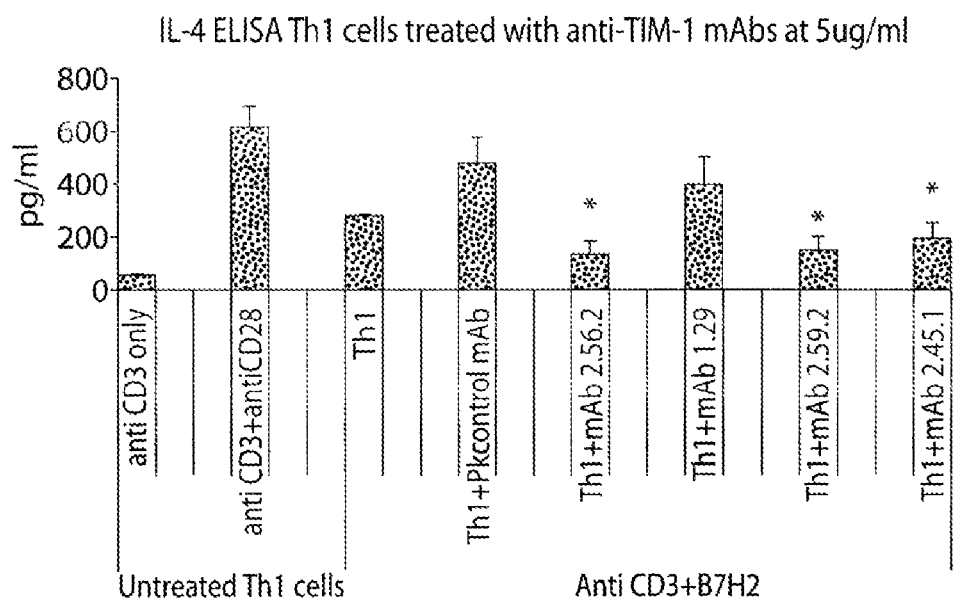
FIG. 8 is a bar graph showing that anti-TIM-1 monoclonal antibodies 2.59.2, 2.56.2 and 2.45.1 significantly inhibit IL-4 release from Th1 cells compared to the control PK16.3 mAb.
Figure 9:
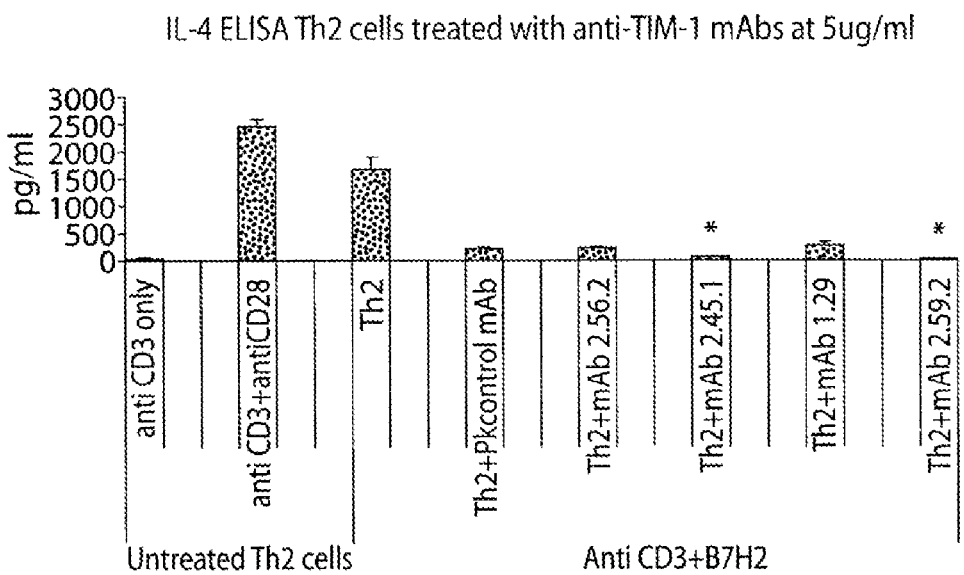
FIG. 9 is a bar graph showing that anti-TIM-1 monoclonal antibodies 2.59.2 and 2.45.1 significantly inhibit IL-4 release from Th2 cells compared to control PK16.3 mAb.
Figure 10:
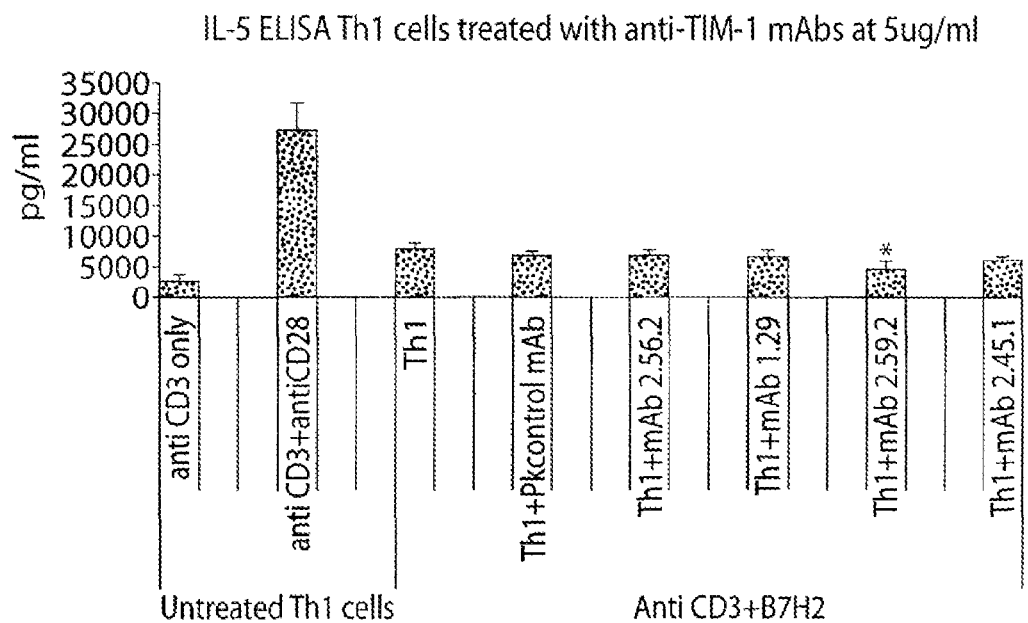
FIG. 10 is a bar graph showing that anti-TIM-1 monoclonal antibody 2.59.2 significantly inhibited IL-5 release from Th1 cells compared to control PK16.3 mAb.
Figure 11:
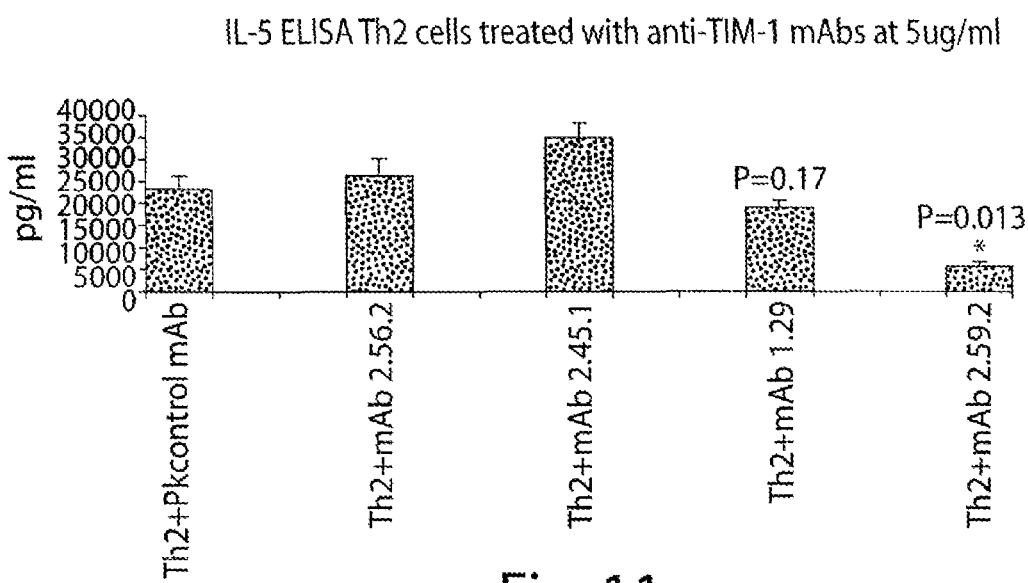
FIG. 11 is a bar graph showing that anti-TIM-1 monoclonal antibodies 2.59.2 and 1.29 significantly inhibited IL-5 release from Th2 cells compared to control PK16.3 mAb.
Figure 12:
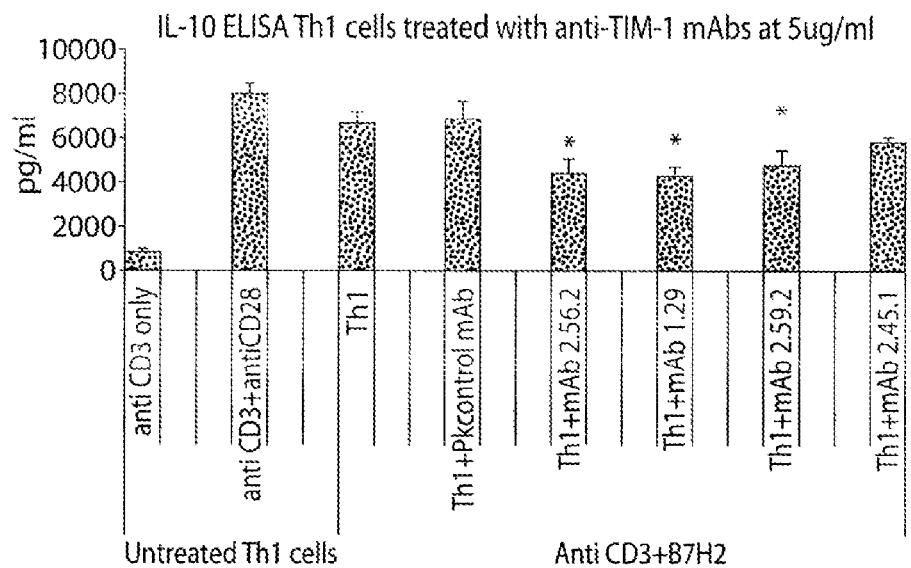
FIG. 12 is a bar graph showing that anti-TIM-1 monoclonal antibodies 2.59.2, 1.29 and 2.56.2 significantly inhibited IL-10 release from Th1 cells compared to control PK16.3 mAb.
Figure 13:
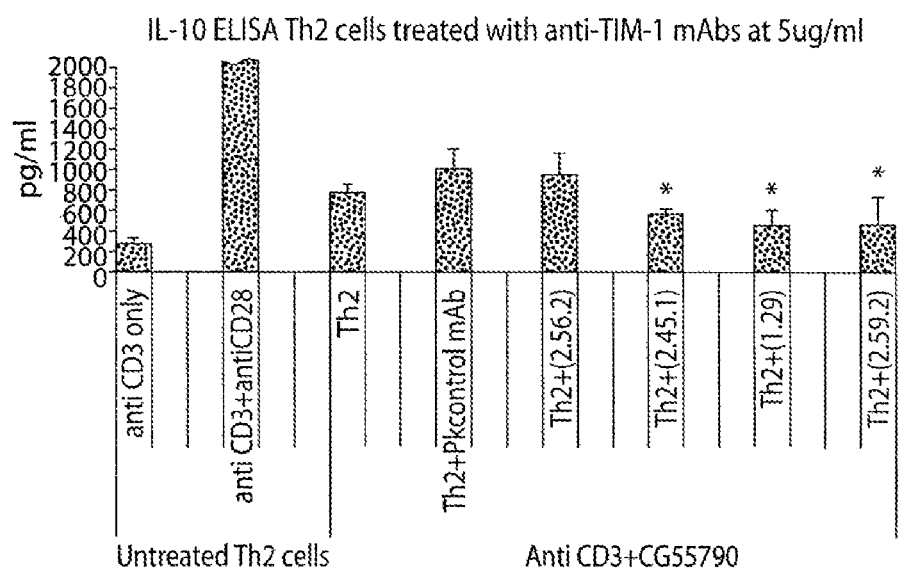
FIG. 13 is a bar graph showing that anti-TIM-1 monoclonal antibodies 2.59.2, 1.29 and 2.45.1 significantly inhibited IL-10 release from Th2 cells compared to control PK16.3 mAb.
Figure 14:
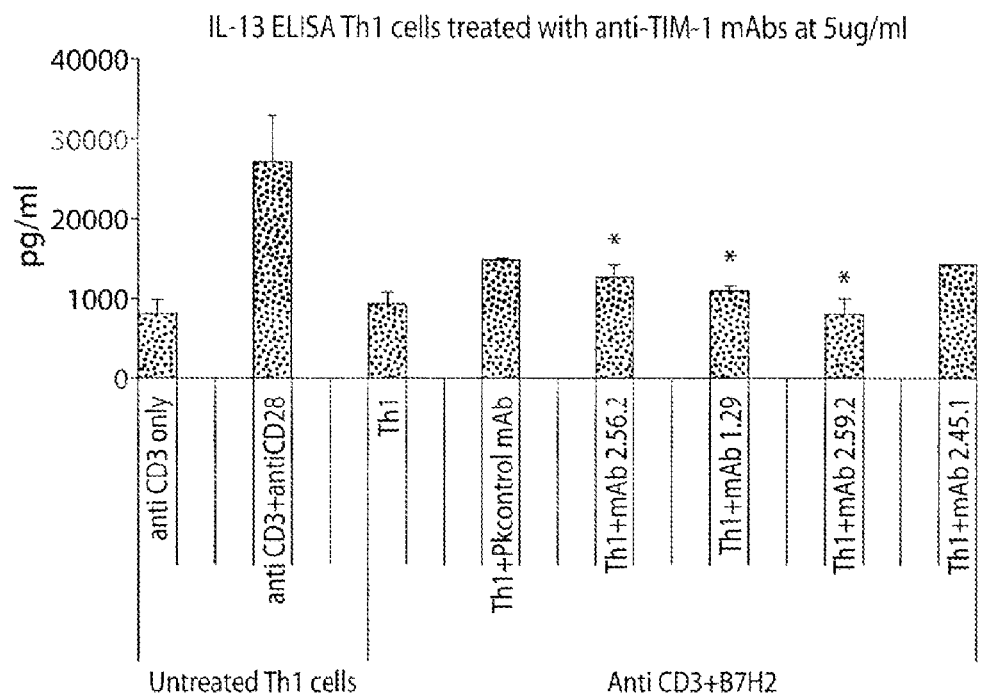
FIG. 14 is a bar graph showing that anti-TIM-1 monoclonal antibodies 2.59.2, 1.29 and 2.56.2 significantly inhibited IL-13 release from Th1 cells compared to control PK16.3 mAb.
Figure 15:
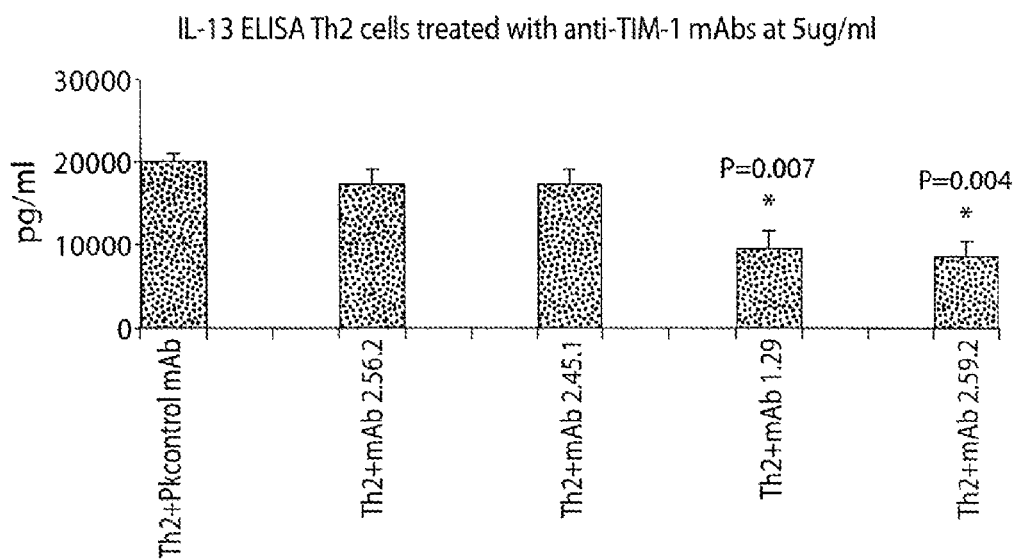
FIG. 15 is a bar graph showing that anti-TIM-1 monoclonal antibodies 2.59.2 and 1.29 significantly inhibited IL-13 release from Th2 cells compared to control PK16.3 mAb.
Figure 16:
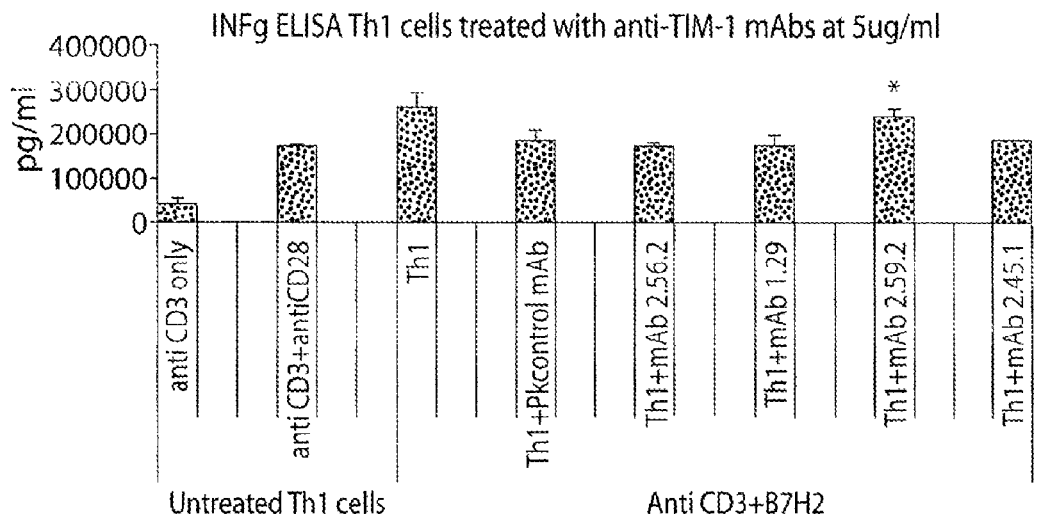
FIG. 16 is a bar graph showing that anti-TIM-1 monoclonal antibodies did not inhibit IFNγ release from Th1 cells compared to control PK16.3 mAb.
Figure 17:
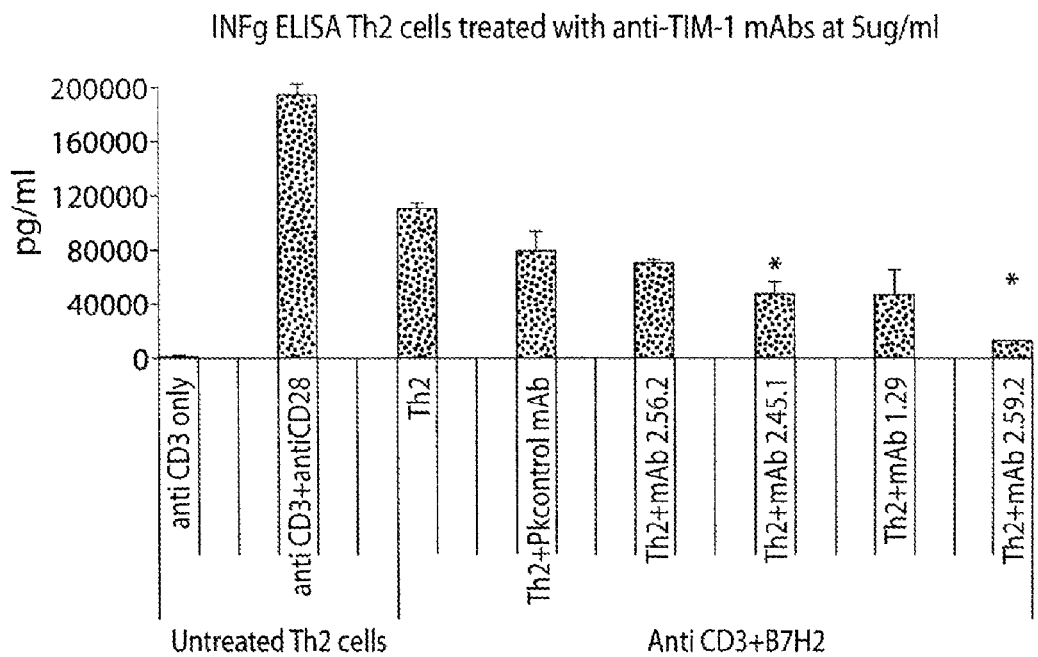
FIG. 17 is a bar graph showing that anti-TIM-1 monoclonal antibodies 2.59.2 and 2.45.1 significantly inhibited IFNγ release from Th2 cells compared to control PK16.3 mAb.

The percent viability in antigen positive CAKI-1 and antigen negative BT549 cell lines are presented in FIGS. 6 and 7, respectively.

The results indicate that unconjugated and AE-conjugated isotype control mAb had no effect on growth of both CAKI-1 and BT549 cells. However, both cell lines were susceptible to AE-EGFR mAb mediated toxin killing in a dose-dependent fashion. At the maximum dose, both anti-TIM-1 mAbs (2.59.2 and 2.70.2) induced over 90% CAKI-1 cell death when compared to their unconjugated counterparts. The response was dose dependent. At the same dose range, both anti-TIM-1 mAbs 2.59.2 and 2.70.2 did not affect the survival of BT549 cells.

Example 9

Human Tumor Xenograft Growth Delay Assay

A tumor growth inhibition model is used according to standard testing methods. Geran et al., *Cancer Chemother. Rep.* 3:1-104 (1972). Athymic nude mice (nu/nu) are implanted with either tumor cells or tumor fragments from an existing host, in particular, renal (CaKi-1) or ovarian (OVCAR) carcinoma tumor fragments are used. These animals are then treated with an anti-TIM-1 antibody immunotoxin conjugate, for example, mAb 2.70.2 AE conjugate at doses ranging from 1 to 20 mg/kg body weight, twice weekly for a period of 2 weeks. Tumor volume for treated animals is assessed and compared to untreated control tumors, thus determining the tumor growth delay.

After reaching a volume of 100 mm3 animals are randomized and individually identified in groups of 5 individuals per cage. Protein or antibody of interest is administered via conventional routes (intraperitoneal, subcutaneous, intravenous, or intramuscular) for a period of 2 weeks. Twice weekly, the animals are evaluated for tumor size using calipers. Daily individual animal weights are recorded throughout the dosing period and twice weekly thereafter. Tumor volume is determined using the formula: Tumor volume (in mm3)=(length×width×height)×0.536. The volume determinations for the treated groups are compared to the untreated tumor bearing control group. The difference in time for the treated tumors to reach specific volumes is calculated for 500 1000, 1500 and 2000 mm3. Body weights are evaluated for changes when compared to untreated tumor bearing control animals. Data are reported as tumor growth in volume plotted against time. Body weights for each experimental group are also plotted in graph form.

Results show that the treatment is well tolerated by the mice. Treatment with anti-TIM-1 mAb AE conjugate inhibits tumor growth of established CaKi-1 and OVCAR tumors.

Example 10

Treatment of Renal Carcinoma with Anti-TIM-1 Antibodies

A patient in need of treatment for a renal carcinoma is given an intravenous injection of anti-TIM-1 antibodies coupled to a cytotoxic chemotherapic agent or radiotherapic agent. The progress of the patient is monitored and additional administrations of anti-TIM-1 antibodies are given as needed to inhibit growth of the renal carcinoma. Following such treatment, the level of carcinoma in the patient is decreased.

Example 11

FACS Analysis of Expression of TIM-1 Protein on CD4+ T Cells

Mononuclear cells were isolated from human blood diluted 1:1 in PBS, by spinning over Ficoll for 20 minutes. The mononuclear cells were washed twice at 1000 rpm with PBS—Mg and Ca and re-suspended in Miltenyi buffer (Miltenyi Biotec Inc., Auburn, Calif.); PBS, 0.5% BSA, 5 mM EDTA at approximately 108 cells/mL. 20 µL of CD4 Miltenyi beads were added per 107 cells and incubated for 15 minutes on ice. Cells were washed with a 10-fold excess volume of Miltenyi buffer. A positive selection column (type VS+) (Miltenyi Biotec Inc., Auburn, Calif.) was washed with 3 mL of Miltenyi buffer. The pelleted cells were re-suspended at 108 cells per mL of Miltenyi buffer and applied to the washed VS column. The column was then washed three times with 3 mL of Miltenyi buffer. Following this, the VS column was removed from the magnetic field and CD4+ cells were eluted from the column with 5 mL of Miltenyi buffer. Isolated CD4+ lymphocytes were pelleted and re-suspended in DMEM 5% FCS plus additives (non-essential amino acids, sodium pyruvate, mercaptoethanol, glutamine, penicillin, and streptomycin) at 106 cells/mL. 1×106 freshly isolated resting CD4+ T cells were transferred into flow cytometry tubes and washed with 2 mL/tube FACS staining buffer (FSB) containing PBS, 1% BSA and 0.05% NaN3. Cells were spun down and supernatant removed.

Cells were blocked with 20% goat serum in FSB for 30 minutes on ice. Cells were washed as above and incubated with 10 μg/mL of primary human anti-TIM-1 mAb or control PK16.3 mAb in FSB (200 μL) for 45 minutes on ice followed by washing. Secondary goat anti-human PE conjugated antibody was added at 1:50 dilution for 45 minutes on ice in the dark, washed, resuspended in 500 μL of PBS containing 1% formaldehyde and kept at 4° C. until flow cytometry analysis was performed.

FACS analysis was performed to determine the expression of TIM-1 protein as detected with five anti-TIM-1 monoclonal antibodies (2.59.2, 1.29, 2.70.2, 2.56.2, 2.45.1) on human and mouse resting CD4+ T cells, as well as human activated and human polarized CD4+ T cells. These analyses demonstrate that freshly isolated resting human CD4+ T cells do not express TIM-1, while a major fraction of polarized human Th2 and Th1 cells do express TIM-1.

FACS Analysis of the Expression of the TIM-1 protein on human CD4+ Th2 cells using five anti-TIM-1 monoclonal antibodies is shown in Table 13. The experiment is described in the left-hand column and the labeled antibody is specified along the top row. Data is reported as the geometric mean of the fluorescence intensity.

TABLE 13

FACS Analysis of the Expression of the TIM-1 protein on human CD4+ Th2 cells

| | Geometric mean of fluorescence intensity | | | | | |
|---|---|---|---|---|---|---|
| | Control | Anti-TIM-1 mAb | | | | |
| Experiment | PK16.3 | 1.29 | 2.45.1 | 2.56.2 | 2.59.2 | 2.70.2 |
| Resting Human CD4+ T cells | 4.6 | 4.7 | 5.1 | 6 | 4.9 | N/A |
| Polarized Human CD4+ Th2 Cells | 8.4 | 22.3 | 42.4 | 564.1 | 22 | 27.8 |

Table 14 demonstrates that over the course of 5 days, continual stimulation of T cells results in an increase in TIM-1 expression, as measured by anti-TIM-1 mAb 2.70.2, as compared to the control PK16.3 antibody. Furthermore, addition of matrix metalloproteinase inhibitor (MMPI) did not measurably increase TIM-1 expression, demonstrating that the receptor is not shed from T cells under these experimental conditions. Thus, expression of the TIM-1 protein and specific antibody binding is specific to activated Th1 and Th2 cells, which in turn, are characteristic of inflammatory response, specifically asthma.

TABLE 14

Percent of activated T cells that express TIM-1

| | | Day 0 | Day 1 | Day 2 | Day 4 | Day 5 |
|---|---|---|---|---|---|---|
| Control PK16.3 | − MMPI | 1 | 3 | 3 | 1 | 1 |
| | + MMPI | 1 | 2 | 6 | 2 | 2 |
| TIM-1 2.70.2 | − MMPI | 1 | 8 | 10 | 5 | 13 |
| | + MMPI | 1 | 10 | 14 | 10 | 19 |

Example 12

Cytokine Assays

IL-4, IL-5, IL-10, IL-13, and IFNγ production levels by activated Th1 and Th2 cell were measured in culture supernatants treated with anti-TIM-1 antibodies using standard ELISA protocols. Cytokine production by Th1 or Th2 cells treated with anti-TIM-1 antibodies was compared to Th1 or Th2 cells treated with the control PK16.3 antibody. In addition, the following samples were run in parallel as internal controls: i) anti-CD3 treated Th1 or Th2 cells, where no cytokine production is expected because of the absence of co-stimulation, ii) anti-CD3/anti-CD28 stimulated Th1 or Th2 cells, expected to show detectable cytokine production, and iii) untreated Th1 or Th2 cells. CD4+ T cells were isolated as described in the Example above. Isolated CD4+ lymphocytes were then spun down and re-suspended in DMEM 5% FCS plus additives (non-essential amino acids, sodium pyruvate, mercaptoethanol, glutamine, penicillin, and streptomycin) at $10^6$ cells/mL. Falcon 6-well non-tissue culture treated plates were pre-coated overnight with anti-CD3 (2 μg/mL) and anti-CD28 (10 μg/mL) (600 μL total in Dulbecco's PBS) overnight at 4° C. The plates were washed with PBS and CD4+ lymphocytes were suspended at 500,000 cells/mL in Th2 medium: DMEM+10% FCS plus supplements and IL-2 5 ng/mL, IL-4 5 ng/mL, anti-IFN gamma 5 μg/mL and cells were stimulated 4-6 days at 37° C. and 5% CO2 in the presence of 5 μg/mL of mAb recognizing the TIM-1 protein or isotype matched negative control mAb PK16.3.

In another set of experiments, CD4+ lymphocytes were suspended at 500,000 cells/mL in Th1 medium: DMEM+ 10% FCS plus supplements and IL-2 5 ng/mL, IL12 5 ng/mL, anti-IL-4 5 μg/mL and stimulated 4-6 days 37° C. temp and 5% CO2 in the presence of 5 μg/mL TIM-1 or isotype matched control mAb PK16.3. Cells were washed two times in DMEM and resuspended in DMEM, 10% FCS plus supplements and 2 ng/mL IL-2 (500,000 cells/mL) in the presence of 5 μg/mL TIM-1 mAb or control PK16.3 mAb and cultured (rested) for 4-6 days at 37° C. and 5% CO2. The process of activation and resting was repeated at least once more as described above with the addition of anti-CD95L (anti-FAS ligand) to prevent FAS-mediated apoptosis of cells. Falcon 96-well non-tissue culture treated plates pre-coated overnight with anti-CD3 mAb at 500 ng/mL and costimulatory molecule B7H2 (B7 homolog 2) 5 μg/mL were washed and 100 μL of TIM-1 mAb treated Th1 or Th2 (200,000 cells) added per well. After 3 days of culture, the supernatants were removed and IL-4, IL-5, IL-10, IL-13, and IFNγ levels were determined by ELISA (Pharmingen, San Diego, Calif. or R&D Systems, Minneapolis, Minn.).

As demonstrated below, anti-TIM-1 mAb significantly inhibited release of the tested cytokines by Th1 and Th2 cells (see FIGS. 8-17). Results where inhibition of cytokine production is significant (p=0.02-0.008), are marked on the bar graphs with an asterisk. Tables 15 and 16 summarize the bar graphs in FIGS. 8-17.

TABLE 15

Cytokine Inhibition in CD4+ Th1 cells using anti-TIM-1 antibodies in two independent human donors Donor 12 + 17

| | Cytokines Anti-TIM-1 | Percentage of Control Antibody | | | | |
|---|---|---|---|---|---|---|
| | mAbs | IL-5 | IL-4 | IL-10 | IL-13 | INF γ |
| TH1 | 2.56.2 | 100.17 | 28.49 * | 63.76 * | 86.45 | 93.69 |
| | 2.45.1 | 90.23 | 39.78 * | 83.98 | 96.25 | 100.6 |
| | 1.29 | 94.63 | 81.05 | 60.77 ** | 73.95 *** | 93.51 |
| | 2.59.2 | 66.62 * | 31.40 * | 68.99 * | 54.5 *** | 128.12 |

Experiments that demonstrate significant inhibition of cytokine production are marked with an asterisk: P = 0.01 to 0.05 *; P = 0.005 to 0.009 ; P = 0.001 to 0.004 *

TABLE 16

Cytokine Inhibition in CD4+ Th2 cells using anti-TIM-1 antibodies in two independent human donors Donor 12 + 17

| | Cytokines Anti-TIM-1 | Percentage of Control Antibody | | | | |
|---|---|---|---|---|---|---|
| | mAbs | IL-5 | IL-4 | IL-10 | IL-13 | INF γ |
| TH2 | 2.56.2 | 112.07 | 103.46 | 93.97 | 86.45 | 88.30 |
| | 2.45.1 | 148.7 | 25.66 *** | 55.97 * | 86.81 | 25.66 * |
| | 1.29 | 80.26 | 112.54 | 44.45 * | 48.91 ** | 112.54 |
| | 2.59.2 | 23.62 * | 19.17 ** | 43.86 * | 43.71 *** | 19.18 * |

Experiments that demonstrate significant inhibition of cytokine production are marked with an asterisk: P = 0.01 to 0.05 *; P = 0.005 to 0.009 ; P = 0.001 to 0.004 *

A summary of Th2 cytokine inhibition data obtained from multiple experiments with different donors is provided in Table 17. Each experiment used purified CD4+ cells isolated from whole blood samples from two independent donors. Cytokine production is reported as the percent of cytokine production detected using the control PK16.3 mAb. The anti-TIM-1 mAb used in each experiment is specified along the bottom row. Results that report significant cytokine inhibition are underlined in Table 17 below. The use of "ND" indicates that the experiment was not performed. These results do reflect donor dependent variability but show that mAbs 2.59.2 and 1.29 reproducibly block one or more of the Th2 cytokines

TABLE 17

Summary of Cytokine Inhibition using anti-TIM-1 mAbs 2.59.2 and 1.29 in 5 independent human donor groups

| Donor ID Cytokine | 12 + 17 | 12 + 14 | 13 + 14 | 14 | 12 |
|---|---|---|---|---|---|
| IL-4 | <u>19</u> | 626 | 130 | ND | ND |
| IL-5 | <u>24</u> | 5 | 122 | 67 | <u>2</u> |
| IL-10 | <u>44</u> | 83 | <u>19</u> | <u>45</u> | 109 |
| IL-13 | <u>44</u> | ND | <u>17</u> | 100 | 91 |
| | Anti-TIM-1 mAb 2.59.2 | | Anti-TIM-1 mAb 1.29 | | |

Results of experiments that report inhibition greater than 50% of that seen using the control PK16.3 antibody are underlined.

Example 13

Construction, Expression and Purification of Anti-TIM-1 scFv

The VL and VH domains of mAb 2.70 were used to make a scFv construct. The sequence of the anti-TIM-1 scFv was synthesized by methods known in the art.

The nucleotide sequence of anti-TIM-1 scFv is as follows:

(SEQ ID NO: 108)
ATGAAATACCTGCTGCCGACCGCTGCTGCTGGTCTGCTGCTCCTCGCT

GCCCAGCCGGCCATGGCCGATATTGTGATGACCCAGACTCCACTCTCC

CTGCCCGTCACCCCTGGAGAGCCGGCCTCCATCTCCTGCAGGTCTAGT

CGGAGCCTCTTGGATAGTGATGATGGAAACACCTATTTGGACTGGTAC

CTGCAGAAGCCAGGGCAGTCTCCACAGCTCCTGATCTACACGCTTTCC

TATCGGGCCTCTGGAGTCCCAGACAGGTTCAGTGGCAGTGGGTCAGGC

ACTGATTTCACACTGAAAATCAGCAGGGTGGAGGCTGAGGATGTTGGA

GTTTATTACTGCATGCAACGTGTAGAGTTTCCTATCACCTTCGGCCAA

GGGACACGACTGGAGATTAAACTTTCCGCGGACGATGCGAAAAAGGAT

GCTGCGAAGAAAGATGACGCTAAGAAAGACGATGCTAAAAAGGACCTC

CAGGTGCAGCTGGTGGAGTCTGGGGGAGGCGTGGTCCAGCCTGGGAGG

TCCCTGAGACTCTCCTGTGCAGCGTCTGGATTCATCTTCAGTCGCTAT

```
GGCATGCACTGGGTCCGCCAGGCTCCAGGCAAGGGGCTGAAATGGGTG

GCAGTTATATGGTATGATGGAAGTAATAAACTCTATGCAGACTCCGTG

AAGGGCCGATTCACCATCTCCAGAGACAATTCCAAGAACACGCTGTAT

CTGCAAATGAACAGCCTGAGAGCCGAGGACACGGCTGTGTATTACTGT

GCGAGAGATTACTATGATAATAGTAGACATCACTGGGGGTTTGACTAC

TGGGGCCAGGGAACCCTGGTCACCGTCTCCTCAGCTAGCGATTATAAG

GACGATGATGACAAATAG
```

The amino acid sequence of mature anti-TIM-1 scFv is as follows:

```
                                         (SEQ ID NO: 109)
DIVMTQTPLSLPVTPGEPASISCRSSRSLLDSDDGNTYLDWYLQKPGQ

SPQLLIYTLSYRASGVPDRFSGSGSGTDFTLKISRVEAEDVGVYYCMQ

RVEFPITFGQGTRLEIKLSADDAKKDAAKKDDAKKDDAKKDLQVQLVE

SGGGVVQPGRSLRLSCAASGFIFSRYGMHWVRQAPGKGLKWVAVIWYD

GSNKLYADSVKGRFTISRDNSKNTLYLQMNSLRAEDTAVYYCARDYYD

NSRHHWGFDYWGQGTLVTVSSASDYKDDDDK
```

The synthesized DNA can be inserted into the pET-20b(+) expression vector, for periplasmic expression in *E. coli*. Cells are grown and the periplasmic proteins prepared using standard protocols. Purification of the anti-TIM-1 scFv is achieved using an anti-FLAG M2 affinity column as per the manufacturer's directions. The predicted molecular weight of the mature protein is 30222.4 daltons. This purified scFv is used in the assays described below to test for biological activity. The scFv construct is comprised of a signal peptide (SP), VL (VL1) derived from mAb 2.70, a linker (L4) based on the 25 amino acid linker 205C, the VH (VH1) derived from mAb 2.70, and a Tag (in this case the FLAG tag). It will be obvious to those skilled in the art that other SP, linker and tag sequences could be utilized to get the same activity as the anti-TIM-1 scFv antibody described herein.

Example 14

Construction, Expression and Purification of Anti-TIM-1 and Anti-CD3 Bispecific scFv1

The basic formula for the construction of this therapeutic protein is as follows:

SP1-VL1-L1-VH1-L2-VH2-L3-VL2-Tag

The signal peptide SP1 is the same as IgG kappa signal peptide VKIII A27 from Medical Research Council (MRC) Centre for Protein Engineering, University of Cambridge, UK.

Other signal peptides can also be used and will be obvious to those skilled in the art. This protein is designed to be expressed from mammalian cells. The predicted molecular weight of the mature cleaved protein is 54833.3 dalton. L1 corresponds to the (Gly4Ser)$_3$ linker, while linker 2 (L2) corresponds to the short linker sequence: GGGGS. L3 is an 18 amino acid linker. VH2 corresponds to the anti-CD3 variable heavy chain domain from Genbank (accession number CAE85148) while VL1 corresponds to the anti-CD3 variable light chain domain from Genbank (accession number CAE85148). The tag being used for this construct is a His tag to facilitate purification and detection of this novel protein. Standard protocols are used to express and purify this His tagged protein, which is tested for activity and tumor cell killing in the protocols described below.

The amino acid and nucleic acid numbering for the components comprising the anti-TIM-1 and anti-CD3 bispecific scFv1 is as follows:
SP: −20 to −1 aa; −60 to −1 nt
VL1: 1-113 aa; 1-339 nt
L1: 114-128 aa; 340-384 nt
VH1: 129-251 aa; 385-753 nt
L2: 252-256 aa; 754-768 nt
VH2: 257-375 aa; 769-1125 nt
L3: 376-393 aa; 1126-1179 nt
VL2: 394-499 aa; 1180-1497 nt
Tag: 500-505 aa; 1498-1515 nt The nucleotide sequence of anti-TIM-1 and anti-CD3 bispecific scFv1 is as follows:

```
                                         (SEQ ID NO: 110)
ATGGAAACCCCAGCGCAGCTTCTCTTCCTCCTGCTACTCTGGCTCCCA

GATACCACCGGAGATATTGTGATGACCCAGACTCCACTCTCCCTGCCC

GTCACCCCTGGAGAGCCGGCCTCCATCTCCTGCAGGTCTAGTCGGAGC

CTCTTGGATAGTGATGATGGAAACACCTATTTGGACTGGTACCTGCAG

AAGCCAGGGCAGTCTCCACAGCTCCTGATCTACACGCTTTCCTATCGG

GCCTCTGGAGTCCCAGACAGGTTCAGTGGCAGTGGGTCAGGCACTGAT

TTCACACTGAAAATCAGCAGGGTGGAGGCTGAGGATGTTGGAGTTTAT

TACTGCATGCAACGTGTAGAGTTTCCTATCACCTTCGGCCAAGGGACA

CGACTGGAGATTAAAGGTGGTGGTGGTTCTGGCGGCGGCGGCTCCGGT

GGTGGTGGTTCCCAGGTGCAGCTGGTGGAGTCTGGGGGAGGCGTGGTC

CAGCCTGGGAGGTCCCTGAGACTCTCCTGTGCAGCGTCTGGATTCATC

TTCAGTCGCTATGGCATGCACTGGGTCCGCCAGGCTCCAGGCAAGGGG

CTGAAATGGGTGGCAGTTATATGGTATGATGGAAGTAATAAACTCTAT

GCAGACTCCGTGAAGGGCCGATTCACCATCTCCAGAGACAATTCCAAG

AACACGCTGTATCTGCAAATGAACAGCCTGAGAGCCGAGGACACGGCT

GTGTATTACTGTGCGAGAGATTACTATGATAATAGTAGACATCACTGG

GGGTTTGACTACTGGGGCCAGGGAACCCTGGTCACCGTCTCCTCAGGA

GGTGGTGGATCCGATATCAAACTGCAGCAGTCAGGGGCTGAACTGGCA

AGACCTGGGGCCTCAGTGAAGATGTCCTGCAAGACTTCTGGCTACACC

TTTACTAGGTACACGATGCACTGGGTAAAACAGAGGCCTGGACAGGGT

CTGGAATGGATTGGATACATTAATCCTAGCCGTGGTTATACTAATTAC

AATCAGAAGTTCAAGGACAAGGCCACATTGACTACAGACAAATCCTCC

AGCACAGCCTACATGCAACTGAGCAGCCTGACATCTGAGGACTCTGCA

GTCTATTACTGTCAAGATATTATGATGATCATTACTGCCTTGACTAC

TGGGGCCAAGGCACCACTCTCACAGTCTCCTCAGTCGAAGGTGGAAGT

GGAGGTTCTGGTGGAAGTGGAGGTTCAGGTGGAGTCGACGACATTCAG

CTGACCCAGTCTCCAGCAATCATGTCTGCATCTCCAGGGGAGAAGGTC

ACCATGACCTGCAGAGCCAGTTCAAGTGTAAGTTACATGAACTGGTAC

CAGCAGAAGTCAGGCACCTCCCCCAAAAGATGGATTTATGACACATCC
```

-continued

```
AAAGTGGCTTCTGGAGTCCCTTATCGCTTCAGTGGCAGTGGGTCTGGG

ACCTCATACTCTCTCACAATCAGCAGCATGGAGGCTGAAGATGCTGCC

ACTTATTACTGCCAACAGTGGAGTAGTAACCCGCTCACGTTCGGTGCT

GGGACCAAGCTGGAGCTGAAATAG
```

The protein sequence of mature anti-TIM-1 and anti-CD3 bispecific scFv1 is as follows:

```
                                       (SEQ ID NO: 111)
DIVMTQTPLSLPVTPGEPASISCRSSRSLLDSDDGNTYLDWYLQKPGQ

SPQLLIYTLSYRASGVPDRFSGSGSGTDFTLKISRVEAEDVGVYYCMQ

RVEFPITFGQGTRLEIKGGGGSGGGGSGGGGSQVQLVESGGGVVQPGR

SLRLSCAASGFIFSRYGMHWVRQAPGKGLKWVAVIWYDGSNKLYADSV

KGRFTISRDNSKNTLYLQMNSLRAEDTAVYYCARDYYDNSRHHWGFDY

WGQGTLVTVSSGGGGSDIKLQQSGAELARPGASVKMSCKTSGYTFTRY

TMHWVKQRPGQGLEWIGYINPSRGYTNYNQKFKDKATLTTDKSSSTAY

MQLSSLTSEDSAVYYCARYYDDHYCLDYWGQGTTLTVSSVEGGSGGSG

GSGGSGGVDDIQLTQSPAIMSASPGEKVTMTCRASSSVSYMNWYQQKS

GTSPKRWIYDTSKVASGVPYRFSGSGSGTSYSLTISSMEAEDAATYYC

QQWSSNPLTFGAGTKLELK
```

Example 15

Construction, Expression and Purification of Anti-TIM-1 and Anti-CD3 Bispecific scFv2

The basic formula for the construction of this novel therapeutic protein is as follows:

SP1-VL1-L4-VH1-L2-VH2-L4-VL2-Tag

The signal peptide SP1 is IgG kappa signal peptide VKIII A27 from Medical Research Council (MRC) Centre for Protein Engineering, University of Cambridge, UK. For more information see mrc-cpe.cam.ac.uk/ALIGN-MENTS.php?menu=901. Other signal peptides and linkers could also be used to get additional biologically active bispecific single chain antibodies. The protein being described in this example is also designed to be expressed from mammalian cells and is similar to the anti-TIM-1 and anti-CD3 bispecific scFv1, except that it utilizes a different linker as indicated in the basic formula above (L4, as described earlier), and that a Flag tag is used instead of the His tag as in the first example.

The predicted molecular weight of the mature cleaved protein is 58070.0 dalton. The tag being used for this construct is a FLAG tag to facilitate purification and detection of this novel protein. Standard protocols are used to express this secreted protein and purify it, which is tested for activity and tumor cell killing in the protocols described below.

The amino acid and nucleic acid numbering for the components comprising the anti-TIM-1 and anti-CD3 bispecific scFv2 is as follows:

SP: −20 to −1 aa; −60 to −1 nt

VL1: 1-113 aa; 1-339 nt

L1: 114-138 aa; 340-414 nt

VH1: 139-261 aa; 415-783 nt

L2: 262-266 aa; 784-798 nt

VH2: 267-385 aa; 799-1155 nt

L3: 386-410 aa; 1156-1230 nt

VL2: 411-516 aa; 1231-1548 nt

Tag: 517-524 aa; 1549-1572 nt

The nucleotide sequence of anti-TIM-1 and anti-CD3 bispecific scFv2 is as follows:

```
                                       (SEQ ID NO: 112)
ATGGAAACCCCAGCGCAGCTTCTCTTCCTCCTGCTACTCTGGCTCCCAGATACCACC

GGAGATATTGTGATGACCCAGACTCCACTCTCCCTGCCCGTCACCCCTGGAGAGCCG

GCCTCCATCTCCTGCAGGTCTAGTCGGAGCCTCTTGGATAGTGATGATGGAAACACC

TATTTGGACTGGTACCTGCAGAAGCCAGGGCAGTCTCCACAGCTCCTGATCTACACG

CTTTCCTATCGGGCCTCTGGAGTCCCAGACAGGTTCAGTGGCAGTGGGTCAGGCACT

GATTTCACACTGAAAATCAGCAGGGTGGAGGCTGAGGATGTTGGAGTTTATTACTGC

ATGCAACGTGTAGAGTTTCCTATCACCTTCGGCCAAGGGACACGACTGGAGATTAAA

CTTTCCGCGGACGATGCGAAAAGGATGCTGCGAAGAAAGATGACGCTAAGAAAGA

CGATGCTAAAAAGGACCTGCAGGTGCAGCTGGTGGAGTCTGGGGGAGGCGTGGTCC

AGCCTGGGAGGTCCCTGAGACTCTCCTGTGCAGCGTCTGGATTCATCTTCAGTCGCT

ATGGCATGCACTGGGTCCGCCAGGCTCCAGGCAAGGGGCTGAAATGGGTGGCAGTT

ATATGGTATGATGGAAGTAATAAACTCTATGCAGACTCCGTGAAGGGCCGATTCACC

ATCTCCAGAGACAATTCCAAGAACACGCTGTATCTGCAAATGAACAGCCTGAGAGC

CGAGGACACGGCTGTGTATTACTGTGCGAGAGATTACTATGATAATAGTAGACATCA

CTGGGGGTTTGACTACTGGGGCCAGGGAACCCTGGTCACCGTCTCCTCAGGAGGTGG
```

```
-continued
TGGATCCGATATCAAACTGCAGCAGTCAGGGGCTGAACTGGCAAGACCTGGGGCCT

CAGTGAAGATGTCCTGCAAGACTTCTGGCTACACCTTTACTAGGTACACGATGCACT

GGGTAAAACAGAGGCCTGGACAGGGTCTGGAATGGATTGGATACATTAATCCTAGC

CGTGGTTATACTAATTACAATCAGAAGTTCAAGGACAAGGCCACATTGACTACAGA

CAAATCCTCCAGCACAGCCTACATGCAACTGAGCAGCCTGACATCTGAGGACTCTGC

AGTCTATTACTGTGCAAGATATTATGATGATCATTACTGCCTTGACTACTGGGGCCA

AGGCACCACTCTCACAGTCTCCTCACTTTCCGCGGACGATGCGAAAAAGGATGCTGC

GAAGAAAGATGACGCTAAGAAAGACGATGCTAAAAAGGACCTGGACATTCAGCTGA

CCCAGTCTCCAGCAATCATGTCTGCATCTCCAGGGGAGAAGGTCACCATGACCTGCA

GAGCCAGTTCAAGTGTAAGTTACATGAACTGGTACCAGCAGAAGTCAGGCACCTCC

CCCAAAAGATGGATTTATGACACATCCAAAGTGGCTTCTGGAGTCCCTTATCGCTTC

AGTGGCAGTGGGTCTGGGACCTCATACTCTCTCACAATCAGCAGCATGGAGGCTGA

AGATGCTGCCACTTATTACTGCCAACAGTGGAGTAGTAACCCGCTCACGTTCGGTGC

TGGGACCAAGCTGGAGCTGAAAGATTATAAGGACGATGATGACAAATAG
```

The protein sequence of mature anti-TIM-1 and anti-CD3 bispecific scFv2 is as follows:

(SEQ ID NO: 113)
DIVMTQTPLSLPVTPGEPASISCRSSRSLLDSDDGNTYLDWYLQKPGQ

SPQLLIYTLSYRASGVPDRFSGSGSGTDFTLKISRVEAEDVGVYYCMQ

RVEFPITFGQGTRLEIKLSADDAKKDAAKKDDAKKDDAKKDLQVQLVE

SGGGVVQPGRSLRLSCAASGFIFSRYGMHWVRQAPGKGLKWVAVIWYD

GSNKLYADSVKGRFTISRDNSKNTLYLQMNSLRAEDTAVYYCARDYYD

NSRHHWGFDYWGQGTLVTVSSGGGGSDIKLQQSGAELARPGASVKMSC

KTSGYTFTRYTMHWVKQRPGQGLEWIGYINPSRGYTNYNQKFKDKATL

TTDKSSSTAYMQLSSLTSEDSAVYYCARYYDDHYCLDYWGQGTTLTVS

SLSADDAKKDAAKKDDAKKDDAKKDLDIQLTQSPAIMSASPGEKVTMT

CRASSSVSYMNWYQQKSGTSPKRWIYDTSKVASGVPYRFSGSGSGTSY

SLTISSMEAEDAATYYCQQWSSNPLTFGAGTKLELKDYKDDDDK

Example 16

Anti-TIM-1 scFv Species Biological Activity

ELISA Analysis:

To determine if the anti-TIM-1 and anti-CD3 bispecific scFv1 and scFv2 antibodies bind to specific antigen, ELISA analysis is performed. 1 ug/ml of specific antigen (TIM-1 antigen (CG57008-02) is bound to ELISA plates overnight in carbonate/bicarbonate buffer (pH approximately 9.2-9.4). Plates are blocked with assay diluent buffer purchased from Pharmingen San Diego, Calif.), and various concentrations of the anti-TIM-1 scFv bispecific antibodies are added for 1 hour at room temp. Plates are washed in 0.01% Tween 20 in PBS, followed by addition of HRP-conjugated mAb to either the 6-His tag (Invitrogen, Carlsbad, Calif.) or the FLAG peptide tag or (Sigma, St. Louis, Mo.) in assay diluent for 60 minutes at room temperature. Color is developed with TMB substrate (Pharmingen), and the reaction stopped with $H_2SO_4$. Plates are read at A450 nm, and the O.D. value taken as a measure of protein binding.

FACS Analysis

Binding of the anti-TIM-1 and anti-CD3 bispecific scFv1 and scFv2 antibodies, as well as the anti-TIM-1 scFv antibody to cells expressing the antigens recognized by the anti-TIM-1 human mAbs is examined by FACS analysis. Cells (such as ACHN) are washed in PBS and resuspended in FACS buffer consisting of ice cold PBS with addition of 1% BSA or 1% FBS. The resuspended cells are then incubated on ice with various concentrations of the bispecific antibody for 30 minutes. Cells are washed to remove non-bound antibody. Bound antibody is detected by binding of a secondary labeled mAb (phycoerythrin or FITC labeled) that specifically recognizes the 6-his tag or the FLAG-tag that is engineered on the bispecific antibody sequence. Cells are washed and analyzed for binding of the anti-tag mAb by FACS analysis. Binding of bispecific mAb plus anti-tag mAb is compared to binding of the anti-tag mAb alone.

Cytotoxicity Analysis

To determine if the bispecific antibody has functional activity as defined by the ability of the bispecific to target T cells to TIM-1 expressing normal or tumor cells, the bispecific antibody is tested in a Cytotoxicity assay. T cells are obtained from the low density cells derived from centrifugation of blood over density separation medium (specific density 1.077). T cells can be used in a heterogeneous mix from the peripheral blood mononuclear cell fraction (which also contains B cells, NK cells and monocytes) or further purified from the low-density cells using MACS separation and negative or positive selection. Killing in assays with T cells derived from the blood directly will have less cytolytic activity than cells that have been stimulated in vitro with PHA, cytokines, activating monoclonal antibodies or other stimulators of polyclonal T cell activation. Therefore, these activators will be used to further boost the activity of T cells in the functional assays. Many variations of cytotoxicity assays are available. Cytotoxicity assays measure the release of natural products of the cells metabolism upon lysis, such as LDH. Other assays are based around labeling cells with various agents such as radioactive chromium (51Cr), DEL- FIA BATDA, CSFE or similar labeling agents and detecting release or change in live cells bound by the agent.

DELFIA cytotoxicity assays (PerkinElmer Life and Analytical Sciences, Inc. Boston, Mass.) offer a non-radioactive method to be used in cell mediated cytotoxicity studies. The method is based on loading cells with an acetoxymethyl ester of a fluorescence enhancing ligand. After the ligand has penetrated the cell membrane the ester bonds are hydrolyzed within the cell to form a hydrophilic ligand, which no longer passes through the membrane. After cytolysis the released ligand is introduced to a europium solution to form a fluorescent chelate. The measured signal correlates directly with the amount of lysed cells. Target cells are resuspended to a concentration of $2 \times 10^6$/ml. 10 µl of DELFIA BATDA was mixed in a tube with 2 ml of target cells according to the manufacturers instructions. Various concentrations of T cells are added to a fixed concentration of labeled target cells (5000 cells per well) in 96 well U-bottom plates, and incubated for at least 2 hours at 37° C. The plates are spun at approximately 200 g, followed by the aspiration of 20 µl of supernatant, which was then added to a europium solution (200 µl) in a separate plate. The plate is incubated for 15 minutes at room temperature, followed by analysis on a SAFIRE (Tecan, Maennedorf, Switzerland) according to the manufacturer's instructions. Signal in the test wells are compared to signal in 100% lysis well (10% lysis buffer in place of T cells) and cell with medium alone (spontaneous release), and % specific lysis is calculated from the formula % specific lysis=(test−spontaneous release)/100% lysis×100.

BIAcore Kinetic Analysis of scFv Constructs

Kinetic measurements to determine the affinity for the scFv constructs (monomer as well as bispecific, containing at least 1 scFv moiety binding to TIM-1) are measured using the methods described earlier for the whole antibodies of this invention. scFv-containing antibody protein affinities to TIM-1 are expected to be within a factor of 10, i.e. between 0.271-27.1 nM, of the affinity given for mAb 2.70.

Example 17

Ability of Anti-TIM-1 mAb to Inhibit the Proliferation of Human Ovary Carcinoma Cells Several fully human monoclonal antibody clones were isolated from the immunizations described above and their ability to inhibit the proliferative potential of OVCAR-5 (human ovary carcinoma) cells was analyzed using the 5-bromo-2-deoxyuridine (BrdU) incorporation assay (described in International Patent Application No. WO 01/25433).

In the BrdU assay, OVCAR-5 cancer cells (Manassas, Va.) were cultured in Dulbeccos Modification of Eagles Medium (DMEM) supplemented with 10% fetal bovine serum or 10% calf serum respectively. The ovarian cancer cell line was grown to confluence at 37° C. in 10% $CO_2$/air. Cells were then starved in DMEM for 24 hours. Enriched conditioned medium was added (10 µL/100 µL of culture) for 18 hours. BrdU (10 µM) was then added and incubated with the cells for 5 hours. BrdU incorporation was assayed by colorimetric immunoassay according to the manufacturer's specifications (Boehringer Mannheim, Indianapolis, Ind.).

Figure 18B:
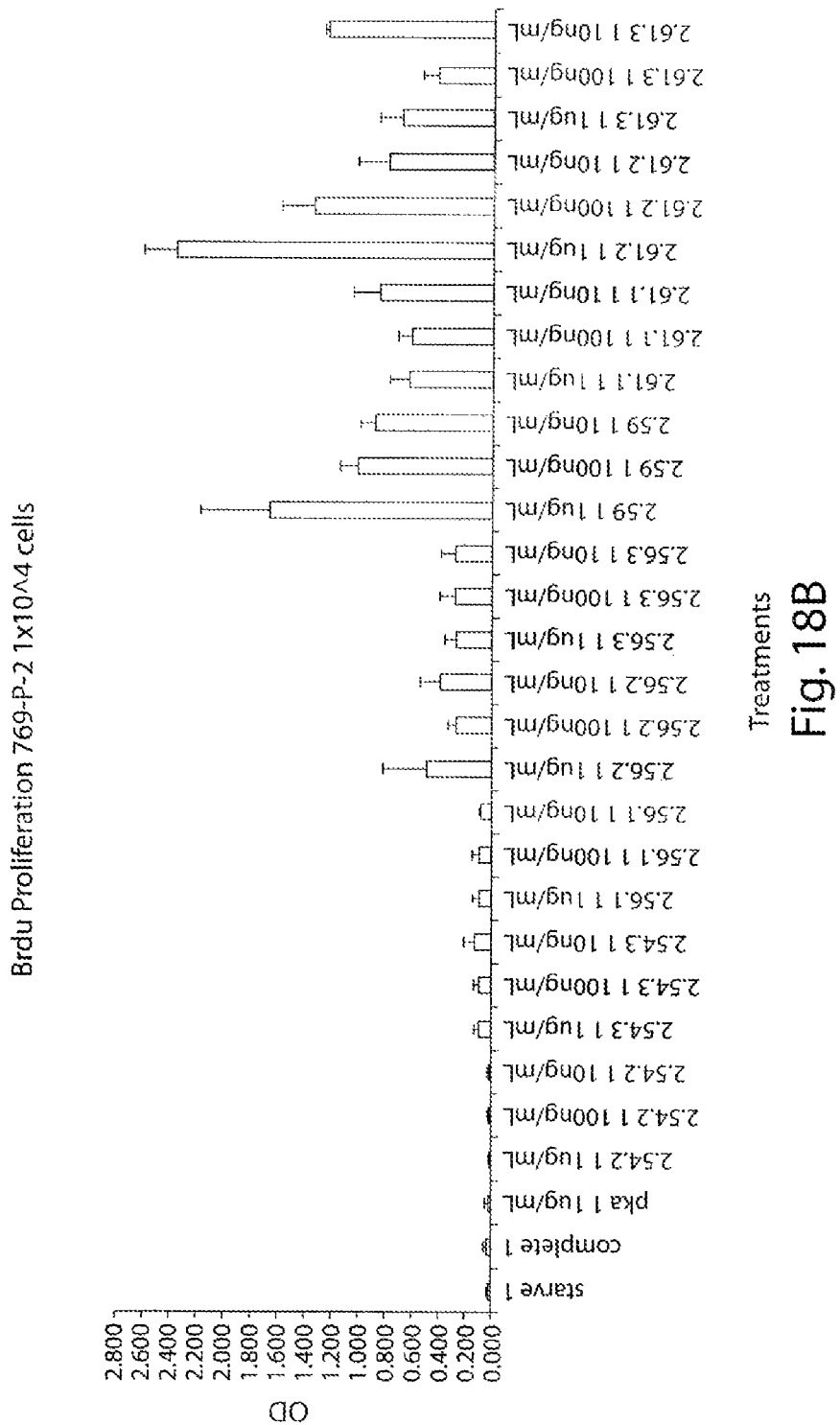
FIGS. 18A-18T are bar graphs showing BrdU incorporation assay results from experiments in which the neutralization of various human anti-TIM-1 monoclonal antibodies was assessed.
Figure 18C:
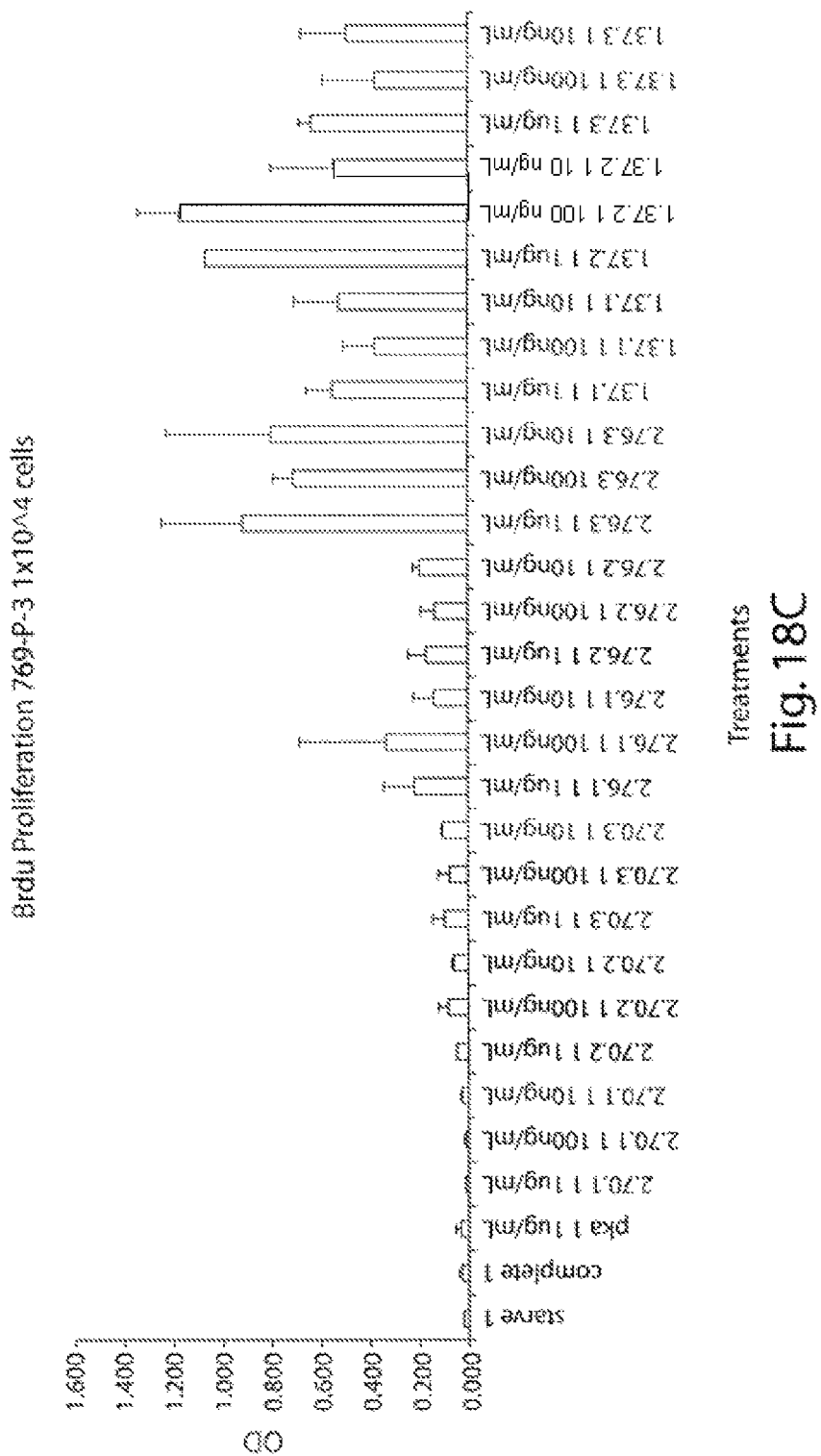
Figure 18D:
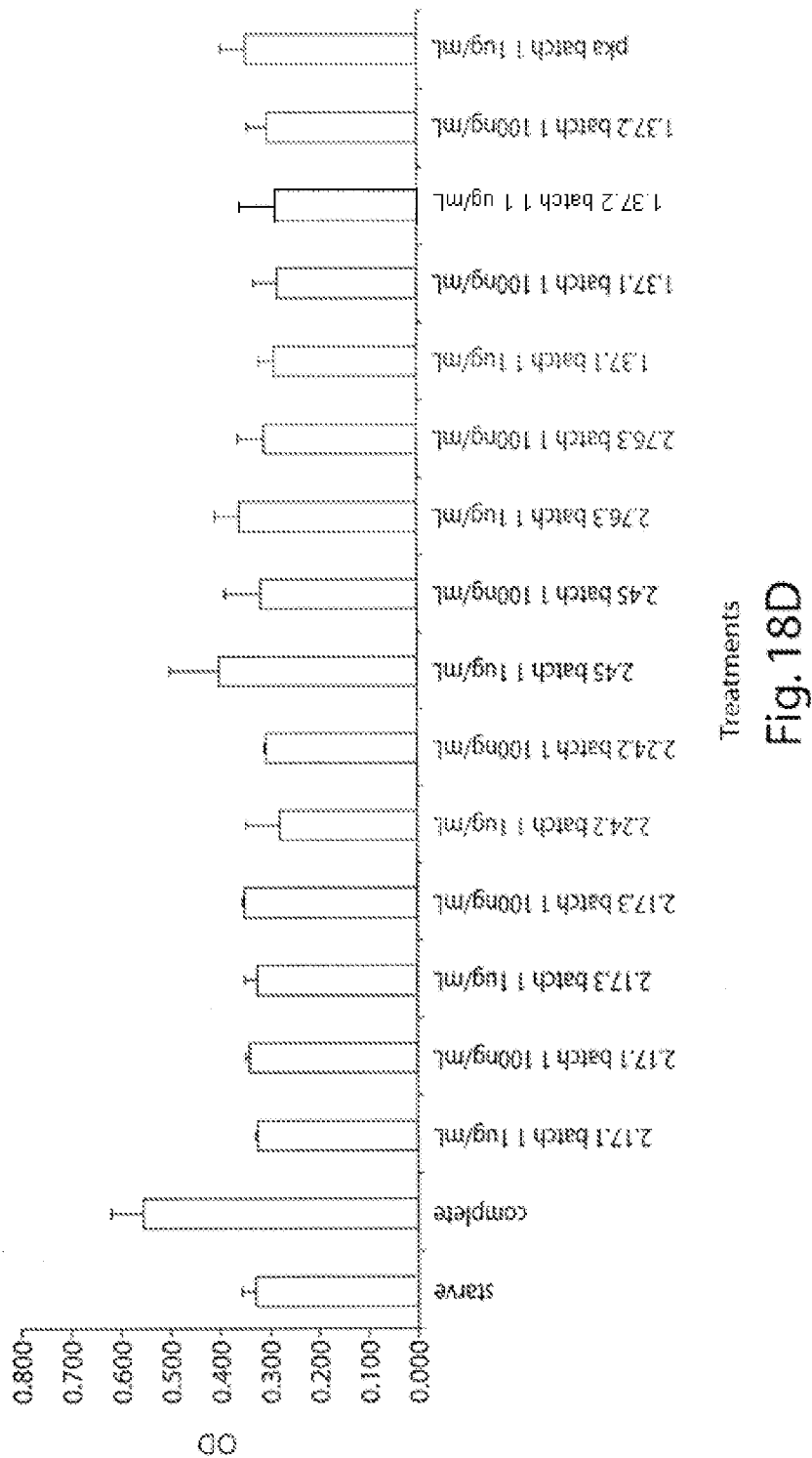
Figure 18E:
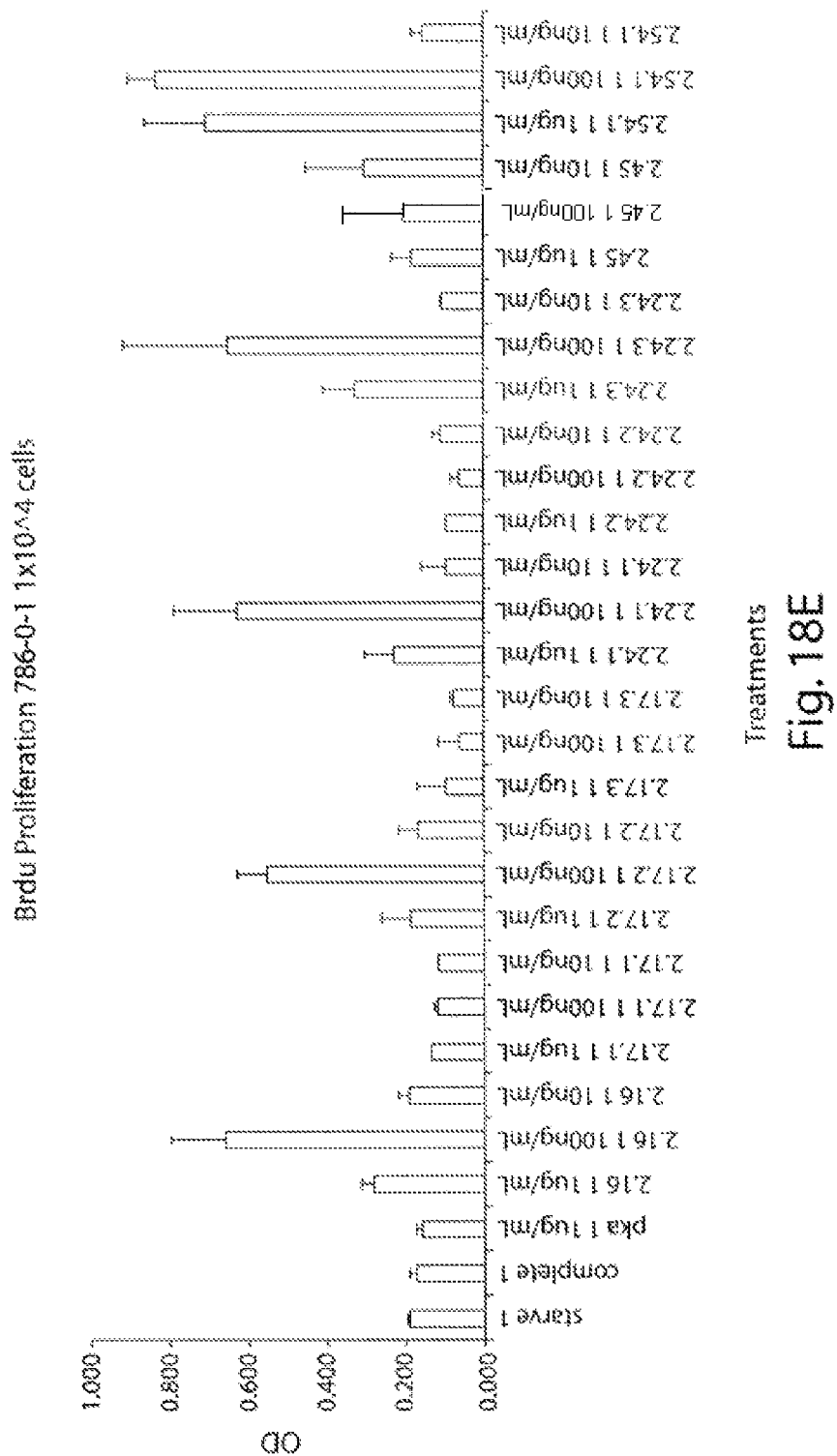
Figure 18F:
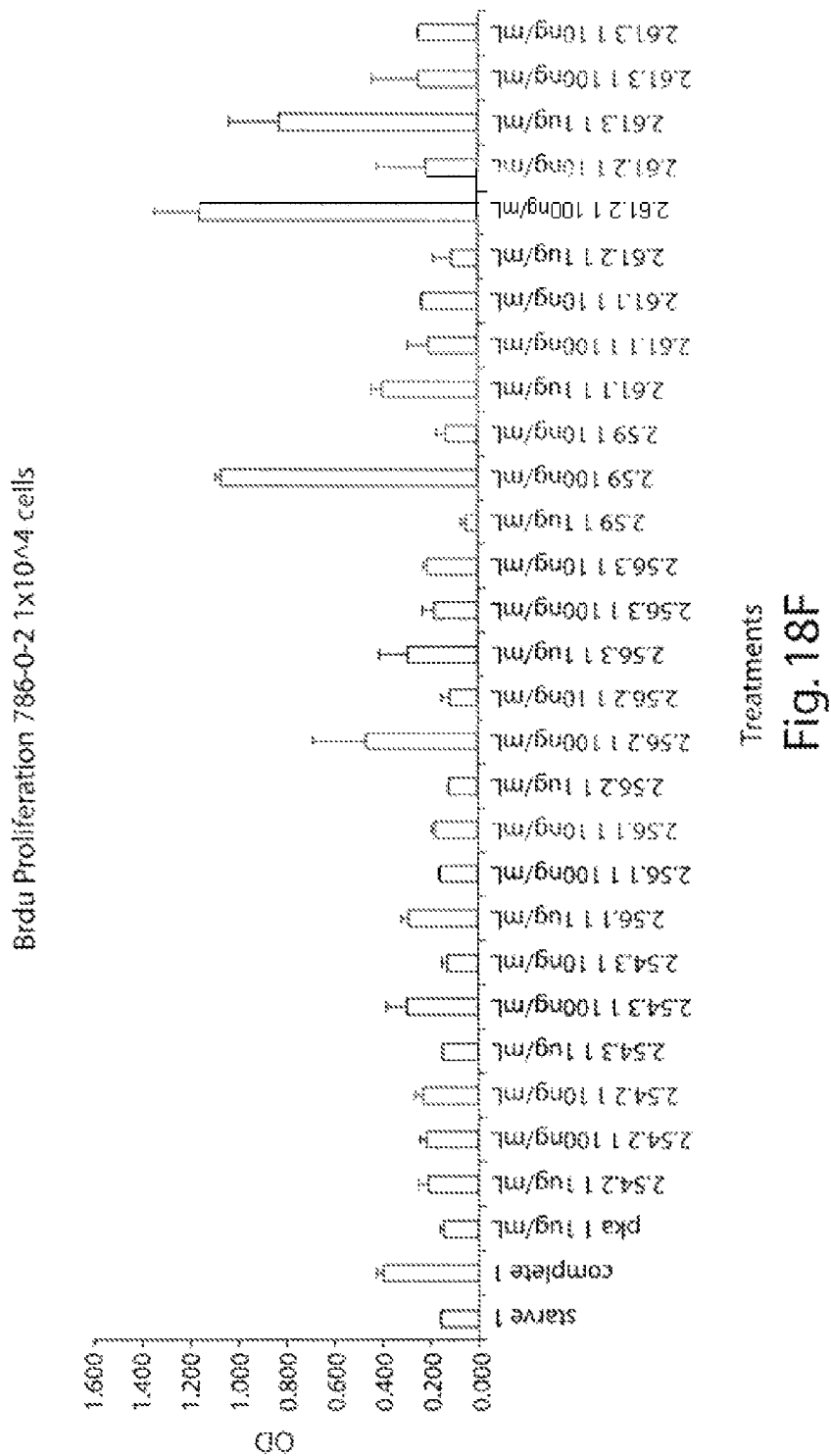
Figure 18G:
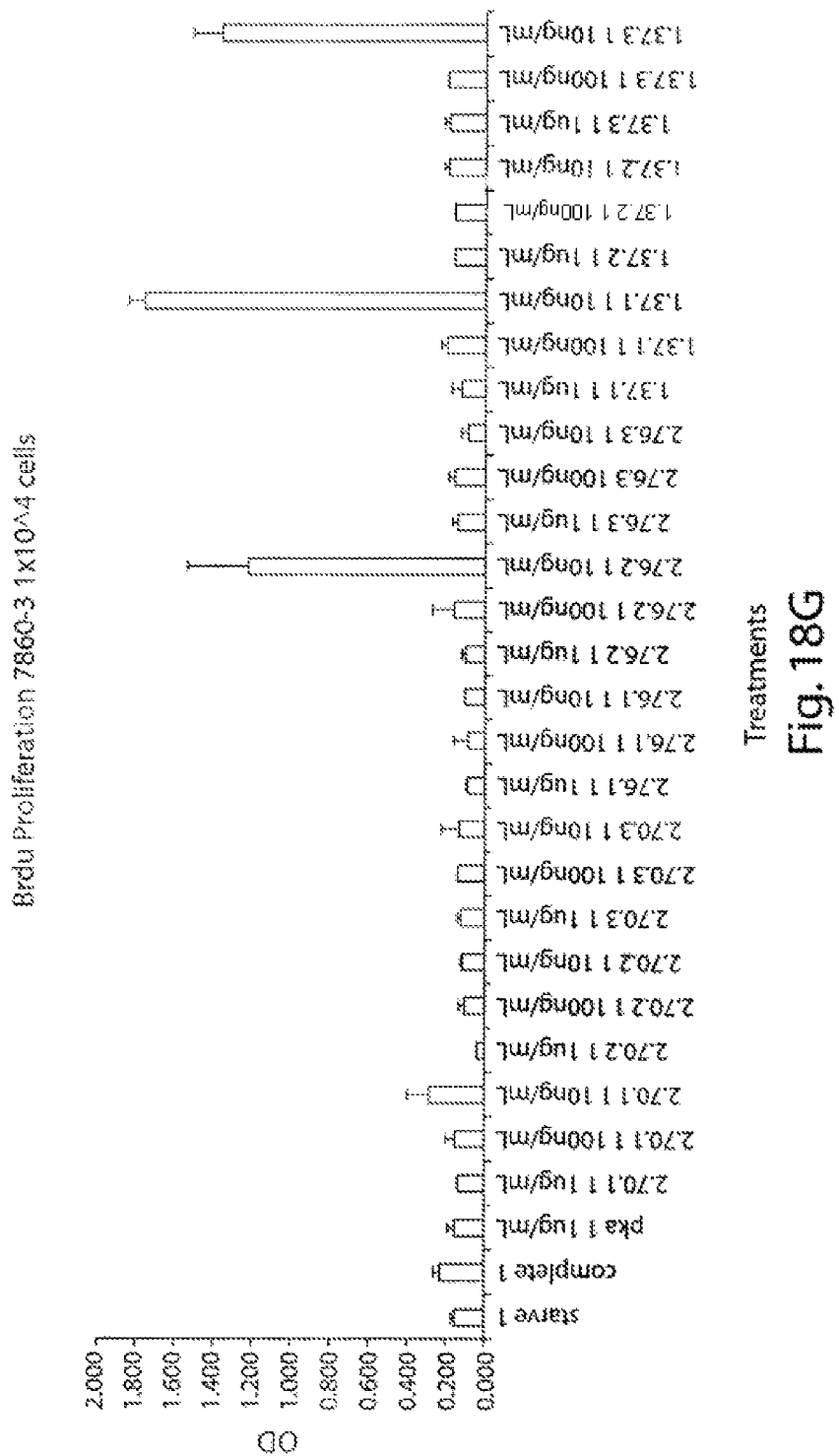
Figure 18H:
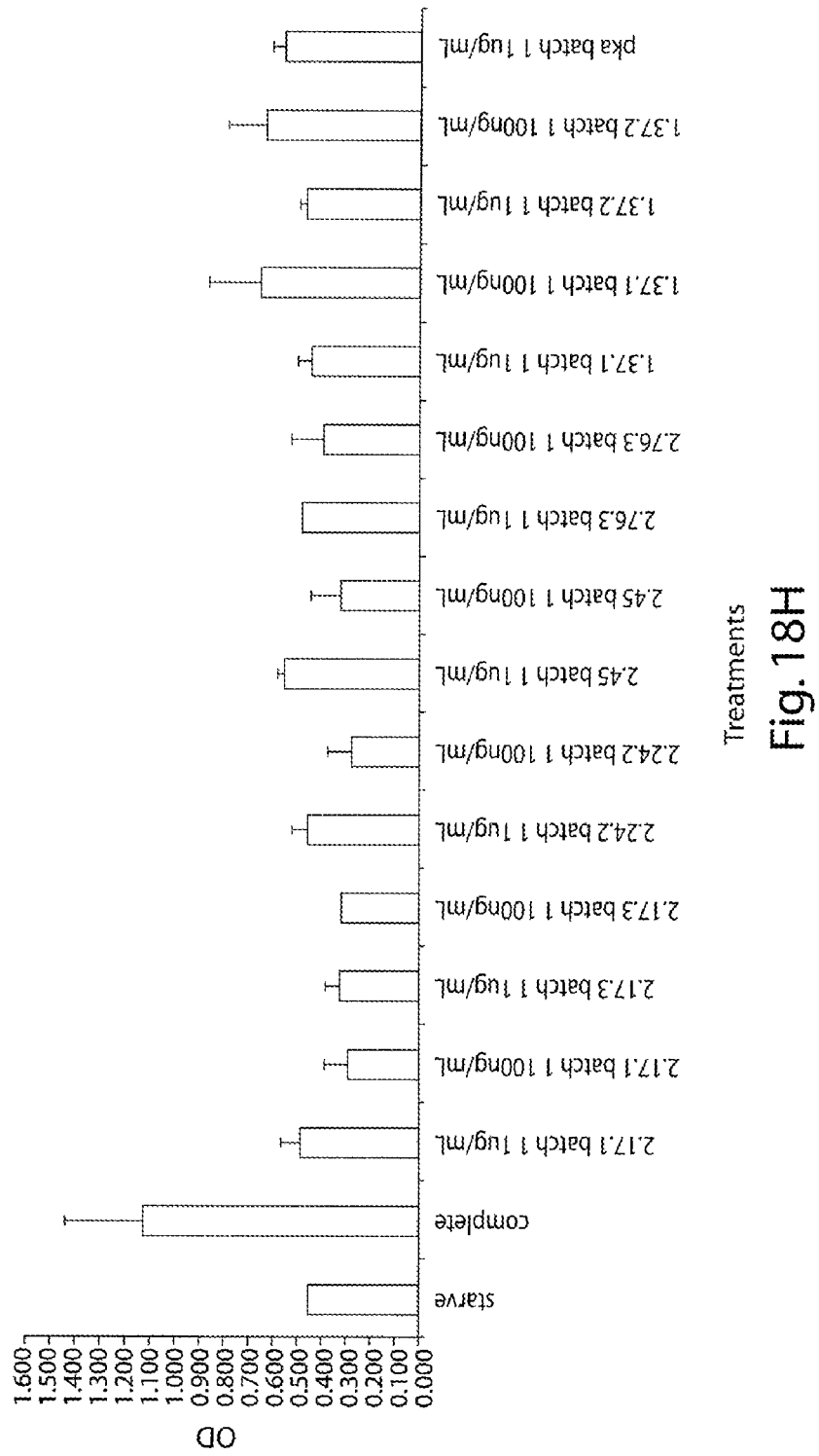
Figure 18I:
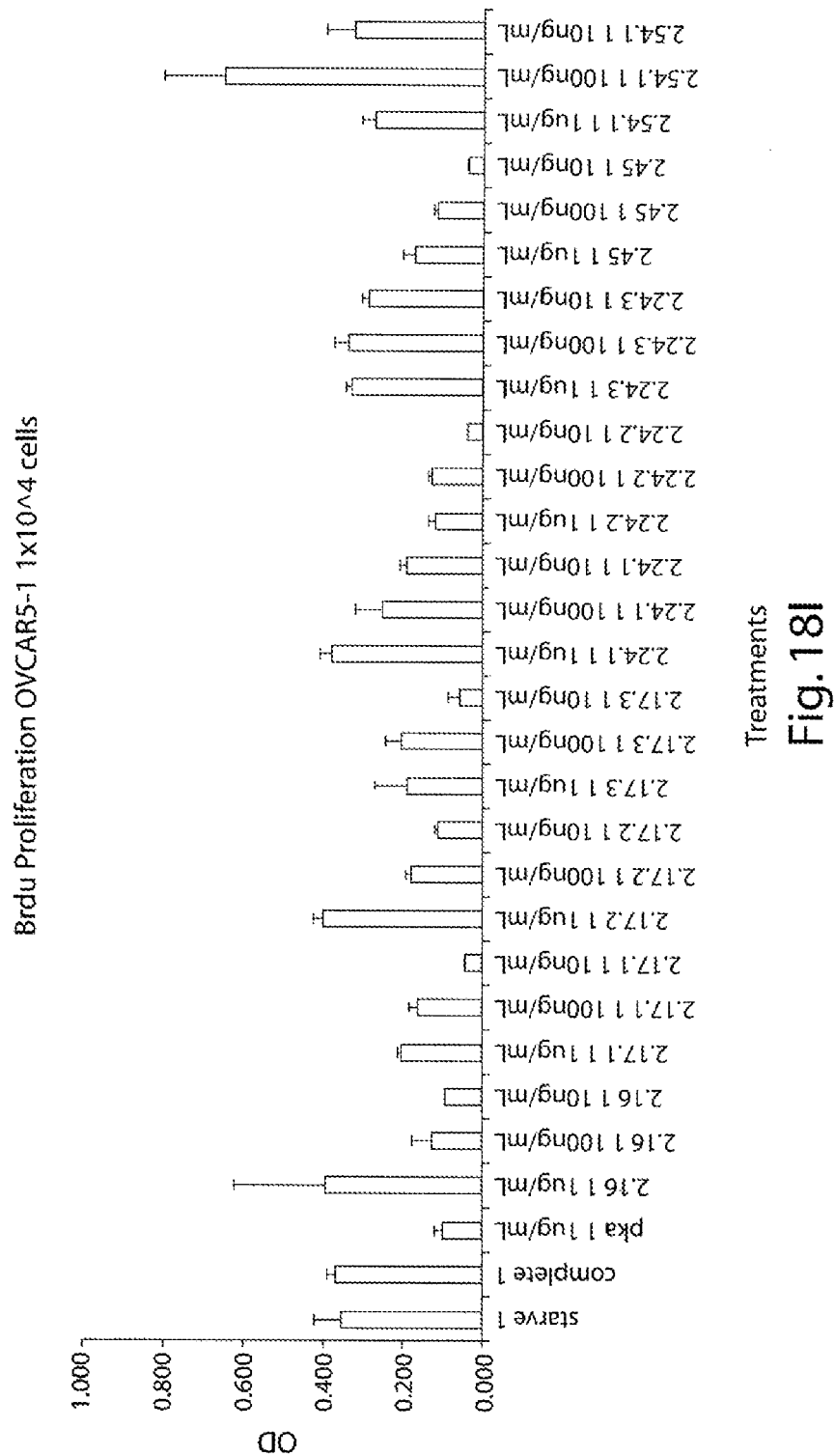
Figure 18J:
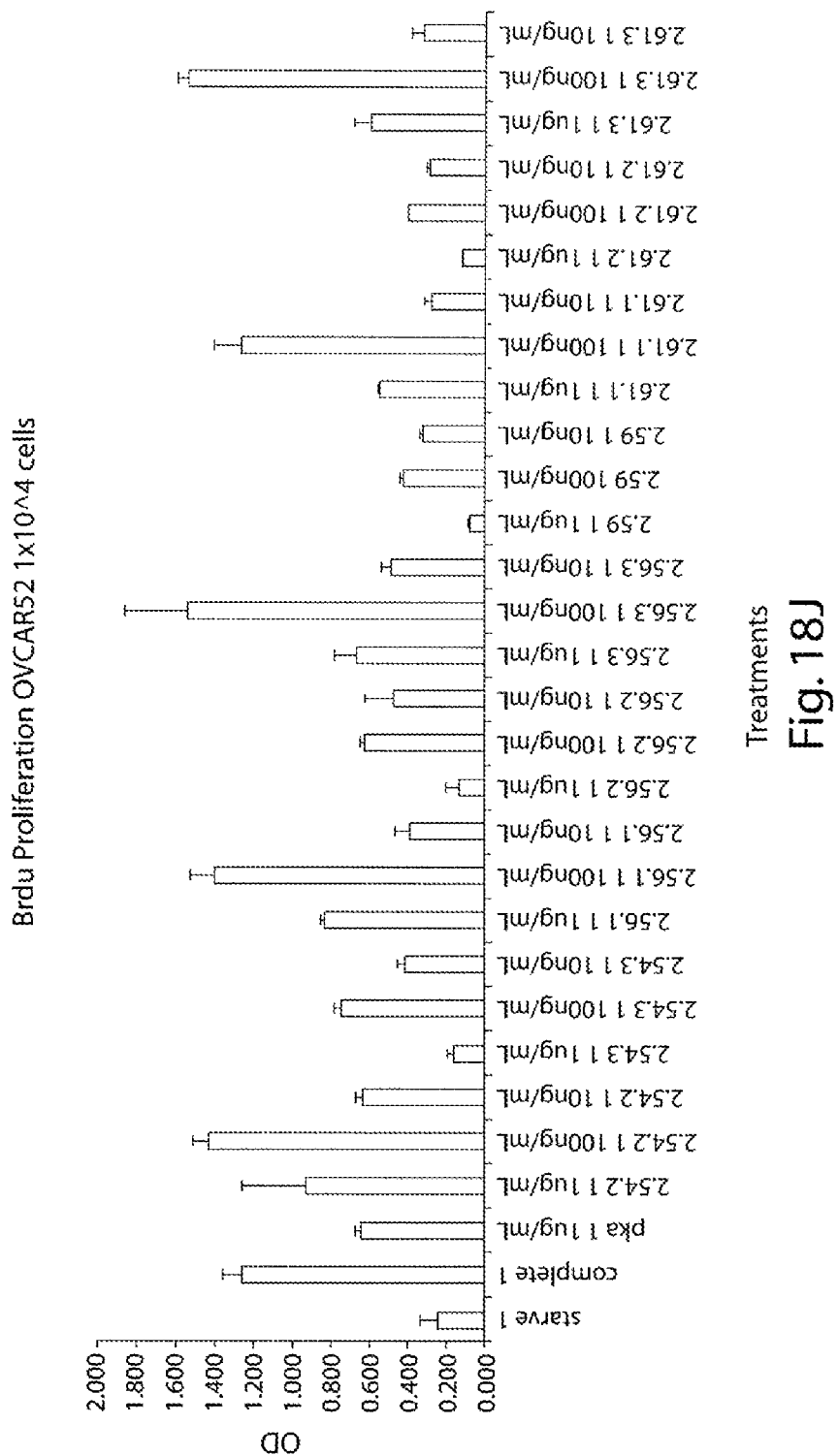
Figure 18K:
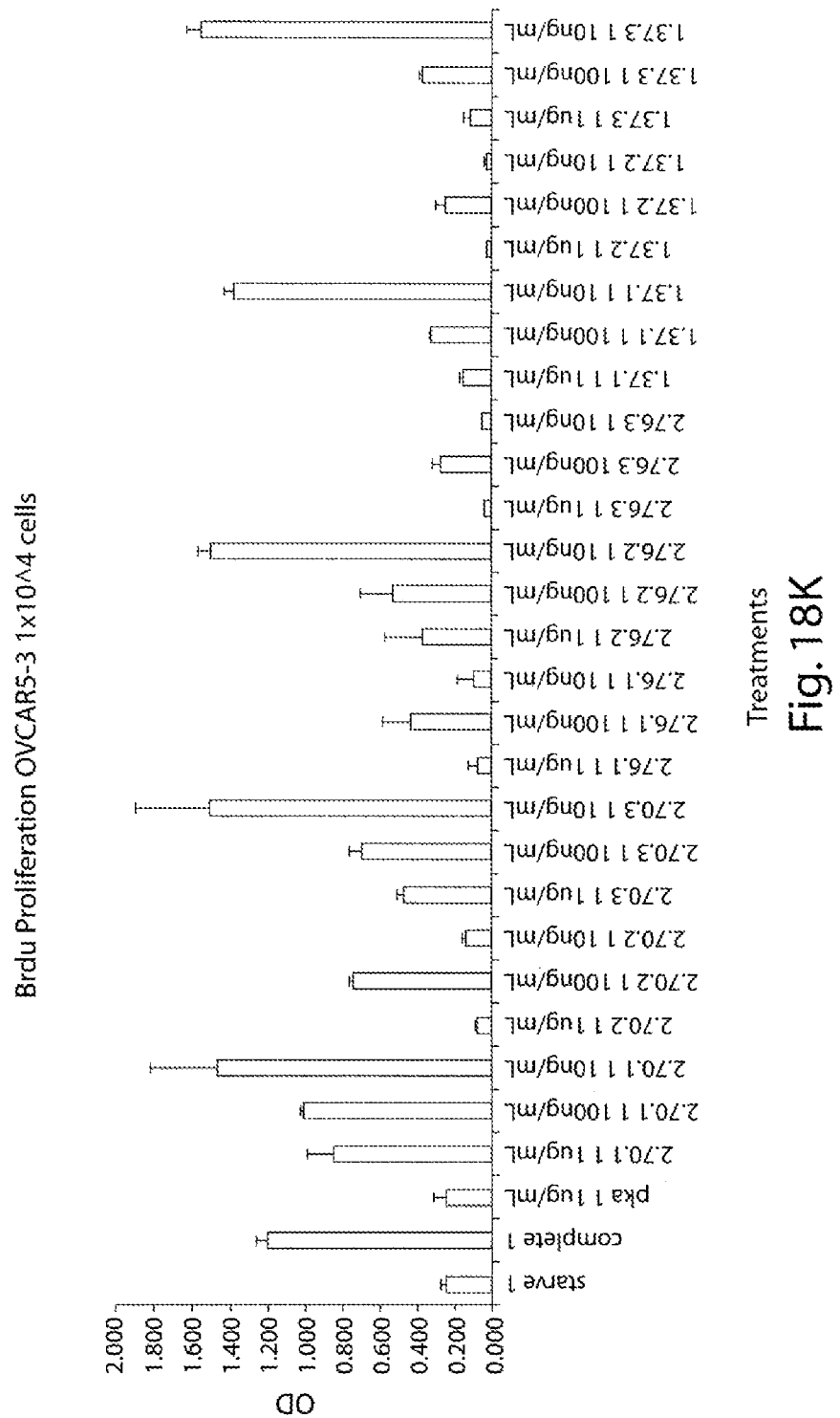
Figure 18L:
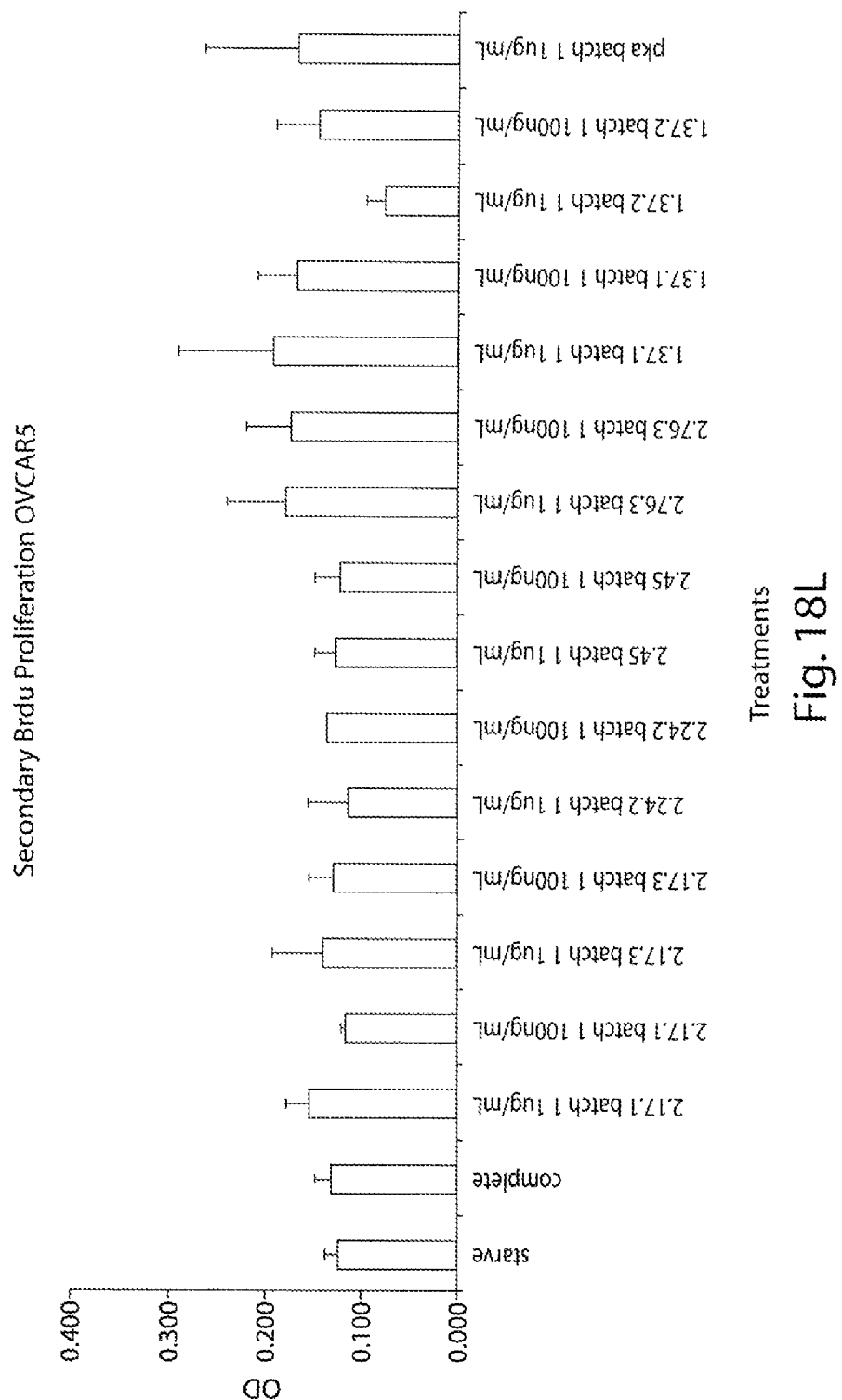
Figure 18N:
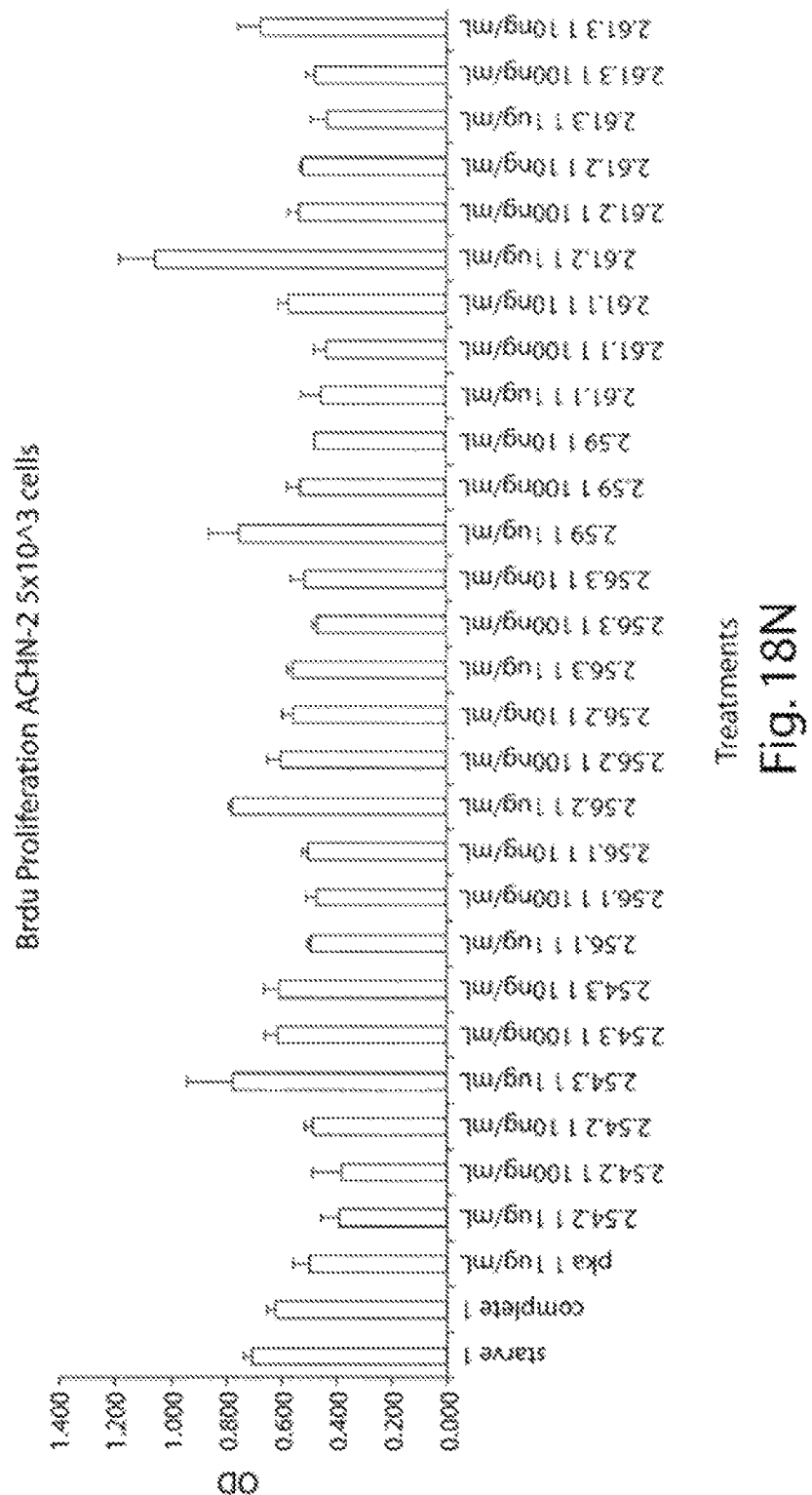
Figure 18O:
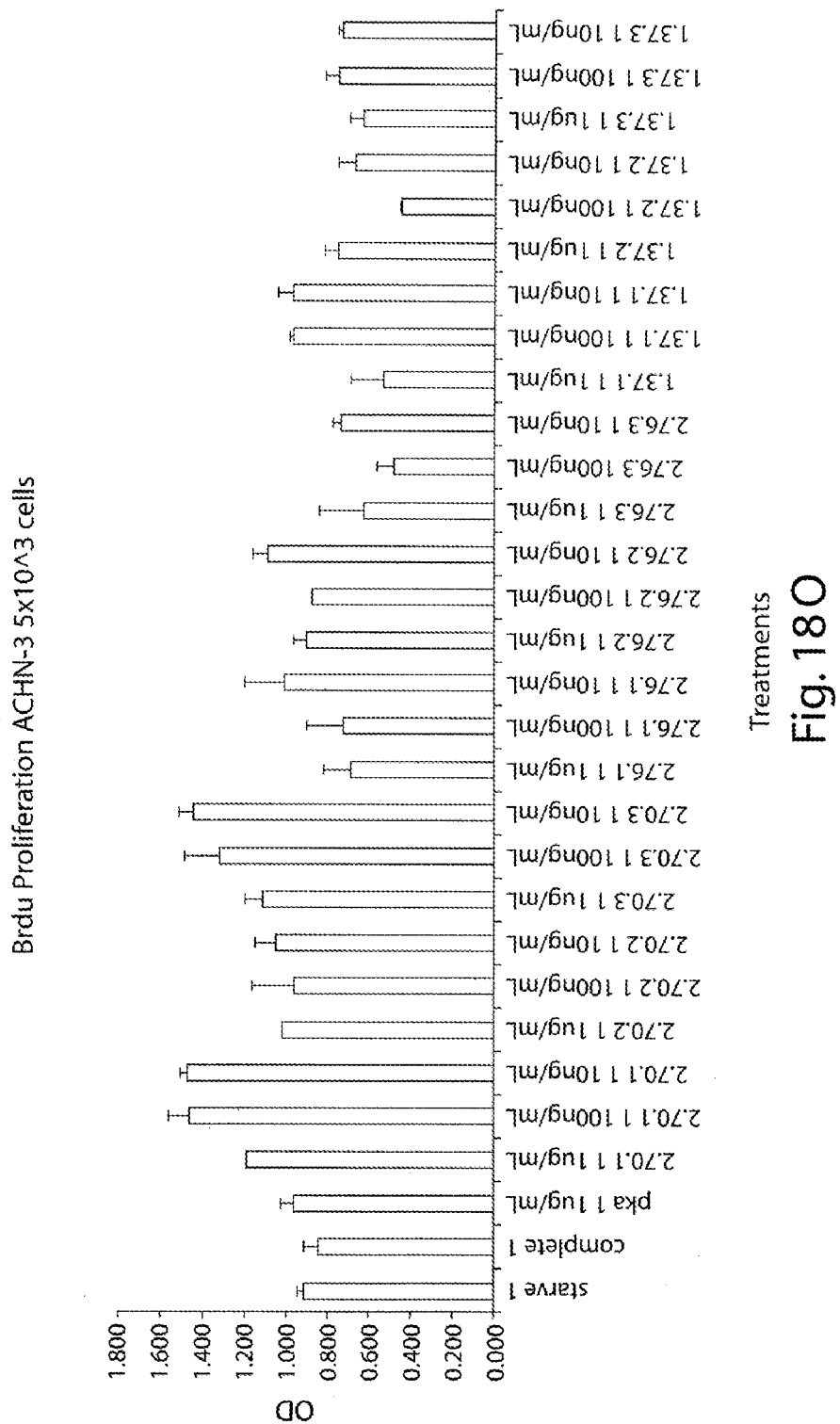
Figure 18P:
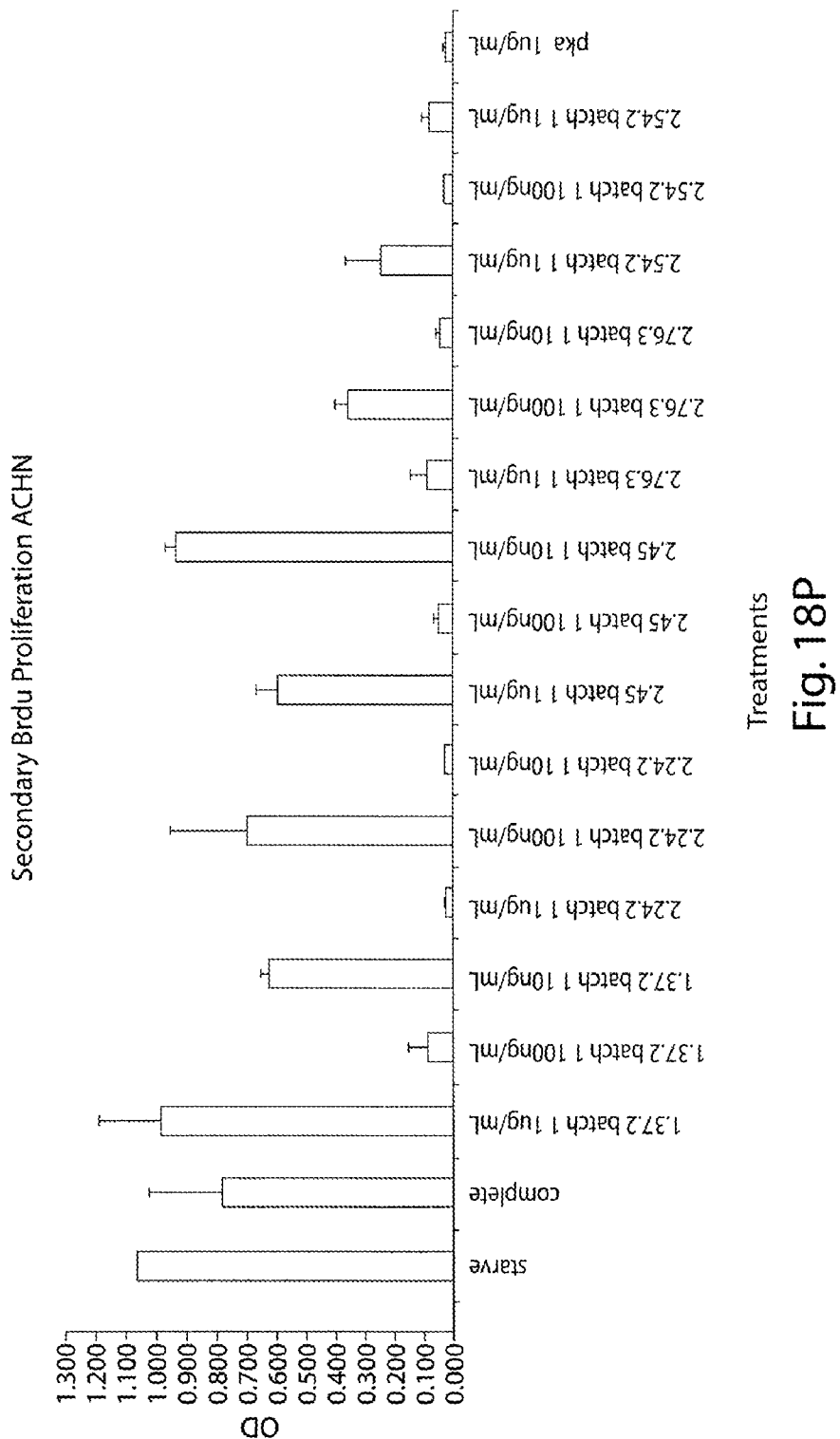
Figure 18Q:
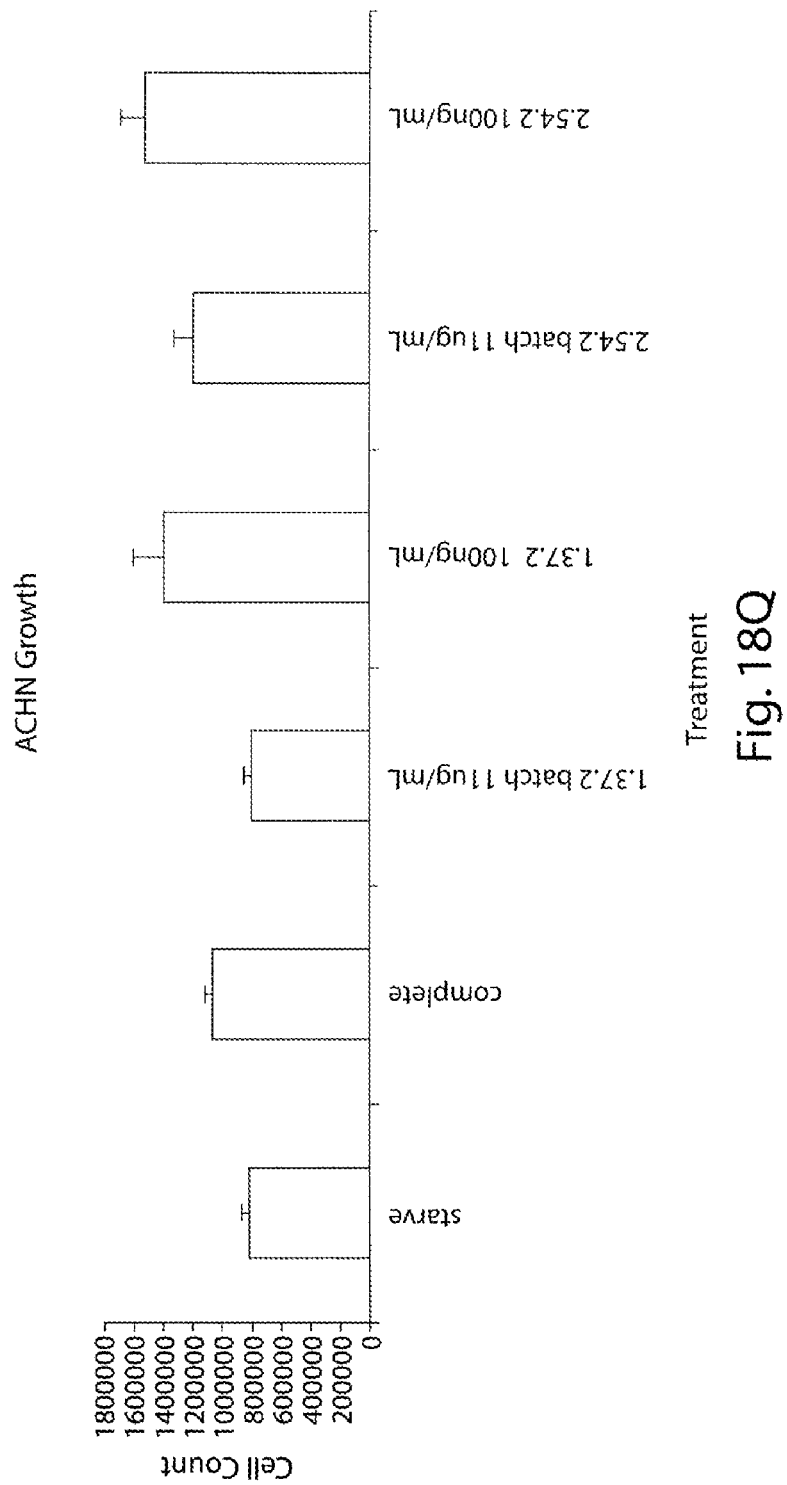
Figure 18R:
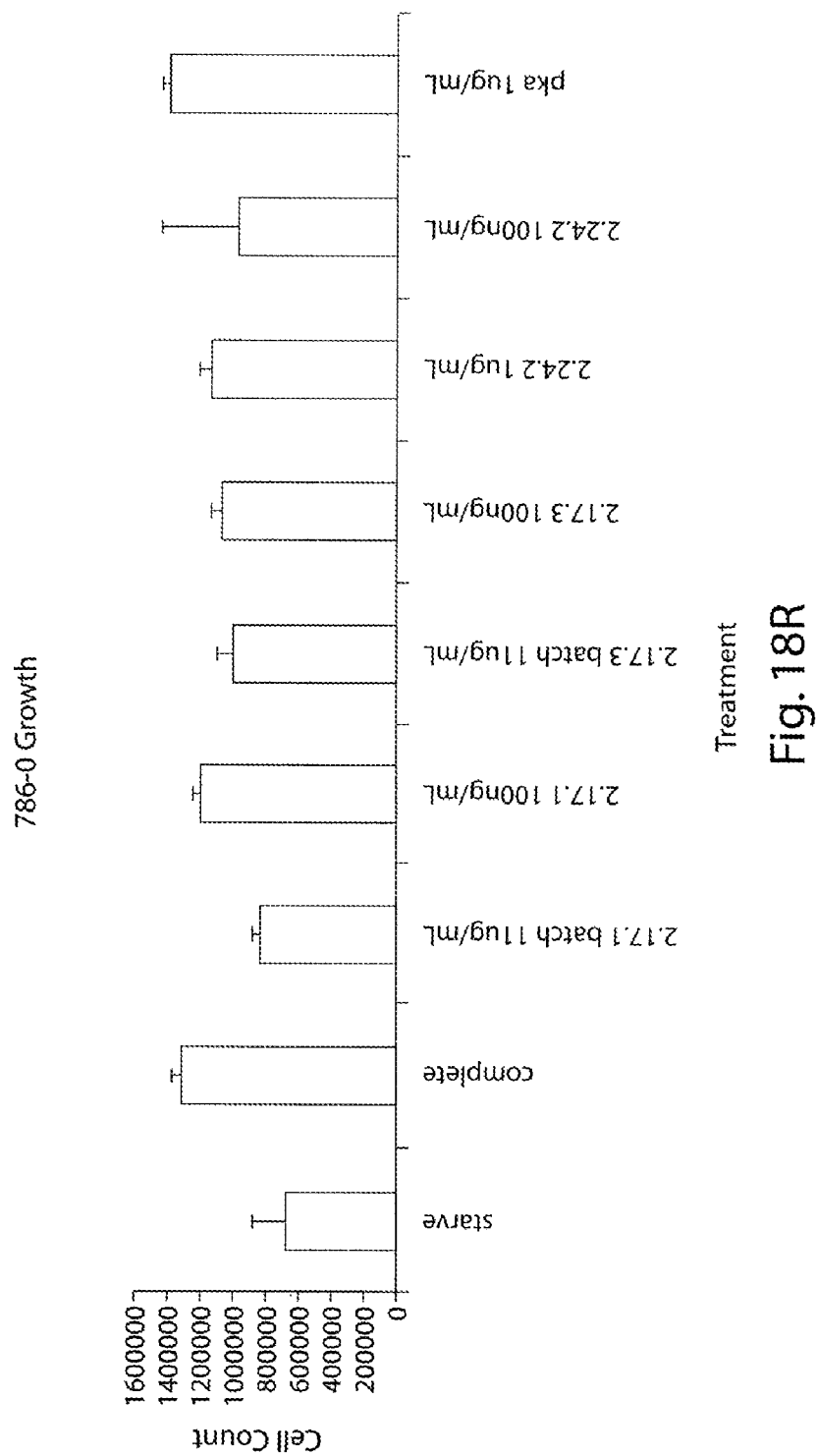
Figure 18S:
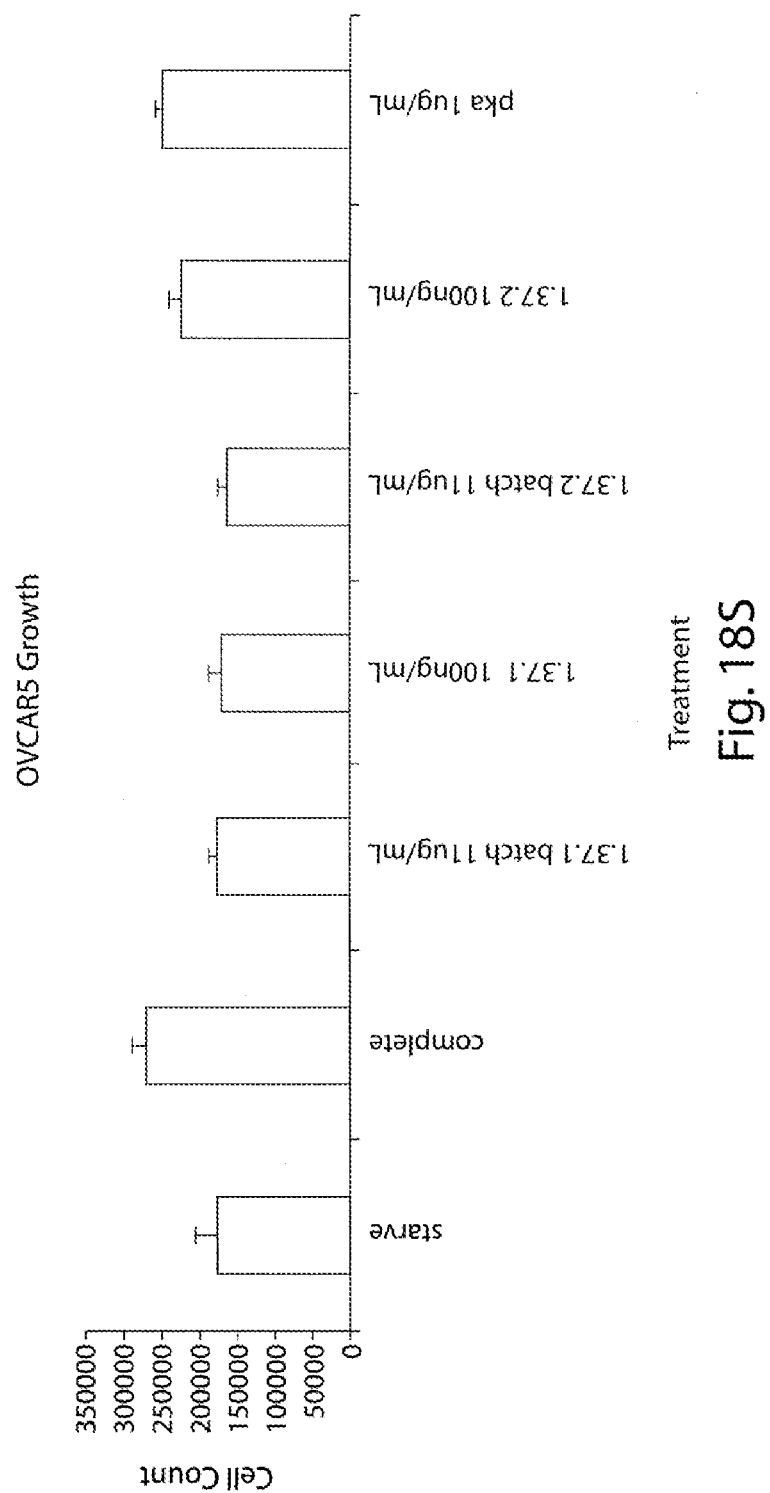
Figure 18T:
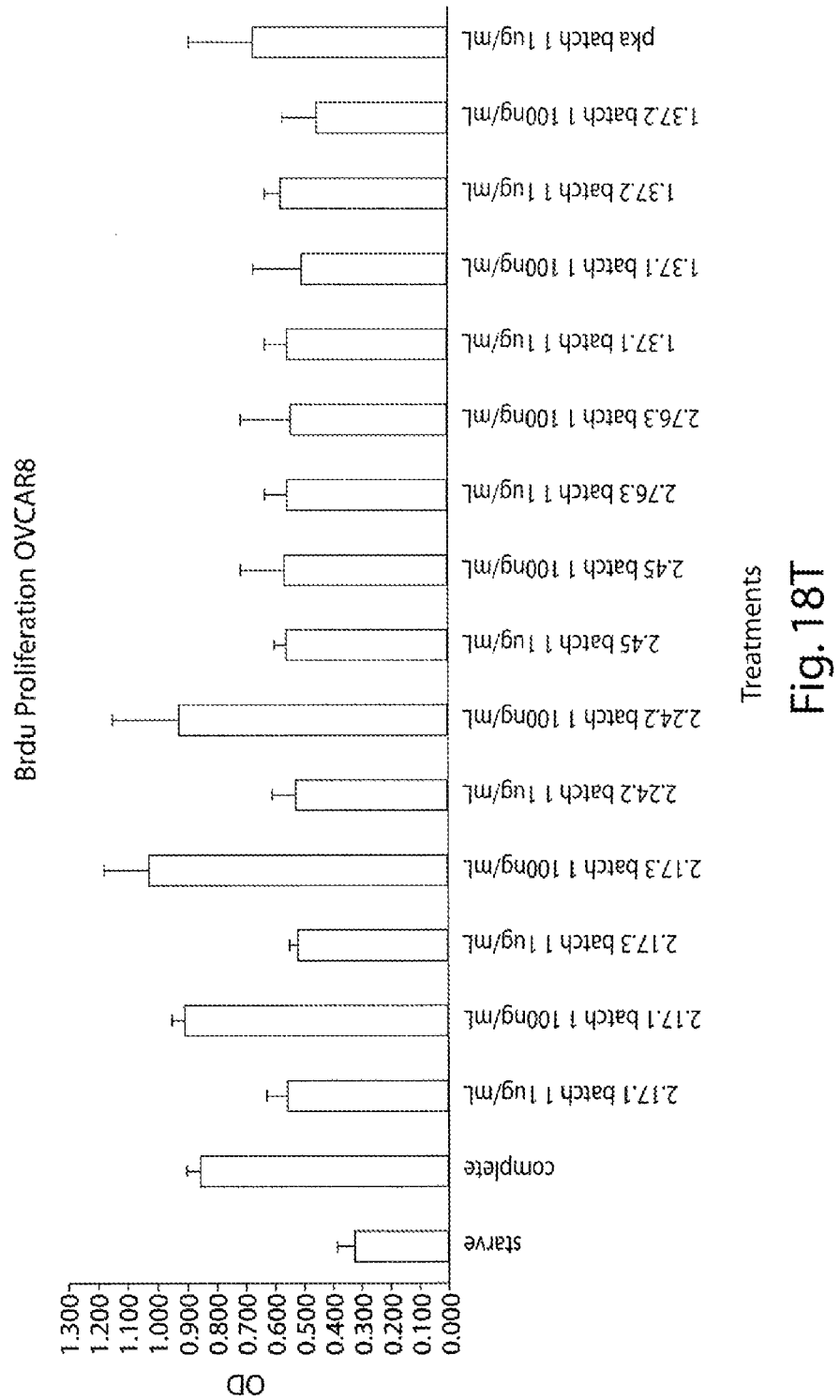

The capability of various human anti-TIM-1 monoclonal antibodies to neutralize was assessed. The results provided in FIGS. 18A-18T are presented in a bar graph format to assist in comparing the levels of BrdU incorporation in OVCAR5 cells upon exposure to various human anti-TIM-1 monoclonal antibodies described herein. As positive and negative controls, OVCAR5 cells were cultured in the presence of either complete media (complete) or restricted serum-containing media (starved). In addition, the monoclonal antibody PK16.3 was included as a negative treatment control representing a human IgG antibody of irrelevant specificity. Human anti-TIM-1 monoclonal antibodies described herein were used at varying doses (10-1000 ng/mL) as compared to a control run utilizing varying concentrations.

Example 18

Antibody Conjugate Studies

Figure 19A:
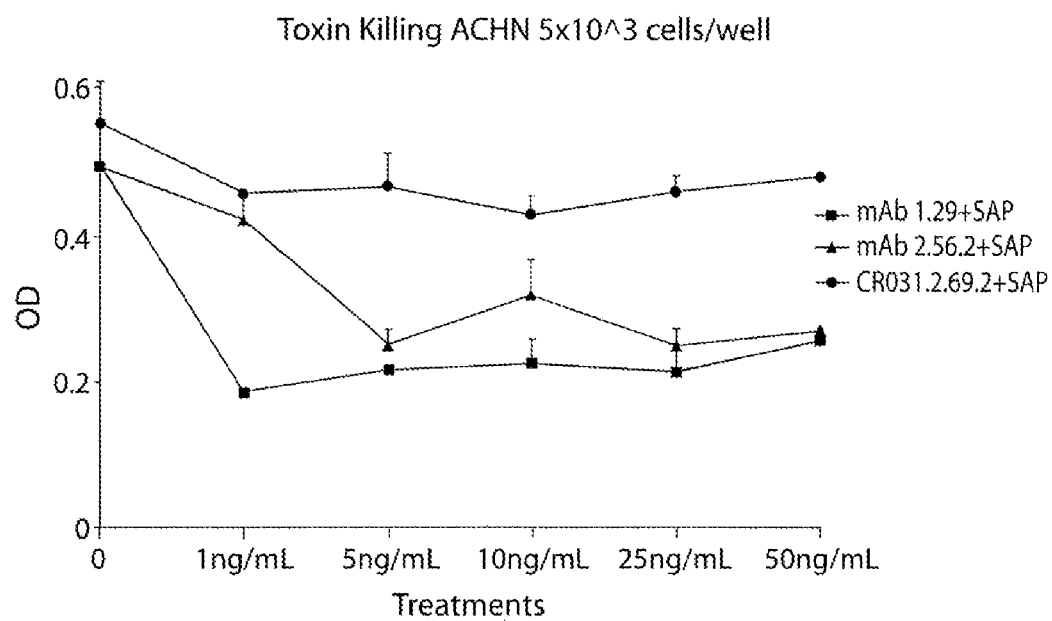
FIGS. 19A through 19D are line graphs showing the results of antibody conjugate studies performed using the plant toxin Saporin conjugated to TIM-1-specific antibodies and irrelevant antibodies (FIGS. 19A-19C). Additional negative controls included irrelevant antibodies alone without toxin (FIG. 19D).
Figure 19B:
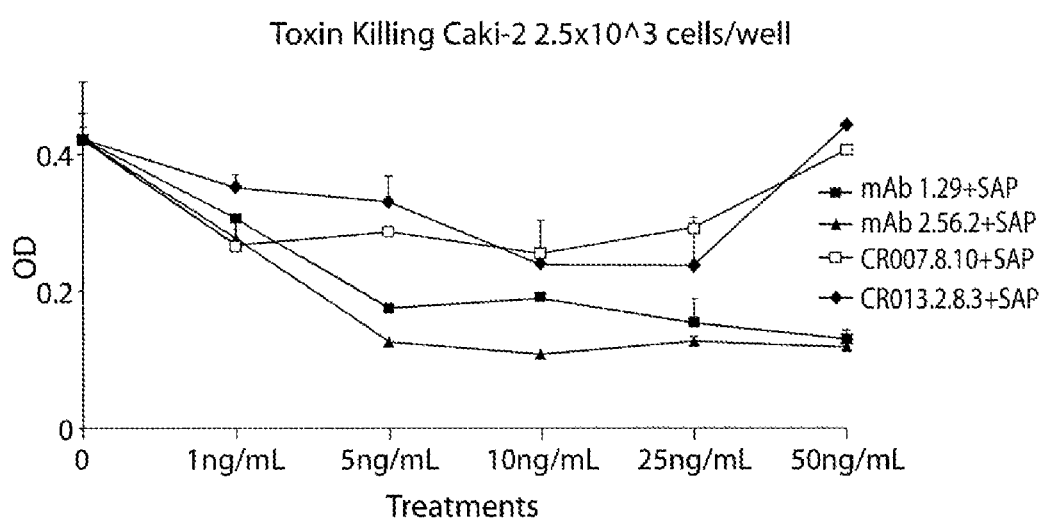
Figure 19C:
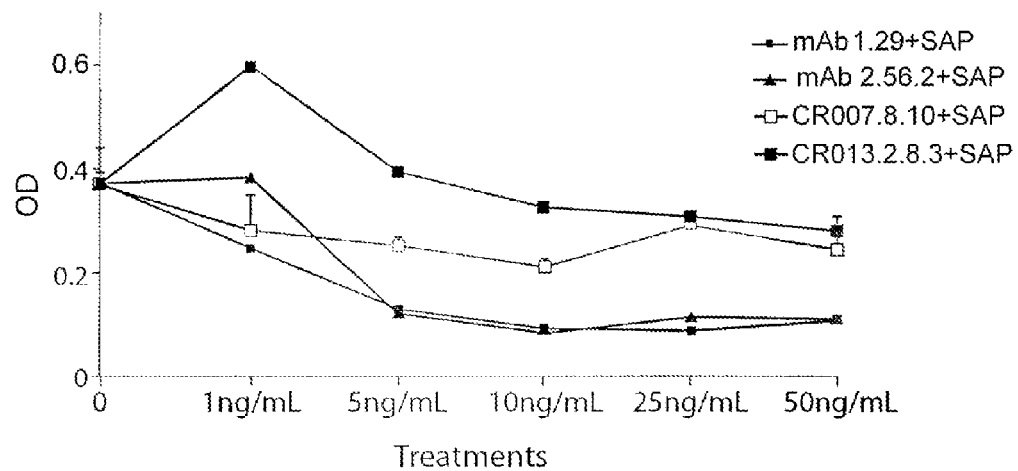
Figure 19D:
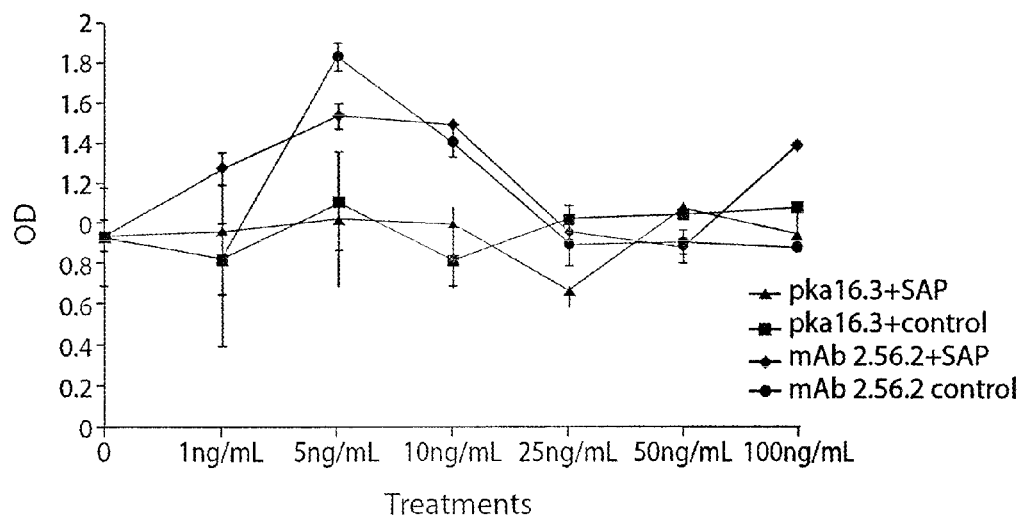

Additional antibody conjugate studies were performed using the plant toxin saporin conjugated to anti-TIM-1-specific mABs (1.29 and 2.56.2) and various irrelevant antibodies, including, PK16.3 (FIGS. 19A-19C). Additional negative controls included anti-TIM-1-specific mAB 2.56.2 and irrelevant antibody PK16.3 without toxin (FIG. 19D). Four cancer cell lines, three kidney cancer cell lines (ACHN, CAKI, and 7860) and one breast cancer cell line (BT549), were treated for 72 hours with saporin-antibody conjugates or antibodies alone, after which time BrdU was added to monitor proliferation over a 24 hour period. The results are described in FIGS. 19A-20C for the kidney cancer cell lines and FIG. 19D for the breast cancer cell line. All three kidney cancer cell lines were sensitive to treatment with saporin-TIM-1-specific antibody conjugates as evidenced by a measurable decrease in BrdU incorporation. Treatment of the same cell lines with conjugated irrelevant antibodies had little or no effect demonstrating antigen dependent antiproliferative effects. The same studies performed with the BT549 cell line showed that the TIM-1-specific antibody 2.56.2 showed no antiproliferative effect either alone or when conjugated to saporin. The negative controls for these studies appeared to work well with no cytotoxic effects Example 19

Sequences

Below are sequences related to monoclonal antibodies against TIM-1. With regard to the amino acid sequences, bold indicates framework regions, underlining indicates CDR regions, and italics indicates constant regions.
Anti-TIM-1 mAb 1.29

Nucleotide sequence of heavy chain variable region and a portion of constant region:

(SEQ ID NO: 1)
5'TGGGTCCTGTCCCAGGTGCAGCTGCAGGAGTCGGGCCCAGGACTGG

TGAAGCCTTCGGAGACCCTGTCCCTCACCTGCACTGTCTCTGGTGGCT

CCGTCAGCAGTGGTGGTTACTACTGGAGCTGGATCCGGCAGCCCCCAG

GGAAGGGACTGGAGTGGATTGGGTTTATCTATTACACTGGGAGCACCA

ACTACAACCCCTCCCTCAAGAGTCGAGTCTCCATATCAGTAGACACGT

CCAAGAACCAGTTCTCCCTGAAGCTGAGCTCTGTGACCGCTGCGGACG

CGGCCGTGTATTACTGTGCGAGAGATTATGACTGGAGCTTCCACTTTG

-continued
ACTACTGGGGCCAGGGAACCCTGGTCACCGTCTCCTCAGCCTCCACCA

AGGGCCCATCGGTCTTCCCCCTGGCGCCCTGCTCCAGGAGCACCTCCG

AGAGCACAGCGGCCCTGGGCTGCCTGGTCAAGGACTACTTCCCCGAAC

CGGTGACGGTGTCGTGGAACTCAGGCGCTCT3'

Amino acid sequence of heavy chain variable region and a portion of constant region encoded by SEQ ID NO:1:

(SEQ ID NO: 114)
WVLSQVQLQESGPGLVKPSETLSLTCTVSGGSVSSGGYYWSWIRQPPG

KGLEWIGFIYYTGSTNYNPSLKSRVSISVDTSKNQFSLKLSSVTAADA

AVYYCARDYDWSFHFDYWGQGTLVTVSSASTKGPSVFPLAPCSRSTSE

STAALGCLVKDYFPEPVTVSWNSGA

Nucleotide sequence of light chain variable region and a portion of constant region:

(SEQ ID NO: 3)
5'CAGCTCCTGGGGCTCCTGCTGCTCTGGTTCCCAGGTGCCAGGTGTG

ACATCCAGATGACCCAGTCTCCATCCTCCCTGTCTGCATCTATAGGAG

ACAGAGTCACCATCACTTGCCGGGCAAGTCAGGGCATTAGAAATGATT

TAGGCTGGTATCAGCAGAAACCAGGGAAAGCCCCTAAGCGCCTGATCT

ATGCTGCATCCAGTTTGCAAAGTGGGGTCCCATCAAGGTTCAGCGGCA

GTGGATCTGGGACAGAATTCACTCTCACAATCAGCAGCCTGCAGCCTG

AAGATTTTGCAACTTATTACTGTCTACAGCATAATAGTTACCCTCTCA

CTTTCGGCGGAGGGACCAAGGTGGAGATCAAACGAACTGTGGCTGCAC

CATCTGTCTTCATCTTCCCGCCATCTGATGAGCAGTTGAAATCTGGAA

CTGCCTCTGTTGTGTGCCTGCTGAATAACTTCTATCCCAGAGAGGCCA

AAGTACAGTGGAAGGTGGATAACGCC3'

Amino acid sequence of light chain variable region and a portion of constant region encoded by SEQ ID NO:3:

(SEQ ID NO: 115)
QLLGLLLLWFPGARCDIQMTQSPSSLSASIGDRVTITCRASQGIRNDL

GWYQQKPGKAPKRLIYAASSLQSGVPSRFSGSGSGTEFTLTISSLQPE

DFATYYCLQHNSYPLTFGGGTKVEIKRTVAAPSVFIFPPSDEQLKSGT

ASVVCLLNNFYPREAKVQWKVDNA

Anti-TIM-1 mAb 1.37

Nucleotide sequence of heavy chain variable region and a portion of constant region:

(SEQ ID NO: 5)
5'CAGTGTGAGGTGCAGCTGGTGGAGTCTGGGGGAGGCTTGGTCCAGC

CTGGGGGGTCCCTGAGACTCTCCTGTGCAGCCTCTGGATTCACCTTTA

CTAACTATTGGATGAGCTGGGTCCGCCAGGCTCCAGGGAAGGGGCTGG

AGTGGGTGGCCAACATACAGCAAGATGGAAGTGAGAAATACTATGTGG

ACTCTGTGAGGGGCCGATTCACCATCTCCAGAGACAACGCCAAGAACT

CACTGTATCTGCAAATGAACAGCCTGAGAGCCGAGGACTCGGCTGTGT

ATTACTGTGCGAGATGGGACTACTGGGGCCAGGGAACCCTGGTCACCG

TCTCCTCAGCCTCCACCAAGGGCCCATCGGTCTTCCCCCTGGCGCCCT

GCTCCAGGAGCACCTCCGAGAGCACAGCGGCCCTGGGCTGCCTGGTCA

AGGACTACTTCCCCGAACCGGTGAGCGGTGTCGTGGAAC3'

Amino acid sequence of heavy chain variable region and a portion of constant region encoded by SEQ ID NO:5:

(SEQ ID NO: 116)
QCEVQLVESGGGLVQPGGSLRLSCAASGFTFTNYWMSWVRQAPGKGLE

WVANIQQDGSEKYYVDSVRGRFTISRDNAKNSLYLQMNSLRAEDSAVY

YCARWDYWGQGTLVTVSSASTKGPSVFPLAPCSRSTSESTAALGCLVK

DYFPEPVSGVVE

Nucleotide sequence of light chain variable region and a portion of constant region:

(SEQ ID NO: 7)
5'CTTCTGGGGCTGCTAATGCTCTGGGTCCCTGGATCCAGTGGGGATA

TTGTGATGACCCAGACTCCACTCTCCTCAACTGTCATCCTTGGACAGC

CGGCCTCCATCTCCTGCAGGTCTAGTCAAAGCCTCGTACACAGTGATG

GAAACACCTACTTGAATTGGCTTCAGCAGAGGCCAGGCCAGCCTCCAA

GACTCCTAATTTATATGATTTCTAACCGGTTCTCTGGGGTCCCAGACA

GATTCAGTGGCAGTGGGGCAGGGACAGATTTCACACTGAAAATCAGCA

GGGTGGAAGCTGAGGATGTCGGGGTTTATTACTGCATGCAAGCTACAG

AATCTCCTCAGACGTTCGGCCAAGGGACCAAGGTGGAAATCAAACGAA

CTGTGGCTGCACCATCTGTCTTCATCTTCCCGCCATCTGATGAGCAGT

TGAAATCTGGAAGGGCCTCTGTTG3'

Amino acid sequence of light chain variable region and a portion of constant region encoded by SEQ ID NO:7:

(SEQ ID NO: 117)
LLGLLMLWVPGSSGDIVMTQTPLSSTVILGQPASISCRSSQSLVHSDG

NTYLNWLQQRPGQPPRLLIYMISNRFSGVPDRFSGSGAGTDFTLKISR

VEAEDVGVYYCMQATESPQTFGQGTKVEIKRTVAAPSVFIFPPSDEQL

KSGRASV

Anti-TIM-1 mAb 2.16

Nucleotide sequence of heavy chain variable region and a portion of constant:

(SEQ ID NO: 9)
5'GAGCAGTCGGGGGAGGCGTGGTAAAGCCTGGGGGGTCTCTTAGA

CTCTCCTGTGCAGCCTCTGGATTCACTTTCAGTAACGCCTGGATGAC

CTGGGTCCGCCAGGCTCCAGGGAAGGGGCTGGAGTGGGTTGGCCGTA

TTAAAAGGAGAACTGATGGTGGGCAACAGACTACGCTGCACCCGTG

AAAGGCAGATTCACCATCTCAAGAGATGATTCAAAAAACACGCTGTA

TCTGCAAATGAACAACCTGAAAAACGAGGACACAGCCGTGTATTACT

-continued
GTACCTCAGTCGATAATGACGTGGACTACTGGGGCCAGGGAACCCTG

GTCACCGTCTCCTCAGCTTCCACCAAGGGCCCATCCGTCTTCCCCCT

GGCGCCCTGCTCCAGGAGCACCTCCGAGAGCACAGCCGCCCTGGGCT

GCCTGGTCAAGGACTACTTCCCCGAACCGGTGACGGTGTCGTGGAAC

GTCAGGCGCCCTGACCAGCGGCGTGCACACCTTCCCGGCTTCCTACA

GTCCTCAGGACTCT3'

Amino acid sequence of heavy chain variable region and a portion of constant region encoded by SEQ ID NO:9:

(SEQ ID NO: 118)
XXXXEQSGGGVVKPGGSLRLSCAASGFTFSNAWMTWVRQAPGKGLEW

VGRIKRRTDGGTTDYAAPVKGRFTISRDDSKNTLYLQMNNLKNEDTA

VYYCTSVDNDVDYWGQGTLVTVSSASTKGPSVFPLAPCSRSTSESTA

ALGCLVKDYFPEPVTVSWNSGALTSGVHTFPAVLQSSGL

Nucleotide sequence of light chain variable region and a portion of constant region:

(SEQ ID NO: 11)
5'CTGACTCAGTCTCCACTCTCCCTGCCCGTCACCCCTGGAGAGCCG

GCCTCCATCTCCTGCAGGTCTAGTCAGAGCCTCCTGCATAGTAATGG

ATACAACTATTTGGATTGGTACCTGCAGAAGCCAGGGCAGTCTCCAC

AGCTCCTGATCTATTTGGGTTCTAATCGGGCCTCCGGGGTCCCTGAC

AGGTTCAGTGGCAGTGGATCAGGCACAGATTTTACACTGAAAATCAG

CAGAGTGGAGGCTGAGGATATTGGTCTTTATTACTGCATGCAAGCTC

TACAAACTCCGCTCACTTTCGGCGGAGGGACCAAGGTGGACATCAAA

CGAACTGTGGCTGCACCATCTGTCTTCATCTTCCCGCCATCTGATGA

GCAGTTGAAATCTGGAACTGCCTCTGTTGTGTGCCTGCTGAATAACT

TCTATCCCAGAGAGGCCAAAGTACAG3'

Amino acid sequence of light chain variable region and a portion of constant region encoded by SEQ ID NO:11:

(SEQ ID NO: 119)
XXXLTQSPLSLPVTPGEPASISCRSSQSLLHSNGYNYLDWYLQKPGQ

SPQLLIYLGSNRASGVPDRFSGSGSGTDFTLKISRVEAEDIGLYYCM

QALQTPLTFGGGTKVDIKRTVAAPSVFIFPPSDEQLKSGTASVVCLL

NNFYPREAKVQ

Anti-TIM-1 mAb 2.17
Nucleotide sequence of heavy chain variable region and a portion of constant region:

(SEQ ID NO: 13)
5'CAGGTGCAGCTGGAGCAGTCGGGGGGAGGCTTGGTACAGCCTGGG

GGGTCCCTGAGACTCTCCTGTGCAGCCTCTGGATTCACCTTCAGTAC

CTATAGCATGAACTGGGTCCGCCAGGCTCCAGGGAAGGGGCTGGAGT

GGGTTTCATACATTAGAAGTAGTACTAGTACCATATACTATGCAGAG

TCCCTGAAGGGCCGATTCACCATCTCCAGCGACAATGCCAAGAATTC

-continued
ACTATATCTGCAAATGAACAGCCTGAGAGACGAGGACACGGCTGTGT

ATTACTGTGCGCGGGACTTTGACTACTGGGGCCAGGGAACCCTGGTC

ACCGTCTCCTCAGCTTCCACCAAGGGCCCATCCGTCTTCCCCCTGGC

GCCCTGCTCCAGGAGCACCTCCGAGAGCACAGCCGCCCTGGGCTGCC

TGGTCAAGGACTACTTCCCCGAACCGGTGACGGTGTCGTGGAACTCA

GGCGCCCTGACCAGCGGCGTGCACACCTTCCCGGCTGTCCTACAGTC

CTCAGGACTCTACTCCCTCAGCA3'

Amino acid sequence of heavy chain variable region and a portion of constant region encoded by SEQ ID NO:13:

(SEQ ID NO: 120)
QVQLEQSGGGLVQPGGSLRLSCAASGFTFSTYSMNWVRQAPGKGLEW

VSYIRSSTSTIYYAESLKGRFTISSDNAKNSLYLQMNSLRDEDTAVY

YCARDFDYWGQGTLVTVSSASTKGPSVFPLAPCSRSTSESTAALGCL

VKDYFPEPVTVSWNSGALTSGVHTFPAVLQSSGLYSLS

Nucleotide sequence of light chain variable region and a portion of constant region:

(SEQ ID NO: 15)
5'GAAATCCAGCTGACTCAGTCTCCACTCTCCTCACCTGTCACCCTT

GGACAGCCGGCCTCCATCTCCTGCAGGTCTAGTCAAAGCCTCGTACA

CAGTGATGGAGACACCTACTTGAATTGGCTTCAGCAGAGGCCAGGCC

AGCCTCCAAGACTCCTAATTTATAAGATTTCTACCCGGTTCTCTGGG

GTCCCTGACAGATTCAGTGGCAGTGGGGCAGGGACAGATTTCACACT

GAAAATCAGCAGGGTGGAGACTGACGATGTCGGGATTTATTACTGCA

TGCAAACTACACAAATTCCTCAAATCACCTTCGGCCAAGGGACACGA

CTGGAGATTAAACGAACTGTGGCTGCACCATCTGTCTTCATCTTCCC

TGCCATCTGATGAGCAGTTGAAACTGGAACTGCCTCTGTTGTGTGCC

TGCTGAATAACTTCTATCCCAGAGAGGCCAAAGTACAGTGGAAGGTG

GATAACGCCCTCCAATCGGGTA3'

Amino acid sequence of light chain variable region and a portion of constant region encoded by SEQ ID NO:15:

(SEQ ID NO: 121)
EIQLTQSPLSSPVTLGQPASISCRSSQSLVHSDGDTYLNWLQQRPGQ

PPRLLIYKISTRFSGVPDRFSGSGAGTDFTLKISRVETDDVGIYYCM

QTTQIPQITFGQGTRLEIKRTVAAPSVFIFPPSDEQLKSGTASVVCL

LNNFYPREAKVQWKVDNALQSG

Anti-TIM-1 mAb 2.24
Nucleotide sequence of heavy chain variable region and a portion of constant region:

(SEQ ID NO: 17)
5'CAGGTGCAGCTGGAGCAGTCGGGGGGAGGCGTGGTCCAGCCTGGG

AGGTCCCTGAGACTCTCCTGTGCAGCGTCTGGATTCACCTTCAGTCG

-continued
CTATGGCATGCACTGGGTCCGCCAGGCTCCAGGCAAGGGGCTGAAAT

GGGTGGCAGTTATATGGTATGATGGAAGTAATAAACTCTATGCAGAC

TCCGTGAAGGGCCGATTCACCATCTCCAGAGACAATTCCAAGAACAC

GCTGTATCTGCAAATGAACAGCCTGAGAGCCGAGGACACGGCTGTGT

ATTACTGTGCGAGAGATTACTATGATAATAGTAGACATCACTGGGGG

TTTGACTACTGGGGCCAGGGAACCCTGGTCACCGTCTCCTCAGCTTC

CACCAAGGGCCCATCCGTCTTCCCCCTGGCGCCCTGCTCCAGGAGCA

CCTCCGAGAGCACAGCCGCCCTGGGCTGCCTGGTCAAGGACTACTTC

CCCGAACCGGTGACGGTGTCGTGGAACTCAGGCGCCCTGACCAGCGG

CGTGCACACCTTCCCGGCTGTCCTACAGTCCTCAGGACTCTACTCCC

TCAGCA

Amino acid sequence of heavy chain variable region and
a portion of constant region encoded by SEQ ID NO:17:

(SEQ ID NO: 122)
QVQLEQSGGGVVQPGRSLRLSCAAS<u>GFTFSRYGMH</u>WVRQAPGKGLK

WVA<u>VIWYDGSNKLYADSVK</u>GRFTISRDNSKNTLYLQMNSLRAEDTA

VYYCAR<u>DYYDNSRHHWGFDY</u>WGQGTLVTVSSA*STKGPSVFPLAPCS*

*RSTSESTAALGCLVKDYFPEPVTVSWNSGALTSGVHTFPAVLQSSG*

*LYSLS*

Nucleotide sequence of light chain variable region and a portion of constant region:

(SEQ ID NO: 19)
5'GACATCCAGCTGACCCAGTCTCCATCCTCCCTGTCTGCATCTGT

AGGAGACAGAGTCACCATCACTTGCCGGGCAAGTCAGAGTATTTAT

AGTTATTTAAATTGGTATCAGCAGAAACCAGGGAAAGCCCCTAAGC

TCCTGATCTATGCTGCATCCAGTTTGCAAAGTGGGGTCCCATCCAG

GTTCAGTGGCAGTGGATCTGGGACAGATTTCACTCTCACCATCAGC

AGTCTGCAACCTGAAGATTTTGCAACTTACTACTGTCAACAGAGTT

ACAGTACCCCTCCGACGTTCGGCCAAGGGACCAAGGTGGAAATCAA

ACGAACTGTGGCTGCACCATCTGTCTTCATCTTCCCGCCATCTGAT

GAGCAGTTGAAATCTGGAACTGCCTCTGTTGTGTGCCTGCTGAATA

ACTTCTATCCCAGAGAGGCCAAAGTACAGTGGAAGGTGGATAACGC

CCTCCAATCGGGTA3'

Amino acid sequence of light chain variable region and a portion of constant region encoded by SEQ ID NO:19:

(SEQ ID NO: 123)
DIQL/MT/LQSPSSLSASVGDRVTITC<u>RASQSIYSYLN</u>WYQQKPGKAP

KLLIY<u>AASSLQS</u>GVPSRFSGSGSGTDFTLTISSLQPEDFATYYC<u>QQSY</u>

<u>STPPT</u>FGQGTKVEIKR*TVAAPSVFIFPPSDEQLKSGTASVVCLLNNFY*

*PREAKVQWKVDNALQSG*

Anti-TIM-1 mAb 2.45

Nucleotide sequence of heavy chain variable region and a portion of constant region:

(SEQ ID NO: 21)
5'CAGTCGGGGGGAGGCTTGGTAAAGCCTGGGGGGTCCCTTAGACTCT

CCTGTGCAGCCTCTGGATTCACTTTCAGTAACGCCTGGATGACCTGGG

TCCGCCAGGCTCCAGGGAAGGGGCTGGAGTGGGTTGGCCGTATTAAAA

GGAAAACTGATGGTGGGACAACAGACTACGCTGCACCCGTGAAAGGCA

GATTCACCATCTCAAGAGATGATTCAGAAAACACGCTGTATCTGCAAA

TGAACAGCCTGGAAACCGAGGACACAGCCGTGTATTACTGTACCACAG

TCGATAACAGTGGTGACTACTGGGGCCAGGGAACCCTGGTCACCGTCT

CCTCAGCTTCCACCAAGGGCCCATCCGTCTTCCCCCTGGCGCCCTGCT

CCAGGAGCACCTCCGAGAGCACAGCCGCCCTGGGCTGCCTGGTCAAGG

ACTACTTCCCCGAACCGGTGACGGTGTCGTGGAACTCAGGCGCCCTGA

CCAGCGGCGTGCACACCTTCCCGGCTGTCCTACAGTCCTCAGGACTCT

CT3'

Amino acid sequence of heavy chain variable region and a portion of constant region encoded by SEQ ID NO:21:

(SEQ ID NO: 124)
XXXXXQSGGGLVKPGGSLRLSCAAS<u>GFTFSNAWMT</u>WVRQAPGKGLEWV

G<u>RIKRKTDGGTTDYAAPV</u>KGRFTISRDDSENTLYLQMNSLETEDTAVY

YCTT<u>VDNSGDY</u>WGQGTLVTVSSA*STKGPSVFPLAPCSRSTSESTAALG*

*CLVKDYFPEPVTVSWNSGALTSGVHTFPAVLQSSGLS*

Nucleotide sequence of light chain variable region and a portion of constant region:

(SEQ ID NO: 23)
5'ACTCAGTCTCCACTCTCCCTGCCCGTCACCCCTGGAGAGCCGGCCT

CCATCTCCTGCAGGTCTAGTCAGAGCCTCCTGCATAGTAATGGATACA

ACTATTTGGATTGGTACCTGCAGAAGCCAGGGCAGTCTCCACAGCTCC

TGATCTATTTGGGTTCTAATCGGGCCTCCGGGGTCCCTGACAGGTTCA

GTGGCAGTGGATCAGGCACAGATTTTACACTGAAAATCAGCAGAGTGG

AGGCTGAGGATGTTGGGGTTTATTACTGCATGCAAGCTCTACAAACTC

CGCTCACTTTCGGCGGAGGGACCAAGGTGGAGATCAAACGAACTGTGG

CTGCACCATCTGTCTTCATCTTCCCGCCATCTGATGAGCAGTTGAAAT

CTGGAACTGCCTCTGTTGTGTGCCTGCTGAATAACTTCTATCCCAGAG

AGGCCAAAGTACAGTGGAAGGTGGATAACGCCCTCCA3'

Amino acid sequence of light chain variable region and a portion of constant region encoded by SEQ ID NO:23:

(SEQ ID NO: 125)
XXXXTQSPLSLPVTPGEPASISC<u>RSSQSLLHSNGYNYLD</u>WYLQKPGQS

PQLLIY<u>LGSNRAS</u>GVPDRFSGSGSGTDFTLKISRVEAEDVGVYYC<u>MQA</u>

-continued

LQTPLTFGGGTKVEIKRTVAAPSVFIFPPSDEQLKSGTASVVCLLNNF

YPREAKVQWKVDNAL

Anti-TIM-1 mAb 2.54

Nucleotide sequence of heavy chain variable region and a portion of constant region:

(SEQ ID NO: 25)
5'CAGGTGCAGCTGGAGCAGTCGGGGGGAGGCGTGGTCCAGCCTGGGA

GGTCCCTGAGACTCTCCTGTGCAGCGTCTGGATTCACCTTCACTAACT

ATGGCTTGCACTGGGTCCGCCAGGCTCCAGGCAAGGGGCTGGATTGGG

TGGCAGTTATATGGTATGATGGAAGTCATAAATTCTATGCAGACTCCG

TGAAGGGCCGATTCACCATCTCCAGAGACAATTCCAAGAACACGCTCT

TTCTGCAAATGAACAGCCTGAGAGCCGAGGACACGGCTGTGTATTACT

GTACGCGAGATCTTGACTACTGGGGCCAGGGAACCCTGGTCACCGTCT

CCTCAGCTTCCACCAAGGGCCCATCCGTCTTCCCCCTGGCGCCCTGCT

CCAGGAGCACCTCCGAGAGCACAGCCGCCCTGGGCTGCCTGGTCAAGG

ACTACTTCCCCGAACCGGTGACGGTGTCGTGGAACTCAGGCGCCCTGA

CCAGCGGCGTGCACACCTTCCCGGCTGTCCTACAGTCCTCAGGACTCT

ACTCCCTCAGC3'

Amino acid sequence of heavy chain variable region and a portion of constant region encoded by SEQ ID NO:25:

(SEQ ID NO: 126)
QVQLEQSGGGVVQPGRSLRLSCAAS<u>GFTFTNYGLH</u>WVRQAPGKGLDWV

A<u>VIWYDGSHKFYADSVK</u>GRFTISRDNSKNTLFLQMNSLRAEDTAVYYC

TR<u>DLDY</u>WGQGTLVTVSSASTKGPSVFPLAPCSRSTSESTAALGCLVK

DYFPEPVTVSWNSGALTSGVHTFPAVLQSSGLYSLS

Nucleotide sequence of light chain variable region and a portion of constant region:

(SEQ ID NO: 27)
5'GAAACGCAGCTGACGCAGTCTCCAGGCACCCTGTCTTTGTCTCCAG

GGGAAAGAGTCACCCTCTCCTGCAGGGCCAGTCAGAGTGTTAGCAACA

ACTACTTAGCCTGGTACCAGCAGAAACCTGGCCAGGCTCCCAGGCTCC

TCATCTATGGTGCATCCAGCAGGGCCACTGGCATCCCAGACAGGTTCA

GTGGCAGTGGGTCTGGGACAGACTTCACTCTCACCATCAGCAGACTGG

AGCCTGAAGATTGTGCAGAGTGTTACTGTCAGCAATATGGTAGCTCAC

TCCCGCTCACTTTCGGCGGAGGGACCAAGGTGGAGATCAAACGAACTG

TGGCTGCACCATCTGTCTTCATCTTCCCGCCATCTGATGAGCAGTTGA

AATCTGGAACTGCCTCTGTTGTGTGCCTGCTGAATAACTTCTATCCCA

GAGAGGCCAAAGTACAGTGGGAAGGTGGGATAACGCCCTCCAATCGGG

TA3'

Amino acid sequence of light chain variable region and a portion of constant region encoded by SEQ ID NO:27:

(SEQ ID NO: 127)
ETQLTQSPGTLSLSPGERVTLSC<u>RASQSVSNNYLA</u>WYQQKPGQAPRLL

IY<u>GASSRAT</u>GIPDRFSGSGSGTDFTLTISRLEPEDCAECYC<u>QQYGSSL</u>

<u>PLT</u>FGGGTKVEIKRTVAAPSVFIFPPSDEQLKSGTASVVCLLNNFYPR

EAKVQWEGGITPSNRV

Anti-TIM-1 mAb 2.56

Nucleotide sequence of heavy chain variable region and a portion of constant region:

(SEQ ID NO: 29)
5'GTCCAGTGTCAGGTGCAGCTGGTGGAGTCTGGGGGAGGCGTGGTCC

AGCCTGGGAGGTCCCTGAGACTCTCCTGTGCAGCGTCTGGATTCACCT

TCAGTAGCTATGGCATGCACTGGGTCCGCCAGGCTCCAGGCAAGGGGC

TGGAGTGGGTGGCAGTTATATGGTATGATGGAAGTCATAAATACTATG

CAGACTCCGTGAAGGGCCGATTCACCATCTCCAGAGACAATTCCAAGA

ACACGCTGTATCTGCAAATGAACAGCCTGAGAGCCGAGGACACGGCTG

TGTATTACTCTGCGAGAGATTACTATGATACGAGTCGGCATCACTGGG

GGTTTGACTGCTGGGGCCAGGGAACCCTGGTCACCGTCTCCTCTGCTT

CCACCAAGGGCCCATCCGTCTTCCCCCTGGCGCCCTGCTCCAGGAGCA

CCTCCGAGAGCACAGCCGCCCTGGGCTGCCTGGTCAAGGACTACTTCC

CCGAACCGGTGACGGTGTCGTGGAACTCAGGCGCCCTGACCAGCGGCG

TGCACACCTTCCCGGC3'

Amino acid sequence of heavy chain variable region and a portion of constant region encoded by SEQ ID NO: 29:

(SEQ ID NO: 128)
VQCQVQLVESGGGVVQPGRSLRLSCAAS<u>GFTFSSYGMH</u>WVRQAPGKGL

EWVA<u>VIWYDGSHKY/LYA/TDSVK</u>GRFTISRDNSKNTLYLQMNSLRAE

DTAVYYSAR<u>DYYDTSRHHWGFDC</u>WGQGTLVTVSSASTKGPSVFPLAPC

SRSTSESTAALGCLVKDYFPEPVTVSWNSGALTSGVHTFP

Nucleotide sequence of light chain variable region and a portion of constant region:

(SEQ ID NO: 31)
5'CAGCTCCTGGGGCTGCTAATGCTCTGGGTCCCTGGATCCAGTGAGG

AAATTGTGATGACCCAGACTCCACTCTCCCTGCCCGTCACCCCTGGAG

AGCCGGCCTCCATCTCCTGCAGGTCTAGTCAGAGCCTCTTGGATAGTG

AAGATGGAAACACCTATTTGGACTGGTACCTGCAGAAGCCAGGGCAGT

CTCCACAGCTCCTGATCTATACGCTTTCCCATCGGGCCTCTGGAGTCC

CAGACAGGTTCAGTGGCAGTGGGTCAGGCACTGATTTCACACTGAAAA

TCAGCAGGGTGGAGGCTGAGGATGTTGGAGTTTATTGCTGCATGCAAC

GTGTAGAGTTTCCTATCACCTTCGGCCAAGGGACACGACTGGAGATTA

AACGAACTGTGGCTGCACCATCTGTCTTCATCTTCCCGCCATCTGATG

AGCAGTTGAAATCTGGAACTGCCTCTGTTGTGTGCCTGCTGAATAACT

TCTATCCCAGAGAGGCCAAAGTACAGTGGAAGGTGGATAACGC3'

Amino acid sequence of light chain variable region and a portion of constant region encoded by SEQ ID NO:31:

(SEQ ID NO: 129)
QLLGLLMLWVPGSSEEIVMTQTPLSLPVTPGEPASISCRSSQSLLDSE

DGNTYLDWYLQKPGQSPQLLIYTLSHRASGVPDRFSGSGSGTDFTLKI

SRVEAEDVGVYCCMQRVEFPITFGQGTRLEIKRTVAAPSVFIFPPSDE

QLKSGTASVVCLLNNFYPREAKVQWKVDN

Anti-TIM-1 mAb 2.59

Nucleotide sequence of heavy chain variable region and a portion of constant region:

(SEQ ID NO: 33)
5'CAGTCGGGCCCAAGACTGGTGAAGCCTTCACAGACCCTGTCCCTCA

CCTGCACTGTCTCTGGTGGCTCCATCAGTAGTGATGGTTACTACTGGA

GCTGGATCCGCCAGCACCCAGGGAAGGGCCTGGAGTGGATTGGGTACA

TCTATTACAGTGGGAGCACCTTCTACAACCCGTCCCTCAAGAGTCGAG

TTGCCATATCAGTGGACACGTCTAAGAACCAGTTCTCCCTGAAGCTGA

GCTCTGTGACTGCCGCGGACACGGCCGTGTATTACTGTGCGAGAGAAT

CCCCTCATAGCAGCAACTGGTACTCGGGCTTTGACTGCTGGGGCCAGG

GAACCCTGGTCACCGTCTCCTCAGCTTCCACCAAGGGCCCATCCGTCT

TCCCCCTGGCGCCCTGCTCCAGGAGCACCTCCGAGAGCACAGCCGCCC

TGGGCTGCCTGGTCAAGGACTACTTTCCCCGAACCGGTGACGGTGTCG

TGGAACTCAGGCGCCCTGACCAGCGGCGTGCACACCTTCCCGGCTGTC

CTACAGTCCTCAGGACTCTCT3'

Amino acid sequence of heavy chain variable region and a portion of constant region encoded by SEQ ID NO:33:

(SEQ ID NO: 130)
XXXXXQSGPRLVKPSQTLSLTCTVSGGSISSDGYYWSWIRQHPGKGLE

WIGYIYYSGSTFYNPSLKSRVAISVDTSKNQFSLKLSSVTAADTAVYY

CARESPHSSNWYSGFDCWGQGTLVTVSSASTKGPSVFPLAPCSRSTSE

PSTAALGCLVKDYFPRTGDGVVELRRPDQRRAHLGCPTVLRTL

Nucleotide sequence of light chain variable region and a portion of constant region:

(SEQ ID NO: 35)
5'ACTCAGTCTCCAGACTTTCAGTCTGTGACTCCAAAGGAGAAAGTCA

CCATCACCTGCCGGGCCAGTCAGAGCATTGGTAGTAGGTTACACTGGT

AACCAGCAGAAACCAGATCGTCTCCAAAGCTCCTCATCAAGTATGCTT

CCCAGTCCTTCTCAGGGGTCCCCTCGAGGTTCAGTGGCAGTGGATCTG

CGGACAGATTTCACCCTCACCATCAATAGCCTGGAAGTGAAGATGCTG

CAACGTATTACTGTCATCAGAGTAGTAATTTACCATTCACTTTCGGCC

CTGGGACCAAAGTGGATATCAAACGAACTGTGGCTGCACCATCTGTCT

TCATCTTCCCGCCATCTGATGAGCAGTTGAAATCTGGAACTGCCTCTG

TTGTGTGCCTGCTGAATAACTTCTATCCCAGAGAGGCCAAAGTACAGT

GGAAGGTGGATAACGCCCTC3'

Amino acid sequence of light chain variable region and a portion of constant region encoded by SEQ ID NO:35:

(SEQ ID NO: 131)
XXXXTQSPDFQSVTPKEKVTITCRASQSIGSRLHWYQQKPDQSPKLLI

KYASQSFSGVPSRFSGSGSGTDFTLTINSLEAEDAATYYCHQSSNLPF

TFGPGTKVDIKR*TVAAPSVFIFPPSDEQLKSGTASVVCLLNNFYPREA*

*KVQWKVDNAL*

Anti-TIM-1 mAb 2.61

Nucleotide sequence of heavy chain variable region and a portion of constant region:

(SEQ ID NO: 37)
5'CAGGTGCAGCTGGTGGAGGCTGGGGGAGGCGTGGTCCAGCCTGGGA

GGTCCCTGAGACTCTCCTGTGCAGCGTCTGGATTCACCTTCAGAAGCT

ATGGCATGCACTGGGTCCGCCAGGCTCCAGGCAAGGGGCTGAAATGGG

TGGCAGTTATATGGTATGATGGAAGTAATAAATACTATACAGACTCCG

TGAAGGGCCGATTCACCATCTCCAGAGACAATTCCAAGAACACGCTGT

ATCTGCAAATGAACAGCCTGAGAGCCGAGGACACGGCTGTGTATTACT

GTGTGAGAGATTACTATGATAATAGTAGACATCACTGGGGGTTTGACT

ACTGGGGCCAGGGAACCCTGGTCACCGTCTCCTCAGCTTCCACCAAGG

GCCCATCCGTCTTCCCCCTGGCGCCCTGCTCCAGGAGCACCTCCGAGA

GCACAGCCGCCCTGGGCTGCCTGGTCAAGGACTACTTCCCCGAACCGG

TGACGGTGTCGTGGAACTCAGGCGCCCTGACCAGCGGCGTGCACACC

TTCCCGGC3'

Amino acid sequence of heavy chain variable region and a portion of constant region encoded by SEQ ID NO:37:

(SEQ ID NO: 132)
QVQLVE/QAGGGVVQPGRSLRLSCAASGFTFRSYGMHWVRQAPGKGLKWVAVIWY

DGSNKY/LYTDSVKGRFTISRDNSKNTLYLQMNSLRAEDTAVYYCVRDYYDNSRHH

WGFDYWGQGTLVTVSSASTKGPSVFPLAPCSRSTSESTAALGCLVKDYFPEPVTVSWNSGA

LTRRRAHLPG

Nucleotide sequence of light chain variable region and a portion of constant region:

(SEQ ID NO: 39)
5'GACATCCAGATGACCCAGTCTCCATCCTCCCGGTGTGCATCCGTAGGA
GACAGAGTCACCATCACTTGCCGGGCAAGTCAGGGCATCAGAAATGATTT
AGCTTGGTATCAGCAGAAACCAGGGAAAGCCCCTAAGCGCCTGATCTATG
CTGCATCCAGTTTGCAAAGTGGGGTCCCATCAAGGTTCAGCGGCAGTAGA
TCTGGGACAGAATTCACTCTCACAATCAGCAGCCTGCAGCCTGAAGATTT
TGCAGCTTATTACTGTCTCCAGCATAATAGTTACCCTCCCAGTTTTGGCC
AGGGGACCAAGCTGGAGATCAAACGAACTGTGGCTGCACCATCTGTCTTC
ATCTTCCCGCCATCTGATGAGCAGTTGAAATCTGGAACTGCTAGCGTTGT
GTGCCTGCTGAATAACTTCTATCCCAGAGAGGCCAAAGTACAGTGGAAGG
TGGATAACGCCCTCCAATCGGG3'

Amino acid sequence of light chain variable region and a portion of constant region encoded by SEQ ID NO:39:

(SEQ ID NO: 133)
DIQMTQSPSSRCASVGDRVTITC<u>RASQGIRNDLA</u>WYQQKPGKAPKRLIY<u>AASSLQS</u>G
VPSRFSGSRSGTEFTLTISSLQPEDFAAVYC<u>LQHNSYPPS</u>FGQGTKLEIKR*TVAAPSVFI*
*FPPSDEQLKSGTASVVCLLNNFYPREAKVQWKVDNALQS*

Anti-TIM-1 mAb 2.70

Nucleotide sequence of heavy chain variable region and a portion of constant region:

(SEQ ID NO: 41)
5'CATGTGCAGGTGCAGCTGGTGGAGTCTGGGGGAGGCGTGGTCCAGCCT
GGGAGGTCCCTGAGACTCTCCTGTGCAGCGTCTGGATTCATCTTCAGTCG
CTATGGCATGCACTGGGTCCGCCAGGCTCCAGGCAAGGGGCTGAAATGGG
TGGCAGTTATATGGTATGATGGAAGTAATAAACTCTATGCAGACTCCGTG
AAGGGCCGATTCACCATCTCCAGAGACAATTCCAAGAACACGCTGTATCT
GCAAATGAACAGCCTGAGAGCCGAGGACACGGCTGTGTATTACTGTGCGA
GAGATTACTATGATAATAGTAGACATCACTGGGGGTTTGACTACTGGGGC
CAGGGAACCCTGGTCACCGTCTCCTCAGCTTCCACCAAGGGCCCATCCGT
CTTCCCCCTGGCGCCCTGCTCCAGGAGCACCTCCGAGAGCACAGCCGCCC
TGGGCTGCCTGGTCAAGGACTACTTCCCCGAACCGGTGACGGTGTCGTGG
AACTCAGGCGCCCTGA3'

Amino acid sequence of heavy chain variable region and a portion of constant region encoded by SEQ ID NO:41:

(SEQ ID NO: 134)
*H*VQVQLVESGGGVVQPGRSLRLSCAAS<u>GFIFSRYGMH</u>WVRQAPGKGLKWVA<u>VIWY
DGSNKLYADSVK</u>GRFTISRDNSKNTLYLQMNSLRAEDTAVYYCAR<u>DYYDNSRHHWG
FDY</u>WGQGTLVTVSSA*STKGPSVFPLAPCSRSTSESTAALGCLVKDYFPEPVTVSWNSGAL*

Nucleotide sequence of light chain variable region and a portion of constant region:

(SEQ ID NO: 43)
5'TCAGCTCCTGGGGCTGCTAATGCTCTGGGTCCCTGGATCAGTGAGGAT
ATTGTGATGACCCAGACTCCACTCTCCCTGCCCGTCACCCCTGGAGAGCC
GGCCTCCATCTCCTGCAGGTCTAGTCGGAGCCTCTTGGATAGTGATGATG
GAAACACCTATTTGGACTGGTACCTGCAGAAGCCAGGGCAGTCTCCACAG
CTCCTGATCTACACGCTTTCCTATCGGGCCTCTGGAGTCCCAGACAGGTT
CAGTGGCAGTGGGTCAGGCACTGATTTCACACTGAAAATCAGCAGGGTGG
AGGCTGAGGATGTTGGAGTTTATTACTGCATGCAACGTGTAGAGTTTCCT
ATCACCTTCGGCCAAGGGACACGACTGGAGATTAAACGAACTGTGGCTGC
ACCATCTGTCTTCATCTTCCCGCCATCTGATGAGCAGTTGAAATCTGGAA
CTGCCTCTGTTGTGTGCCTGCTGAATAACTTCTATCCCAGAGAGGCCAAA
GTACAGTGGAAGGTGGATAACGCCT3'

Amino acid sequence of light chain variable region and a portion of constant region encoded by SEQ ID NO:43:

(SEQ ID NO: 135)
SAPGAANALGPWISEDIVMTQTPLSLPVTPGEPASISCRSSRSLLDSDDGNTYLD**WYLQK
PGQSPQLLIYTLSYRASGVPDRFSGSGSGTDFTLKISRVEAEDVGVYYC**MQRVEFPITF
GQGTRLEIKR**TVAAPSVFIFPPSDEQLKSGTASVVCLLNNFYPREAKVQWKVDNA

Anti-TIM-1 mAb 2.70.2

Nucleotide sequence of heavy chain variable region and a portion of constant region:

(SEQ ID NO: 49)
5'CGGCCGCCTATTTACCCAGAGACAGGGAGAGGCTCTTCTGTGTGTAGT
GGTTGTGCAGAGCCTCATGCATCACGGAGCATGAGAAGACATTCCCCTCC
TGCCACCTGCTCTTGTCCACGGTTAGCCTGCTGTAGAGGAAGAAGGAGCC
GTCGGAGTCCAGCACGGGAGGCGTGGTCTTGTAGTTGTTCTCCGGCTGCC
CATTGCTCTCCCACTCCACGGCGATGTCGCTGGGGTAGAAGCCTTTGACC
AGGCAGGTCAGGCTGACCTGGTTCTTGGTCATCTCCTCCTGGGATGGGGG
CAGGGTGTACACCTGTGGCTCTCGGGGCTGCCCTTTGGCTTTGGAGATGG
TTTTCTCGATGGAGGACGGGAGGCCTTTGTTGGAGACCTTGCACTTGTAC
TCCTTGCCGTTCAGCCAGTCCTGGTGCAGGACGGTGAGGACGCTGACCAC
ACGGTACGTGCTGTTGAACTGCTCCTCCCGCGGCTTTGTCTTGGCATTAT
GCACCTCCACGCCATCCACGTACCAGTTGAACTGGACCTCGGGGTCTTCC
TGGCTCACGTCCACCACCACGCACGTGACCTCAGGGGTCCGGGAGATCAT
GAGAGTGTCCTTGGGTTTTGGGGGGAACAGGAAGACTGATGGTCCCCCCA
GGAACTCAGGTGCTGGGCATGATGGGCATGGGGGACCATATTTGGACTCA
ACTCTCTTGTCCACCTTGGTGTTGCTGGGCTTGTGATCTACGTTGCAGGT
GTAGGTCTTCGTGCCCAAGCTGCTGGAGGGCACGGTCACCACGCTGCTGA
GGGAGTAGAGTCCTGAGGACTGTAGGACAGCCGGGAAGGTGTGCACGCCG
CTGGTCAGGGCGCCTGAGTTCCACGACACCGTCACCGGTTCGGGGAAGTA
GTCCTTGACCAGGCAGCCCAGGGCGGCTGTGCTCTCGGAGGTGCTCCTGG
AGCAGGGCGCCAGGGGGAAGACGGATGGGCCCTTGGTGGAAGCTGAGGAG
ACGGTGACCAGGGTTCCCTGGCCCCAGTAGTCAAACCCCCAGTGATGTCT
ACTATTATCATAGTAATCTCTCGCACAGTAATACACAGCCGTGTCCTCGG
CTCTCAGGCTGTTCATTTGCAGATACAGCGTGTTCTTGGAATTGTCTCTG

Amino acid sequence of heavy chain variable region and a portion of constant region encoded by SEQ ID NO:49:

(SEQ ID NO: 50)
MEFGLSWLFLVAILKGVQCQVQLVESGGGVVQPGRSLRLSCAASGFIFSRYGMH**WVRQ
APGKGLKWVAVIWYDGSNKLYADSVKGRFTISRDNSKNTLYLQMNSLRAEDTAVY
YCARDYYDNSRHHWGFDYWGQGTLVTVSSA**STKGPSVFPLAPCSRSTSESTAALGCLVK
DYFPEPVTVSWNSGALTSGVHTFPAVLQSSGLYSLSSVVTVPSSSLGTKTYTCNVDHKPSNTKV
DKRVESKYGPPCPSCPAPEFLGGPSVFLFPPKPKDTLMISRTPEVTCVVVDVSQEDPEVQFN
WYVDGVEVHNAKTKPREEQFNSTYRVVSVLTVLHQDWLNGKEYKCKVSNKGLPSSIEKTISKA

KGQPREPQVYTLPPSQEEMTKNQVSLTCLVKGFYPSDIAVEWESNGQPENNYKTTPPVLDSD

GSFFLYSRLTVDKSRWQEGNVFSCSVMHEALHNHYTQKSLSLSLGK

Nucleotide sequence of light chain variable region and a portion of constant region:

(SEQ ID NO: 51)
5'AGTCGACCACCATGGAAACCCCAGCGCAGCTTCTCTTCCTCCTGCTAC

TCTGGCTCCCAGATACCACCGGAGATATTGTGATGACCCAGACTCCACTC

TCCCTGCCCGTCACCCCTGGAGAGCCGGCCTCCATCTCCTGCAGGTCTAG

TCGGAGCCTCTTGGATAGTGATGATGGAAACACCTATTTGGACTGGTACC

TGCAGAAGCCAGGGCAGTCTCCACAGCTCCTGATCTACACGCTTTCCTAT

CGGGCCTCTGGAGTCCCAGACAGGTTCAGTGGCAGTGGGTCAGGCACTGA

TTTCACACTGAAAATCAGCAGGGTGGAGGCTGAGGATGTTGGAGTTTATT

ACTGCATGCAACGTGTAGAGTTTCCTATCACCTTCGGCCAAGGGACACGA

CTGGAGATTAAACGAACTGTGGCTGCACCATCTGTCTTCATCTTCCCGCC

ATCTGATGAGCAGTTGAAATCTGGAACTGCCTCTGTTGTGTGCCTGCTGA

CCGCCAGGCTCCAGGCAAGGGGCTGGAGTGGGTGGCAGTTATATGGTATG

ATGGAAGCAATAAATACTATGCAGACTCCGTGAAGGGCCGATTCACCATC

TCCAGAGACAATTCCAAGAACACGCTGTATCTGCAAATGAACAGCCTGAG

AGCCGAGGACACGGCTGTGTATTACTGTGCGAGGGATTTCTATGATAGTA

GTCGTTACCACTACGGTATGGACGTCTGGGGCCAAGGGACCACGGTCACC

GTCTCCTCAGCTTCCACCAAGGGCCCATCCGTCTTCCCCCTGGCGCCCTG

CTCCAGGAGCACCTCCGAGAGCACAGCCGCCCTGGGCTGCCTGGTCAAGG

ACTACTTCCCCGAACCGGTGACGGTGTCGTGGAACTCAGGCGCCCTGACC

AGCGGCGTGCACACCTTCCCGGCTGTCCTACAGTCCTCAGGACTCTCT 3'

Amino acid sequence of heavy chain variable region and a portion of constant region encoded by SEQ ID NO:45:

(SEQ ID NO: 136)
XXXXEQSGGGVVQPGRSLRLSCAAS GFTFSSYGMY WVRQAPGKGLEWVA VIWYDG

SNKYYADSVK GRFTISRDNSKNTLYLQMNSLRAEDTAVYYCAR DFYDSSRYHYGMD

VWGQGTTVTVSSA STKGPSVFPLAPCSRSTSESTAALGCLVKDYFPEPVTVSWNSGALTSGV

HTFPAVLQSSGLS

Nucleotide sequence of light chain variable region and a portion of constant region:

(SEQ ID NO: 47)
5'ACTCAGTGTCCACTCTCCCTGCCCGTCACCCCTGGAGAGCCGGCCTCC

ATCTCCTGCAGGTCTAGTCAGAGCCTCTTGGATAGTGATGATGGAAACAC

CTATTTGGACTGGTACCTGCAGAAGCCAGGGCAGTCTCCACAGCTCCTGA

TCTATACGGTTTCCTATCGGGCCTCTGGAGTCCCAGACAGGTTCAGTGGC

AGTGGGTCAGGCACTGATTTCACACTGAAAATCAGCAGGGTGGAGGCTGA

GGATGTTGGAGTTTATTACTGCATGCAACGTATAGAGTTTCCGATCACCT

TCGGCCAAGGGACCCGACTGGAGATTAAACGAACTGTGGCTGCACCATCT

GTCTTCATCTTCCCGCCATCTGATGAGCAGTTGAAATCTGGAACTGCCTC

TGTTGTGTGCCTGCTGAATAA3'

ATAACTTCTATCCCAGAGAGGCCAAAGTACAGTGGAAGGTGGATAACGCC

CTCCAATCGGGTAACTCCCAGGAGAGTGTCACAGAGCAGGACAGCAAGGA

CAGCACCTACAGCCTCAGCAGCACCCTGACGCTGAGCAAAGCAGACTACG

AGAAACACAAAGTCTACGCCTGCGAAGTCACCCATCAGGGCCTGAGCTCG

CCCGTCACAAAGAGCTTCAACAGGGGAGAGTGTTAGGCGGCCG3'

Amino acid sequence of light chain variable region and portion constant region by SEQ ID NO:51:

(SEQ ID NO: 52)
METPAQLLFLLLLWLPDTTG DIVMTQTPLSLPVTPGEPASISC RSSRSLLDSDDGNTYLD

WYLQKPGQSPQLLIY TLSYRAS GVPDRFSGSGSGTDFTLKISRVEAEDVGVYYC MQR

VEFPIT FGQGTRLEIKR TVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSPVTKSFNRGEC

Anti-TIM-1 mAb 2.76

Nucleotide sequence of heavy chain variable region and a portion of constant region:

(SEQ ID NO: 45)
5'GAGCAGTCGGGGGGCGGCGTGGTCCAGCCTGGGAGGTCCCTGAGACTC

TCCTGTGCAGCGTCTGGATTCACCTTCAGTAGCTATGGCATGTACTGGGT

Amino acid sequence of light chain variable region and a portion of constant region encoded by SEQ ID NO:47:

(SEQ ID NO: 137)
XXXXTQCPLSLPVTPGEPASISCRSSQSLLDSDDGNTYLDWYLQKPGQSP

QLLIYTVSYRASGVPDRFSGSGSGTDFTLKISRVEAEDVGVYYCMQRIEF

PITFGQGTRLEIKRTVAAPSVFIFPPSDEQLKSGTASVVCLLN

INCORPORATION BY REFERENCE

All references cited herein, including patents, patent applications, papers, text books, and the like, and the references cited therein, to the extent that they are not already, are hereby incorporated herein by reference in their entirety. In addition, the following references are also incorporated by reference herein in their entirety, including the references cited in such references:

EQUIVALENTS

While the preferred embodiment of the invention has been illustrated and described, it is to be understood that this invention is capable of variation and modification by those skilled in the art to which it pertains, and is therefore not limited to the precise terms set forth, but also such changes and alterations which may be made for adapting the invention to various usages and conditions. Accordingly, such changes and alterations are properly intended to be within the full range of equivalents, and therefore within the purview of the following claims.

The invention and the manner and a process of making and using it has been described in such full, clear, concise and exact terms so as to enable any person skilled in the art to which it pertains, or with which it is most nearly connected, to make and use the same.

What is claimed is:

1. A method of treating renal cancer in a subject in need thereof, the method comprising:

administering to said subject a therapeutically effective dose of an isolated human antibody or antigen-binding fragment thereof, that specifically binds T cell, immunoglobulin domain and mucin domain 1 (TIM-1), wherein the antibody or the antigen-binding fragment thereof comprises a heavy chain amino acid sequence comprising three complementarity determining regions (CDRs) and a light chain amino acid sequence comprising three CDRs, wherein the three heavy chain CDRs and the three light chain CDRs are selected from the group consisting of:

(a) a heavy chain CDR1 comprising the amino acid sequence of residues 45-54 of SEQ ID NO: 50, a heavy chain CDR2 comprising the amino acid sequence of residues 69-85 of SEQ ID NO: 50, a heavy chain CDR3 comprising the amino acid sequence of residues 118-131 of SEQ ID NO: 50, a light chain CDR1 comprising the amino acid sequence of residues 44-60 of SEQ ID NO: 52, a light chain CDR2 comprising the amino acid sequence of residues 76-82 of SEQ ID NO: 52, and a light chain CDR3 comprising the amino acid sequence of residues 115-123 of SEQ ID NO: 52;

(b) a heavy chain CDR1 comprising the amino acid sequence of residues 26-35 of SEQ ID NO: 126, a heavy chain CDR2 comprising the amino acid sequence of residues 50-66 of SEQ ID NO: 126, a heavy chain CDR3 comprising the amino acid sequence of residues 99-102 of SEQ ID NO: 126, a light chain CDR1 comprising the amino acid sequence of residues 24-35 of SEQ ID NO: 127, a light chain CDR2 comprising the amino acid sequence of residues 51-57 of SEQ ID NO: 127, and a light chain CDR3 comprising the amino acid sequence of residues 90-99 of SEQ ID NO: 127;

(c) a heavy chain CDR1 comprising the amino acid sequence of residues 26-35 of SEQ ID NO: 136, a heavy chain CDR2 comprising the amino acid sequence of residues 50-66 of SEQ ID NO: 136, a heavy chain CDR3 comprising the amino acid sequence of residues 99-112 of SEQ ID NO: 136, a light chain CDR1 comprising the amino acid sequence of residues 24-40 of SEQ ID NO: 137, a light chain CDR2 comprising the amino acid sequence of residues 52-62 of SEQ ID NO: 137, and a light chain CDR3 comprising the amino acid sequence of residues 95-103 of SEQ ID NO: 137;

(d) a heavy chain CDR1 comprising the amino acid sequence of residues 26-37 of SEQ ID NO: 130, a heavy chain CDR2 comprising the amino acid sequence of residues 52-67 of SEQ ID NO: 130, a heavy chain CDR3 comprising the amino acid sequence of residues 100-113 of SEQ ID NO: 130, a light chain CDR1 comprising the amino acid sequence of residues 24-34 of SEQ ID NO: 131, a light chain CDR2 comprising the amino acid sequence of residues 50-56 of SEQ ID NO: 131, and a light chain CDR3 comprising the amino acid sequence of residues 89-97 of SEQ ID NO: 131;

(e) a heavy chain CDR1 comprising the amino acid sequence of residues 26-35 of SEQ ID NO: 122, a heavy chain CDR2 comprising the amino acid sequence of residues 50-66 of SEQ ID NO: 122, a heavy chain CDR3 comprising the amino acid sequence of residues 99-112 of SEQ ID NO: 122, a light chain CDR1 comprising the amino acid sequence of residues 24-34 of SEQ ID NO: 123, a light chain CDR2 comprising the amino acid sequence of residues 50-56 of SEQ ID NO: 123, and a light chain CDR3 comprising the amino acid sequence of residues 89-97 of SEQ ID NO: 123;

(f) a heavy chain CDR1 comprising the amino acid sequence of residues 26-35 of SEQ ID NO: 132, a heavy chain CDR2 comprising the amino acid sequence of residues 50-66 of SEQ ID NO: 132, a heavy chain CDR3 comprising the amino acid sequence of residues 99-112 of SEQ ID NO: 132, a light chain CDR1 comprising the amino acid sequence of residues 24-34 of SEQ ID NO: 133, a light chain CDR2 comprising the amino acid sequence of residues 50-56 of SEQ ID NO: 133, and a light chain CDR3 comprising the amino acid sequence of residues 89-97 of SEQ ID NO: 133;

(g) a heavy chain CDR1 comprising the amino acid sequence of residues 29-38 of SEQ ID NO: 128, a heavy chain CDR2 comprising the amino acid sequence of residues 53-69 of SEQ ID NO: 128, a heavy chain CDR3 comprising the amino acid sequence of residues 102-115 of SEQ ID NO: 128, a light chain CDR1 comprising the amino acid sequence of residues 39-55 of SEQ ID NO: 129, a light chain CDR2 comprising the amino acid sequence of residues 71-77 of SEQ ID NO: 129, and a light chain CDR3 comprising the amino acid sequence of residues 110-118 of SEQ ID NO: 129;
(h) a heavy chain CDR1 comprising the amino acid sequence of residues 26-35 of SEQ ID NO: 118, a heavy chain CDR2 comprising the amino acid sequence of residues 50-68 of SEQ ID NO: 118, a heavy chain CDR3 comprising the amino acid sequence of residues 101-107 of SEQ ID NO: 118, a light chain CDR1 comprising the amino acid sequence of residues 24-39 of SEQ ID NO: 119, a light chain CDR2 comprising the amino acid sequence of residues 55-61 of SEQ ID NO: 119, and a light chain CDR3 comprising the amino acid sequence of residues 94-102 of SEQ ID NO: 119;
(i) a heavy chain CDR1 comprising the amino acid sequence of residues 30-41 of SEQ ID NO: 114, a heavy chain CDR2 comprising the amino acid sequence of residues 56-71 of SEQ ID NO: 114, a heavy chain CDR3 comprising the amino acid sequence of residues 104-113 of SEQ ID NO: 114, a light chain CDR1 comprising the amino acid sequence of residues 39-49 of SEQ ID NO: 115, a light chain CDR2 comprising the amino acid sequence of residues 65-71 of SEQ ID NO: 115, and a light chain CDR3 comprising the amino acid sequence of residues 104-112 of SEQ ID NO: 115;
(j) a heavy chain CDR1 comprising the amino acid sequence of residues 26-35 of SEQ ID NO: 124, a heavy chain CDR2 comprising the amino acid sequence of residues 50-68 of SEQ ID NO: 124, a heavy chain CDR3 comprising the amino acid sequence of residues 101-107 of SEQ ID NO: 124, a light chain CDR1 comprising the amino acid sequence of residues 24-39 of SEQ ID NO: 125, a light chain CDR2 comprising the amino acid sequence of residues 55-61 of SEQ ID NO: 125, and a light chain CDR3 comprising the amino acid sequence of residues 94-102 of SEQ ID NO: 125;
(k) a heavy chain CDR1 comprising the amino acid sequence of residues 28-37 of SEQ ID NO: 116, a heavy chain CDR2 comprising the amino acid sequence of residues 52-68 of SEQ ID NO: 116, a heavy chain CDR3 comprising the amino acid sequence of residues 101-103 of SEQ ID NO: 116, a light chain CDR1 comprising the amino acid sequence of residues 38-53 of SEQ ID NO: 117, a light chain CDR2 comprising the amino acid sequence of residues 69-75 of SEQ ID NO: 117, and a light chain CDR3 comprising the amino acid sequence of residues 108-116 of SEQ ID NO: 117; and
(l) a heavy chain CDR1 comprising the amino acid sequence of residues 26-35 of SEQ ID NO: 120, a heavy chain CDR2 comprising the amino acid sequence of residues 50-66 of SEQ ID NO: 120, a heavy chain CDR3 comprising the amino acid sequence of residues 99-102 of SEQ ID NO: 120, a light chain CDR1 comprising the amino acid sequence of residues 24-39 of SEQ ID NO: 121, a light chain CDR2 comprising the amino acid sequence of residues 55-61 of SEQ ID NO: 121, and a light chain CDR3 comprising the amino acid sequence of residues 94-103 of SEQ ID NO: 121.

2. A method of treating ovarian cancer in a subject in need thereof, the method comprising:
administering to said subject a therapeutically effective dose of an isolated human antibody or antigen-binding fragment thereof, that specifically binds T cell, immunoglobulin domain and mucin domain 1 (TIM-1), wherein the antibody or the antigen-binding fragment thereof comprises a heavy chain amino acid sequence comprising three complementarity determining regions (CDRs) and a light chain amino acid sequence comprising three CDRs, wherein the three heavy chain CDRs and the three light chain CDRs are selected from the group consisting of:
(a) a heavy chain CDR1 comprising the amino acid sequence of residues 45-54 of SEQ ID NO: 50, a heavy chain CDR2 comprising the amino acid sequence of residues 69-85 of SEQ ID NO: 50, a heavy chain CDR3 comprising the amino acid sequence of residues 118-131 of SEQ ID NO: 50, a light chain CDR1 comprising the amino acid sequence of residues 44-60 of SEQ ID NO: 52, a light chain CDR2 comprising the amino acid sequence of residues 76-82 of SEQ ID NO: 52, and a light chain CDR3 comprising the amino acid sequence of residues 115-123 of SEQ ID NO: 52;
(b) a heavy chain CDR1 comprising the amino acid sequence of residues 26-35 of SEQ ID NO: 126, a heavy chain CDR2 comprising the amino acid sequence of residues 50-66 of SEQ ID NO: 126, a heavy chain CDR3 comprising the amino acid sequence of residues 99-102 of SEQ ID NO: 126, a light chain CDR1 comprising the amino acid sequence of residues 24-35 of SEQ ID NO: 127, a light chain CDR2 comprising the amino acid sequence of residues 51-57 of SEQ ID NO: 127, and a light chain CDR3 comprising the amino acid sequence of residues 90-99 of SEQ ID NO: 127;
(c) a heavy chain CDR1 comprising the amino acid sequence of residues 26-35 of SEQ ID NO: 136, a heavy chain CDR2 comprising the amino acid sequence of residues 50-66 of SEQ ID NO: 136, a heavy chain CDR3 comprising the amino acid sequence of residues 99-112 of SEQ ID NO: 136, a light chain CDR1 comprising the amino acid sequence of residues 24-40 of SEQ ID NO: 137, a light chain CDR2 comprising the amino acid sequence of residues 56-62 of SEQ ID NO: 137, and a light chain CDR3 comprising the amino acid sequence of residues 95-103 of SEQ ID NO: 137;
(d) a heavy chain CDR1 comprising the amino acid sequence of residues 26-37 of SEQ ID NO: 130, a heavy chain CDR2 comprising the amino acid sequence of residues 52-67 of SEQ ID NO: 130, a heavy chain CDR3 comprising the amino acid sequence of residues 100-113 of SEQ ID NO: 130, a light chain CDR1 comprising the amino acid sequence of residues 24-34 of SEQ ID NO: 131, a light chain CDR2 comprising the amino acid sequence of residues 50-56 of SEQ ID NO: 131, and a light chain CDR3 comprising the amino acid sequence of residues 89-97 of SEQ ID NO: 131;
(e) a heavy chain CDR1 comprising the amino acid sequence of residues 26-35 of SEQ ID NO: 122, a heavy chain CDR2 comprising the amino acid sequence of residues 50-66 of SEQ ID NO: 122, a heavy chain CDR3 comprising the amino acid sequence of residues 99-112 of SEQ ID NO: 122, a light chain CDR1 comprising the amino acid sequence of residues 24-34 of SEQ ID NO: 123, a light chain CDR2 comprising the amino acid sequence of residues 50-56 of SEQ ID NO: 123, and a light chain CDR3 comprising the amino acid sequence of residues 89-97 of SEQ ID NO: 123;

(f) a heavy chain CDR1 comprising the amino acid sequence of residues 26-35 of SEQ ID NO: 132, a heavy chain CDR2 comprising the amino acid sequence of residues 50-66 of SEQ ID NO: 132, a heavy chain CDR3 comprising the amino acid sequence of residues 99-112 of SEQ ID NO: 132, a light chain CDR1 comprising the amino acid sequence of residues 24-34 of SEQ ID NO: 133, a light chain CDR2 comprising the amino acid sequence of residues 50-56 of SEQ ID NO: 133, and a light chain CDR3 comprising the amino acid sequence of residues 89-97 of SEQ ID NO: 133;

(g) a heavy chain CDR1 comprising the amino acid sequence of residues 29-38 of SEQ ID NO: 128, a heavy chain CDR2 comprising the amino acid sequence of residues 53-69 of SEQ ID NO: 128, a heavy chain CDR3 comprising the amino acid sequence of residues 102-115 of SEQ ID NO: 128, a light chain CDR1 comprising the amino acid sequence of residues 39-55 of SEQ ID NO: 129, a light chain CDR2 comprising the amino acid sequence of residues 71-77 of SEQ ID NO: 129, and a light chain CDR3 comprising the amino acid sequence of residues 110-118 of SEQ ID NO: 129;

(h) a heavy chain CDR1 comprising the amino acid sequence of residues 26-35 of SEQ ID NO: 118, a heavy chain CDR2 comprising the amino acid sequence of residues 50-68 of SEQ ID NO: 118, a heavy chain CDR3 comprising the amino acid sequence of residues 101-107 of SEQ ID NO: 118, a light chain CDR1 comprising the amino acid sequence of residues 24-39 of SEQ ID NO: 119, a light chain CDR2 comprising the amino acid sequence of residues 55-61 of SEQ ID NO: 119, and a light chain CDR3 comprising the amino acid sequence of residues 94-102 of SEQ ID NO: 119;

(i) a heavy chain CDR1 comprising the amino acid sequence of residues 30-41 of SEQ ID NO: 114, a heavy chain CDR2 comprising the amino acid sequence of residues 56-71 of SEQ ID NO: 114, a heavy chain CDR3 comprising the amino acid sequence of residues 104-113 of SEQ ID NO: 114, a light chain CDR1 comprising the amino acid sequence of residues 39-49 of SEQ ID NO: 115, a light chain CDR2 comprising the amino acid sequence of residues 65-71 of SEQ ID NO: 115, and a light chain CDR3 comprising the amino acid sequence of residues 104-112 of SEQ ID NO: 115;

(j) a heavy chain CDR1 comprising the amino acid sequence of residues 26-35 of SEQ ID NO: 124, a heavy chain CDR2 comprising the amino acid sequence of residues 50-68 of SEQ ID NO: 124, a heavy chain CDR3 comprising the amino acid sequence of residues 101-107 of SEQ ID NO: 124, a light chain CDR1 comprising the amino acid sequence of residues 24-39 of SEQ ID NO: 125, a light chain CDR2 comprising the amino acid sequence of residues 55-61 of SEQ ID NO: 125, and a light chain CDR3 comprising the amino acid sequence of residues 94-102 of SEQ ID NO: 125;

(k) a heavy chain CDR1 comprising the amino acid sequence of residues 28-37 of SEQ ID NO: 116, a heavy chain CDR2 comprising the amino acid sequence of residues 52-68 of SEQ ID NO: 116, a heavy chain CDR3 comprising the amino acid sequence of residues 101-103 of SEQ ID NO: 116, a light chain CDR1 comprising the amino acid sequence of residues 38-53 of SEQ ID NO: 117, a light chain CDR2 comprising the amino acid sequence of residues 69-75 of SEQ ID NO: 117, and a light chain CDR3 comprising the amino acid sequence of residues 108-116 of SEQ ID NO: 117; and (l) a heavy chain CDR1 comprising the amino acid sequence of residues 26-35 of SEQ ID NO: 120, a heavy chain CDR2 comprising the amino acid sequence of residues 50-66 of SEQ ID NO: 120, a heavy chain CDR3 comprising the amino acid sequence of residues 99-102 of SEQ ID NO: 120, a light chain CDR1 comprising the amino acid sequence of residues 24-39 of SEQ ID NO: 121, a light chain CDR2 comprising the amino acid sequence of residues 55-61 of SEQ ID NO: 121, and a light chain CDR3 comprising the amino acid sequence of residues 94-103 of SEQ ID NO: 121.

3. The method of claim 1, wherein said antibody is a monoclonal antibody.

4. The method of claim 2, wherein said antibody is a monoclonal antibody.

5. The method of claim 1, wherein said binding fragment comprises a Fab, Fab', F(ab')$_2$, or Fv fragment of said antibody.

6. The method of claim 2, wherein said binding fragment comprises a Fab, Fab', F(ab')$_2$, or Fv fragment of said antibody.

7. The method of claim 1, wherein said antibody is a single chain antibody.

8. The method of claim 2, wherein said antibody is a single chain antibody.

9. The method of claim 1, wherein the antibody or binding fragment is conjugated to a therapeutic agent.

10. The method of claim 9, wherein the therapeutic agent is a toxin.

11. The method of claim 9, wherein the therapeutic agent is a radioactive isotope.

12. The method of claim 9, wherein the therapeutic agent is a chemotherapeutic agent.

13. The method of claim 2, wherein the antibody or binding fragment is conjugated to a therapeutic agent.

14. The method of claim 13, wherein the therapeutic agent is a toxin.

15. The method of claim 13, wherein the therapeutic agent is a radioactive isotope.

16. The method of claim 13, wherein the therapeutic agent is a chemotherapeutic agent.

* * * * *

SEQUENCE LISTING

```
<160> NUMBER OF SEQ ID NOS: 199

<210> SEQ ID NO 1
<211> LENGTH: 509
<212> TYPE: DNA
<213> ORGANISM: Homo sapiens

<400> SEQUENCE: 1
tgggtcctgt cccaggtgca gctgcaggag tcgggcccag gactggtgaa gccttcggag     60
accctgtccc tcacctgcac tgtctctggt ggctccgtca gcagtggtgg ttactactgg    120
agctggatcc ggcagccccc agggaaggga ctggagtgga ttgggtttat ctattacact    180
gggagcacca actacaaccc ctccctcaag agtcgagtct ccatatcagt agacacgtcc    240
aagaaccagt tctccctgaa gctgagctct gtgaccgctg cggacgcggc cgtgtattac    300
tgtgcgagag attatgactg gagcttccac tttgactact ggggccaggg aaccctggtc    360
accgtctcct cagcctccac caagggccca tcggtcttcc ccctggcgcc ctgctccagg    420
agcacctccg agagcacagc ggccctgggc tgcctggtca aggactactt ccccgaaccg    480
gtgacggtgt cgtggaactc aggcgctct                                      509

<210> SEQ ID NO 2
<211> LENGTH: 121
<212> TYPE: PRT
<213> ORGANISM: Homo sapiens

<400> SEQUENCE: 2

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
                20                  25                  30

Gly Tyr Tyr Trp Ser Trp Ile Arg Gln Pro Pro Gly Lys Gly Leu Glu
            35                  40                  45

Trp Ile Gly Phe Ile Tyr Tyr Thr Gly Ser Thr Asn Tyr Asn Pro Ser
    50                  55                  60

Leu Lys Ser Arg Val Ser Ile Ser Val Asp Thr Ser Lys Asn Gln Phe
65                  70                  75                  80

Ser Leu Lys Leu Ser Ser Val Thr Ala Ala Asp Ala Ala Val Tyr Tyr
                85                  90                  95
```

Cys Ala Arg Asp Tyr Asp Trp Ser Phe His Phe Asp Tyr Trp Gly Gln
            100                 105                 110

Gly Thr Leu Val Thr Val Ser Ser Ala
        115                 120

<210> SEQ ID NO 3
<211> LENGTH: 504
<212> TYPE: DNA
<213> ORGANISM: Homo sapiens

<400> SEQUENCE: 3
cagctcctgg ggctcctgct gctctggttc ccaggtgcca ggtgtgacat ccagatgacc    60
cagtctccat cctccctgtc tgcatctata ggagacagag tcaccatcac ttgccgggca   120
agtcagggca ttagaaatga tttaggctgg tatcagcaga aaccagggaa agcccctaag   180
cgcctgatct atgctgcatc cagtttgcaa agtggggtcc catcaaggtt cagcggcagt   240
ggatctggga cagaattcac tctcacaatc agcagcctgc agcctgaaga ttttgcaact   300
tattactgtc tacagcataa tagttaccct ctcactttcg gcggagggac caaggtggag   360
atcaaacgaa ctgtggctgc accatctgtc ttcatcttcc cgccatctga tgagcagttg   420
aaatctggaa ctgcctctgt tgtgtgcctg ctgaataact ctatcccag agaggccaaa    480 gtacagtgga aggtggataa cgcc                                          504

<210> SEQ ID NO 4
<211> LENGTH: 108
<212> TYPE: PRT
<213> ORGANISM: Homo sapiens

<400> SEQUENCE: 4

Asp Ile Gln Met Thr Gln Ser Pro Ser Ser Leu Ser Ala Ser Ile Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys Arg
            100                 105

<210> SEQ ID NO 5
<211> LENGTH: 469
<212> TYPE: DNA
<213> ORGANISM: Homo sapiens

<400> SEQUENCE: 5
cagtgtgagg tgcagctggt ggagtctggg ggaggcttgg tccagcctgg ggggtccctg    60
agactctcct gtgcagcctc tggattcacc tttactaact attggatgag ctgggtccgc   120
caggctccag ggaaggggct ggagtgggtg gccaacatac agcaagatgg aagtgagaaa   180
tactatgtgg actctgtgag gggccgattc accatctcca gagacaacgc caagaactca   240
ctgtatctgc aaatgaacag cctgagagcc gaggactcgg ctgtgtatta ctgtgcgaga   300

```
tgggactact ggggccaggg aaccctggtc accgtctcct cagcctccac caagggccca    360
tcggtcttcc ccctggcgcc ctgctccagg agcacctccg agagcacagc ggccctgggc    420
tgcctggtca aggactactt ccccgaaccg gtgagcggtg tcgtggaac                469
```

<210> SEQ ID NO 6
<211> LENGTH: 113
<212> TYPE: PRT
<213> ORGANISM: Homo sapiens

<400> SEQUENCE: 6

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Trp Met Ser Trp Val Arg Gln Ala Pro Gly Lys Gly Leu Glu Trp Val
        35                  40                  45

Ala Asn Ile Gln Gln Asp Gly Ser Glu Lys Tyr Tyr Val Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Ser Ala Val Tyr Tyr Cys
                85                  90                  95

Ala Arg Trp Asp Tyr Trp Gly Gln Gly Thr Leu Val Thr Val Ser Ser
            100                 105                 110

Ala
```

<210> SEQ ID NO 7
<211> LENGTH: 454
<212> TYPE: DNA
<213> ORGANISM: Homo sapiens

<400> SEQUENCE: 7

```
cttctggggc tgctaatgct ctgggtccct ggatccagtg gggatattgt gatgacccag     60
actccactct cctcaactgt catccttgga cagccggcct ccatctcctg caggtctagt    120
caaagcctcg tacacagtga tggaaacacc tacttgaatt ggcttcagca gaggccaggc    180
cagcctccaa gactcctaat ttatatgatt tctaaccggt tctctggggt cccagacaga    240
ttcagtggca gtggggcagg gacagatttc acactgaaaa tcagcagggt ggaagctgag    300
gatgtcgggg tttattactg catgcaagct acagaatctc ctcagacgtt cggccaaggg    360
accaaggtgg aaatcaaacg aactgtggct gcaccatctg tcttcatctt cccgccatct    420
gatgagcagt tgaaatctgg aagggcctct gttg                                454
```

<210> SEQ ID NO 8
<211> LENGTH: 113
<212> TYPE: PRT
<213> ORGANISM: Homo sapiens

<400> SEQUENCE: 8

```
Asp Ile Val Met Thr Gln Thr Pro Leu Ser Ser Thr Val Ile Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Leu Gln Gln Arg Pro Gly Gln Pro
        35                  40                  45

Pro Arg Leu Leu Ile Tyr Met Ile Ser Asn Arg Phe Ser Gly Val Pro
```

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Glu Ser Pro Gln Thr Phe Gly Gln Gly Thr Lys Val Glu Ile Lys
            100                 105                 110

Arg

<210> SEQ ID NO 9
<211> LENGTH: 529
<212> TYPE: DNA
<213> ORGANISM: Homo sapiens

<400> SEQUENCE: 9
gagcagtcgg ggggaggcgt ggtaaagcct gggggtctc ttagactctc ctgtgcagcc      60
tctggattca ctttcagtaa cgcctggatg acctgggtcc gccaggctcc agggaagggg    120
ctggagtggg ttggccgtat taaaaggaga actgatggtg ggacaacaga ctacgctgca    180
cccgtgaaag gcagattcac catctcaaga gatgattcaa aaaacacgct gtatctgcaa    240
atgaacaacc tgaaaaacga ggacacagcc gtgtattact gtacctcagt cgataatgac    300
gtggactact ggggccaggg aaccctggtc accgtctcct cagcttccac caagggccca    360
tccgtcttcc ccctggcgcc ctgctccagg agcacctccg agagcacagc cgccctgggc    420
tgcctggtca aggactactt ccccgaaccg gtgacggtgt cgtggaactc aggcgccctg    480
accagcggcg tgcacacctt cccggctgtc ctacagtcct caggactct                529

<210> SEQ ID NO 10
<211> LENGTH: 119
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: Xaa is any amino acid

<400> SEQUENCE: 10

Xaa Xaa Xaa Xaa Glu Gln Ser Gly Gly Gly Val Val Lys Pro Gly Gly
1               5                   10                  15

Ser Leu Arg Leu Ser Cys Ala Ala Ser Gly Phe Thr Phe Ser Asn Ala
            20                  25                  30

Trp Met Thr Trp Val Arg Gln Ala Pro Gly Lys Gly Leu Glu Trp Val
        35                  40                  45

Gly Arg Ile Lys Arg Arg Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Asn Leu Lys Asn Glu Asp Thr Ala Val Tyr
                85                  90                  95

Tyr Cys Thr Ser Val Asp Asn Asp Val Asp Tyr Trp Gly Gln Gly Thr
            100                 105                 110

Leu Val Thr Val Ser Ser Ala
        115

<210> SEQ ID NO 11
<211> LENGTH: 447
<212> TYPE: DNA

<213> ORGANISM: Homo sapiens

<400> SEQUENCE: 11

```
ctgactcagt ctccactctc cctgcccgtc accctggag agccggcctc catctcctgc      60
aggtctagtc agagcctcct gcatagtaat ggatacaact atttggattg gtacctgcag     120
aagccagggc agtctccaca gctcctgatc tatttgggtt ctaatcgggc ctccggggtc     180
cctgacaggt tcagtggcag tggatcaggc acagatttta cactgaaaat cagcagagtg     240
gaggctgagg atattggtct ttattactgc atgcaagctc tacaaactcc gctcactttc     300
ggcggaggga ccaaggtgga catcaaacga actgtggctg caccatctgt cttcatcttc     360
ccgccatctg atgagcagtt gaaatctgga actgcctctg ttgtgtgcct gctgaataac     420
ttctatccca gagaggccaa agtacag                                         447
```

<210> SEQ ID NO 12
<211> LENGTH: 113
<212> TYPE: PRT
<213> ORGANISM: Homo sapiens
<220> FEATURE:
<221> NAME/KEY: MISC_FEATURE
<222> LOCATION: (1)..(3)
<223> OTHER INFORMATION: Xaa is any amino acid

<400> SEQUENCE: 12

Xaa Xaa Xaa Leu Thr Gln Ser Pro Leu Ser Leu Pro Val Thr Pro Gly
1               5                   10                  15
Glu Pro Ala Ser Ile Ser Cys Arg Ser Ser Gln Ser Leu Leu His Ser
            20                  25                  30
Asn Gly Tyr Asn Tyr Leu Asp Trp Tyr Leu Gln Lys Pro Gly Gln Ser
        35                  40                  45
Pro Gln Leu Leu Ile Tyr Leu Gly Ser Asn Arg Ala Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Ile Gly Leu Tyr Tyr Cys Met Gln Ala
                85                  90                  95
Leu Gln Thr Pro Leu Thr Phe Gly Gly Gly Thr Lys Val Asp Ile Lys
            100                 105                 110
Arg

<210> SEQ ID NO 13
<211> LENGTH: 538
<212> TYPE: DNA
<213> ORGANISM: Homo sapiens

<400> SEQUENCE: 13

```
caggtgcagc tggagcagtc ggggggaggc ttggtacagc ctgggggtc cctgagactc       60
tcctgtgcag cctctggatt caccttcagt acctatagca tgaactgggt ccgccaggct     120
ccagggaagg ggctggagtg ggtttcatac attagaagta gtactagtac catatactat     180
gcagagtccc tgaagggccg attcaccatc tccagcgaca atgccaagaa ttcactatat     240
ctgcaaatga acagcctgag agacgaggac acggctgtgt attactgtgc gcgggacttt     300
gactactggg gccagggaac cctggtcacc gtctcctcag cttccaccaa gggcccatcc     360
gtcttccccc tggcgccctg ctccaggagc acctccgaga gcacagccgc cctgggctgc     420
ctggtcaagg actacttccc cgaaccggtg acggtgtcgt ggaactcagg cgccctgacc     480
```

```
agcggcgtgc acaccttccc ggctgtccta cagtcctcag gactctactc cctcagca      538
```

<210> SEQ ID NO 14
<211> LENGTH: 114
<212> TYPE: PRT
<213> ORGANISM: Homo sapiens

<400> SEQUENCE: 14

```
Gln Val Gln Leu Glu Gln Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ser Met Asn Trp Val Arg Gln Ala Pro Gly Lys Gly Leu Glu Trp Val
        35                  40                  45

Ser Tyr Ile Arg Ser Ser Thr Ser Thr Ile Tyr Tyr Ala Glu Ser Leu
    50                  55                  60

Lys Gly Arg Phe Thr Ile Ser Ser Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp Phe Asp Tyr Trp Gly Gln Gly Thr Leu Val Thr Val Ser
            100                 105                 110

Ser Ala
```

<210> SEQ ID NO 15
<211> LENGTH: 490
<212> TYPE: DNA
<213> ORGANISM: Homo sapiens

<400> SEQUENCE: 15

```
gaaatccagc tgactcagtc tccactctcc tcacctgtca cccttggaca gccggcctcc      60
atctcctgca ggtctagtca aagcctcgta cacagtgatg gagacaccta cttgaattgg     120
cttcagcaga ggccaggcca gcctccaaga ctcctaattt ataagatttc tacccggttc     180
tctggggtcc ctgacagatt cagtggcagt ggggcaggga cagatttcac actgaaaatc     240
agcagggtgg agactgacga tgtcgggatt tattactgca tgcaaactac acaaattcct     300
caaatcacct tcggccaagg gacacgactg gagattaaac gaactgtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta                                                            490
```

<210> SEQ ID NO 16
<211> LENGTH: 114
<212> TYPE: PRT
<213> ORGANISM: Homo sapiens

<400> SEQUENCE: 16

```
Glu Ile Gln Leu Thr Gln Ser Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asp Thr Tyr Leu Asn Trp Leu Gln Gln Arg Pro Gly Gln Pro
        35                  40                  45

Pro Arg Leu Leu Ile Tyr Lys Ile Ser Thr Arg Phe Ser Gly Val Pro
    50                  55                  60
```

Asp Arg Phe Ser Gly Ser Gly Ala Gly Thr Asp Phe Thr Leu Lys Ile
 65                  70                  75                  80

Ser Arg Val Glu Thr Asp Asp Val Gly Ile Tyr Tyr Cys Met Gln Thr
                 85                  90                  95

Thr Gln Ile Pro Gln Ile Thr Phe Gly Gln Gly Thr Arg Leu Glu Ile
            100                 105                 110

Lys Arg

<210> SEQ ID NO 17
<211> LENGTH: 568
<212> TYPE: DNA
<213> ORGANISM: Homo sapiens

<400> SEQUENCE: 17
caggtgcagc tggagcagtc ggggggaggc gtggtccagc ctggggaggtc cctgagactc      60 tcctgtgcag cgtctggatt caccttcagt cgctatggca tgcactgggt ccgccaggct     120
ccaggcaagg ggctgaaatg ggtggcagtt atatggtatg atggaagtaa taaactctat     180
gcagactccg tgaagggccg attcaccatc tccagagaca attccaagaa cacgctgtat     240
ctgcaaatga acagcctgag agccgaggac acggctgtgt attactgtgc gagagattac     300
tatgataata gtagacatca ctgggggttt gactactggg gccagggaac cctggtcacc     360
gtctcctcag cttccaccaa gggcccatcc gtcttccccc tggcgccctg ctccaggagc     420
acctccgaga gcacagccgc cctgggctgc ctggtcaagg actacttccc cgaaccggtg     480
acggtgtcgt ggaactcagg cgccctgacc agcggcgtgc acaccttccc ggctgtccta     540
cagtcctcag gactctactc cctcagca                                        568

<210> SEQ ID NO 18
<211> LENGTH: 124
<212> TYPE: PRT
<213> ORGANISM: Homo sapiens

<400> SEQUENCE: 18

Gln Val Gln Leu Glu Gln Ser Gly Gly Gly Val Val Gln Pro Gly Arg
 1               5                  10                  15

Ser Leu Arg Leu Ser Cys Ala Ala Ser Gly Phe Thr Phe Ser Arg Tyr
             20                  25                  30

Gly Met His Trp Val Arg Gln Ala Pro Gly Lys Gly Leu Lys Trp Val
         35                  40                  45

Ala Val Ile Trp Tyr Asp Gly Ser Asn Lys Leu Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Tyr Tyr Asp Asn Ser Arg His His Trp Gly Phe Asp Tyr
            100                 105                 110

Trp Gly Gln Gly Thr Leu Val Thr Val Ser Ser Ala
        115                 120

<210> SEQ ID NO 19
<211> LENGTH: 472
<212> TYPE: DNA
<213> ORGANISM: Homo sapiens

<400> SEQUENCE: 19

```
gacatccagc tgacccagtc tccatcctcc ctgtctgcat ctgtaggaga cagagtcacc    60
atcacttgcc gggcaagtca gagtatttat agttatttaa attggtatca gcagaaacca   120
gggaaagccc ctaagctcct gatctatgct gcatccagtt tgcaaagtgg ggtcccatcc   180
aggttcagtg gcagtggatc tgggacagat ttcactctca ccatcagcag tctgcaacct   240
gaagattttg caacttacta ctgtcaacag agttacagta cccctccgac gttcggccaa   300
gggaccaagg tggaaatcaa acgaactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg ta           472
```

<210> SEQ ID NO 20
<211> LENGTH: 108
<212> TYPE: PRT
<213> ORGANISM: Homo sapiens

<400> SEQUENCE: 20

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Tyr Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys Arg
            100                 105

<210> SEQ ID NO 21
<211> LENGTH: 528
<212> TYPE: DNA
<213> ORGANISM: Homo sapiens

<400> SEQUENCE: 21

```
cagtcggggg gaggcttggt aaagcctggg gggtccctta gactctcctg tgcagcctct    60
ggattcactt tcagtaacgc ctggatgacc tgggtccgcc aggctccagg aaggggctg    120 gagtgggttg gccgtattaa aggaaaaact gatggtggga caacagacta cgctgcaccc   180
gtgaaaggca gattcaccat ctcaagagat gattcagaaa acacgctgta tctgcaaatg   240
aacagcctgg aaaccgagga cacagccgtg tattactgta ccacagtcga taacagtggt   300
gactactggg gccagggaac cctggtcacc gtctcctcag cttccaccaa gggcccatcc   360
gtcttccccc tggcgccctg ctccaggagc acctccgaga gcagccgc cctgggctgc    420 ctggtcaagg actacttccc cgaaccggtg acggtgtcgt ggaactcagg cgccctgacc   480
agcggcgtgc acaccttccc ggctgtccta cagtcctcag gactctct               528
```

<210> SEQ ID NO 22
<211> LENGTH: 119
<212> TYPE: PRT
<213> ORGANISM: Homo sapiens
<220> FEATURE:
<221> NAME/KEY: MISC_FEATURE
<222> LOCATION: (1)..(5)

<223> OTHER INFORMATION: Xaa is any amino acid

<400> SEQUENCE: 22

```
Xaa Xaa Xaa Xaa Xaa Gln Ser Gly Gly Gly Leu Val Lys Pro Gly
1               5                   10                  15
Ser Leu Arg Leu Ser Cys Ala Ala Ser Gly Phe Thr Phe Ser Asn Ala
            20                  25                  30
Trp Met Thr Trp Val Arg Gln Ala Pro Gly Lys Gly Leu Glu Trp Val
        35                  40                  45
Gly Arg Ile Lys Arg Lys Thr Asp Gly Gly Thr Thr Asp Tyr Ala Ala
    50                  55                  60
Pro Val Lys Gly Arg Phe Thr Ile Ser Arg Asp Asp Ser Glu Asn Thr
65                  70                  75                  80
Leu Tyr Leu Gln Met Asn Ser Leu Glu Thr Glu Asp Thr Ala Val Tyr
                85                  90                  95
Tyr Cys Thr Thr Val Asp Asn Ser Gly Asp Tyr Trp Gly Gln Gly Thr
            100                 105                 110
Leu Val Thr Val Ser Ser Ala
            115
```

<210> SEQ ID NO 23
<211> LENGTH: 466
<212> TYPE: DNA
<213> ORGANISM: Homo sapiens

<400> SEQUENCE: 23

```
actcagtctc cactctccct gcccgtcacc cctggagagc cggcctccat ctcctgcagg      60
tctagtcaga gcctcctgca tagtaatgga tacaactatt tggattggta cctgcagaag    120
ccagggcagt ctccacagct cctgatctat ttgggttcta atcgggcctc cggggtccct    180
gacaggttca gtggcagtgg atcaggcaca gattttacac tgaaaatcag cagagtggag    240
gctgaggatg ttggggttta ttactgcatg caagctctac aaactccgct cactttcggc    300
ggagggacca aggtggagat caaacgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctca              466
```

<210> SEQ ID NO 24
<211> LENGTH: 113
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: Xaa is any amino acid

<400> SEQUENCE: 24

```
Xaa Xaa Xaa Xaa Thr Gln Ser Pro Leu Ser Leu Pro Val Thr Pro Gly
1               5                   10                  15
Glu Pro Ala Ser Ile Ser Cys Arg Ser Ser Gln Ser Leu Leu His Ser
            20                  25                  30
Asn Gly Tyr Asn Tyr Leu Asp Trp Tyr Leu Gln Lys Pro Gly Gln Ser
        35                  40                  45
Pro Gln Leu Leu Ile Tyr Leu Gly Ser Asn Arg Ala Ser Gly Val Pro
    50                  55                  60
Asp Arg Phe Ser Gly Ser Gly Ser Gly Thr Asp Phe Thr Leu Lys Ile
65                  70                  75                  80
```

Ser Arg Val Glu Ala Glu Asp Val Gly Val Tyr Tyr Cys Met Gln Ala
            85                  90                  95

Leu Gln Thr Pro Leu Thr Phe Gly Gly Gly Thr Lys Val Glu Ile Lys
        100                 105                 110

Arg

<210> SEQ ID NO 25
<211> LENGTH: 537
<212> TYPE: DNA
<213> ORGANISM: Homo sapiens

<400> SEQUENCE: 25
caggtgcagc tggagcagtc ggggggaggc gtggtccagc ctggggaggtc cctgagactc      60 tcctgtgcag cgtctggatt caccttcact aactatggct tgcactgggt ccgccaggct     120
ccaggcaagg ggctggattg ggtggcagtt atatggtatg atggaagtca taaattctat     180
gcagactccg tgaagggccg attcaccatc tccagagaca attccaagaa cacgctcttt     240
ctgcaaatga acagcctgag agccgaggac acggctgtgt attactgtac gcgagatctt     300
gactactggg gccagggaac cctggtcacc gtctcctcag cttccaccaa gggcccatcc     360
gtcttccccc tggcgccctg ctccaggagc acctccgaga gcacagccgc cctgggctgc     420
ctggtcaagg actacttccc cgaaccggtg acggtgtcgt ggaactcagg cgccctgacc     480
agcggcgtgc acaccttccc ggctgtccta cagtcctcag gactctactc cctcagc       537

<210> SEQ ID NO 26
<211> LENGTH: 114
<212> TYPE: PRT
<213> ORGANISM: Homo sapiens

<400> SEQUENCE: 26

Gln Val Gln Leu Glu Gln Ser Gly Gly Gly Val Val Gln Pro Gly Arg
1               5                   10                  15

Ser Leu Arg Leu Ser Cys Ala Ala Ser Gly Phe Thr Phe Thr Asn Tyr
            20                  25                  30

Gly Leu His Trp Val Arg Gln Ala Pro Gly Lys Gly Leu Asp Trp Val
        35                  40                  45

Ala Val Ile Trp Tyr Asp Gly Ser His Lys Phe Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
            85                  90                  95

Thr Arg Asp Leu Asp Tyr Trp Gly Gln Gly Thr Leu Val Thr Val Ser
        100                 105                 110

Ser Ala

<210> SEQ ID NO 27
<211> LENGTH: 480
<212> TYPE: DNA
<213> ORGANISM: Homo sapiens

<400> SEQUENCE: 27
gaaacgcagc tgacgcagtc tccaggcacc ctgtctttgt ctccagggga aagagtcacc      60
ctctcctgca gggccagtca gagtgttagc aacaactact tagcctggta ccagcagaaa     120
cctggccagg ctcccaggct cctcatctat ggtgcatcca gcagggccac tggcatccca     180

```
gacaggttca gtggcagtgg gtctgggaca gacttcactc tcaccatcag cagactggag    240
cctgaagatt gtgcagagtg ttactgtcag caatatggta gctcactccc gctcactttc    300
ggcggaggga ccaaggtgga gatcaaacga actgtggctg caccatctgt cttcatcttc    360
ccgccatctg atgagcagtt gaaatctgga actgcctctg ttgtgtgcct gctgaataac    420
ttctatccca gagaggccaa agtacagtgg aaggtggga taacgccctc caatcgggta     480
```

<210> SEQ ID NO 28
<211> LENGTH: 110
<212> TYPE: PRT
<213> ORGANISM: Homo sapiens

<400> SEQUENCE: 28

Glu Thr Gln Leu Thr Gln Ser Pro Gly Thr Leu Ser Leu Ser Pro Gly
1               5                   10                  15

Glu Arg Val Thr Leu Ser Cys Arg Ala Ser Gln Ser Val Ser Asn Asn
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Cys Ala Glu Cys Tyr Cys Gln Gln Tyr Gly Ser Ser Leu
                85                  90                  95

Pro Leu Thr Phe Gly Gly Gly Thr Lys Val Glu Ile Lys Arg
            100                 105                 110

<210> SEQ ID NO 29
<211> LENGTH: 542
<212> TYPE: DNA
<213> ORGANISM: Homo sapiens

<400> SEQUENCE: 29

```
gtccagtgtc aggtgcagct ggtggagtct gggggaggcg tggtccagcc tggggaggtcc    60 ctgagactct cctgtgcagc gtctggattc accttcagta gctatggcat gcactgggtc    120
cgccaggctc caggcaaggg gctggagtgg gtggcagtta tatggtatga tggaagtcat    180
aaatactatg cagactccgt gaagggccga ttcaccatct ccagagacaa ttccaagaac    240
acgctgtatc tgcaaatgaa cagcctgaga gccgaggaca cggctgtgta ttactctgcg    300
agagattact atgatacgag tcggcatcac tgggggtttg actgctgggg ccagggaacc    360
ctggtcaccg tctcctctgc ttccaccaag ggcccatccg tcttccccct ggcgccctgc    420
tccaggagca cctccgagag cacagccgcc ctgggctgcc tggtcaagga ctacttcccc    480
gaaccggtga cggtgtcgtg gaactcaggc gccctgacca gcggcgtgca caccttcccg    540
gc                                                                   542
```

<210> SEQ ID NO 30
<211> LENGTH: 124
<212> TYPE: PRT
<213> ORGANISM: Homo sapiens

<400> SEQUENCE: 30

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr

```
            20                  25                  30
Gly Met His Trp Val Arg Gln Ala Pro Gly Lys Gly Leu Glu Trp Val
         35                  40                  45
Ala Val Ile Trp Tyr Asp Gly Ser His Lys Tyr Tyr Ala Asp Ser Val
         50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Ser
                 85                  90                  95
Ala Arg Asp Tyr Tyr Asp Thr Ser Arg His His Trp Gly Phe Asp Cys
                100                 105                 110
Trp Gly Gln Gly Thr Leu Val Thr Val Ser Ser Ala
                115                 120
```

<210> SEQ ID NO 31
<211> LENGTH: 521
<212> TYPE: DNA
<213> ORGANISM: Homo sapiens

<400> SEQUENCE: 31

```
cagctcctgg ggctgctaat gctctgggtc cctggatcca gtgaggaaat tgtgatgacc      60
cagactccac tctccctgcc cgtcacccct ggagagccgg cctccatctc ctgcaggtct     120
agtcagagcc tcttggatag tgaagatgga aacacctatt tggactggta cctgcagaag     180
ccagggcagt ctccacagct cctgatctat acgctttccc atcgggcctc tggagtccca     240
gacaggttca gtggcagtgg gtcaggcact gatttcacac tgaaaatcag cagggtggag     300
gctgaggatg ttggagttta ttgctgcatg caacgtgtag agtttcctat caccttcggc     360
caagggacac gactggagat taaacgaact gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg c                         521
```

<210> SEQ ID NO 32
<211> LENGTH: 114
<212> TYPE: PRT
<213> ORGANISM: Homo sapiens

<400> SEQUENCE: 32

```
Glu Ile Val Met Thr Gln Thr Pro Leu Ser Leu Pro Val Thr Pro Gly
 1               5                  10                  15
Glu Pro Ala Ser Ile Ser Cys Arg Ser Ser Gln Ser Leu Leu Asp Ser
             20                  25                  30
Glu Asp Gly Asn Thr Tyr Leu Asp Trp Tyr Leu Gln Lys Pro Gly Gln
         35                  40                  45
Ser Pro Gln Leu Leu Ile Tyr Thr Leu Ser His Arg Ala Ser Gly Val
     50                  55                  60
Pro Asp Arg Phe Ser Gly Ser Gly Ser Gly Thr Asp Phe Thr Leu Lys
 65                  70                  75                  80
Ile Ser Arg Val Glu Ala Glu Asp Val Gly Val Tyr Cys Cys Met Gln
                 85                  90                  95
Arg Val Glu Phe Pro Ile Thr Phe Gly Gln Gly Thr Arg Leu Glu Ile
                100                 105                 110
Lys Arg
```

<210> SEQ ID NO 33

```
<211> LENGTH: 547
<212> TYPE: DNA
<213> ORGANISM: Homo sapiens

<400> SEQUENCE: 33
cagtcgggcc caagactggt gaagccttca cagaccctgt ccctcacctg cactgtctct    60
ggtggctcca tcagtagtga tggttactac tggagctgga tccgccagca cccagggaag   120
ggcctggagt ggattgggta catctattac agtgggagca ccttctacaa cccgtccctc   180
aagagtcgag ttgccatatc agtggacacg tctaagaacc agttctccct gaagctgagc   240
tctgtgactg ccgcggacac ggccgtgtat tactgtgcga gagaatcccc tcatagcagc   300
aactggtact cgggctttga ctgctggggc cagggaaccc tggtcaccgt ctcctcagct   360
tccaccaagg gcccatccgt cttccccctg gcgccctgct ccaggagcac ctccgagagc   420
acagccgccc tgggctgcct ggtcaaggac tactttcccc gaaccggtga cggtgtcgtg   480
gaactcaggc gccctgacca gcggcgtgca ccttcccg gctgtcctac agtcctcagg   540
actctct                                                              547

<210> SEQ ID NO 34
<211> LENGTH: 125
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: Xaa is any amino acid

<400> SEQUENCE: 34

Xaa Xaa Xaa Xaa Xaa Gln Ser Gly Pro Arg Leu Val Lys Pro Ser Gln
1               5                   10                  15

Thr Leu Ser Leu Thr Cys Thr Val Ser Gly Gly Ser Ile Ser Ser Asp
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Phe Tyr Asn Pro Ser
    50                  55                  60

Leu Lys Ser Arg Val Ala Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Ser Pro His Ser Ser Asn Trp Tyr Ser Gly Phe Asp
            100                 105                 110

Cys Trp Gly Gln Gly Thr Leu Val Thr Val Ser Ser Ala
        115                 120                 125

<210> SEQ ID NO 35
<211> LENGTH: 450
<212> TYPE: DNA
<213> ORGANISM: Homo sapiens

<400> SEQUENCE: 35
actcagtctc cagactttca gtctgtgact ccaaaggaga agtcaccat cacctgccgg    60
gccagtcaga gcattggtag taggttacac tggtaccagc agaaaccaga tcagtctcca   120
aagctcctca tcaagtatgc ttcccagtcc ttctcagggg tccctcgag gttcagtggc   180
agtggatctg gacagatt cacctcacc atcaatagcc tggaagctga agatgctgca   240
acgtattact gtcatcagag tagtaattta ccattcactt tcggccctgg gaccaaagtg   300
```

```
gatatcaaac gaactgtggc tgcaccatct gtcttcatct tcccgccatc tgatgagcag    360
ttgaaatctg gaactgcctc tgttgtgtgc ctgctgaata acttctatcc cagagaggcc    420
aaagtacagt ggaaggtgga taacgccctc                                     450
```

```
<210> SEQ ID NO 36
<211> LENGTH: 108
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: Xaa is any amino acid

<400> SEQUENCE: 36
```

Xaa Xaa Xaa Xaa Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Arg
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Asn Leu Pro Phe
                85                  90                  95

Thr Phe Gly Pro Gly Thr Lys Val Asp Ile Lys Arg
            100                 105

```
<210> SEQ ID NO 37
<211> LENGTH: 534
<212> TYPE: DNA
<213> ORGANISM: Homo sapiens

<400> SEQUENCE: 37
```

```
caggtgcagc tggtggaggc tgggggaggc gtggtccagc ctgggaggtc cctgagactc    60
tcctgtgcag cgtctggatt caccttcaga agctatggca tgcactgggt ccgccaggct    120
ccaggcaagg ggctgaaatg ggtggcagtt atatggtatg atggaagtaa taaatactat    180
acagactccg tgaagggccg attcaccatc tccagagaca attccaagaa cacgctgtat    240
ctgcaaatga acagcctgag agccgaggac acggctgtgt attactgtgt gagagattac    300
tatgataata gtagacatca ctgggggttt gactactggg gccagggaac cctggtcacc    360
gtctcctcag cttccaccaa gggcccatcg gtcttccccc tggcgccctg ctccaggagc    420
acctccgaga gcacagccgc cctgggctgc ctggtcaagg actacttccc cgaaccggtg    480
acggtgtcgt ggaactcagg cgccctgacc agcggcgtg cacaccttcc cggc           534
```

```
<210> SEQ ID NO 38
<211> LENGTH: 124
<212> TYPE: PRT
<213> ORGANISM: Homo sapiens

<400> SEQUENCE: 38
```

Gln Val Gln Leu Val Glu Ala Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Lys Trp Val
        35                  40                  45

Ala Val Ile Trp Tyr Asp Gly Ser Asn Lys Tyr Tyr Thr Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Asp Tyr Tyr Asp Asn Ser Arg His His Trp Gly Phe Asp Tyr
                100                 105                 110

Trp Gly Gln Gly Thr Leu Val Thr Val Ser Ser Ala
        115                 120

<210> SEQ ID NO 39
<211> LENGTH: 470
<212> TYPE: DNA
<213> ORGANISM: Homo sapiens

<400> SEQUENCE: 39

```
gacatccaga tgacccagtc tccatcctcc cggtgtgcat ccgtaggaga cagagtcacc      60
atcacttgcc gggcaagtca gggcatcaga aatgatttag cttggtatca gcagaaacca    120
gggaaagccc ctaagcgcct gatctatgct gcatccagtt tgcaaagtgg ggtcccatca    180
aggttcagcg gcagtagatc tgggacagaa ttcactctca caatcagcag cctgcagcct    240
gaagattttg cagcttatta ctgtctccag cataatagtt accctcccag ttttggccag    300
gggaccaagc tggagatcaa acgaactgtg gctgcaccat ctgtcttcat cttcccgcca    360
tctgatgagc agttgaaatc tggaactgct agcgttgtgt gcctgctgaa taacttctat    420
cccagagagg ccaaagtaca gtggaaggtg gataacgccc tccaatcggg              470
```

<210> SEQ ID NO 40
<211> LENGTH: 108
<212> TYPE: PRT
<213> ORGANISM: Homo sapiens

<400> SEQUENCE: 40

Asp Ile Gln Met Thr Gln Ser Pro Ser Ser Arg Cys Ala Ser Val Gly
1               5                   10                  15

Asp Arg Val Thr Ile Thr Cys Arg Ala Ser Gln Gly Ile Arg Asn Asp
                20                  25                  30

Leu Ala Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
        50                  55                  60

Ser Arg Ser Gly Thr Glu Phe Thr Leu Thr Ile Ser Ser Leu Gln Pro
65                  70                  75                  80

Glu Asp Phe Ala Ala Tyr Tyr Cys Leu Gln His Asn Ser Tyr Pro Pro
                85                  90                  95

Ser Phe Gly Gln Gly Thr Lys Leu Glu Ile Lys Arg
                100                 105

<210> SEQ ID NO 41
<211> LENGTH: 514
<212> TYPE: DNA
<213> ORGANISM: Homo sapiens

<400> SEQUENCE: 41

```
catgtgcagg tgcagctggt ggagtctggg ggaggcgtgg tccagcctgg gaggtccctg      60
agactctcct gtgcagcgtc tggattcatc ttcagtcgct atggcatgca ctgggtccgc     120
caggctccag gcaaggggct gaaatgggtg gcagttatat ggtatgatgg aagtaataaa     180
ctctatgcag actccgtgaa gggccgattc accatctcca gagacaattc caagaacacg     240
ctgtatctgc aaatgaacag cctgagagcc gaggacacgg ctgtgtatta ctgtgcgaga     300
gattactatg ataatagtag acatcactgg gggtttgact actggggcca gggaaccctg     360
gtcaccgtct cctcagcttc caccaagggc ccatccgtct tccccctggc gcctgctcc      420 aggagcacct ccgagagcac agccgccctg ggctgcctgg tcaaggacta cttccccgaa     480
ccggtgacgg tgtcgtggaa ctcaggcgcc ctga                                 514
```

<210> SEQ ID NO 42
<211> LENGTH: 124
<212> TYPE: PRT
<213> ORGANISM: Homo sapiens

<400> SEQUENCE: 42

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Arg Tyr
            20                  25                  30

Gly Met His Trp Val Arg Gln Ala Pro Gly Lys Gly Leu Lys Trp Val
        35                  40                  45

Ala Val Ile Trp Tyr Asp Gly Ser Asn Lys Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Tyr Asp Asn Ser Arg His His Trp Gly Phe Asp Tyr
            100                 105                 110

Trp Gly Gln Gly Thr Leu Val Thr Val Ser Ser Ala
        115                 120
```

<210> SEQ ID NO 43
<211> LENGTH: 523
<212> TYPE: DNA
<213> ORGANISM: Homo sapiens

<400> SEQUENCE: 43

```
tcagctcctg gggctgctaa tgctctgggt ccctggatca gtgaggatat tgtgatgacc      60
cagactccac tctccctgcc cgtcacccct ggagagccgg cctccatctc ctgcaggtct     120
agtcggagcc tcttggatag tgatgatgga acacctatt ggactggta cctgcagaag      180 ccagggcagt ctccacagct cctgatctac acgctttcct atcgggcctc tggagtccca     240
gacaggttca gtggcagtgg gtcaggcact gatttcacac tgaaaatcag cagggtggag     300
gctgaggatg ttggagttta ttactgcatg caacgtgtag agtttcctat caccttcggc     360
caagggacac gactggagat taaacgaact gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg cct                      523
```

<210> SEQ ID NO 44

<211> LENGTH: 114
<212> TYPE: PRT
<213> ORGANISM: Homo sapiens

<400> SEQUENCE: 44

Asp Ile Val Met Thr Gln Thr Pro Leu Ser Leu Pro Val Thr Pro Gly
1               5                   10                  15

Glu Pro Ala Ser Ile Ser Cys Arg Ser Ser Arg Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Val Glu Phe Pro Ile Thr Phe Gly Gln Gly Thr Arg Leu Glu Ile
            100                 105                 110

Lys Arg

<210> SEQ ID NO 45
<211> LENGTH: 546
<212> TYPE: DNA
<213> ORGANISM: Homo sapiens

<400> SEQUENCE: 45
gagcagtcgg ggggcggcgt ggtccagcct gggaggtccc tgagactctc ctgtgcagcg      60
tctggattca ccttcagtag ctatggcatg tactgggtcc gccaggctcc aggcaagggg     120
ctggagtggg tggcagttat atggtatgat ggaagcaata atactatgc agactccgtg      180 aagggccgat tcaccatctc cagagacaat tccaagaaca cgctgtatct gcaaatgaac     240
agcctgagag ccgaggacac ggctgtgtat tactgtgcga gggatttcta tgatagtagt     300
cgttaccact acggtatgga cgtctggggc caagggacca cggtcaccgt ctcctcagct     360
tccaccaagg gcccatccgt cttcccctg gcgccctgct ccaggagcac ctccgagagc      420
acagccgccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctct                                                                546

<210> SEQ ID NO 46
<211> LENGTH: 124
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: Xaa is any amino acid

<400> SEQUENCE: 46

Xaa Xaa Xaa Xaa Glu Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val

```
            50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Phe Tyr Asp Ser Ser Arg Tyr His Tyr Gly Met Asp Val
            100                 105                 110

Trp Gly Gln Gly Thr Thr Val Thr Val Ser Ser Ala
            115                 120

<210> SEQ ID NO 47
<211> LENGTH: 419
<212> TYPE: DNA
<213> ORGANISM: Homo sapiens

<400> SEQUENCE: 47
actcagtgtc cactctccct gcccgtcacc cctggagagc cggcctccat ctcctgcagg    60
tctagtcaga gcctcttgga tagtgatgat ggaaacacct atttggactg gtacctgcag   120
aagccagggc agtctccaca gctcctgatc tatacggttt cctatcgggc ctctggagtc   180
ccagacaggt tcagtggcag tgggtcaggc actgatttca cactgaaaat cagcagggtg   240
gaggctgagg atgttggagt ttattactgc atgcaacgta tagagtttcc gatcaccttc   300
ggccaaggga cccgactgga gattaaacga actgtggctg caccatctgt cttcatcttc   360
ccgccatctg atgagcagtt gaaatctgga actgcctctg ttgtgtgcct gctgaataa    419

<210> SEQ ID NO 48
<211> LENGTH: 114
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: Xaa is any amino acid

<400> SEQUENCE: 48

Xaa Xaa Xaa Xaa Thr Gln Cys Pro Leu Ser Leu Pro Val Thr Pro Gly
 1               5                  10                  15

Glu Pro Ala Ser Ile Ser Cys Arg Ser Ser Gln Ser Leu Leu Asp Ser
                 20                  25                  30

Asp Asp Gly Asn Thr Tyr Leu Asp Trp Tyr Leu Gln Lys Pro Gly Gln
             35                  40                  45

Ser Pro Gln Leu Leu Ile Tyr Thr Val Ser Tyr Arg Ala Ser Gly Val
         50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Met Gln
                 85                  90                  95

Arg Ile Glu Phe Pro Ile Thr Phe Gly Gln Gly Thr Arg Leu Glu Ile
            100                 105                 110

Lys Arg

<210> SEQ ID NO 49
<211> LENGTH: 1428
<212> TYPE: DNA
<213> ORGANISM: Homo sapiens

<400> SEQUENCE: 49
```

```
cggccgccta tttacccaga gacagggaga ggctcttctg tgtgtagtgg ttgtgcagag      60
cctcatgcat cacggagcat gagaagacat tccctcctg ccacctgctc ttgtccacgg      120
ttagcctgct gtagaggaag aaggagccgt cggagtccag cacgggaggc gtggtcttgt     180
agttgttctc cggctgccca ttgctctccc actccacggc gatgtcgctg ggtagaagc      240
ctttgaccag gcaggtcagg ctgacctggt tcttggtcat ctcctcctgg gatggggca      300
gggtgtacac ctgtggctct cggggctgcc ctttggcttt ggagatggtt ttctcgatgg     360
aggacgggag gcctttgttg gagaccttgc acttgtactc cttgccgttc agccagtcct     420
ggtgcaggac ggtgaggacg ctgaccacac ggtacgtgct gttgaactgc cctcccgcg     480
gctttgtctt ggcattatgc acctccacgc catccacgta ccagttgaac tggacctcgg     540
ggtcttcctg gctcacgtcc accaccacgc acgtgacctc aggggtccgg agatcatga     600
gagtgtcctt gggttttggg gggaacagga agactgatgg tccccccagg aactcaggtg     660
ctgggcatga tgggcatggg ggaccatatt tggactcaac tctcttgtcc accttggtgt     720
tgctgggctt gtgatctacg ttgcaggtgt aggtcttcgt gcccaagctg ctggagggca     780
cggtcaccac gctgctgagg gagtagagtc ctgaggactg taggacagcc gggaaggtgt     840
gcacgccgct ggtcagggcg cctgagttcc acgacaccgt caccggttcg gggaagtagt     900
ccttgaccag cagcccagg gcggctgtgc tctcggaggt gctcctggag cagggcgcca     960
gggggaagac ggatgggccc ttggtggaag ctgaggagac ggtgaccagg ttccctggc     1020
cccagtagtc aaaccccag tgatgtctac tattatcata gtaatctctc gcacagtaat     1080
acacagccgt gtcctcggct ctcaggctgt tcatttgcag atacagcgtg ttcttggaat    1140
tgtctctgga gatggtgaat cggcccttca cggagtctgc atagagttta ttacttccat    1200
cataccatat aactgccacc catttcagcc ccttgcctgg agcctggcgg acccagtgca    1260
tgccatagcg actgaagatg aatccagacg ctgcacagga gagtctcagg acctcccag    1320
gctggaccac gcctccccca gactccacca gctgcacctg cactggaca cctttttaaaa   1380
tagccacaag aaaaagccag ctcagcccaa actccatggt ggtcgact                 1428
```

<210> SEQ ID NO 50  
<211> LENGTH: 469  
<212> TYPE: PRT  
<213> ORGANISM: Homo sapiens

<400> SEQUENCE: 50

```
Met Glu Phe Gly Leu Ser Trp Leu Phe Leu Val Ala Ile Leu Lys Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Ile Phe
        35                  40                  45

Ser Arg Tyr Gly Met His Trp Val Arg Gln Ala Pro Gly Lys Gly Leu
    50                  55                  60

Lys Trp Val Ala Val Ile Trp Tyr Asp Gly Ser Asn Lys Leu Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Tyr Tyr Asp Asn Ser Arg His His Trp Gly
        115                 120                 125
```

```
Phe Asp Tyr Trp Gly Gln Gly Thr Leu Val Thr Val Ser Ser Ala Ser
            130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Lys Thr Tyr Thr
    210                 215                 220

Cys Asn Val Asp His Lys Pro Ser Asn Thr Lys Val Asp Lys Arg Val
225                 230                 235                 240

Glu Ser Lys Tyr Gly Pro Pro Cys Pro Ser Cys Pro Ala Pro Glu Phe
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser Gln Glu Asp Pro Glu Val Gln Phe Asn Trp Tyr Val Asp Gly Val
    290                 295                 300

Glu Val His Asn Ala Lys Thr Lys Pro Arg Glu Glu Gln Phe Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Gly Leu Pro Ser
            340                 345                 350

Ser Ile Glu Lys Thr Ile Ser Lys Ala Lys Gly Gln Pro Arg Glu Pro
        355                 360                 365

Gln Val Tyr Thr Leu Pro Pro Ser Gln Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Arg Leu
            420                 425                 430

Thr Val Asp Lys Ser Arg Trp Gln Glu Gly Asn Val Phe Ser Cys Ser
        435                 440                 445

Val Met His Glu Ala Leu His Asn His Tyr Thr Gln Lys Ser Leu Ser
    450                 455                 460

Leu Ser Leu Gly Lys
465

<210> SEQ ID NO 51
<211> LENGTH: 741
<212> TYPE: DNA
<213> ORGANISM: Homo sapiens

<400> SEQUENCE: 51
agtcgaccac catggaaacc ccagcgcagc ttctcttcct cctgctactc tggctcccag      60
ataccaccgg agatattgtg atgacccaga ctccactctc cctgcccgtc acccctggag     120
```

```
agccggcctc catctcctgc aggtctagtc ggagcctctt ggatagtgat gatggaaaca      180
cctatttgga ctggtacctg cagaagccag ggcagtctcc acagctcctg atctacacgc      240
tttcctatcg ggcctctgga gtcccagaca ggttcagtgg cagtgggtca ggcactgatt      300
tcacactgaa aatcagcagg gtggaggctg aggatgttgg agtttattac tgcatgcaac      360
gtgtagagtt tcctatcacc ttcggccaag ggacacgact ggagattaaa cgaactgtgg      420
ctgcaccatc tgtcttcatc ttcccgccat ctgatgagca gttgaaatct ggaactgcct      480
ctgttgtgtg cctgctgaat aacttctatc ccagagaggc caaagtacag tggaaggtgg      540
ataacgccct ccaatcgggt aactcccagg agagtgtcac agagcaggac agcaaggaca      600
gcacctacag cctcagcagc accctgacgc tgagcaaagc agactacgag aaacacaaag      660
tctacgcctg cgaagtcacc catcagggcc tgagctcgcc cgtcacaaag agcttcaaca      720
ggggagagtg ttaggcggcc g                                               741
```

<210> SEQ ID NO 52
<211> LENGTH: 240
<212> TYPE: PRT
<213> ORGANISM: Homo sapiens

<400> SEQUENCE: 52

```
Met Glu Thr Pro Ala Gln Leu Leu Phe Leu Leu Leu Trp Leu Pro
1               5                  10                  15

Asp Thr Thr Gly Asp Ile Val Met Thr Gln Thr Pro Leu Ser Leu Pro
                20                  25                  30

Val Thr Pro Gly Glu Pro Ala Ser Ile Ser Cys Arg Ser Ser Arg Ser
            35                  40                  45

Leu Leu Asp Ser Asp Asp Gly Asn Thr Tyr Leu Asp Trp Tyr Leu Gln
        50                  55                  60

Lys Pro Gly Gln Ser Pro Gln Leu Leu Ile Tyr Thr Leu Ser Tyr Arg
65                  70                  75                  80

Ala Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Val Gly Val Tyr
            100                 105                 110

Tyr Cys Met Gln Arg Val Glu Phe Pro Ile Thr Phe Gly Gln Gly Thr
        115                 120                 125

Arg Leu Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 53
<211> LENGTH: 789
<212> TYPE: DNA

<213> ORGANISM: Homo sapiens

<400> SEQUENCE: 53

```
tctgtaaagg ttggtggaga ggcaggtcca tctgtcacac taccctgcca ctacagtgga    60
gctgtcacat caatgtgctg aatagaggc tcatgttctc tattcacatg ccaaaatggc   120
attgtctgga ccaatggaac ccacgtcacc tatcggaagg acacacgcta taagctattg   180
ggggaccttt caagaaggga tgtctctttg accatagaaa atacagctgt gtctgacagt   240
ggcgtatatt gttgccgtgt tgagcaccgt gggtggttca atgacatgaa aatcaccgta   300
tcattggaga ttgtgccacc caaggtcacg actactccaa ttgtcacaac tgttccaacc   360
gtcacgactg ttcgaacgag caccactgtt ccaacgacaa cgactgttcc aacgacaact   420
gttccaacaa caatgagcat tccaacgaca acgactgttc cgacgacaat gactgtttca   480
acgacaacga gcgttccaac gacaacgagc attccaacaa caacaagtgt tccagtgaca   540
acaacggtct ctacctttgt tcctccaatg cctttgccca ggcagaacca tgaaccagta   600
gccacttcac catcttcacc tcagccagca gaaacccacc ctacgacact gcagggagca   660
ataaggagag aacccaccag ctcaccattg tactcttaca caacagatgg gaatgacacc   720
gtgacagagt cttcagatgg cctttggaat aacaatcaaa ctcaactgtt cctagaacat   780
agtctactg                                                           789
```

<210> SEQ ID NO 54
<211> LENGTH: 263
<212> TYPE: PRT
<213> ORGANISM: Homo sapiens

<400> SEQUENCE: 54

```
Ser Val Lys Val Gly Gly Glu Ala Gly Pro Ser Val Thr Leu Pro Cys
  1               5                  10                  15

His Tyr Ser Gly Ala Val Thr Ser Met Cys Trp Asn Arg Gly Ser Cys
             20                  25                  30

Ser Leu Phe Thr Cys Gln Asn Gly Ile Val Trp Thr Asn Gly Thr His
         35                  40                  45

Val Thr Tyr Arg Lys Asp Thr Arg Tyr Lys Leu Leu Gly Asp Leu Ser
     50                  55                  60

Arg Arg Asp Val Ser Leu Thr Ile Glu Asn Thr Ala Val Ser Asp Ser
 65                  70                  75                  80

Gly Val Tyr Cys Cys Arg Val Glu His Arg Gly Trp Phe Asn Asp Met
                 85                  90                  95

Lys Ile Thr Val Ser Leu Glu Ile Val Pro Pro Lys Val Thr Thr Thr
            100                 105                 110

Pro Ile Val Thr Thr Val Pro Thr Val Thr Val Arg Thr Ser Thr
        115                 120                 125

Thr Val Pro Thr Thr Thr Thr Val Pro Thr Thr Thr Val Pro Thr Thr
    130                 135                 140

Met Ser Ile Pro Thr Thr Thr Val Pro Thr Thr Met Thr Val Ser
145                 150                 155                 160

Thr Thr Thr Ser Val Pro Thr Thr Thr Ser Ile Pro Thr Thr Thr Ser
                165                 170                 175

Val Pro Val Thr Thr Thr Val Ser Thr Phe Val Pro Pro Met Pro Leu
            180                 185                 190

Pro Arg Gln Asn His Glu Pro Val Ala Thr Ser Pro Ser Ser Pro Gln
        195                 200                 205
```

-continued

Pro Ala Glu Thr His Pro Thr Thr Leu Gln Gly Ala Ile Arg Arg Glu
210                 215                 220

Pro Thr Ser Ser Pro Leu Tyr Ser Tyr Thr Thr Asp Gly Asn Asp Thr
225                 230                 235                 240

Val Thr Glu Ser Ser Asp Gly Leu Trp Asn Asn Asn Gln Thr Gln Leu
                245                 250                 255

Phe Leu Glu His Ser Leu Leu
            260

<210> SEQ ID NO 55
<211> LENGTH: 114
<212> TYPE: PRT
<213> ORGANISM: Homo sapiens
<220> FEATURE:
<221> NAME/KEY: MISC_FEATURE
<222> LOCATION: (99)..(100)
<223> OTHER INFORMATION: Xaa is any amino acid

<400> SEQUENCE: 55

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Xaa Xaa Asp Tyr Trp Gly Gln Gly Thr Leu Val Thr Val Ser
            100                 105                 110

Ser Ala

<210> SEQ ID NO 56
<211> LENGTH: 124
<212> TYPE: PRT
<213> ORGANISM: Homo sapiens
<220> FEATURE:
<221> NAME/KEY: MISC_FEATURE
<222> LOCATION: (98)..(100)
<223> OTHER INFORMATION: Xaa is any amino acid
<220> FEATURE:
<221> NAME/KEY: MISC_FEATURE
<222> LOCATION: (105)..(107)
<223> OTHER INFORMATION: Xaa is any amino acid

<400> SEQUENCE: 56

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                    85                  90                  95
Ala Xaa Xaa Xaa Tyr Asp Ser Ser Xaa Xaa Tyr Gly Met Asp Val
            100                 105                 110

Trp Gly Gln Gly Thr Thr Val Thr Val Ser Ser Ala
        115                 120

<210> SEQ ID NO 57
<211> LENGTH: 125
<212> TYPE: PRT
<213> ORGANISM: Homo sapiens
<220> FEATURE:
<221> NAME/KEY: MISC_FEATURE
<222> LOCATION: (100)..(103)
<223> OTHER INFORMATION: Xaa is any amino acid
<220> FEATURE:
<221> NAME/KEY: MISC_FEATURE
<222> LOCATION: (109)..(110)
<223> OTHER INFORMATION: Xaa is any amino acid

<400> SEQUENCE: 57

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Xaa Xaa Xaa Xaa Ser Ser Ser Trp Tyr Xaa Xaa Phe Asp
            100                 105                 110

Tyr Trp Gly Gln Gly Thr Leu Val Thr Val Ser Ser Ala
        115                 120                 125

<210> SEQ ID NO 58
<211> LENGTH: 124
<212> TYPE: PRT
<213> ORGANISM: Homo sapiens
<220> FEATURE:
<221> NAME/KEY: MISC_FEATURE
<222> LOCATION: (105)..(109)
<223> OTHER INFORMATION: Xaa is any amino acid

<400> SEQUENCE: 58

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Tyr Asp Ser Ser Xaa Xaa Xaa Xaa Xaa Phe Asp Tyr
```

```
              100                 105                 110

Trp Gly Gln Gly Thr Leu Val Thr Val Ser Ser Ala
        115                 120

<210> SEQ ID NO 59
<211> LENGTH: 119
<212> TYPE: PRT
<213> ORGANISM: Homo sapiens
<220> FEATURE:
<221> NAME/KEY: MISC_FEATURE
<222> LOCATION: (100)..(101)
<223> OTHER INFORMATION: Xaa is any amino acid
<220> FEATURE:
<221> NAME/KEY: MISC_FEATURE
<222> LOCATION: (103)..(105)
<223> OTHER INFORMATION: Xaa is any amino acid

<400> SEQUENCE: 59

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Xaa Xaa Asp Xaa Xaa Xaa Asp Tyr Trp Gly Gln Gly Thr
            100                 105                 110

Leu Val Thr Val Ser Ser Ala
        115

<210> SEQ ID NO 60
<211> LENGTH: 121
<212> TYPE: PRT
<213> ORGANISM: Homo sapiens
<220> FEATURE:
<221> NAME/KEY: MISC_FEATURE
<222> LOCATION: (100)..(102)
<223> OTHER INFORMATION: Xaa is any amino acid
<220> FEATURE:
<221> NAME/KEY: MISC_FEATURE
<222> LOCATION: (104)..(106)
<223> OTHER INFORMATION: Xaa is any amino acid

<400> SEQUENCE: 60

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Gly Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95
```

```
Cys Ala Arg Xaa Xaa Xaa Trp Xaa Xaa Xaa Phe Asp Tyr Trp Gly Gln
                100                 105                 110

Gly Thr Leu Val Thr Val Ser Ser Ala
        115                 120

<210> SEQ ID NO 61
<211> LENGTH: 119
<212> TYPE: PRT
<213> ORGANISM: Homo sapiens
<220> FEATURE:
<221> NAME/KEY: MISC_FEATURE
<222> LOCATION: (101)..(103)
<223> OTHER INFORMATION: Xaa is any amino acid

<400> SEQUENCE: 61

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Xaa Xaa Xaa Ser Gly Asp Tyr Trp Gly Gln Gly Thr
            100                 105                 110

Leu Val Thr Val Ser Ser Ala
        115

<210> SEQ ID NO 62
<211> LENGTH: 113
<212> TYPE: PRT
<213> ORGANISM: Homo sapiens
<220> FEATURE:
<221> NAME/KEY: MISC_FEATURE
<222> LOCATION: (099)..(099)
<223> OTHER INFORMATION: Xaa is any amino acid

<400> SEQUENCE: 62

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Xaa Asp Tyr Trp Gly Gln Gly Thr Leu Val Thr Val Ser Ser
            100                 105                 110

Ala

<210> SEQ ID NO 63
```

-continued

```
<211> LENGTH: 114
<212> TYPE: PRT
<213> ORGANISM: Homo sapiens
<220> FEATURE:
<221> NAME/KEY: MISC_FEATURE
<222> LOCATION: (98)..(99)
<223> OTHER INFORMATION: Xaa is any amino acid

<400> SEQUENCE: 63

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Xaa Xaa Phe Asp Tyr Trp Gly Gln Gly Thr Leu Val Thr Val Ser
            100                 105                 110

Ser Ala

<210> SEQ ID NO 64
<211> LENGTH: 110
<212> TYPE: PRT
<213> ORGANISM: Homo sapiens
<220> FEATURE:
<221> NAME/KEY: MISC_FEATURE
<222> LOCATION: (96)..(97)
<223> OTHER INFORMATION: Xaa is any amino acid

<400> SEQUENCE: 64

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Xaa
                85                  90                  95

Xaa Leu Thr Phe Gly Gly Gly Thr Lys Val Glu Ile Lys Arg
            100                 105                 110

<210> SEQ ID NO 65
<211> LENGTH: 113
<212> TYPE: PRT
<213> ORGANISM: Homo sapiens
<220> FEATURE:
<221> NAME/KEY: MISC_FEATURE
<222> LOCATION: (100)..(101)
<223> OTHER INFORMATION: Xaa is any amino acid

<400> SEQUENCE: 65

Asp Ile Val Met Thr Gln Ser Pro Leu Ser Leu Pro Val Thr Pro Gly
```

```
                1               5                   10                  15
            Glu Pro Ala Ser Ile Ser Cys Arg Ser Ser Gln Ser Leu Leu His Ser
                            20                  25                  30

Asn Gly Tyr Asn Tyr Leu Asp Trp Tyr Leu Gln Lys Pro Gly Gln Ser
                        35                  40                  45

Pro Gln Leu Leu Ile Tyr Leu Gly Ser Asn Arg Ala Ser Gly Val Pro
                50                  55                  60

Asp Arg Phe Ser Gly Ser Gly Ser Gly Thr Asp Phe Thr Leu Lys Ile
             65                  70                  75                  80

Ser Arg Val Glu Ala Glu Asp Val Gly Val Tyr Tyr Cys Met Gln Ala
                            85                  90                  95

Leu Gln Thr Xaa Xaa Thr Phe Gly Gly Gly Thr Lys Val Glu Ile Lys
                            100                 105                 110

Arg
```

<210> SEQ ID NO 66
<211> LENGTH: 108
<212> TYPE: PRT
<213> ORGANISM: Homo sapiens

<400> SEQUENCE: 66

```
            Asp Ile Gln Met Thr Gln Ser Pro Ser Ser Leu Ser Ala Ser Val Gly
             1               5                   10                  15

Asp Arg Val Thr Ile Thr Cys Arg Ala Ser Gln Gly Ile Arg Asn Asp
                            20                  25                  30

Leu Gly Trp Tyr Gln Lys Pro Gly Lys Ala Pro Lys Arg Leu Ile
                        35                  40                  45

Tyr Ala Ala Ser Ser Leu Gln Ser Gly Val Pro Ser Arg Phe Ser Gly
                50                  55                  60

Ser Gly Ser Gly Thr Glu Phe Thr Leu Thr Ile Ser Ser Leu Gln Pro
             65                  70                  75                  80

Glu Asp Phe Ala Thr Tyr Tyr Cys Leu Gln His Asn Ser Tyr Pro Leu
                            85                  90                  95

Thr Phe Gly Gly Gly Thr Lys Val Glu Ile Lys Arg
                            100                 105
```

<210> SEQ ID NO 67
<211> LENGTH: 114
<212> TYPE: PRT
<213> ORGANISM: Homo sapiens
<220> FEATURE:
<221> NAME/KEY: MISC_FEATURE
<222> LOCATION: (101)..(101)
<223> OTHER INFORMATION: Xaa is any amino acid

<400> SEQUENCE: 67

```
            Asp Ile Val Met Thr Gln Thr Pro Leu Ser Ser Pro Val Thr Leu Gly
             1               5                   10                  15

Gln Pro Ala Ser Ile Ser Cys Arg Ser Ser Gln Ser Leu Val His Ser
                            20                  25                  30

Asp Gly Asn Thr Tyr Leu Ser Trp Leu Gln Gln Arg Pro Gly Gln Pro
                        35                  40                  45

Pro Arg Leu Leu Ile Tyr Lys Ile Ser Asn Arg Phe Ser Gly Val Pro
                50                  55                  60

Asp Arg Phe Ser Gly Ser Gly Ala Gly Thr Asp Phe Thr Leu Lys Ile
             65                  70                  75                  80

Ser Arg Val Glu Ala Glu Asp Val Gly Val Tyr Tyr Cys Met Gln Ala
```

```
                    85                  90                  95

Thr Gln Phe Pro Xaa Ile Thr Phe Gly Gln Gly Thr Arg Leu Glu Ile
                100                 105                 110

Lys Arg

<210> SEQ ID NO 68
<211> LENGTH: 108
<212> TYPE: PRT
<213> ORGANISM: Homo sapiens

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys Arg
                100                 105

<210> SEQ ID NO 69
<211> LENGTH: 113
<212> TYPE: PRT
<213> ORGANISM: Homo sapiens

<400> SEQUENCE: 69

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Gln Thr Phe Gly Gln Gly Thr Lys Val Glu Ile Lys
                100                 105                 110

Arg

<210> SEQ ID NO 70
<211> LENGTH: 114
<212> TYPE: PRT
<213> ORGANISM: Homo sapiens

<400> SEQUENCE: 70

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
```

```
                20                  25                  30
Asp Asp Gly Asn Thr Tyr Leu Asp Trp Tyr Leu Gln Lys Pro Gly Gln
            35                  40                  45

Ser Pro Gln Leu Leu Ile Tyr Thr Leu Ser Tyr Arg Ala Ser Gly Val
 50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Met Gln
                85                  90                  95

Arg Ile Glu Phe Pro Ile Thr Phe Gly Gln Gly Thr Arg Leu Glu Ile
               100                 105                 110

Lys Arg

<210> SEQ ID NO 71
<211> LENGTH: 108
<212> TYPE: PRT
<213> ORGANISM: Homo sapiens

<400> SEQUENCE: 71

Glu Ile Val Leu Thr Gln Ser Pro Asp Phe Gln Ser Val Thr Pro Lys
 1               5                  10                  15

Glu Lys Val Thr Ile Thr Cys Arg Ala Ser Gln Ser Ile Gly Ser Ser
                20                  25                  30

Leu His Trp Tyr Gln Gln Lys Pro Asp Gln Ser Pro Lys Leu Leu Ile
            35                  40                  45

Lys Tyr Ala Ser Gln Ser Phe Ser Gly Val Pro Ser Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys His Gln Ser Ser Ser Leu Pro Phe
                85                  90                  95

Thr Phe Gly Pro Gly Thr Lys Val Asp Ile Lys Arg
               100                 105

<210> SEQ ID NO 72
<211> LENGTH: 108
<212> TYPE: PRT
<213> ORGANISM: Homo sapiens
<220> FEATURE:
<221> NAME/KEY: MISC_FEATURE
<222> LOCATION: (96)..(97)
<223> OTHER INFORMATION: Xaa is any amino acid

<400> SEQUENCE: 72

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Xaa
                85                  90                  95

Xaa Phe Gly Gln Gly Thr Lys Leu Glu Ile Lys Arg
```

<210> SEQ ID NO 73
<211> LENGTH: 16
<212> TYPE: DNA
<213> ORGANISM: Homo sapiens

<400> SEQUENCE: 73
ttactatgat aatagt                                                    16

<210> SEQ ID NO 74
<211> LENGTH: 15
<212> TYPE: DNA
<213> ORGANISM: Homo sapiens

<400> SEQUENCE: 74
agacatcact ggggg                                                     15

<210> SEQ ID NO 75
<211> LENGTH: 17
<212> TYPE: DNA
<213> ORGANISM: Homo sapiens

<400> SEQUENCE: 75
atagcagcaa ctggtac                                                   17

<210> SEQ ID NO 76
<211> LENGTH: 16
<212> TYPE: DNA
<213> ORGANISM: Homo sapiens

<400> SEQUENCE: 76
ttactatgat aatagt                                                    16

<210> SEQ ID NO 77
<211> LENGTH: 15
<212> TYPE: DNA
<213> ORGANISM: Homo sapiens

<400> SEQUENCE: 77
agacatcact ggggg                                                     15

<210> SEQ ID NO 78
<211> LENGTH: 16
<212> TYPE: DNA
<213> ORGANISM: Homo sapiens

<400> SEQUENCE: 78
ttactatgat aatagt                                                    16

<210> SEQ ID NO 79
<211> LENGTH: 15
<212> TYPE: DNA
<213> ORGANISM: Homo sapiens

<400> SEQUENCE: 79
agacatcact ggggg                                                     15

<210> SEQ ID NO 80
<211> LENGTH: 13
<212> TYPE: DNA
<213> ORGANISM: Homo sapiens

<400> SEQUENCE: 80

```
ctatgatagt agt                                                          13

<210> SEQ ID NO 81
<211> LENGTH: 11
<212> TYPE: DNA
<213> ORGANISM: Homo sapiens

<400> SEQUENCE: 81
ttactatgat a                                                            11

<210> SEQ ID NO 82
<211> LENGTH: 20
<212> TYPE: DNA
<213> ORGANISM: Homo sapiens

<400> SEQUENCE: 82
cgagtcggca tcactggggg                                                   20

<210> SEQ ID NO 83
<211> LENGTH: 23
<212> TYPE: DNA
<213> ORGANISM: Homo sapiens
<220> FEATURE:
<221> NAME/KEY: misc_feature
<222> LOCATION: (21)..(21)
<223> OTHER INFORMATION: n is inosine

<400> SEQUENCE: 83
caggtgcagc tggagcagtc ngg                                               23

<210> SEQ ID NO 84
<211> LENGTH: 24
<212> TYPE: DNA
<213> ORGANISM: Homo sapiens

<400> SEQUENCE: 84
gctgagggag tagagtcctg agga                                              24

<210> SEQ ID NO 85
<211> LENGTH: 19
<212> TYPE: DNA
<213> ORGANISM: Homo sapiens

<400> SEQUENCE: 85
cacaccgcgg tcacatggc                                                    19

<210> SEQ ID NO 86
<211> LENGTH: 20
<212> TYPE: DNA
<213> ORGANISM: Homo sapiens

<400> SEQUENCE: 86
ctactctagg gcacctgtcc                                                   20

<210> SEQ ID NO 87
<211> LENGTH: 14
<212> TYPE: PRT
<213> ORGANISM: Homo sapiens

<400> SEQUENCE: 87

Pro Met Pro Leu Pro Arg Gln Asn His Glu Pro Val Ala Thr
1               5                   10
```

```
<210> SEQ ID NO 88
<211> LENGTH: 12
<212> TYPE: PRT
<213> ORGANISM: Homo sapiens

<400> SEQUENCE: 88

Pro Met Pro Leu Pro Arg Gln Asn His Glu Pro Val
1               5                   10

<210> SEQ ID NO 89
<211> LENGTH: 10
<212> TYPE: PRT
<213> ORGANISM: Homo sapiens

<400> SEQUENCE: 89

Pro Met Pro Leu Pro Arg Gln Asn His Glu
1               5                   10

<210> SEQ ID NO 90
<211> LENGTH: 8
<212> TYPE: PRT
<213> ORGANISM: Homo sapiens

<400> SEQUENCE: 90

Pro Met Pro Leu Pro Arg Gln Asn
1               5

<210> SEQ ID NO 91
<211> LENGTH: 6
<212> TYPE: PRT
<213> ORGANISM: Homo sapiens

<400> SEQUENCE: 91

Pro Met Pro Leu Pro Arg
1               5

<210> SEQ ID NO 92
<211> LENGTH: 12
<212> TYPE: PRT
<213> ORGANISM: Homo sapiens

<400> SEQUENCE: 92

Pro Leu Pro Arg Gln Asn His Glu Pro Val Ala Thr
1               5                   10

<210> SEQ ID NO 93
<211> LENGTH: 10
<212> TYPE: PRT
<213> ORGANISM: Homo sapiens

<400> SEQUENCE: 93

Pro Arg Gln Asn His Glu Pro Val Ala Thr
1               5                   10

<210> SEQ ID NO 94
<211> LENGTH: 8
<212> TYPE: PRT
<213> ORGANISM: Homo sapiens

<400> SEQUENCE: 94

Gln Asn His Glu Pro Val Ala Thr
1               5

<210> SEQ ID NO 95
<211> LENGTH: 6
```

```
<212> TYPE: PRT
<213> ORGANISM: Homo sapiens

<400> SEQUENCE: 95

His Glu Pro Val Ala Thr
1               5

<210> SEQ ID NO 96
<211> LENGTH: 7
<212> TYPE: PRT
<213> ORGANISM: Homo sapiens

<400> SEQUENCE: 96

Pro Leu Pro Arg Asn His Glu
1               5

<210> SEQ ID NO 97
<211> LENGTH: 6
<212> TYPE: PRT
<213> ORGANISM: Homo sapiens

<400> SEQUENCE: 97

Leu Pro Arg Gln Asn His
1               5

<210> SEQ ID NO 98
<211> LENGTH: 10
<212> TYPE: PRT
<213> ORGANISM: Homo sapiens

<400> SEQUENCE: 98

Pro Met Pro Ala Pro Arg Gln Asn His Glu
1               5                   10

<210> SEQ ID NO 99
<211> LENGTH: 10
<212> TYPE: PRT
<213> ORGANISM: Homo sapiens

<400> SEQUENCE: 99

Pro Met Pro Leu Ala Arg Gln Asn His Glu
1               5                   10

<210> SEQ ID NO 100
<211> LENGTH: 10
<212> TYPE: PRT
<213> ORGANISM: Homo sapiens

<400> SEQUENCE: 100

Pro Met Pro Leu Pro Ala Gln Asn His Glu
1               5                   10

<210> SEQ ID NO 101
<211> LENGTH: 10
<212> TYPE: PRT
<213> ORGANISM: Homo sapiens

<400> SEQUENCE: 101

Pro Met Pro Leu Pro Arg Ala Asn His Glu
1               5                   10

<210> SEQ ID NO 102
<211> LENGTH: 10
<212> TYPE: PRT
<213> ORGANISM: Homo sapiens
```

-continued

<400> SEQUENCE: 102

Pro Met Pro Leu Pro Arg Gln Ala His Glu
1               5                   10

<210> SEQ ID NO 103
<211> LENGTH: 10
<212> TYPE: PRT
<213> ORGANISM: Homo sapiens

<400> SEQUENCE: 103

Pro Met Pro Leu Pro Arg Gln Asn Ala Glu
1               5                   10

<210> SEQ ID NO 104
<211> LENGTH: 8
<212> TYPE: PRT
<213> ORGANISM: Homo sapiens

<400> SEQUENCE: 104

Pro Leu Pro Arg Gln Asn His Glu
1               5

<210> SEQ ID NO 105
<211> LENGTH: 7
<212> TYPE: PRT
<213> ORGANISM: Homo sapiens

<400> SEQUENCE: 105

Leu Pro Arg Gln Asn His Glu
1               5

<210> SEQ ID NO 106
<211> LENGTH: 8
<212> TYPE: PRT
<213> ORGANISM: Homo sapiens

<400> SEQUENCE: 106

Pro Leu Pro Arg Gln Asn His Glu
1               5

<210> SEQ ID NO 107
<211> LENGTH: 7
<212> TYPE: PRT
<213> ORGANISM: Homo sapiens

<400> SEQUENCE: 107

Leu Pro Arg Gln Asn His Glu
1               5

<210> SEQ ID NO 108
<211> LENGTH: 882
<212> TYPE: DNA
<213> ORGANISM: Homo sapiens

<400> SEQUENCE: 108
atgaaatacc tgctgccgac cgctgctgct ggtctgctgc tcctcgctgc ccagccggcc      60
atggccgata ttgtgatgac ccagactcca ctctccctgc ccgtcacccc tggagagccg     120
gcctccatct cctgcaggtc tagtcggagc ctcttggata tgatgatgg aaacacctat     180 ttggactggt acctgcagaa gccagggcag tctccacagc tcctgatcta cacgctttcc     240
tatcgggcct ctggagtccc agacaggttc agtggcagtg ggtcaggcac tgatttcaca     300

```
ctgaaaatca gcagggtgga ggctgaggat gttggagttt attactgcat gcaacgtgta    360
gagtttccta tcaccttcgg ccaagggaca cgactggaga ttaaactttc gcggacgat     420 gcgaaaaagg atgctgcgaa gaaagatgac gctaagaaag acgatgctaa aaaggacctc    480
caggtgcagc tggtggagtc tgggggaggc gtggtccagc ctgggaggtc cctgagactc    540
tcctgtgcag cgtctggatt catcttcagt cgctatggca tgcactgggt ccgccaggct    600
ccaggcaagg ggctgaaatg ggtggcagtt atatggtatg atggaagtaa taaactctat    660
gcagactccg tgaagggccg attcaccatc tccagagaca attccaagaa cacgctgtat    720
ctgcaaatga acagcctgag agccgaggac acggctgtgt attactgtgc gagagattac    780
tatgataata gtagacatca ctgggggttt gactactggg gccagggaac cctggtcacc    840
gtctcctcag ctagcgatta taaggacgat gatgacaaat ag                       882
```

<210> SEQ ID NO 109
<211> LENGTH: 271
<212> TYPE: PRT
<213> ORGANISM: Homo sapiens

<400> SEQUENCE: 109

Asp Ile Val Met Thr Gln Thr Pro Leu Ser Leu Pro Val Thr Pro Gly
1               5                   10                  15

Glu Pro Ala Ser Ile Ser Cys Arg Ser Ser Arg Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Val Glu Phe Pro Ile Thr Phe Gly Gln Gly Thr Arg Leu Glu Ile
            100                 105                 110

Lys Leu Ser Ala Asp Asp Ala Lys Lys Asp Ala Ala Lys Lys Asp Asp
        115                 120                 125

Ala Lys Lys Asp Asp Ala Lys Lys Asp Leu Gln Val Gln Leu Val Glu
    130                 135                 140

Ser Gly Gly Gly Val Val Gln Pro Gly Arg Ser Leu Arg Leu Ser Cys
145                 150                 155                 160

Ala Ala Ser Gly Phe Ile Phe Ser Arg Tyr Gly Met His Trp Val Arg
                165                 170                 175

Gln Ala Pro Gly Lys Gly Leu Lys Trp Val Ala Val Ile Trp Tyr Asp
            180                 185                 190

Gly Ser Asn Lys Leu Tyr Ala Asp Ser Val Lys Gly Arg Phe Thr Ile
        195                 200                 205

Ser Arg Asp Asn Ser Lys Asn Thr Leu Tyr Leu Gln Met Asn Ser Leu
    210                 215                 220

Arg Ala Glu Asp Thr Ala Val Tyr Tyr Cys Ala Arg Asp Tyr Tyr Asp
225                 230                 235                 240

Asn Ser Arg His His Trp Gly Phe Asp Tyr Trp Gly Gln Gly Thr Leu
                245                 250                 255

Val Thr Val Ser Ser Ala Ser Asp Tyr Lys Asp Asp Asp Asp Lys
            260                 265                 270

<210> SEQ ID NO 110
<211> LENGTH: 1560
<212> TYPE: DNA
<213> ORGANISM: Homo sapiens

<400> SEQUENCE: 110

```
atggaaaccc cagcgcagct tctcttcctc ctgctactct ggctcccaga taccaccgga      60
gatattgtga tgacccagac tccactctcc ctgcccgtca cccctggaga gccggcctcc     120
atctcctgca ggtctagtcg gagcctcttg gatagtgatg atggaaacac ctatttggac     180
tggtacctgc agaagccagg gcagtctcca cagctcctga tctacacgct ttcctatcgg     240
gcctctggag tcccagacag gttcagtggc agtgggtcag gcactgattt cacactgaaa     300
atcagcaggg tggaggctga ggatgttgga gtttattact gcatgcaacg tgtagagttt     360
cctatcacct tcggccaagg gacacgactg gagattaaag gtggtggtgg ttctggcggc     420
ggcggctccg gtggtggtgg ttcccaggtg cagctggtgg agtctggggg aggcgtggtc     480
cagcctggga ggtccctgag actctcctgt gcagcgtctg gattcatctt cagtcgctat     540
ggcatgcact gggtccgcca ggctccaggc aaggggctga atgggtggc agttatatgg      600
tatgatggaa gtaataaact ctatgcagac tccgtgaagg gccgattcac catctccaga     660
gacaattcca agaacacgct gtatctgcaa atgaacagcc tgagagccga ggacacggct     720
gtgtattact gtgcgagaga ttactatgat aatagtagca tcactgggg gtttgactac      780
tggggccagg gaaccctggt caccgtctcc tcaggaggtg gtggatccga tatcaaactg     840
cagcagtcag gggctgaact ggcaagacct ggggcctcag tgaagatgtc ctgcaagact     900
tctggctaca cctttactag gtacacgatg cactgggtaa acagaggcc tggacagggt      960
ctggaatgga ttggatacat taatcctagc cgtggttata ctaattacaa tcagaagttc    1020
aaggacaagg ccacattgac tacagacaaa tcctccagca cagcctacat gcaactgagc    1080
agcctgacat ctgaggactc tgcagtctat tactgtgcaa gatattatga tgatcattac    1140
tgccttgact actggggcca aggcaccact ctcacagtct cctcagtcga aggtggaagt    1200
ggaggttctg gtggaagtgg aggttcaggt ggagtcgacg acattcagct gacccagtct    1260
ccagcaatca tgtctgcatc tccaggggag aaggtcacca tgacctgcag agccagttca    1320
agtgtaagtt acatgaactg gtaccagcag aagtcaggca cctcccccaa agatgggatt    1380
tatgacacat ccaaagtggc ttctggagtc ccttatcgct tcagtggcag tgggtctggg    1440
acctcatact ctctcacaat cagcagcatg gaggctgaag atgctgccac ttattactgc    1500
caacagtgga gtagtaaccc gctcacgttc ggtgctggga ccaagctgga gctgaaatag    1560
```

<210> SEQ ID NO 111
<211> LENGTH: 499
<212> TYPE: PRT
<213> ORGANISM: Homo sapiens

<400> SEQUENCE: 111

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Arg Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60
```

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
            85                  90                  95

Arg Val Glu Phe Pro Ile Thr Phe Gly Gln Gly Thr Arg Leu Glu Ile
        100                 105                 110

Lys Gly Gly Gly Gly Ser Gly Gly Gly Gly Ser Gly Gly Gly Gly Ser
    115                 120                 125

Gln Val Gln Leu Val Glu Ser Gly Gly Val Val Gln Pro Gly Arg
130                 135                 140

Ser Leu Arg Leu Ser Cys Ala Ala Ser Gly Phe Ile Phe Ser Arg Tyr
145                 150                 155                 160

Gly Met His Trp Val Arg Gln Ala Pro Gly Lys Gly Leu Lys Trp Val
            165                 170                 175

Ala Val Ile Trp Tyr Asp Gly Ser Asn Lys Leu Tyr Ala Asp Ser Val
        180                 185                 190

Lys Gly Arg Phe Thr Ile Ser Arg Asp Asn Ser Lys Asn Thr Leu Tyr
    195                 200                 205

Leu Gln Met Asn Ser Leu Arg Ala Glu Asp Thr Ala Val Tyr Tyr Cys
210                 215                 220

Ala Arg Asp Tyr Tyr Asp Asn Ser Arg His His Trp Gly Phe Asp Tyr
225                 230                 235                 240

Trp Gly Gln Gly Thr Leu Val Thr Val Ser Ser Gly Gly Gly Gly Ser
            245                 250                 255

Asp Ile Lys Leu Gln Gln Ser Gly Ala Glu Leu Ala Arg Pro Gly Ala
        260                 265                 270

Ser Val Lys Met Ser Cys Lys Thr Ser Gly Tyr Thr Phe Thr Arg Tyr
    275                 280                 285

Thr Met His Trp Val Lys Gln Arg Pro Gly Gln Gly Leu Glu Trp Ile
290                 295                 300

Gly Tyr Ile Asn Pro Ser Arg Gly Tyr Thr Asn Tyr Asn Gln Lys Phe
305                 310                 315                 320

Lys Asp Lys Ala Thr Leu Thr Thr Asp Lys Ser Ser Ser Thr Ala Tyr
            325                 330                 335

Met Gln Leu Ser Ser Leu Thr Ser Glu Asp Ser Ala Val Tyr Tyr Cys
        340                 345                 350

Ala Arg Tyr Tyr Asp Asp His Tyr Cys Leu Asp Tyr Trp Gly Gln Gly
    355                 360                 365

Thr Thr Leu Thr Val Ser Ser Val Glu Gly Gly Ser Gly Gly Ser Gly
370                 375                 380

Gly Ser Gly Gly Ser Gly Gly Val Asp Asp Ile Gln Leu Thr Gln Ser
385                 390                 395                 400

Pro Ala Ile Met Ser Ala Ser Pro Gly Glu Lys Val Thr Met Thr Cys
            405                 410                 415

Arg Ala Ser Ser Ser Val Ser Tyr Met Asn Trp Tyr Gln Gln Lys Ser
        420                 425                 430

Gly Thr Ser Pro Lys Arg Trp Ile Tyr Asp Thr Ser Lys Val Ala Ser
    435                 440                 445

Gly Val Pro Tyr Arg Phe Ser Gly Ser Gly Ser Gly Thr Ser Tyr Ser
450                 455                 460

Leu Thr Ile Ser Ser Met Glu Ala Glu Asp Ala Ala Thr Tyr Tyr Cys
465                 470                 475                 480

Gln Gln Trp Ser Ser Asn Pro Leu Thr Phe Gly Ala Gly Thr Lys Leu
            485                 490                 495

Glu Leu Lys

<210> SEQ ID NO 112
<211> LENGTH: 1635
<212> TYPE: DNA
<213> ORGANISM: Homo sapiens

<400> SEQUENCE: 112

| | |
|---|---:|
| atggaaaccc cagcgcagct tctcttcctc ctgctactct ggctcccaga taccaccgga | 60 |
| gatattgtga tgacccagac tccactctcc ctgcccgtca cccctggaga gccggcctcc | 120 |
| atctcctgca ggtctagtcg gagcctcttg atagtgatg atggaaacac ctatttggac | 180 |
| tggtacctgc agaagccagg gcagtctcca cagctcctga tctacacgct ttcctatcgg | 240 |
| gcctctggag tcccagacag gttcagtggc agtgggtcag gcactgattt cacactgaaa | 300 |
| atcagcaggg tggaggctga ggatgttgga gtttattact gcatgcaacg tgtagagttt | 360 |
| cctatcacct tcggccaagg gacacgactg gagattaaac tttccgcgga cgatgcgaaa | 420 |
| aaggatgctg cgaagaaaga tgacgctaag aaagacgatg ctaaaaagga cctgcaggtg | 480 |
| cagctggtgg agtctggggg aggcgtggtc cagcctggga ggtccctgag actctcctgt | 540 |
| gcagcgtctg gattcatctt cagtcgctat ggcatgcact gggtccgcca ggctccaggc | 600 |
| aaggggctga atgggtggc agttatatgg tatgatggaa gtaataaact ctatgcagac | 660 |
| tccgtgaagg gccgattcac catctccaga gacaattcca agaacacgct gtatctgcaa | 720 |
| atgaacagcc tgagagccga ggacacggct gtgtattact gtgcgagaga ttactatgat | 780 |
| aatagtagac atcactgggg gtttgactac tggggccagg gaaccctggt caccgtctcc | 840 |
| tcaggaggtg gtggatccga tatcaaactg cagcagtcag gggctgaact ggcaagacct | 900 |
| ggggcctcag tgaagatgtc ctgcaagact tctggctaca cctttactag gtacacgatg | 960 |
| cactgggtaa acagaggcc tggacaggt ctggaatgga ttggatacat taatcctagc | 1020 |
| cgtggttata ctaattacaa tcagaagttc aaggacaagg ccacattgac tacagacaaa | 1080 |
| tcctccagca cagcctacat gcaactgagc agcctgacat ctgaggactc tgcagtctat | 1140 |
| tactgtgcaa gatattatga tgatcattac tgccttgact actggggcca aggcaccact | 1200 |
| ctcacagtct cctcactttc gcggacgat gcgaaaaagg atgctgcgaa gaaagatgac | 1260 |
| gctaagaaag acgatgctaa aaaggacctg acattcagc tgacccagtc tccagcaatc | 1320 |
| atgtctgcat ctccagggga aaggtcacc atgacctgca gagccagttc aagtgtaagt | 1380 |
| tacatgaact ggtaccagca gaagtcaggc acctccccca aaagatggat ttatgacaca | 1440 |
| tccaaagtgg cttctggagt cccttatcgc ttcagtggca gtgggtctgg gacctcatac | 1500 |
| tctctcacaa tcagcagcat ggaggctgaa gatgctgcca cttattactg ccaacagtgg | 1560 |
| agtagtaacc cgctcacgtt cggtgctggg accaagctgg agctgaaaga ttataaggac | 1620 |
| gatgatgaca aatag | 1635 |

<210> SEQ ID NO 113
<211> LENGTH: 524
<212> TYPE: PRT
<213> ORGANISM: Homo sapiens

<400> SEQUENCE: 113

Asp Ile Val Met Thr Gln Thr Pro Leu Ser Leu Pro Val Thr Pro Gly
1               5                  10                  15

Glu Pro Ala Ser Ile Ser Cys Arg Ser Ser Arg Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Val Glu Phe Pro Ile Thr Phe Gly Gln Gly Thr Arg Leu Glu Ile
                100                 105                 110

Lys Leu Ser Ala Asp Asp Ala Lys Lys Asp Ala Ala Lys Lys Asp Asp
            115                 120                 125

Ala Lys Lys Asp Asp Ala Lys Lys Asp Leu Gln Val Gln Leu Val Glu
    130                 135                 140

Ser Gly Gly Gly Val Val Gln Pro Gly Arg Ser Leu Arg Leu Ser Cys
145                 150                 155                 160

Ala Ala Ser Gly Phe Ile Phe Ser Arg Tyr Gly Met His Trp Val Arg
                165                 170                 175

Gln Ala Pro Gly Lys Gly Leu Lys Trp Val Ala Val Ile Trp Tyr Asp
                180                 185                 190

Gly Ser Asn Lys Leu Tyr Ala Asp Ser Val Lys Gly Arg Phe Thr Ile
            195                 200                 205

Ser Arg Asp Asn Ser Lys Asn Thr Leu Tyr Leu Gln Met Asn Ser Leu
    210                 215                 220

Arg Ala Glu Asp Thr Ala Val Tyr Tyr Cys Ala Arg Asp Tyr Tyr Asp
225                 230                 235                 240

Asn Ser Arg His His Trp Gly Phe Asp Tyr Trp Gly Gln Gly Thr Leu
                245                 250                 255

Val Thr Val Ser Ser Gly Gly Gly Ser Asp Ile Lys Leu Gln Gln
                260                 265                 270

Ser Gly Ala Glu Leu Ala Arg Pro Gly Ala Ser Val Lys Met Ser Cys
    275                 280                 285

Lys Thr Ser Gly Tyr Thr Phe Thr Arg Tyr Thr Met His Trp Val Lys
    290                 295                 300

Gln Arg Pro Gly Gln Gly Leu Glu Trp Ile Gly Tyr Ile Asn Pro Ser
305                 310                 315                 320

Arg Gly Tyr Thr Asn Tyr Asn Gln Lys Phe Lys Asp Lys Ala Thr Leu
                325                 330                 335

Thr Thr Asp Lys Ser Ser Ser Thr Ala Tyr Met Gln Leu Ser Ser Leu
            340                 345                 350

Thr Ser Glu Asp Ser Ala Val Tyr Tyr Cys Ala Arg Tyr Tyr Asp Asp
    355                 360                 365

His Tyr Cys Leu Asp Tyr Trp Gly Gln Gly Thr Thr Leu Thr Val Ser
    370                 375                 380

Ser Leu Ser Ala Asp Asp Ala Lys Lys Asp Ala Ala Lys Lys Asp Asp
385                 390                 395                 400

Ala Lys Lys Asp Asp Ala Lys Lys Asp Leu Asp Ile Gln Leu Thr Gln
                405                 410                 415

Ser Pro Ala Ile Met Ser Ala Ser Pro Gly Glu Lys Val Thr Met Thr
                420                 425                 430

```
Cys Arg Ala Ser Ser Val Ser Tyr Met Asn Trp Tyr Gln Gln Lys
            435                 440                 445

Ser Gly Thr Ser Pro Lys Arg Trp Ile Tyr Asp Thr Ser Lys Val Ala
450                 455                 460

Ser Gly Val Pro Tyr Arg Phe Ser Gly Ser Gly Ser Gly Thr Ser Tyr
465                 470                 475                 480

Ser Leu Thr Ile Ser Ser Met Glu Ala Glu Asp Ala Ala Thr Tyr Tyr
                485                 490                 495

Cys Gln Gln Trp Ser Ser Asn Pro Leu Thr Phe Gly Ala Gly Thr Lys
                500                 505                 510

Leu Glu Leu Lys Asp Tyr Lys Asp Asp Asp Lys
            515                 520

<210> SEQ ID NO 114
<211> LENGTH: 169
<212> TYPE: PRT
<213> ORGANISM: Homo sapiens

<400> SEQUENCE: 114

Trp Val Leu Ser Gln Val Gln Leu Gln Glu Ser Gly Pro Gly Leu Val
1               5                   10                  15

Lys Pro Ser Glu Thr Leu Ser Leu Thr Cys Thr Val Ser Gly Gly Ser
            20                  25                  30

Val Ser Ser Gly Tyr Tyr Trp Ser Trp Ile Arg Gln Pro Pro Gly
        35                  40                  45

Lys Gly Leu Glu Trp Ile Gly Phe Ile Tyr Tyr Thr Gly Ser Thr Asn
    50                  55                  60

Tyr Asn Pro Ser Leu Lys Ser Arg Val Ser Ile Ser Val Asp Thr Ser
65                  70                  75                  80

Lys Asn Gln Phe Ser Leu Lys Leu Ser Ser Val Thr Ala Ala Asp Ala
                85                  90                  95

Ala Val Tyr Tyr Cys Ala Arg Asp Tyr Asp Trp Ser Phe His Phe Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala
                165

<210> SEQ ID NO 115
<211> LENGTH: 168
<212> TYPE: PRT
<213> ORGANISM: Homo sapiens

<400> SEQUENCE: 115

Gln Leu Leu Gly Leu Leu Leu Trp Phe Pro Gly Ala Arg Cys Asp
1               5                   10                  15

Ile Gln Met Thr Gln Ser Pro Ser Ser Leu Ser Ala Ser Ile Gly Asp
            20                  25                  30

Arg Val Thr Ile Thr Cys Arg Ala Ser Gln Gly Ile Arg Asn Asp Leu
        35                  40                  45

Gly Trp Tyr Gln Gln Lys Pro Gly Lys Ala Pro Lys Arg Leu Ile Tyr
    50                  55                  60
```

Ala Ala Ser Ser Leu Gln Gly Val Pro Ser Arg Phe Ser Gly Ser
65                  70                  75                  80

Gly Ser Gly Thr Glu Phe Thr Leu Thr Ile Ser Ser Leu Gln Pro Glu
                85                  90                  95

Asp Phe Ala Thr Tyr Tyr Cys Leu Gln His Asn Ser Tyr Pro Leu Thr
            100                 105                 110

Phe Gly Gly Gly Thr Lys Val Glu Ile Lys Arg Thr Val Ala Ala Pro
        115                 120                 125

Ser Val Phe Ile Phe Pro Pro Ser Asp Glu Gln Leu Lys Ser Gly Thr
    130                 135                 140

Ala Ser Val Val Cys Leu Leu Asn Asn Phe Tyr Pro Arg Glu Ala Lys
145                 150                 155                 160

Val Gln Trp Lys Val Asp Asn Ala
                165

<210> SEQ ID NO 116
<211> LENGTH: 156
<212> TYPE: PRT
<213> ORGANISM: Homo sapiens

<400> SEQUENCE: 116

Gln Cys Glu Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Phe Thr
                20                  25                  30

Asn Tyr Trp Met Ser Trp Val Arg Gln Ala Pro Gly Lys Gly Leu Glu
            35                  40                  45

Trp Val Ala Asn Ile Gln Gln Asp Gly Ser Glu Lys Tyr Tyr Val Asp
    50                  55                  60

Ser Val Arg Gly Arg Phe Thr Ile Ser Arg Asp Asn Ala Lys Asn Ser
65                  70                  75                  80

Leu Tyr Leu Gln Met Asn Ser Leu Arg Ala Glu Asp Ser Ala Val Tyr
                85                  90                  95

Tyr Cys Ala Arg Trp Asp Tyr Trp Gly Gln Gly Thr Leu Val Thr Val
            100                 105                 110

Ser Ser Ala Ser Thr Lys Gly Pro Ser Val Phe Pro Leu Ala Pro Cys
        115                 120                 125

Ser Arg Ser Thr Ser Glu Ser Thr Ala Ala Leu Gly Cys Leu Val Lys
    130                 135                 140

Asp Tyr Phe Pro Glu Pro Val Ser Gly Val Val Glu
145                 150                 155

<210> SEQ ID NO 117
<211> LENGTH: 151
<212> TYPE: PRT
<213> ORGANISM: Homo sapiens

<400> SEQUENCE: 117

Leu Leu Gly Leu Leu Met Leu Trp Val Pro Gly Ser Ser Gly Asp Ile
1               5                   10                  15

Val Met Thr Gln Thr Pro Leu Ser Ser Thr Val Ile Leu Gly Gln Pro
                20                  25                  30

Ala Ser Ile Ser Cys Arg Ser Ser Gln Ser Leu Val His Ser Asp Gly
            35                  40                  45

Asn Thr Tyr Leu Asn Trp Leu Gln Gln Arg Pro Gly Gln Pro Pro Arg
    50                  55                  60

Leu Leu Ile Tyr Met Ile Ser Asn Arg Phe Ser Gly Val Pro Asp Arg
65                  70                  75                  80

Phe Ser Gly Ser Gly Ala Gly Thr Asp Phe Thr Leu Lys Ile Ser Arg
            85                  90                  95

Val Glu Ala Glu Asp Val Gly Val Tyr Tyr Cys Met Gln Ala Thr Glu
        100                 105                 110

Ser Pro Gln Thr Phe Gly Gln Gly Thr Lys Val Glu Ile Lys Arg Thr
    115                 120                 125

Val Ala Ala Pro Ser Val Phe Ile Phe Pro Pro Ser Asp Glu Gln Leu
130                 135                 140

Lys Ser Gly Arg Ala Ser Val
145                 150

<210> SEQ ID NO 118
<211> LENGTH: 180
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: Xaa is any amino acid

<400> SEQUENCE: 118

Xaa Xaa Xaa Xaa Glu Gln Ser Gly Gly Gly Val Val Lys Pro Gly Gly
1               5                   10                  15

Ser Leu Arg Leu Ser Cys Ala Ala Ser Gly Phe Thr Phe Ser Asn Ala
            20                  25                  30

Trp Met Thr Trp Val Arg Gln Ala Pro Gly Lys Gly Leu Glu Trp Val
        35                  40                  45

Gly Arg Ile Lys Arg Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Asn Leu Lys Asn Glu Asp Thr Ala Val Tyr
            85                  90                  95

Tyr Cys Thr Ser Val Asp Asn Asp Val Asp Tyr Trp Gly Gln Gly Thr
        100                 105                 110

Leu Val Thr Val Ser Ser Ala Ser Thr Lys Gly Pro Ser Val Phe Pro
    115                 120                 125

Leu Ala Pro Cys Ser Arg Ser Thr Ser Glu Ser Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu
            180

<210> SEQ ID NO 119
<211> LENGTH: 152
<212> TYPE: PRT
<213> ORGANISM: Homo sapiens
<220> FEATURE:
<221> NAME/KEY: MISC_FEATURE
<222> LOCATION: (1)..(3)
<223> OTHER INFORMATION: Xaa is any amino acid

<400> SEQUENCE: 119

Xaa Xaa Xaa Leu Thr Gln Ser Pro Leu Ser Leu Pro Val Thr Pro Gly

```
  1               5                  10                 15
Glu Pro Ala Ser Ile Ser Cys Arg Ser Ser Gln Ser Leu Leu His Ser
            20                  25                 30

Asn Gly Tyr Asn Tyr Leu Asp Trp Tyr Leu Gln Lys Pro Gly Gln Ser
            35                  40                 45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Ile Gly Leu Tyr Tyr Cys Met Gln Ala
                85                  90                  95

Leu Gln Thr Pro Leu Thr Phe Gly Gly Gly Thr Lys Val Asp Ile Lys
            100                 105                110

Arg Thr Val Ala Ala Pro Ser Val Phe Ile Phe Pro Pro Ser Asp Glu
            115                 120                125

Gln Leu Lys Ser Gly Thr Ala Ser Val Val Cys Leu Leu Asn Asn Phe
            130                 135                140

Tyr Pro Arg Glu Ala Lys Val Gln
145                 150
```

<210> SEQ ID NO 120
<211> LENGTH: 179
<212> TYPE: PRT
<213> ORGANISM: Homo sapiens

<400> SEQUENCE: 120

```
Gln Val Gln Leu Glu Gln Ser Gly Gly Gly Leu Val Gln Pro Gly Gly
1               5                  10                 15

Ser Leu Arg Leu Ser Cys Ala Ala Ser Gly Phe Thr Phe Ser Thr Tyr
            20                  25                 30

Ser Met Asn Trp Val Arg Gln Ala Pro Gly Lys Gly Leu Glu Trp Val
            35                  40                 45

Ser Tyr Ile Arg Ser Ser Thr Ser Thr Ile Tyr Tyr Ala Glu Ser Leu
    50                  55                  60

Lys Gly Arg Phe Thr Ile Ser Ser Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp Phe Asp Tyr Trp Gly Gln Gly Thr Leu Val Thr Val Ser
            100                 105                110

Ser Ala Ser Thr Lys Gly Pro Ser Val Phe Pro Leu Ala Pro Cys Ser
            115                 120                125

Arg Ser Thr Ser Glu Ser Thr Ala Ala Leu Gly Cys Leu Val Lys Asp
            130                 135                140

Tyr Phe Pro Glu Pro Val Thr Val Ser Trp Asn Ser Gly Ala Leu Thr
145                 150                 155                160

Ser Gly Val His Thr Phe Pro Ala Val Leu Gln Ser Ser Gly Leu Tyr
                165                 170                175

Ser Leu Ser
```

<210> SEQ ID NO 121
<211> LENGTH: 163
<212> TYPE: PRT
<213> ORGANISM: Homo sapiens

<400> SEQUENCE: 121

Glu Ile Gln Leu Thr Gln Ser Pro Leu Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asp Thr Tyr Leu Asn Trp Leu Gln Gln Arg Pro Gly Gln Pro
        35                  40                  45

Pro Arg Leu Leu Ile Tyr Lys Ile Ser Thr Arg Phe Ser Gly Val Pro
    50                  55                  60

Asp Arg Phe Ser Gly Ser Gly Ala Gly Thr Asp Phe Thr Leu Lys Ile
65              70                  75                  80

Ser Arg Val Glu Thr Asp Asp Val Gly Ile Tyr Tyr Cys Met Gln Thr
                85                  90                  95

Thr Gln Ile Pro Gln Ile Thr Phe Gly Gln Gly Thr Arg Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly

<210> SEQ ID NO 122
<211> LENGTH: 189
<212> TYPE: PRT
<213> ORGANISM: Homo sapiens

<400> SEQUENCE: 122

Gln Val Gln Leu Glu Gln Ser Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Lys Trp Val
        35                  40                  45

Ala Val Ile Trp Tyr Asp Gly Ser Asn Lys Leu Tyr Ala Asp Ser Val
    50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Arg Asp Tyr Tyr Asp Asn Ser Arg His His Trp Gly Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser
            180                 185

<210> SEQ ID NO 123

<211> LENGTH: 157
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa is Leu or Met
<220> FEATURE:
<221> NAME/KEY: MISC_FEATURE
<222> LOCATION: (5)..(5)
<223> OTHER INFORMATION: Xaa is Thr or Leu

<400> SEQUENCE: 123

```
Asp Ile Gln Xaa Xaa Gln Ser Pro Ser Ser Leu Ser Ala Ser Val Gly
1               5                   10                  15

Asp Arg Val Thr Ile Thr Cys Arg Ala Ser Gln Ser Ile Tyr Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly
145                 150                 155
```

<210> SEQ ID NO 124
<211> LENGTH: 181
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: Xaa is any amino acid

<400> SEQUENCE: 124

```
Xaa Xaa Xaa Xaa Xaa Gln Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Thr Trp Val Arg Gln Ala Pro Gly Lys Gly Leu Glu Trp Val
        35                  40                  45

Gly Arg Ile Lys Arg Lys Thr Asp Gly Gly Thr Thr Asp Tyr Ala Ala
50                  55                  60

Pro Val Lys Gly Arg Phe Thr Ile Ser Arg Asp Asp Ser Glu Asn Thr
65                  70                  75                  80

Leu Tyr Leu Gln Met Asn Ser Leu Glu Thr Glu Asp Thr Ala Val Tyr
                85                  90                  95

Tyr Cys Thr Thr Val Asp Asn Ser Gly Asp Tyr Trp Gly Gln Gly Thr
            100                 105                 110

Leu Val Thr Val Ser Ser Ala Ser Thr Lys Gly Pro Ser Val Phe Pro
        115                 120                 125
```

Leu Ala Pro Cys Ser Arg Ser Thr Ser Glu Ser Thr Ala Ala Leu Gly
         130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Ser
            180

<210> SEQ ID NO 125
<211> LENGTH: 159
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: Xaa is any amino acid

<400> SEQUENCE: 125

Xaa Xaa Xaa Xaa Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu
145                 150                 155

<210> SEQ ID NO 126
<211> LENGTH: 179
<212> TYPE: PRT
<213> ORGANISM: Homo sapiens

<400> SEQUENCE: 126

Gln Val Gln Leu Glu Gln Ser Gly Gly Gly Val Val Gln Pro Gly Arg
1               5                   10                  15

Ser Leu Arg Leu Ser Cys Ala Ala Ser Gly Phe Thr Phe Thr Asn Tyr
            20                  25                  30

Gly Leu His Trp Val Arg Gln Ala Pro Gly Lys Gly Leu Asp Trp Val
        35                  40                  45

Ala Val Ile Trp Tyr Asp Gly Ser His Lys Phe Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys

```
                      85                  90                  95

Thr Arg Asp Leu Asp Tyr Trp Gly Gln Gly Thr Leu Val Thr Val Ser
                    100                 105                 110

Ser Ala Ser Thr Lys Gly Pro Ser Val Phe Pro Leu Ala Pro Cys Ser
                    115                 120                 125

Arg Ser Thr Ser Glu Ser Thr Ala Ala Leu Gly Cys Leu Val Lys Asp
                130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser

<210> SEQ ID NO 127
<211> LENGTH: 160
<212> TYPE: PRT
<213> ORGANISM: Homo sapiens

<400> SEQUENCE: 127

Glu Thr Gln Leu Thr Gln Ser Pro Gly Thr Leu Ser Leu Ser Pro Gly
1               5                   10                  15

Glu Arg Val Thr Leu Ser Cys Arg Ala Ser Gln Ser Val Ser Asn Asn
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Cys Ala Glu Cys Tyr Cys Gln Gln Tyr Gly Ser Ser Leu
                85                  90                  95

Pro Leu Thr Phe Gly Gly Gly Thr Lys Val Glu Ile Lys Arg Thr Val
                100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
        130                 135                 140

Glu Ala Lys Val Gln Trp Glu Gly Gly Ile Thr Pro Ser Asn Arg Val
145                 150                 155                 160

<210> SEQ ID NO 128
<211> LENGTH: 180
<212> TYPE: PRT
<213> ORGANISM: Homo sapiens
<220> FEATURE:
<221> NAME/KEY: MISC_FEATURE
<222> LOCATION: (62)..(62)
<223> OTHER INFORMATION: Xaa is Tyr or Leu
<220> FEATURE:
<221> NAME/KEY: MISC_FEATURE
<222> LOCATION: (64)..(64)
<223> OTHER INFORMATION: Xaa is Ala or Thr

<400> SEQUENCE: 128

Val Gln Cys Gln Val Gln Leu Val Glu Ser Gly Gly Gly Val Val Gln
1               5                   10                  15

Pro Gly Arg Ser Leu Arg Leu Ser Cys Ala Ala Ser Gly Phe Thr Phe
                20                  25                  30
```

```
Ser Ser Tyr Gly Met His Trp Val Arg Gln Ala Pro Gly Lys Gly Leu
        35                  40                  45

Glu Trp Val Ala Val Ile Trp Tyr Asp Gly Ser His Lys Xaa Tyr Xaa
 50                  55                  60

Asp Ser Val Lys Gly Arg Phe Thr Ile Ser Arg Asp Asn Ser Lys Asn
 65                  70                  75                  80

Thr Leu Tyr Leu Gln Met Asn Ser Leu Arg Ala Glu Asp Thr Ala Val
                 85                  90                  95

Tyr Tyr Ser Ala Arg Asp Tyr Tyr Asp Thr Ser Arg His His Trp Gly
            100                 105                 110

Phe Asp Cys Trp Gly Gln Gly Thr Leu Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro
        180

<210> SEQ ID NO 129
<211> LENGTH: 173
<212> TYPE: PRT
<213> ORGANISM: Homo sapiens

<400> SEQUENCE: 129

Gln Leu Leu Gly Leu Leu Met Leu Trp Val Pro Gly Ser Ser Glu Glu
 1               5                  10                  15

Ile Val Met Thr Gln Thr Pro Leu Ser Leu Pro Val Thr Pro Gly Glu
                 20                  25                  30

Pro Ala Ser Ile Ser Cys Arg Ser Ser Gln Ser Leu Leu Asp Ser Glu
            35                  40                  45

Asp Gly Asn Thr Tyr Leu Asp Trp Tyr Leu Gln Lys Pro Gly Gln Ser
 50                  55                  60

Pro Gln Leu Leu Ile Tyr Thr Leu Ser His Arg Ala Ser Gly Val Pro
 65                  70                  75                  80

Asp Arg Phe Ser Gly Ser Gly Ser Gly Thr Asp Phe Thr Leu Lys Ile
                 85                  90                  95

Ser Arg Val Glu Ala Glu Asp Val Gly Val Tyr Cys Cys Met Gln Arg
            100                 105                 110

Val Glu Phe Pro Ile Thr Phe Gly Gln Gly Thr Arg Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn
                165                 170

<210> SEQ ID NO 130
<211> LENGTH: 187
<212> TYPE: PRT
<213> ORGANISM: Homo sapiens
<220> FEATURE:
<221> NAME/KEY: MISC_FEATURE
<222> LOCATION: (1)..(5)
```

<223> OTHER INFORMATION: Xaa is any amino acid

<400> SEQUENCE: 130

```
Xaa Xaa Xaa Xaa Xaa Gln Ser Gly Pro Arg Leu Val Lys Pro Ser Gln
1               5                   10                  15
Thr Leu Ser Leu Thr Cys Thr Val Ser Gly Gly Ser Ile Ser Ser Asp
            20                  25                  30
Gly Tyr Tyr Trp Ser Trp Ile Arg Gln His Pro Gly Lys Gly Leu Glu
        35                  40                  45
Trp Ile Gly Tyr Ile Tyr Tyr Ser Gly Ser Thr Phe Tyr Asn Pro Ser
    50                  55                  60
Leu Lys Ser Arg Val Ala Ile Ser Val Asp Thr Ser Lys Asn Gln Phe
65                  70                  75                  80
Ser Leu Lys Leu Ser Ser Val Thr Ala Ala Asp Thr Ala Val Tyr Tyr
                85                  90                  95
Cys Ala Arg Glu Ser Pro His Ser Ser Asn Trp Tyr Ser Gly Phe Asp
            100                 105                 110
Cys Trp Gly Gln Gly Thr Leu Val Thr Val Ser Ser Ala Ser Thr Lys
        115                 120                 125
Gly Pro Ser Val Phe Pro Leu Ala Pro Cys Ser Arg Ser Thr Ser Glu
    130                 135                 140
Ser Thr Ala Ala Leu Gly Cys Leu Val Lys Asp Tyr Phe Pro Arg Thr
145                 150                 155                 160
Gly Asp Gly Val Val Glu Leu Arg Arg Pro Asp Gln Arg Ala His
                165                 170                 175
Leu Pro Gly Cys Pro Thr Val Leu Arg Thr Leu
            180                 185
```

<210> SEQ ID NO 131
<211> LENGTH: 154
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: Xaa is any amino acid

<400> SEQUENCE: 131

```
Xaa Xaa Xaa Xaa Thr Gln Ser Pro Asp Phe Gln Ser Val Thr Pro Lys
1               5                   10                  15
Glu Lys Val Thr Ile Thr Cys Arg Ala Ser Gln Ser Ile Gly Ser Arg
            20                  25                  30
Leu His Trp Tyr Gln Gln Lys Pro Asp Gln Ser Pro Lys Leu Leu Ile
        35                  40                  45
Lys Tyr Ala Ser Gln Ser Phe Ser Gly Val Pro Ser Arg Phe Ser Gly
    50                  55                  60
Ser Gly Ser Gly Thr Asp Phe Thr Leu Thr Ile Asn Ser Leu Glu Ala
65                  70                  75                  80
Glu Asp Ala Ala Thr Tyr Tyr Cys His Gln Ser Ser Asn Leu Pro Phe
                85                  90                  95
Thr Phe Gly Pro Gly Thr Lys Val Asp Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
```

Lys Val Gln Trp Lys Val Asp Asn Ala Leu
145                 150

<210> SEQ ID NO 132
<211> LENGTH: 178
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa is Glu or Gln
<220> FEATURE:
<221> NAME/KEY: MISC_FEATURE
<222> LOCATION: (59)..(59)
<223> OTHER INFORMATION: Xaa is Tyr or Leu

<400> SEQUENCE: 132

Gln Val Gln Leu Val Xaa Ala Gly Gly Val Val Gln Pro Gly Arg
1               5                   10                  15

Ser Leu Arg Leu Ser Cys Ala Ala Ser Gly Phe Thr Phe Arg Ser Tyr
                20                  25                  30

Gly Met His Trp Val Arg Gln Ala Pro Gly Lys Gly Leu Lys Trp Val
            35                  40                  45

Ala Val Ile Trp Tyr Asp Gly Ser Asn Lys Xaa Tyr Thr Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Asp Tyr Tyr Asp Asn Ser Arg His His Trp Gly Phe Asp Tyr
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Arg Arg Ala His Leu
                165                 170                 175

Pro Gly

<210> SEQ ID NO 133
<211> LENGTH: 156
<212> TYPE: PRT
<213> ORGANISM: Homo sapiens

<400> SEQUENCE: 133

Asp Ile Gln Met Thr Gln Ser Pro Ser Ser Arg Cys Ala Ser Val Gly
1               5                   10                  15

Asp Arg Val Thr Ile Thr Cys Arg Ala Ser Gln Gly Ile Arg Asn Asp
                20                  25                  30

Leu Ala Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Arg Ser Gly Thr Glu Phe Thr Leu Thr Ile Ser Ser Leu Gln Pro
65                  70                  75                  80

Glu Asp Phe Ala Ala Tyr Tyr Cys Leu Gln His Asn Ser Tyr Pro Pro
                85                  90                  95

```
Ser Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser
145                 150                 155

<210> SEQ ID NO 134
<211> LENGTH: 171
<212> TYPE: PRT
<213> ORGANISM: Homo sapiens

<400> SEQUENCE: 134

His Val Gln Val Gln Leu Val Glu Ser Gly Gly Val Val Gln Pro
1               5                   10                  15

Gly Arg Ser Leu Arg Leu Ser Cys Ala Ala Ser Gly Phe Ile Phe Ser
            20                  25                  30

Arg Tyr Gly Met His Trp Val Arg Gln Ala Pro Gly Lys Gly Leu Lys
        35                  40                  45

Trp Val Ala Val Ile Trp Tyr Asp Gly Ser Asn Lys Leu Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Tyr Tyr Asp Asn Ser Arg His His Trp Gly Phe
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu
                165                 170

<210> SEQ ID NO 135
<211> LENGTH: 174
<212> TYPE: PRT
<213> ORGANISM: Homo sapiens

<400> SEQUENCE: 135

Ser Ala Pro Gly Ala Ala Asn Ala Leu Gly Pro Trp Ile Ser Glu Asp
1               5                   10                  15

Ile Val Met Thr Gln Thr Pro Leu Ser Leu Pro Val Thr Pro Gly Glu
            20                  25                  30

Pro Ala Ser Ile Ser Cys Arg Ser Arg Ser Leu Leu Asp Ser Asp
        35                  40                  45

Asp Gly Asn Thr Tyr Leu Asp Trp Tyr Leu Gln Lys Pro Gly Gln Ser
    50                  55                  60

Pro Gln Leu Leu Ile Tyr Thr Leu Ser Tyr Arg Ala Ser Gly Val Pro
65                  70                  75                  80

Asp Arg Phe Ser Gly Ser Gly Ser Gly Thr Asp Phe Thr Leu Lys Ile
                85                  90                  95
```

```
Ser Arg Val Glu Ala Glu Asp Val Gly Val Tyr Tyr Cys Met Gln Arg
            100                 105                 110

Val Glu Phe Pro Ile Thr Phe Gly Gln Gly Thr Arg Leu Glu Ile Lys
            115                 120                 125

Arg Thr Val Ala Ala Pro Ser Val Phe Ile Phe Pro Pro Ser Asp Glu
            130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala
                165                 170

<210> SEQ ID NO 136
<211> LENGTH: 186
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: Xaa is any amino acid

<400> SEQUENCE: 136

Xaa Xaa Xaa Xaa Glu Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Phe Tyr Asp Ser Ser Arg Tyr His Tyr Gly Met Asp Val
            100                 105                 110

Trp Gly Gln Gly Thr Thr Val Thr Val Ser Ser Ala Ser Thr Lys Gly
            115                 120                 125

Pro Ser Val Phe Pro Leu Ala Pro Cys Ser Arg Ser Thr Ser Glu Ser
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Ser
            180                 185

<210> SEQ ID NO 137
<211> LENGTH: 143
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: Xaa is any amino acid

<400> SEQUENCE: 137

Xaa Xaa Xaa Xaa Thr Gln Cys Pro Leu Ser Leu Pro Val Thr Pro Gly
1               5                   10                  15
```

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Val Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Ile Glu Phe Pro Ile Thr Phe Gly Gln Gly Thr Arg Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn
    130                 135                 140

<210> SEQ ID NO 138
<211> LENGTH: 10
<212> TYPE: PRT
<213> ORGANISM: Homo sapiens

<400> SEQUENCE: 138

Gly Phe Thr Phe Thr Asn Tyr Gly Leu His
1               5                   10

<210> SEQ ID NO 139
<211> LENGTH: 17
<212> TYPE: PRT
<213> ORGANISM: Homo sapiens

<400> SEQUENCE: 139

Val Ile Trp Tyr Asp Gly Ser His Lys Phe Tyr Ala Asp Ser Val Lys
1               5                   10                  15

Gly

<210> SEQ ID NO 140
<211> LENGTH: 4
<212> TYPE: PRT
<213> ORGANISM: Homo sapiens

<400> SEQUENCE: 140

Asp Leu Asp Tyr
1

<210> SEQ ID NO 141
<211> LENGTH: 12
<212> TYPE: PRT
<213> ORGANISM: Homo sapiens

<400> SEQUENCE: 141

Arg Ala Ser Gln Ser Val Ser Asn Asn Tyr Leu Ala
1               5                   10

<210> SEQ ID NO 142
<211> LENGTH: 7
<212> TYPE: PRT
<213> ORGANISM: Homo sapiens

<400> SEQUENCE: 142

Gly Ala Ser Ser Arg Ala Thr

-continued

```
<210> SEQ ID NO 143
<211> LENGTH: 10
<212> TYPE: PRT
<213> ORGANISM: Homo sapiens

<400> SEQUENCE: 143

Gln Gln Tyr Gly Ser Ser Leu Pro Leu Thr
1               5                   10

<210> SEQ ID NO 144
<211> LENGTH: 10
<212> TYPE: PRT
<213> ORGANISM: Homo sapiens

<400> SEQUENCE: 144

Gly Phe Thr Phe Ser Ser Tyr Gly Met Tyr
1               5                   10

<210> SEQ ID NO 145
<211> LENGTH: 17
<212> TYPE: PRT
<213> ORGANISM: Homo sapiens

<400> SEQUENCE: 145

Val Ile Trp Tyr Asp Gly Ser Asn Lys Tyr Tyr Ala Asp Ser Val Lys
1               5                   10                  15

Gly

<210> SEQ ID NO 146
<211> LENGTH: 14
<212> TYPE: PRT
<213> ORGANISM: Homo sapiens

<400> SEQUENCE: 146

Asp Phe Tyr Asp Ser Ser Arg Tyr His Tyr Gly Met Asp Val
1               5                   10

<210> SEQ ID NO 147
<211> LENGTH: 17
<212> TYPE: PRT
<213> ORGANISM: Homo sapiens

<400> SEQUENCE: 147

Arg Ser Ser Gln Ser Leu Leu Asp Ser Asp Asp Gly Asn Thr Tyr Leu
1               5                   10                  15

Asp

<210> SEQ ID NO 148
<211> LENGTH: 7
<212> TYPE: PRT
<213> ORGANISM: Homo sapiens

<400> SEQUENCE: 148

Thr Val Ser Tyr Arg Ala Ser
1               5

<210> SEQ ID NO 149
<211> LENGTH: 9
<212> TYPE: PRT
<213> ORGANISM: Homo sapiens

<400> SEQUENCE: 149
```

Met Gln Arg Ile Glu Phe Pro Ile Thr
1               5

<210> SEQ ID NO 150
<211> LENGTH: 12
<212> TYPE: PRT
<213> ORGANISM: Homo sapiens

<400> SEQUENCE: 150

Gly Gly Ser Ile Ser Ser Asp Gly Tyr Tyr Trp Ser
1               5                   10

<210> SEQ ID NO 151
<211> LENGTH: 16
<212> TYPE: PRT
<213> ORGANISM: Homo sapiens

<400> SEQUENCE: 151

Tyr Ile Tyr Tyr Ser Gly Ser Thr Phe Tyr Asn Pro Ser Leu Lys Ser
1               5                   10                  15

<210> SEQ ID NO 152
<211> LENGTH: 14
<212> TYPE: PRT
<213> ORGANISM: Homo sapiens

<400> SEQUENCE: 152

Glu Ser Pro His Ser Ser Asn Trp Tyr Ser Gly Phe Asp Cys
1               5                   10

<210> SEQ ID NO 153
<211> LENGTH: 11
<212> TYPE: PRT
<213> ORGANISM: Homo sapiens

<400> SEQUENCE: 153

Arg Ala Ser Gln Ser Ile Gly Ser Arg Leu His
1               5                   10

<210> SEQ ID NO 154
<211> LENGTH: 7
<212> TYPE: PRT
<213> ORGANISM: Homo sapiens

<400> SEQUENCE: 154

Tyr Ala Ser Gln Ser Phe Ser
1               5

<210> SEQ ID NO 155
<211> LENGTH: 9
<212> TYPE: PRT
<213> ORGANISM: Homo sapiens

<400> SEQUENCE: 155

His Gln Ser Ser Asn Leu Pro Phe Thr
1               5

<210> SEQ ID NO 156
<211> LENGTH: 10
<212> TYPE: PRT
<213> ORGANISM: Homo sapiens

<400> SEQUENCE: 156

Gly Phe Ile Phe Ser Arg Tyr Gly Met His

-continued

```
1               5                   10
```

<210> SEQ ID NO 157
<211> LENGTH: 17
<212> TYPE: PRT
<213> ORGANISM: Homo sapiens

<400> SEQUENCE: 157

```
Val Ile Trp Tyr Asp Gly Ser Asn Lys Leu Tyr Ala Asp Ser Val Lys
1               5                   10                  15

Gly
```

<210> SEQ ID NO 158
<211> LENGTH: 14
<212> TYPE: PRT
<213> ORGANISM: Homo sapiens

<400> SEQUENCE: 158

```
Asp Tyr Tyr Asp Asn Ser Arg His His Trp Gly Phe Asp Tyr
1               5                   10
```

<210> SEQ ID NO 159
<211> LENGTH: 17
<212> TYPE: PRT
<213> ORGANISM: Homo sapiens

<400> SEQUENCE: 159

```
Arg Ser Ser Arg Ser Leu Leu Asp Ser Asp Asp Gly Asn Thr Tyr Leu
1               5                   10                  15

Asp
```

<210> SEQ ID NO 160
<211> LENGTH: 7
<212> TYPE: PRT
<213> ORGANISM: Homo sapiens

<400> SEQUENCE: 160

```
Thr Leu Ser Tyr Arg Ala Ser
1               5
```

<210> SEQ ID NO 161
<211> LENGTH: 9
<212> TYPE: PRT
<213> ORGANISM: Homo sapiens

<400> SEQUENCE: 161

```
Met Gln Arg Val Glu Phe Pro Ile Thr
1               5
```

<210> SEQ ID NO 162
<211> LENGTH: 10
<212> TYPE: PRT
<213> ORGANISM: Homo sapiens

<400> SEQUENCE: 162

```
Gly Phe Thr Phe Ser Arg Tyr Gly Met His
1               5                   10
```

<210> SEQ ID NO 163
<211> LENGTH: 11
<212> TYPE: PRT
<213> ORGANISM: Homo sapiens

<400> SEQUENCE: 163

Arg Ala Ser Gln Ser Ile Tyr Ser Tyr Leu Asn
1               5                   10

<210> SEQ ID NO 164
<211> LENGTH: 7
<212> TYPE: PRT
<213> ORGANISM: Homo sapiens

<400> SEQUENCE: 164

Ala Ala Ser Ser Leu Gln Ser
1               5

<210> SEQ ID NO 165
<211> LENGTH: 9
<212> TYPE: PRT
<213> ORGANISM: Homo sapiens

<400> SEQUENCE: 165

Gln Gln Ser Tyr Ser Thr Pro Pro Thr
1               5

<210> SEQ ID NO 166
<211> LENGTH: 10
<212> TYPE: PRT
<213> ORGANISM: Homo sapiens

<400> SEQUENCE: 166

Gly Phe Thr Phe Arg Ser Tyr Gly Met His
1               5                   10

<210> SEQ ID NO 167
<211> LENGTH: 17
<212> TYPE: PRT
<213> ORGANISM: Homo sapiens

<400> SEQUENCE: 167

Val Ile Trp Tyr Asp Gly Ser Asn Lys Tyr Tyr Thr Asp Ser Val Lys
1               5                   10                  15

Gly

<210> SEQ ID NO 168
<211> LENGTH: 11
<212> TYPE: PRT
<213> ORGANISM: Homo sapiens

<400> SEQUENCE: 168

Arg Ala Ser Gln Gly Ile Arg Asn Asp Leu Ala
1               5                   10

<210> SEQ ID NO 169
<211> LENGTH: 9
<212> TYPE: PRT
<213> ORGANISM: Homo sapiens

<400> SEQUENCE: 169

Leu Gln His Asn Ser Tyr Pro Pro Ser
1               5

<210> SEQ ID NO 170
<211> LENGTH: 10
<212> TYPE: PRT
<213> ORGANISM: Homo sapiens

<400> SEQUENCE: 170

```
Gly Phe Thr Phe Ser Ser Tyr Gly Met His
1               5                   10

<210> SEQ ID NO 171
<211> LENGTH: 17
<212> TYPE: PRT
<213> ORGANISM: Homo sapiens

<400> SEQUENCE: 171

Val Ile Trp Tyr Asp Gly Ser His Lys Tyr Tyr Ala Asp Ser Val Lys
1               5                   10                  15

Gly

<210> SEQ ID NO 172
<211> LENGTH: 14
<212> TYPE: PRT
<213> ORGANISM: Homo sapiens

<400> SEQUENCE: 172

Asp Tyr Tyr Asp Thr Ser Arg His His Trp Gly Phe Asp Cys
1               5                   10

<210> SEQ ID NO 173
<211> LENGTH: 17
<212> TYPE: PRT
<213> ORGANISM: Homo sapiens

<400> SEQUENCE: 173

Arg Ser Ser Gln Ser Leu Leu Asp Ser Glu Asp Gly Asn Thr Tyr Leu
1               5                   10                  15

Asp

<210> SEQ ID NO 174
<211> LENGTH: 7
<212> TYPE: PRT
<213> ORGANISM: Homo sapiens

<400> SEQUENCE: 174

Thr Leu Ser His Arg Ala Ser
1               5

<210> SEQ ID NO 175
<211> LENGTH: 10
<212> TYPE: PRT
<213> ORGANISM: Homo sapiens

<400> SEQUENCE: 175

Gly Phe Thr Phe Ser Asn Ala Trp Met Thr
1               5                   10

<210> SEQ ID NO 176
<211> LENGTH: 19
<212> TYPE: PRT
<213> ORGANISM: Homo sapiens

<400> SEQUENCE: 176

Arg Ile Lys Arg Arg Thr Asp Gly Gly Thr Thr Asp Tyr Ala Ala Pro
1               5                   10                  15

Val Lys Gly

<210> SEQ ID NO 177
<211> LENGTH: 7
```

```
<212> TYPE: PRT
<213> ORGANISM: Homo sapiens

<400> SEQUENCE: 177

Val Asp Asn Asp Val Asp Tyr
1               5

<210> SEQ ID NO 178
<211> LENGTH: 16
<212> TYPE: PRT
<213> ORGANISM: Homo sapiens

<400> SEQUENCE: 178

Arg Ser Ser Gln Ser Leu Leu His Ser Asn Gly Tyr Asn Tyr Leu Asp
1               5                   10                  15

<210> SEQ ID NO 179
<211> LENGTH: 7
<212> TYPE: PRT
<213> ORGANISM: Homo sapiens

<400> SEQUENCE: 179

Leu Gly Ser Asn Arg Ala Ser
1               5

<210> SEQ ID NO 180
<211> LENGTH: 9
<212> TYPE: PRT
<213> ORGANISM: Homo sapiens

<400> SEQUENCE: 180

Met Gln Ala Leu Gln Thr Pro Leu Thr
1               5

<210> SEQ ID NO 181
<211> LENGTH: 12
<212> TYPE: PRT
<213> ORGANISM: Homo sapiens

<400> SEQUENCE: 181

Gly Gly Ser Val Ser Ser Gly Gly Tyr Tyr Trp Ser
1               5                   10

<210> SEQ ID NO 182
<211> LENGTH: 16
<212> TYPE: PRT
<213> ORGANISM: Homo sapiens

<400> SEQUENCE: 182

Phe Ile Tyr Tyr Thr Gly Ser Thr Asn Tyr Asn Pro Ser Leu Lys Ser
1               5                   10                  15

<210> SEQ ID NO 183
<211> LENGTH: 10
<212> TYPE: PRT
<213> ORGANISM: Homo sapiens

<400> SEQUENCE: 183

Asp Tyr Asp Trp Ser Phe His Phe Asp Tyr
1               5                   10

<210> SEQ ID NO 184
<211> LENGTH: 11
<212> TYPE: PRT
<213> ORGANISM: Homo sapiens
```

<400> SEQUENCE: 184

Arg Ala Ser Gln Gly Ile Arg Asn Asp Leu Gly
1               5                   10

<210> SEQ ID NO 185
<211> LENGTH: 9
<212> TYPE: PRT
<213> ORGANISM: Homo sapiens

<400> SEQUENCE: 185

Leu Gln His Asn Ser Tyr Pro Leu Thr
1               5

<210> SEQ ID NO 186
<211> LENGTH: 19
<212> TYPE: PRT
<213> ORGANISM: Homo sapiens

<400> SEQUENCE: 186

Arg Ile Lys Arg Lys Thr Asp Gly Gly Thr Thr Asp Tyr Ala Ala Pro
1               5                   10                  15

Val Lys Gly

<210> SEQ ID NO 187
<211> LENGTH: 7
<212> TYPE: PRT
<213> ORGANISM: Homo sapiens

<400> SEQUENCE: 187

Val Asp Asn Ser Gly Asp Tyr
1               5

<210> SEQ ID NO 188
<211> LENGTH: 10
<212> TYPE: PRT
<213> ORGANISM: Homo sapiens

<400> SEQUENCE: 188

Gly Phe Thr Phe Thr Asn Tyr Trp Met Ser
1               5                   10

<210> SEQ ID NO 189
<211> LENGTH: 17
<212> TYPE: PRT
<213> ORGANISM: Homo sapiens

<400> SEQUENCE: 189

Asn Ile Gln Gln Asp Gly Ser Glu Lys Tyr Tyr Val Asp Ser Val Arg
1               5                   10                  15

Gly

<210> SEQ ID NO 190
<211> LENGTH: 3
<212> TYPE: PRT
<213> ORGANISM: Homo sapiens

<400> SEQUENCE: 190

Trp Asp Tyr
1

<210> SEQ ID NO 191
<211> LENGTH: 16

<212> TYPE: PRT
<213> ORGANISM: Homo sapiens

<400> SEQUENCE: 191

Arg Ser Ser Gln Ser Leu Val His Ser Asp Gly Asn Thr Tyr Leu Asn
1               5                   10                  15

<210> SEQ ID NO 192
<211> LENGTH: 7
<212> TYPE: PRT
<213> ORGANISM: Homo sapiens

<400> SEQUENCE: 192

Met Ile Ser Asn Arg Phe Ser
1               5

<210> SEQ ID NO 193
<211> LENGTH: 9
<212> TYPE: PRT
<213> ORGANISM: Homo sapiens

<400> SEQUENCE: 193

Met Gln Ala Thr Glu Ser Pro Gln Thr
1               5

<210> SEQ ID NO 194
<211> LENGTH: 10
<212> TYPE: PRT
<213> ORGANISM: Homo sapiens

<400> SEQUENCE: 194

Gly Phe Thr Phe Ser Thr Tyr Ser Met Asn
1               5                   10

<210> SEQ ID NO 195
<211> LENGTH: 17
<212> TYPE: PRT
<213> ORGANISM: Homo sapiens

<400> SEQUENCE: 195

Tyr Ile Arg Ser Ser Thr Ser Thr Ile Tyr Tyr Ala Glu Ser Leu Lys
1               5                   10                  15

Gly

<210> SEQ ID NO 196
<211> LENGTH: 4
<212> TYPE: PRT
<213> ORGANISM: Homo sapiens

<400> SEQUENCE: 196

Asp Phe Asp Tyr
1

<210> SEQ ID NO 197
<211> LENGTH: 16
<212> TYPE: PRT
<213> ORGANISM: Homo sapiens

<400> SEQUENCE: 197

Arg Ser Ser Gln Ser Leu Val His Ser Asp Gly Asp Thr Tyr Leu Asn
1               5                   10                  15

<210> SEQ ID NO 198
<211> LENGTH: 7

```
<212> TYPE: PRT
<213> ORGANISM: Homo sapiens

<400> SEQUENCE: 198

Lys Ile Ser Thr Arg Phe Ser
1               5

<210> SEQ ID NO 199
<211> LENGTH: 10
<212> TYPE: PRT
<213> ORGANISM: Homo sapiens

<400> SEQUENCE: 199

Met Gln Thr Thr Gln Ile Pro Gln Ile Thr
1               5                   10
```